US012745974B2

(12) United States Patent
Booth et al.

(10) Patent No.: US 12,745,974 B2
(45) Date of Patent: Sep. 29, 2026

(54) MEDICAL DECISION SUPPORT SYSTEM

(71) Applicant: AUSCULSCIENCES, INC., Vienna, VA (US)

(72) Inventors: Brian J. Booth, Munster (CA); Marina Vernalis, Silver Spring, MD (US); Bahareh Taji, Ottawa (CA); Fatma Usta, Nepean (CA); David Gloag, Kanata (CA); Sergey A. Telenkov, Ottawa (CA); Robin F. Castelino, Kanata (CA)

(73) Assignee: AUSCULSCIENCES, INC., Vienna, VA (US)

( * ) Notice: Subject to any disclaimer, the term of this patent is extended or adjusted under 35 U.S.C. 154(b) by 123 days.

(21) Appl. No.: 18/735,337

(22) Filed: Jun. 6, 2024

(65) Prior Publication Data

US 2024/0366178 A1 Nov. 7, 2024

Related U.S. Application Data

(63) Continuation of application No. 17/509,018, filed on Oct. 24, 2021, which is a continuation of application
(Continued)

(51) Int. Cl.
*A61B 5/0472* (2006.01)
*A61B 5/00* (2006.01)
(Continued)

(52) U.S. Cl.
CPC .............. *A61B 7/04* (2013.01); *A61B 5/0245* (2013.01); *A61B 5/7246* (2013.01); *A61B 5/725* (2013.01);
(Continued)

(58) Field of Classification Search
CPC ......... A61B 5/316; A61B 5/318; A61B 5/352; A61B 5/6885; A61B 5/7246; A61B 5/7267; A61B 7/026; A61B 7/04
See application file for complete search history.

(56) References Cited

U.S. PATENT DOCUMENTS 4,378,022 A 3/1983 Suobank
4,548,204 A 10/1985 Groch et al.
(Continued)

FOREIGN PATENT DOCUMENTS

CA 3025748 A1 12/2017
EP 2710959 A1 3/2014
(Continued)

OTHER PUBLICATIONS

US 8,740,816 B2, 06/2014, Telfort et al. (withdrawn)
(Continued)

*Primary Examiner* — Jon Eric C Morales
(74) *Attorney, Agent, or Firm* — Kurt L. VanVoorhies

(57) ABSTRACT

A Support Vector Machine trained responsive to mean and median values of standard and Shannon energy for a plurality of time and frequency intervals within a heart cycles provides for detecting coronary artery disease (CAD). A quality of an auscultatory sound time-series vector is assessed responsive to a vector distance and angle thereof in relation to a median heart cycle vector.

28 Claims, 83 Drawing Sheets

Related U.S. Application Data

No. PCT/US2021/044854, filed on Aug. 5, 2021, and a continuation-in-part of application No. PCT/US2020/029970, filed on Apr. 24, 2020, and a continuation-in-part of application No. 16/854,894, filed on Apr. 21, 2020, now Pat. No. 11,284,827, which is a continuation-in-part of application No. PCT/US2018/056956, filed on Oct. 22, 2018.

(60) Provisional application No. 63/062,424, filed on Aug. 6, 2020, provisional application No. 63/061,770, filed on Aug. 5, 2020, provisional application No. 62/838,270, filed on Apr. 24, 2019, provisional application No. 62/838,296, filed on Apr. 24, 2019, provisional application No. 62/575,390, filed on Oct. 21, 2017, provisional application No. 62/575,399, filed on Oct. 21, 2017, provisional application No. 62/575,397, filed on Oct. 21, 2017.

(51) Int. Cl.

| | |
|---|---|
| ***A61B 5/02*** | (2006.01) |
| ***A61B 5/0245*** | (2006.01) |
| ***A61B 5/316*** | (2021.01) |
| ***A61B 5/352*** | (2021.01) |
| ***A61B 7/04*** | (2006.01) |
| ***G16H 50/20*** | (2018.01) |
| ***G16H 50/30*** | (2018.01) |

(52) U.S. Cl.

CPC .......... *A61B 5/7257* (2013.01); *A61B 5/7264* (2013.01); *A61B 5/7267* (2013.01); *G16H 50/20* (2018.01); *G16H 50/30* (2018.01)

(56) References Cited

U.S. PATENT DOCUMENTS

| | | | |
|---|---|---|---|
| 4,594,731 | A | 6/1986 | Lewkowicz |
| 4,628,939 | A | 12/1986 | Little |
| 4,905,706 | A | 3/1990 | Duff et al. |
| 5,109,863 | A | 5/1992 | Semmlow et al. |
| 5,117,833 | A | 6/1992 | Albert |
| 5,289,824 | A | 3/1994 | Mills et al. |
| 6,048,319 | A | 4/2000 | Hudgins et al. |
| 6,050,950 | A | 4/2000 | Mohler |
| 6,053,872 | A | 4/2000 | Mohler |
| 6,572,560 | B1 | 6/2003 | Watrous et al. |
| 6,629,937 | B2 | 10/2003 | Watrous |
| 7,096,060 | B2 | 8/2006 | Arand et al. |
| 7,115,102 | B2 | 10/2006 | Abbruscato |
| 7,190,994 | B2 | 3/2007 | Mohler et al. |
| 7,462,153 | B2 | 12/2008 | Bostian et al. |
| 7,527,597 | B2 | 5/2009 | Sandler et al. |
| 7,753,856 | B2 | 7/2010 | Dziubinski |
| 7,909,772 | B2 | 3/2011 | Popev et al. |
| 8,419,651 | B2 | 4/2013 | Owsley et al. |
| 8,449,471 | B2 | 5/2013 | Tran |
| 8,475,396 | B2 | 7/2013 | Jones et al. |
| 8,684,943 | B2 | 4/2014 | Schmidt et al. |
| 8,690,789 | B2 | 4/2014 | Watrous |
| 8,715,206 | B2 | 5/2014 | Telfort et al. |
| 8,755,535 | B2 | 6/2014 | Telfort et al. |
| 8,771,204 | B2 | 7/2014 | Telfort et al. |
| 8,821,415 | B2 | 9/2014 | Al-Ali et al. |
| 8,827,919 | B2 | 9/2014 | Siejko et al. |
| 8,870,791 | B2 | 10/2014 | Sabatino |
| 8,870,792 | B2 | 10/2014 | Al-Ali et al. |
| 8,920,343 | B2 | 12/2014 | Sabatino |
| 8,968,195 | B2 | 3/2015 | Tran |
| 9,050,007 | B1 | 6/2015 | Brockway et al. |
| 9,125,564 | B2 | 9/2015 | Schmidt et al. |
| 9,125,574 | B2 | 9/2015 | Zia et al. |
| 9,198,634 | B2 | 12/2015 | Pretorius et al. |
| 9,215,980 | B2 | 12/2015 | Tran et al. |
| 9,226,726 | B1 | 1/2016 | Semmlow |
| 9,237,870 | B2 | 1/2016 | Mittal |
| 9,364,193 | B2 | 6/2016 | Patangay et al. |
| 9,386,961 | B2 | 7/2016 | Al-Ali et al. |
| 9,408,549 | B2 | 8/2016 | Brockway et al. |
| 9,636,029 | B1 | 5/2017 | Narasimhan et al. |
| 9,724,016 | B1 | 8/2017 | Al-Ali et al. |
| 9,801,542 | B2 | 10/2017 | Tran et al. |
| 9,848,800 | B1 | 12/2017 | Lee et al. |
| 9,848,848 | B2 | 12/2017 | Emmanouilidou et al. |
| 9,955,887 | B2 | 5/2018 | Hughes et al. |
| 9,955,939 | B2 | 5/2018 | Sezan et al. |
| 9,999,359 | B2 | 6/2018 | Thakur et al. |
| 10,098,559 | B2 | 10/2018 | Hughes et al. |
| 10,441,181 | B1 | 10/2019 | Telfort et al. |
| 10,463,340 | B2 | 11/2019 | Telfort et al. |
| 11,045,144 | B2 | 6/2021 | Zhou et al. |
| 11,045,163 | B2 | 6/2021 | Laska et al. |
| 11,191,486 | B2 | 12/2021 | Griffin et al. |
| 11,284,827 | B2 * | 3/2022 | Telenkov ............... A61B 5/352 |
| 11,896,380 | B2 | 2/2024 | Telenkov et al. |
| 2004/0260188 | A1 | 12/2004 | Syed et al. |
| 2004/0267148 | A1 | 12/2004 | Arand et al. |
| 2006/0064037 | A1 | 3/2006 | Shalon et al. |
| 2006/0161064 | A1 | 7/2006 | Watrous et al. |
| 2007/0055151 | A1 | 3/2007 | Shertukde et al. |
| 2007/0191725 | A1 | 8/2007 | Nelson |
| 2009/0043218 | A1 | 2/2009 | Warner et al. |
| 2010/0087746 | A1 | 4/2010 | Radzievsky et al. |
| 2010/0145210 | A1 | 6/2010 | Graff et al. |
| 2011/0066041 | A1 | 3/2011 | Pandia et al. |
| 2011/0066042 | A1 | 3/2011 | Pandia et al. |
| 2011/0098583 | A1 | 4/2011 | Pandia et al. |
| 2011/0125060 | A1 | 5/2011 | Telfort et al. |
| 2011/0208009 | A1 | 8/2011 | Fu et al. |
| 2012/0130263 | A1 | 5/2012 | Pretorius et al. |
| 2013/0109989 | A1 | 5/2013 | Busse et al. |
| 2014/0276229 | A1 | 9/2014 | Ikeda |
| 2015/0018702 | A1 | 1/2015 | Galloway et al. |
| 2015/0038856 | A1 | 2/2015 | Houlton et al. |
| 2015/0057512 | A1 | 2/2015 | Kapoor |
| 2016/0120434 | A1 | 5/2016 | Park et al. |
| 2016/0242665 | A1 | 8/2016 | Galloway |
| 2017/0079594 | A1 | 3/2017 | Telfort et al. |
| 2018/0020987 | A1 | 1/2018 | Schmidt et al. |
| 2018/0317876 | A1 | 11/2018 | Emmanouilidou et al. |
| 2019/0059748 | A1 | 2/2019 | Kaiser et al. |
| 2019/0117162 | A1 | 4/2019 | Zhou et al. |
| 2019/0117165 | A1 | 4/2019 | Zeng et al. |
| 2019/0117184 | A1 | 4/2019 | Laska et al. |
| 2019/0175072 | A1 | 6/2019 | Schmidt et al. |
| 2019/0298269 | A1 | 10/2019 | Atashbar et al. |
| 2020/0015773 | A9 | 1/2020 | Sabatino |
| 2020/0046241 | A1 | 2/2020 | Lam et al. |
| 2020/0245889 | A1 | 8/2020 | Telenkov et al. |
| 2020/0253509 | A1 | 8/2020 | Al-Ali et al. |
| 2021/0298684 | A1 | 9/2021 | Zeng et al. |
| 2021/0298685 | A1 | 9/2021 | Zeng et al. |
| 2022/0061797 | A1 * | 3/2022 | Vernalis ................. A61B 5/725 |

FOREIGN PATENT DOCUMENTS

| | | | |
|---|---|---|---|
| IN | 202141027484 | A | 7/2021 |
| WO | 2006078954 | A1 | 7/2006 |
| WO | 2008036911 | A2 | 3/2008 |
| WO | 2011015935 | A1 | 2/2011 |
| WO | 2019079829 | A1 | 4/2019 |
| WO | 2020219991 | A1 | 10/2020 |
| WO | 2022032041 | A1 | 2/2022 |

OTHER PUBLICATIONS

Weissler et al., "Systolic Time Intervals in Heart Failure in Man," Circulation, Vo. 37, No. 2, Feb. 1968, pp. 149-159.

Miller et al., "Spectral Analysis of Arterial Bruits (Phonoangiography): Experimental Validation," 61 Circulation (3) pp. 515-520 (Mar. 1980).

(56) References Cited

OTHER PUBLICATIONS

Luisada et al., "Assessment of Left Ventricular Function by Noninvasive Methods," 32 Adv. Cardiol, pp. 111-141 (1985).
Abe et al., "Measurement of Left Atrial Systolic Time Intervals in Hypertensive patients Using Doppler Echocardiography: Relation to Fourth Heart Sound and Left Ventricular Wall Thickness," 11 JACC (4) pp. 800-805 (Apr. 1988).
Daubechies, Ingrid, "Orthonormal Bases of Compactly Supported Wavelets," Communications on Pure and Applied Mathematics, vol. XLI, 909-996 (1988).
Rangayyan et al., "Phonocardiogram Signal Analysis: A Review," 15 CRC Critical Reviews in Biomedical Engineering(3) pp. 211-237 (1988).
Donnerstein, Richard L., "Continuous Spectral Analysis of Heart Murmurs for Evaluating Stenotic Cardiac Lesions," 64 American J, Cardiology pp. 625-630 (Sep. 1989).
Mallat, Stephane G., A theory for multiresolution signal decomposition: the wavelet representation. IEEE Trans. Pattern Anal. Mach. Intell., 11(7), 674-693 (1989).
Hamilton et al., "Compression of the Ambulatory ECG by Average Beat Subtraction and Residual Differencing," IEEE Transactions on Biomedical Engineering, vol. 38, No. 3, pp. 253-259 (Mar. 1991).
Khadra et al., "The Wavelet Transform and its Applications to Phonocardiogram Signal Analysis," 16 Med. Inform. (3), pp. 271-277 (1991).
Thakor et al., "Applications of Adaptive Filtering to ECG Analysis: Noise Cancellation and Arrhythmia Detection," 38 IEEE Transaction on Biomedical Engineering (8) pp. 785-794 (Aug. 1991).
Glower, et al., "Mechanical Correlates of the Third Heart Sound," 19 JACC (2) pp. 450-457 (Feb. 1992).
Wikerhauser, Mladen Victor, Lectures on Wavelet Packet Algorithms, http://citeseerx.ist.psu.edu, Apr. 1992.
MathWorks, "Envelope Detection", MathWorks Help Center, MATLAB & Simulink, Internet document, 6 pp., downloaded on Apr. 15, 2019, https://www.mathworks.com/help/dsp/ug/envelope-detection.html.
Weston, Jason, "Support Vector Machine (and Statistical Learning Theory) Tutorial", NEC Labs America, Internet Document: http://www.cs.columbia.edu/~kathy/cs4701/documents/jason_svm_tutorial.pdf, downloaded on Apr. 17, 2019.
Wikipedia, "Softmax Function", Internet Document, 7 pp., https://en.wikipedia.org/wiki/Softmax_function, downloaded on Apr. 17, 2019.
Wikipedia, "Convolution Neural Network", Internet Document, 22 pp., https://en.wikipedia.org/wiki/Convolutional_neural_network as of Apr. 22, 2019 per https://web.archive.org/web/20190422083506/https://en.wikipedia.org/wiki/convolutional_neural_network, downloaded on Apr. 20, 2020.
Giordano et al., "A Novel Method for Measuring the Timing of Heart Sound Components through Digital Phonocardiography," Sensors 2019, 19, 1868; Publication [online]. Apr. 19, 2019 [retrieved Jul. 6, 2020]. Retrieved from the Internet: <URL: https://www.mdpi.com/1424-8220/19/8/1868 >.
Tan, Andrew, "Principal Components of Electrocardiograms", Internet Document, Medium, Nov. 29, 2016, 8 pp., https://medium.com/@andrewtan_36013/principal-components-of-electrocardiograms-14874b3a96b1.
Schmidt, Samuel, Detection of Coronary Artery Disease with an Electric Stethoscope, PHD Thesis, Aalborg University, Aalborg, Denmark, 2011, 49 pp.
Bogaert et al., Clinical cardiac MRI, Springer Science & Business Media, 2012, p. 517.
Bogaert et al., Clinical cardiac MRI, Springer Science & Business Media, 2012, p. 17.
Zhu et al., "An R-peak detection method based on peaks of Shannon enegy envelope : Abstract",Science Direct, Biomedical Signal Processing and Control, vol. 8, Issue 5, Sep. 2013, pp. 466-474, https://doi.org/10.1016/j.bspc.2013.01.001.
Mohamed et al., "An Approach for ECG Feature Extraction using Daubechies 4 (DB4) Wavelet", International Journal of Computer Applications (0975-8887), vol. 96—No. 12, Jun. 2014.
Sharma et al., "Study and Design of a Shannon-Energy-Envelope based Phonocardiogram Peak Spacing Analysis for Estimating Arrhythmic Heart-Beat", International Journal of Scientific and Research Publications, vol. 4, Issue 9, Sep. 2014, ISSN 2250-3153, 5 pp., www.ijsrp.org/research-paper-0914/ijsrp-p3325.pdf.
Jeong-Seon Park et al: "R Peak Detection Method Using Wavelet Transform and Modified Shannon Energy Envelope", Journal of Healthcare Engineering, vol. 2017, Jul. 5, 2017 (Jul. 5, 2017), pp. 1-14, XP055546974, Brentwood ISSN: 2040-2295, DOI: 10.1155/2017/4901017.
Ray, Sunil, "Understanding Support Vector Machine (SVM) algorithm from examples (along with code)", Sep. 13, 2017, 6 pp., from https://www.analyticsvidhya.com/blog/2017/09/understaing-support-vector-machine-example-code/.
Healio-Learn the Heart, "Heart Sounds Topic Review," Cardiology Review: Topic Reviews, Downloaded on Oct. 18, 2018, 14 pp., https://www.healio.com/cardiology/learn-the-heart/cardiology-review/topic-reviews/heart-sounds.
MathWorks, "Code for Shannon energy envelope?", MATLAB Answers, MATLAB Central, Internet document, 3 pp., Jan. 17, 2019, https://www.mathworks.com/matlabcentral/answers/440144-code-for-shannon-energy-envelope/.
European Patent Office International Search Report and Written Opinion of International Searching Authority in International Application No. PCT/US2018/056956, Feb. 1, 2019, 9 pp.
USPTO, International Preliminary Report On Patentability in International Application No. PCT/US2018/056956, Nov. 26, 2019, 86 pp.
USPTO, Examiner's search strategy and results, Written Opinion of the ISA, International Search Report, and Transmittal in International Application No. PCT/US2020/029970, Oct. 1, 2020, 23 pp.
USPTO, International Search Report and Written Opinion of the ISA and Transmittal thereof, Examiner's search strategy and results in International Application No. in International Application No. PCT/US2021/044854, USPTO, Dec. 29, 2021, 32 pp.
Wood et al., "Time-Frequency Transforms: A New Approach to First Heart Sound Frequency Dynamics," IEEE Transaction on Biomedical Engineering, vol. 39, No. 7, pp. 730-740 (Jul. 1992).
Akay et al., "Noninvasive Characterization of the Sound Pattern Caused by Coronary Artery Stenosis Using FTF/FAEST Zero Tracking Filters: Normal/Abnormal Study," 21 Annals of Biomedical Engineering, pp. 175-182 (1993).
Akay et al., "Noninvasive Acoustical Detection of Coronary Artery Disease: A Comparative Study of Signal Processing Methods," 40 IEEE Transaction on Biomedical Engineering (6) pp. 571-578 (Jun. 1993).
Akay et al., "Acoustical Detection of Coronary Occlusions Using Neural Networks," 15 J. Biomed. Eng pp. 469-473 (1993).
Akay et al., "Application of Adaptive FTF/FAEST Zero Tracking Filters to Noninvasive Characterization of the Sound Pattern Caused by Coronary Artery Stenosis Before and After Angioplasty," 21 Annals of Biomedical Engineering, pp. 9-17 (1993).
Perini et al., "Body Position Affects the Power Spectrum of Heart Rate Variability During Dynamic Exercise," 66 Eur. J. Appl. Physiol. , pp. 207-213 (1993).
Graps, Amara, "An Introduction to Wavelets," IEEE Computational Science and Engineering, Summer 1995, vol. 2, No. 2, 1995, pp. 1-18.
Saito et al., "Local discriminant bases and their applications," J. Math. Imaging and Vision, 5, 337-358 (1995).
Saito et al., "On Local Feature Extraction for Signal Classification," ICIAM, 1995, https://www.math.ucdavis.edu/~saito/publications/saito_iciam95.pdf.
Zhou et al, "A Novel Technique for Muscle Onset Detection Using Surface EMG Signals without Removal of ECG Artifacts," US National Library of Medicine, National Institutes of Health, HHS Public Access, https://www.ncbi.nlm.nih.gov/pmc/articles/PMC4035355/, 1995, 12 pp.

(56) References Cited

OTHER PUBLICATIONS

Richman et al, "Physiological Time-Series Analysis Using Approximate Entropy and Sample Entropy," Am J Physiol Heart Circ Physiol., 278: H2039-H2049, 2000.
Santos et al., "Detection of First and Second Cardiac Sounds Based on Time Frequency Analysis," 23rd Annual International Conference of the IEEE Engineering in Medicine and Biology Society, Oct. 25-28, 2001, Istanbul, Turkey.
Erne, Paul, "Beyond auscultation—acoustic cardiography in the diagnosis and assessment of cardiac disease," Swiss Med. Wkly 2008, 128 (31-32), pp. 439-452.
Kessler et al., "Wavelet Notes", University of Iowa, https://arxiv.org/pdf/nucl-th/0305025.pdf, Feb. 5, 2008.
Wasilewski, Filip, "Wavelet Daubechies 4 (db4) Properties," Pywavelets, Internet Document: http://wavelets.pybytes.com/wavelet/db4/, 2008-2019.
Bogaert et al., Clinical cardiac MRI, Springer Science & Business Media, 2009, pp. 10-11.
Inovise Medical Inc, "Audicor 200S", 2009, 2 pp. brochure downloaded from www.audiocore.com on Sep. 14, 2020.
Xinpei Wang et al: "Detection of the First and Second Heart Sound Using Heart Sound Energy", 2009 2nd International Conference on Biomedical Engineering and Informatics : BMEI 2009 ; Tianjin, China, Oct. 17-19, 2009, Jan. 1, 2009 (Jan. 1, 2009), pp. 1-4, XP055546725, Piscataway, NJ, USA DOI: 10.1109/BMEI.2009.5305640 ISBN: 978-1-4244-4132-7.
Zuber et al., "Acoustic cardiography to improve detection of coronary artery disease with stress testing," World Journal of Cardiology, vol. 2, Issue 5, May 26, 2010, pp. 118-124.

* cited by examiner 16.1, 72

37, 76

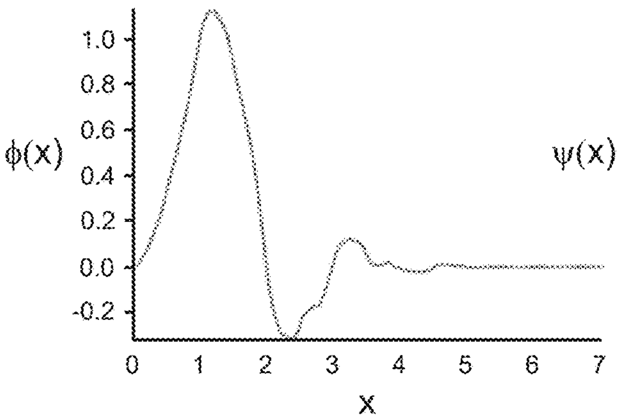
Scaling function φ
$h_0 = -0.0105974018$
$h_1 = 0.0328830117$
$h_2 = 0.0308413818$
$h_3 = -0.1870348117$
$h_4 = -0.0279837694$
$h_5 = 0.6308807679$
$h_6 = 0.7148465706$
$h_7 = 0.2303778133$
FIG. 59
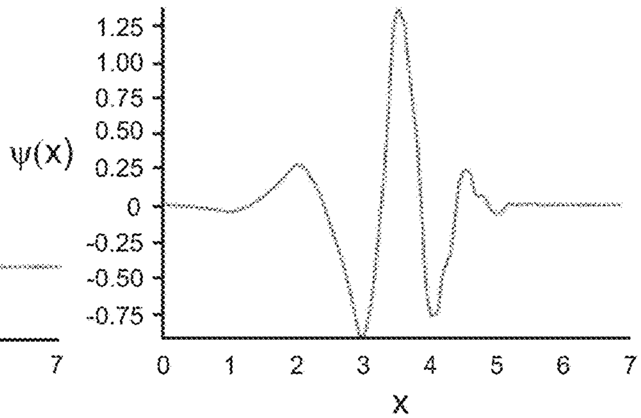
Wavelet function ψ
$g_0 = -0.2303778133$
$g_1 = 0.7148465706$
$g_2 = -0.6308807679$
$g_3 = -0.0279837694$
$g_4 = 0.1870348117$
$g_5 = 0.0308413818$
$g_6 = -0.0328830117$
$g_7 = -0.0105974018$
FIG. 60
61.2g 61.1g
$$w_{j+1,2k+1}[l] = \sqrt{2} \cdot \sum_{m=1}^{M} g_m w_{j,k}[2 \cdot l - m]$$
$$w_{j+1,2k}[l] = \sqrt{2} \cdot \sum_{m=1}^{M} h_m w_{j,k}[2 \cdot l - m]$$
61.2h 61.1h
FIG. 61

9100

$$S3_{SWING}toS1timesS2_{SWING}[b] = S3_{SWING} / (S1_{SWING} \cdot S2_{SWING})$$
$$S4_{SWING}toS1timesS2_{SWING}[b] = S4_{SWING} / (S1_{SWING} \cdot S2_{SWING})$$

$$S3_{SWING}toS1plusS2_{SWING}[b] = S3_{SWING} / (S1_{SWING} + S2_{SWING})$$
$$S4_{SWING}toS1plusS2_{SWING}[b] = S4_{SWING} / (S1_{SWING} + S2_{SWING})$$

$$S3S2_{SWING}plusS3S1_{SWING}[b] = S3S2_{SWING}[b] + S3S1_{SWING}[b]$$
$$S4S2_{SWING}plusS4S1_{SWING}[b] = S4S2_{SWING}[b] + S4S1_{SWING}[b]$$

{X}

*FIG. 91*

9200

$$MS3s\_S1timesS2s = Median( S3_{SWING}toS1timesS2_{SWING}[\{b\}] )$$
$$MS4s\_S1timesS2s = Median( S4_{SWING}toS1timesS2_{SWING}[\{b\}] )$$

$$MS3s\_S1plusS2s = Median( S3_{SWING}toS1plusS2_{SWING}[\{b\}] )$$
$$MS4s\_S1plusS2s = Median( S4_{SWING}toS1plusS2_{SWING}[\{b\}] )$$

$$MS3S2splusS3S1s = Median( S3S2_{SWING}plusS3S1_{SWING}[\{b\}] )$$
$$MS4S2splusS4S1s = Median( S4S2_{SWING}plusS4S1_{SWING}[\{b\}] )$$

{X}

*FIG. 92*

MEDICAL DECISION SUPPORT SYSTEM

CROSS-REFERENCE TO RELATED APPLICATIONS

The instant application is a continuation of U.S. application Ser. No. 17/509,018 filed on 24 Oct. 2021, which is a continuation of International Application No. PCT/US2021/044854 filed on 5 Aug. 2021, which claims benefit of the following: U.S. Provisional Application Ser. No. 63/061,770 filed on 5 Aug. 2020, and U.S. Provisional Application Ser. No. 63/062,424 filed on 6 Aug. 2020. U.S. application Ser. No. 17/509,018 is a continuation-in-part of International Application No. PCT/US2020/029970 filed on 24 Apr. 2020, which claims benefit of the following: U.S. Provisional Application Ser. No. 62/838,270 filed on 24 Apr. 2019, and U.S. Provisional Application Ser. No. 62/838,296 filed on 24 Apr. 2019. U.S. application Ser. No. 17/509,018 is also a continuation-in-part of U.S. application Ser. No. 16/854,894 filed on 21 Apr. 2020, now U.S. Pat. No. 11,284,827 issued on 29 Mar. 2022, which is a continuation-in-part of International Application No. PCT/US2018/056956 filed on 22 Oct. 2018, which claims benefit of the following: U.S. Provisional Application Ser. No. 62/575,390 filed on 21 Oct. 2017, U.S. Provisional Application Ser. No. 62/575,397 filed on 21 Oct. 2017, and U.S. Provisional Application Ser. No. 62/575,399 filed on 21 Oct. 2017. U.S. application Ser. No. 16/854,894 also claims benefit of the following: U.S. Provisional Application Ser. No. 62/838,270 filed on 24 Apr. 2019, and U.S. Provisional Application Ser. No. 62/838,296 filed on 24 Apr. 2019. Each of the above identified applications is incorporated herein by reference in its entirety.

BRIEF DESCRIPTION OF THE DRAWINGS

In the accompanying drawings:

FIGS. 5*b* and 5*c* each illustrate an auscultatory sound sensor that is detached, and therefore fully decoupled, from the skin of a test-subject, wherein FIG. 5*b* illustrates the associated adhesive interface detached from the skin of the test-subject, and FIG. 5*c* illustrates the associated adhesive interface detached from the auscultatory sound sensor;

FIGS. 10*a*-10*f* respectively illustrate a simulation of successively recorded blocks of breath-held, sensor time-series data illustrated in FIG. 9, each illustrated with an expanded time scale, wherein FIGS. 10*a*-10*e* illustrates a condition for which the auscultatory sound sensor is coupled to the skin of the test-subject, and FIG. 10*f* illustrates a condition for which the auscultatory sound sensor is decoupled from the skin of the test-subject;

FIGS. 12*a*-12*f* respectively illustrate time-series of the absolute values of the corresponding time-series data illustrated in FIGS. 10*a*-10*f*, further illustrating a division of the block of breath-held, sensor time-series data into a plurality of associated data segments, with each data segment of sufficient width to nominally include sound from a single heartbeat, and with the peak values in each data segment marked, wherein FIGS. 12*a*-12*e* illustrates a condition for which the auscultatory sound sensor is coupled to the skin of the test-subject, and FIG. 12*f* illustrates a condition for which the auscultatory sound sensor is decoupled from the skin of the test-subject;

FIG. 59 illustrates a scaling function of a Daubechies 4 (db4) wavelet family;

FIG. 60 illustrates a wavelet function of a Daubechies 4 (db4) wavelet family;

FIG. 61 illustrates a kernel discrete wavelet transformation process;

FIG. 91 illustrates a flow chart of a process for optionally determining a plurality of supplemental swing measures from the swing measures determined by the process illustrated in FIG. 90, called from the process illustrated in FIG. 89;

FIG. 92 illustrates flow chart of a process for optionally determining median values of the plurality of supplemental swing measures determined by the process illustrated in FIG. 91, called from the process illustrated in FIG. 89;

DESCRIPTION OF EMBODIMENT(S)

Figure 1:
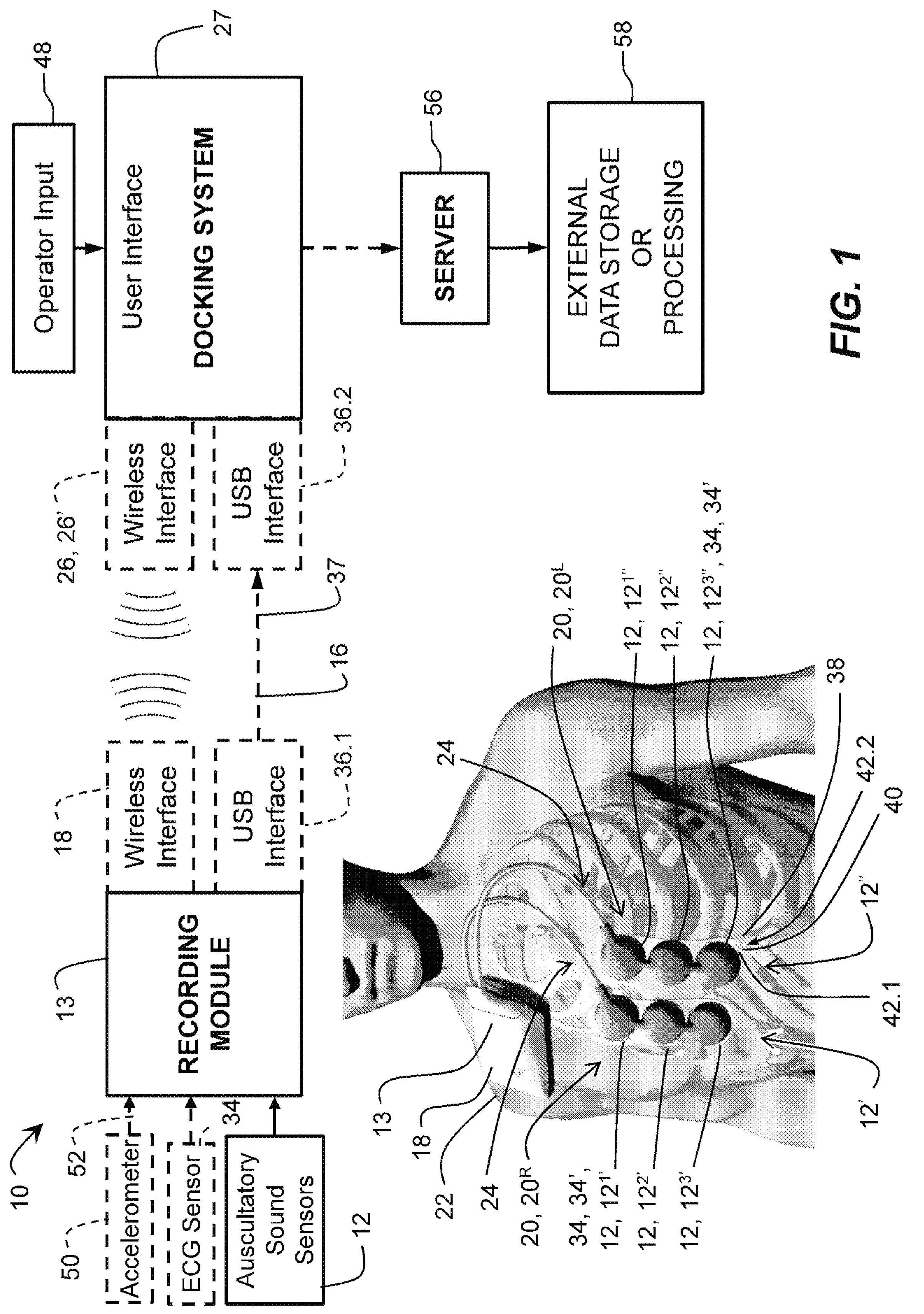
FIG. 1 illustrates a block diagram of a coronary-artery-disease detection system.
Figure 2:
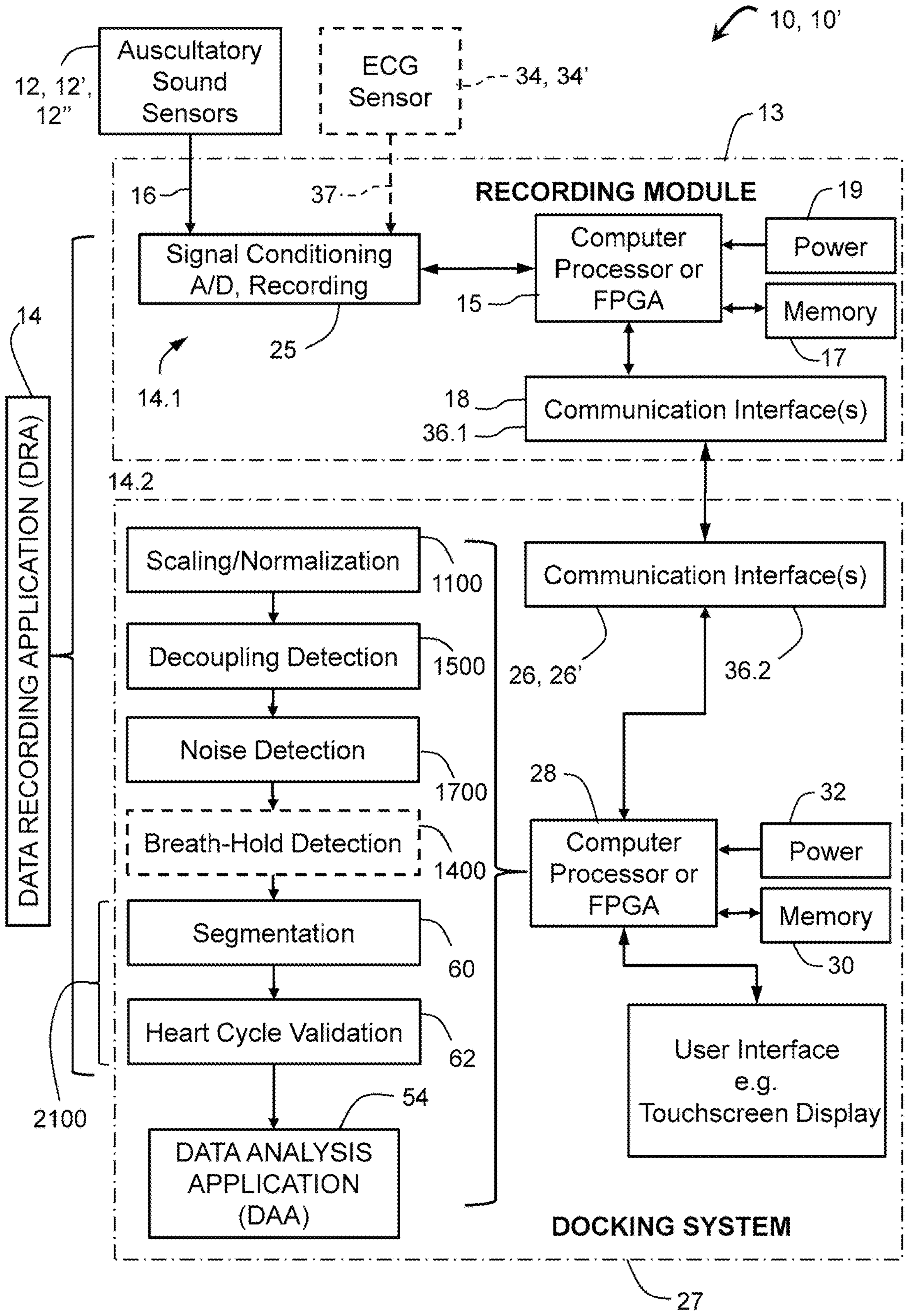
FIG. 2 illustrates a first aspect of a data recording module and a first aspect of an associated docking system, in accordance with a first aspect of the coronary-artery-disease detection system illustrated in FIG. 1.
Figure 3:
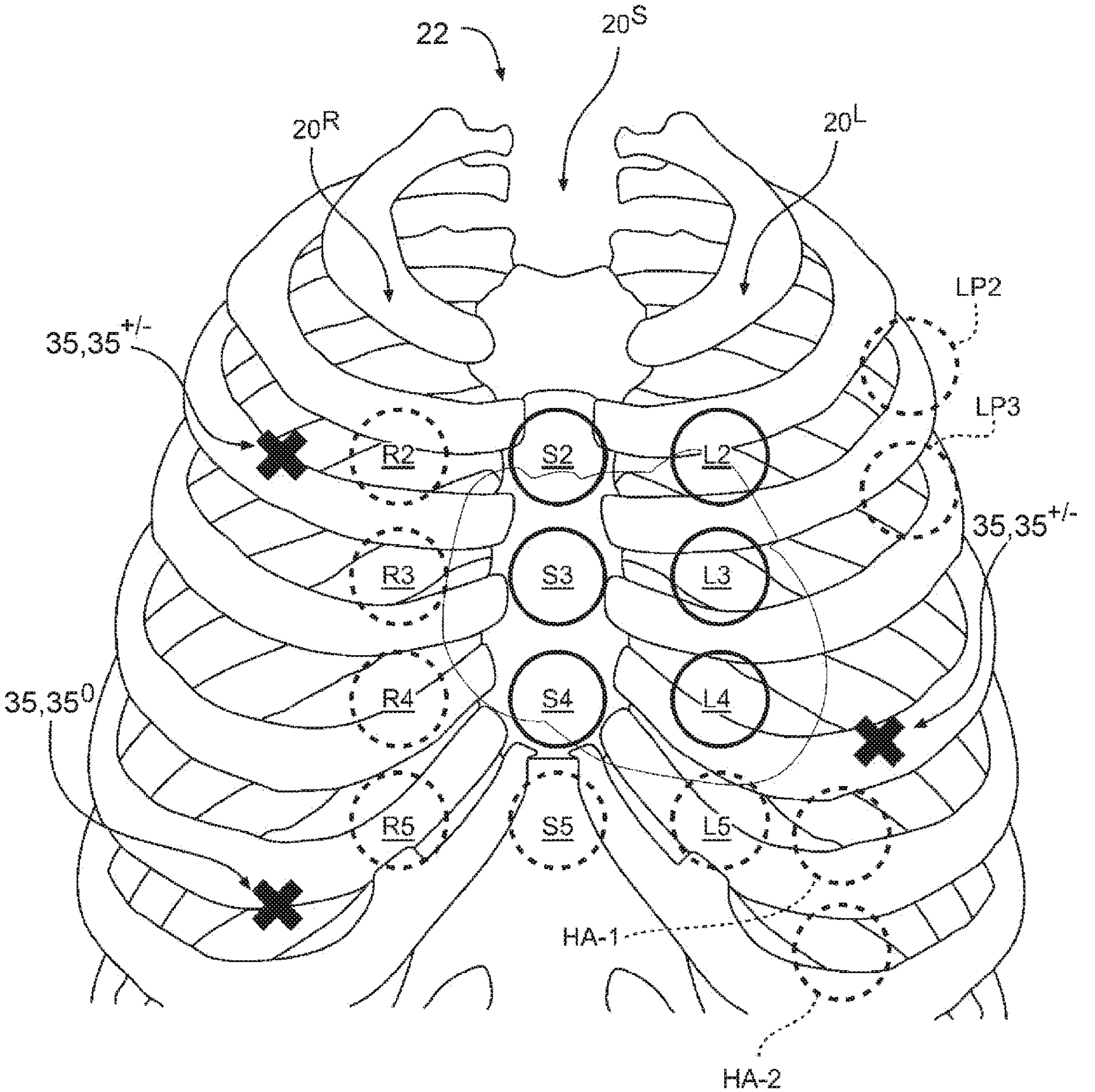
FIG. 3 illustrates a fragmentary view of a human thorax and associated prospective locations of auscultatory sound sensors at associated right, sternum and left, second, third, fourth and fifth, intercostal spaces, left posterior locations at the second and third intercostal spaces, and locations proximate to the heart apex.

Referring to FIGS. 1 and 2, an auscultatory coronary-artery-disease detection system 10 incorporates at least one auscultatory sound sensor 12 that is operatively coupled to a recording module 13 running at least a first portion 14.1 of a Data Recording Application (DRA) 14, 14.1 on a first specialized computer or electronic system comprising a first computer processor or FPGA (Field Programmable Gate Array) 15 and a first memory 17 powered by a first power supply 19, which provides for recording and preprocessing auscultatory sound signals 16 from the at least one auscultatory sound sensor 12. For example, in one set of embodiments, the at least one auscultatory sound sensor 12 comprises a first group 12' of three auscultatory sound sensors 12, $12^{1'}$, $12^{2'}$, $12^{3'}$ physically interconnected end-to-end with one another, and physically and electrically interconnected with a first wireless transceiver 18; and a second group 12" of three auscultatory sound sensors 12, $12^{1''}$, $12^{2''}$, $12^{3''}$ physically interconnected end-to-end with one another, and physically and electrically interconnected with the first wireless transceiver 18, with both groups 12', 12" of auscultatory sound sensors placed on the skin of the thorax 20 of a test-subject 22, in acoustic communication therewith. Referring also to FIG. 3, the placement of the first group of auscultatory sound sensors 12' in FIG. 1 is illustrated with the respective associated auscultatory sound sensors 12, $12^{1'}$, $12^{2'}$, $12^{3'}$ in substantial alignment with the corresponding respective third R3, fourth R4 and fifth R5, intercostal spaces on the right side $20^R$ of the thorax 20, and the placement of the second group of auscultatory sound sensors 12" in FIG. 1 is illustrated with the respective associated auscultatory sound sensors 12, $12^{1''}$, $12^{2''}$, $12^{3''}$ in substantial alignment with the corresponding respective third L3, fourth L4 and fifth L5, intercostal spaces on the left side $20^L$ of the thorax 20. Prospective sensor locations R2-R5, S2-S5, and L2-L5 illustrated in FIG. 3 respectively refer to the second R2 through fifth R5 intercostal spaces on the right side $20^R$ of the thorax 20, the second S2 through fifth S5 intercostal spaces at the center/sternum $20^S$ of the thorax 20, and the second L2 through fifth L5 intercostal spaces on the left side $20^L$ of the thorax 20. Furthermore, prospective left-side posterior sensor locations LP2 and LP3 illustrated in FIG. 3 respectively refer to the second LP2 and third LP3 intercostal spaces locations at the posterior of the thorax 20. Yet further, prospective sensor locations HA-1 and HA-2 are proximate to the apex of the heart, at either the anterior or the posterior of the thorax 20. For example, in one set of embodiments, the auscultatory sound sensors 12, $12^{1'}$, $12^{2'}$, $12^{3'}$, $12^{1''}$, $12^{2''}$, $12^{3''}$ are located at the second S2, L2, third S3, L3 and fourth S4, L4 intercostal spaces at the sternum S2-S4 and left-side L2-L4 of the thorax 20.

As used herein, the term "auscultatory sound" is intended to mean a sound originating from inside a human or animal organism as a result of the biological functioning thereof, for example, as might be generated by action of the heart, lungs, other organs, or the associated vascular system; and is not intended to be limited to a particular range of frequencies—for example, not limited to a range of frequencies or sound intensities that would be audible to a human ear,—but could include frequencies above, below, and in the audible range, and sound intensities that are too faint to be audible to a human ear. Furthermore, the term "auscultatory-sound sensor" is intended to mean a sound sensor that provides for transducing auscultatory sounds into a corresponding electrical or optical signal that can be subsequently processed.

The auscultatory sound sensors 12, $12^{1'}$, $12^{2'}$, $12^{3'}$, $12^{1''}$, $12^{2''}$, $12^{3''}$ provide for transducing the associated sounds received thereby into corresponding auscultatory sound signals 16 that are preprocessed and recorded by an associated hardware-based signal conditioning/preprocessing and recording subsystem 25, then communicated to the first wireless transceiver 18, and then wirelessly transmitted thereby to an associated second wireless transceiver 26 of an associated wireless interface 26' of an associated docking system 27, possibly running a second portion 14.2 of the Data Recording Application (DRA) 14, 14.2 on a corresponding second specialized computer or electronic system comprising an associated second computer processor or FPGA (Field Programmable Gate Array) 28 and second memory 30, both of which are powered by an associated second power supply 32, which together provide for recording and preprocessing the associated auscultatory sound signals 16 from the auscultatory sound sensors 12, $12^{1'}$, $12^{2'}$, $12^{3'}$, $12^{1''}$, $12^{2''}$, $12^{3''}$.

For example, in accordance with one set of embodiments, the hardware-based signal conditioning/preprocessing and recording subsystem 25 includes an amplifier—either of fixed or programmable gain,—a filter, and an analog-to-digital converter (ADC). For example, in one set of embodiments, the analog-to-digital converter (ADC) is a 16-bit analog-to-digital converter (ADC) that converts a −2.25 to +2.25 volt input to a corresponding digital value of −32,768 to +32,767. Furthermore, in accordance with one set of embodiments of the amplifier, the amplifier gain is programmable to one of sixteen different levels respectively identified as levels 0 to 15, with corresponding, respective gain values of 88, 249, 411, 571, 733, 894, 1055, 1216, 1382, 1543, 1705, 1865, 2027, 2188, 2350 and 2510, respectively for one set of embodiments. In accordance with another set of embodiments of the amplifier, the amplifier gain is fixed at the lowest above value, i.e., for this example, 88, so as to provide for avoiding the relative degradation of the associated signal-to-noise ratio (SNR) that naturally occurs with the relatively high gain levels of the programmable-gain set of embodiments.

It should be understood that the associated processes of the Data Recording Application (DRA) 14 could be implemented either in software-controlled hardware, hardware, or a combination of the two.

For example, in one set of embodiments, either or both the recording module 13 or the docking system 27 may be constructed and operated in accordance with the disclosure of U.S. Provisional Application No. 62/575,364 filed on 20 Oct. 2017, entitled CORONARY ARTERY DISEASE DETECTION SYSTEM, or International Application No. PCT/US2018/056832 filed on 22 Oct. 2018, entitled CORONARY ARTERY DISEASE DETECTION SIGNAL PROCESSING SYSTEM AND METHOD, each of which is incorporated by reference in its entirety. Furthermore, in accordance with one set of embodiments, the auscultatory coronary-artery-disease detection system 10 may further incorporate an ECG sensor 34, for example, in one set of embodiments, an ECG sensor 34' comprising a pair of electrodes 35 incorporated in a corresponding pair of auscultatory sound sensors 12, wherein the signal from the ECG sensor 34' is also preprocessed and recorded by a corresponding different signal channel of the same hardware-based signal conditioning/preprocessing and recording subsystem 25 of the recording module 13 that is used to preprocess the signals from the one or more auscultatory sound sensors 12. Alternatively, the ECG sensor 34 may comprise a separate set of a pair or plurality of electrodes 35 that are coupled to the skin of the test-subject, for example, in one set of embodiments, a pair of signal electrodes 35, $\mathbf{35}^{+/-}$ in cooperation with a ground electrode $\mathbf{35}^{0}$, wherein, referring to FIG. 3 (illustrating the locations of the electrodes 35, $\mathbf{35}^{+/-}$, $\mathbf{35}^{0}$), in accordance with one non-limiting embodiment, the signal electrodes 35, $\mathbf{35}^{+/-}$ span the heart from diametrically-opposed quadrants of the torso 44, and the ground electrode $\mathbf{35}^{0}$ is located in a different quadrant, orthogonally displaced from a midpoint of a baseline connecting the signal electrodes 35, $\mathbf{35}^{+/-}$. Alternatively the signal electrodes 35, $\mathbf{35}^{+/-}$ could span across the top of the top of the thorax 20, or at any pair of locations commonly used for conventional ECG tests. Furthermore, in one set of embodiments, the recording module 13 and docking system 27 may each incorporate a corresponding respective USB interface 36.1, 36.2 to provide for transferring corresponding auscultatory sound signals 16 and/or an electrographic signal 37—from an associated ECG sensor 34, 34'—from the recording module 13 to the docking system 27, for example, rather than relying upon the first 18 and second 26 wireless transceivers of an associated wireless interface 26'. Further alternatively, either instead of, or in addition to, the wireless interface 26' or the USB interface 36.1, 36.2, data may be transferred from the recording module 13 to the docking system 27 via a portable memory element, for example, either an SD memory card or a Micro SD memory card.

Figure 4:
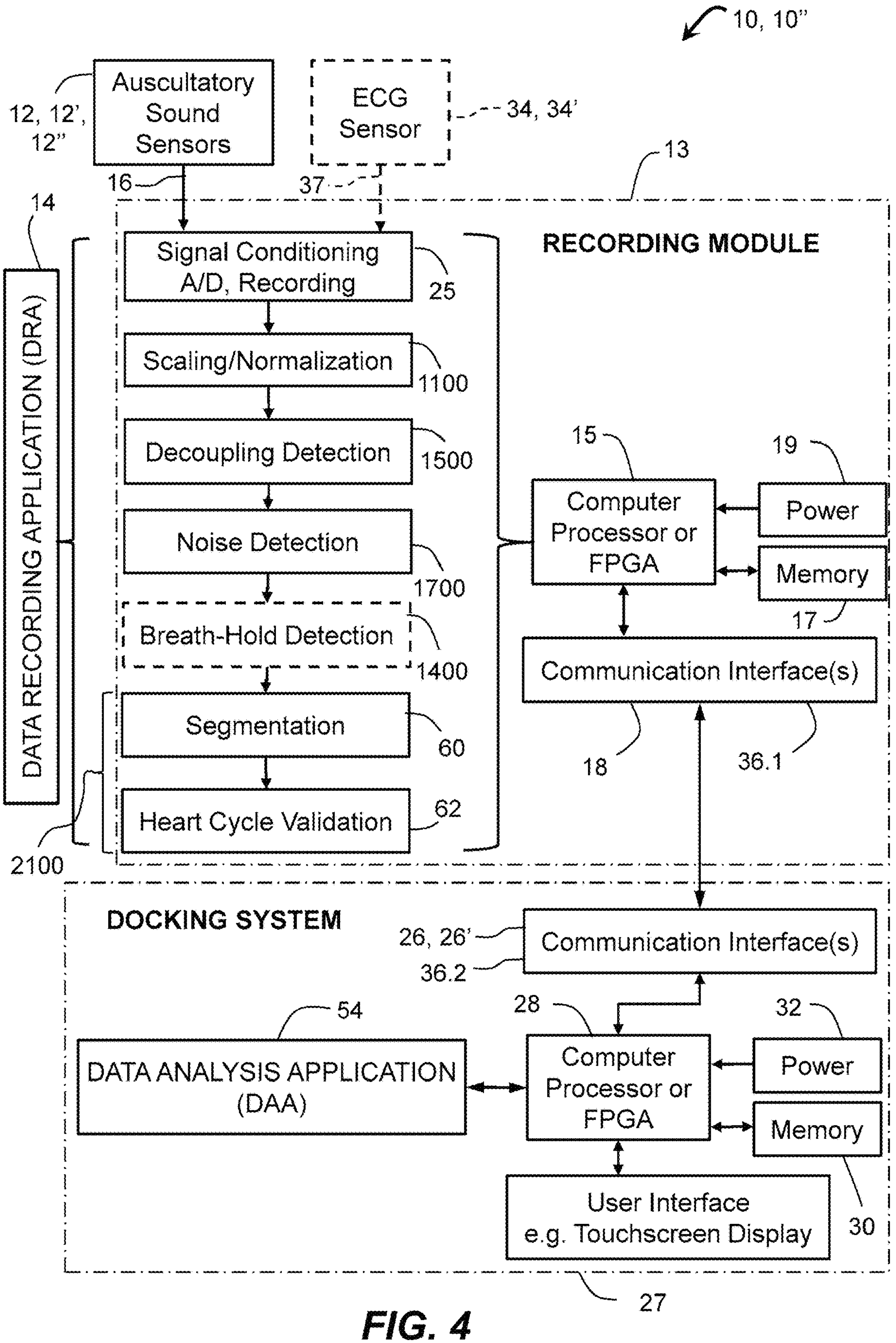
FIG. 4 illustrates a second aspect of a data recording module and a second aspect of an associated docking system, in accordance with a second aspect of the coronary-artery-disease detection system illustrated in FIG. 1.

The functionality of the Data Recording Application (DRA) 14 is distributed across the recording module 13 and the docking system 27. For example, referring to FIG. 2, in accordance with a first aspect 10' of an auscultatory coronary-artery-disease detection system 10, 10', the Data Recording Application (DRA) 14 spans across the recording module 13 and the docking system 27, with a first portion 14.1 comprising the hardware-based signal conditioning/preprocessing and recording subsystem 25 operative on the recording module 13, and a remaining second portion 14.2 operative on the docking system 27. Alternatively, as another example, referring to FIG. 4, in accordance with a second aspect 10" of an auscultatory coronary-artery-disease detection system 10, 10", the Data Recording Application (DRA) 14 is operative entirely on the recording module 13.

The auscultatory sound sensor 12 provides for sensing sound signals that emanate from within the thorax 20 of the test-subject 22 responsive to the operation of the test-subject's heart, and the resulting flow of blood through the arteries and veins, wherein an associated build-up of deposits therewithin can cause turbulence in the associated blood flow that can generate associated cardiovascular-condition-specific sounds, the latter of which can be detected by a sufficiently-sensitive auscultatory sound sensor 12 that is acoustically coupled to the skin 38 of the thorax 20 of the test-subject 22. For some cardiovascular-conditions associated with, or predictive of, a cardiovascular disease, the sound level of these cardiovascular-condition-specific sounds can be below a level that would be detectable by a human using a conventional stethoscope. However, these sound levels are susceptible to detection by sufficiently sensitive auscultatory sound sensor 12 that is sufficiently acoustically coupled to the skin 38 of the thorax 20 of the test-subject 22. For example, in one of embodiments, the auscultatory sound sensor 12 may be constructed in accordance with the teachings of U.S. Provisional Application No. 62/568,155 filed on 4 Oct. 2017, entitled AUSCULTATORY SOUND SENSOR, or International Application No. PCT/US2018/054471 filed on 4 Oct. 2018, entitled AUSCULTATORY SOUND-OR-VIBRATION SENSOR, each of which is incorporated by reference in its entirety. Furthermore, in another set of embodiments, the auscultatory sound sensor 12 may be constructed in accordance with the teachings of U.S. Pat. Nos. 6,050,950, 6,053,872 or 6,179,783, which are incorporated herein by reference.

Figure 5A:
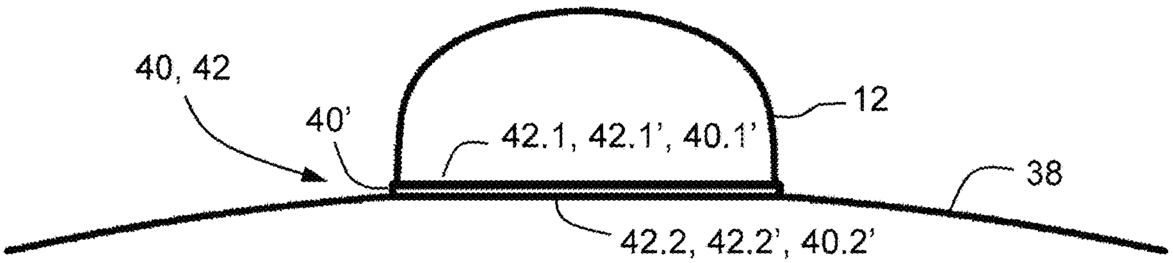
FIG. 5*a* illustrates an auscultatory sound sensor coupled to the skin of a test-subject, by bonding via associated adhesive layers or surfaces on both sides of an adhesive interface.
Figure 5B:
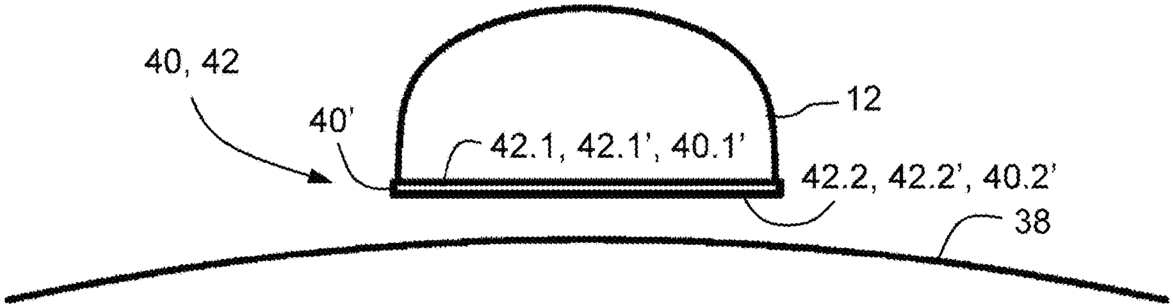
Figure 5C:
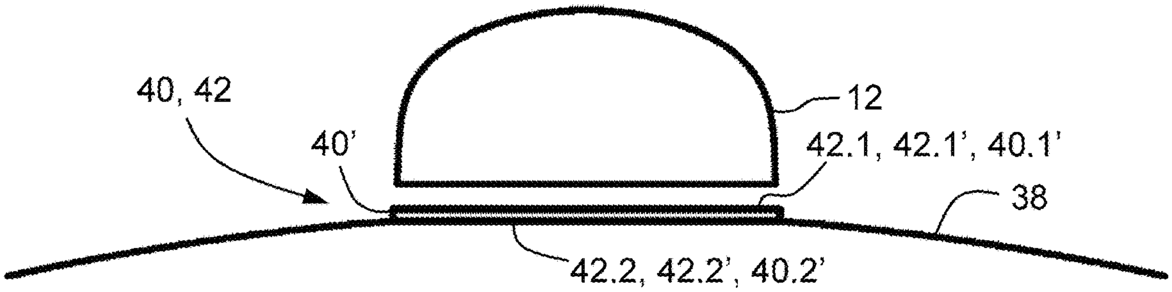
Figure 5D:
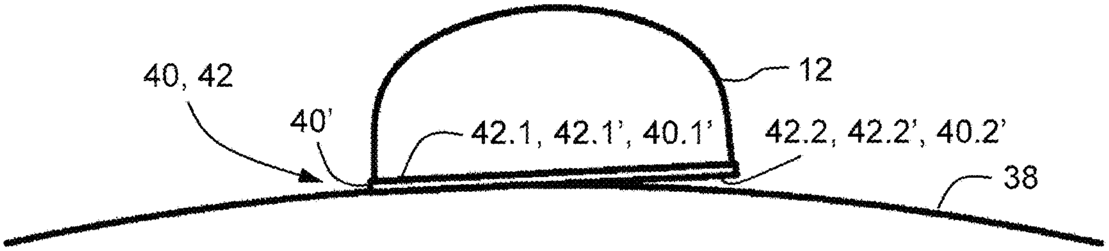
FIGS. 5*d* through 5*g* each illustrate an auscultatory sound sensor that is partially coupled to, but debonded from, the skin of a test-subject.
Figure 5E:
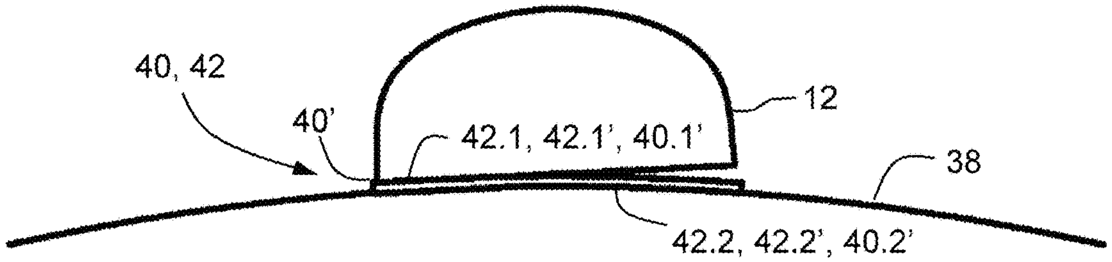
Figure 5F:
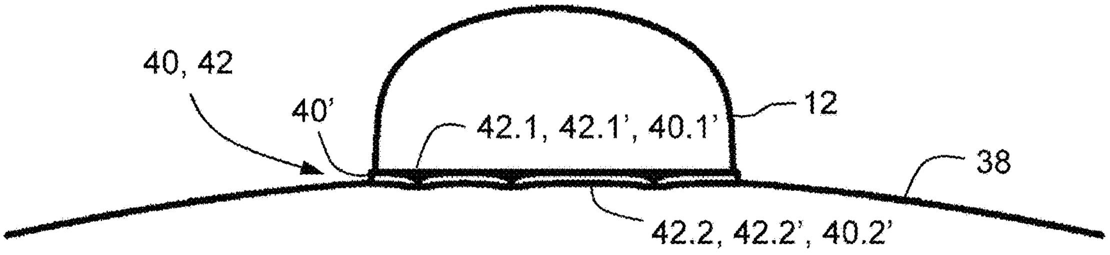
Figure 5G:
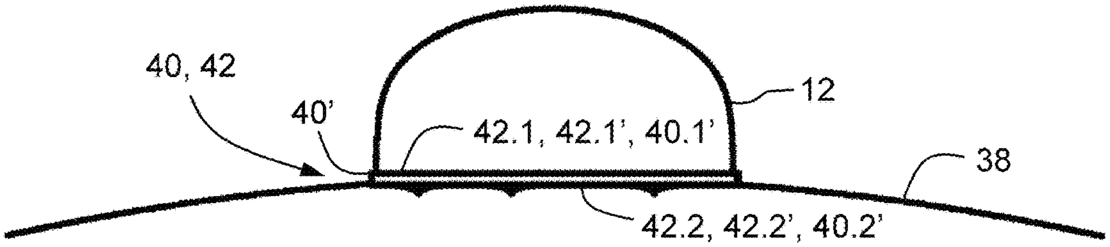

Referring also to FIG. 5*a*, the auscultatory sound sensors 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ are acoustically coupled to the skin 38 of the thorax 20 of the test-subject 22 via an acoustic interface 40, for example, via a hydrogel layer 40', that also functions as an associated adhesive interface 42 that is attached to the associated auscultatory sound sensor 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ with a first adhesive layer 42.1, for example, either a first surface 40.1' of the hydrogel layer 40' or a first layer of double-sided tape 42.1' on a first side of the acoustic/adhesive interface 40, 42, and that is attached to the skin 38 of the thorax 20 of the test-subject 22 with a second adhesive layer 42.2, for example, either a second surface 40.2' of the hydrogel layer 40' or a second layer of double-sided tape 42.2' on the opposing, second side of the acoustic/adhesive interface 40, 42. When fully coupled—as illustrated in FIG. 5*a*,—the auscultatory sound sensor 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ is fully attached to the acoustic/adhesive interface 40, 42 via the first adhesive layer 42.1, 42.1', 40.1', and the acoustic/adhesive interface 40, 42 is fully attached to the skin 38 of the thorax 20 of the test-subject 22 via the second adhesive layer 42.2, 42.2', 40.2', so that sound signals from within the thorax 20 of the test-subject 22 can propagate otherwise unimpeded to the auscultatory sound sensor 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$, thereby providing for a maximum achievable level of the corresponding associated auscultatory sound signals 16, and thereby improving the prospect of detecting an associated abnormal cardiovascular condition—if present—therefrom. Referring to FIGS. 5*b* and 5*c*—with the acoustic/adhesive interface 40, 42 respectively detached from the skin 38 or detached from the auscultatory sound sensor 12, respectively,—if the auscultatory sound sensor 12, 12$^{1'}$, 12$^{2'}$, 12$^{3'}$, 12$^{1''}$, 12$^{2''}$, 12$^{3''}$ is completely detached from the skin 38 of the thorax 20 of the test-subject 22, and thereby fully decoupled therefrom, the resulting auscultatory sound sensor 12, 12$^{1'}$, 12$^{2'}$, 12$^{3'}$, 12$^{1''}$, 12$^{2''}$, 12$^{3''}$ would be substantially non-responsive to sound signals from within the thorax 20 of the test-subject 22. Referring to FIGS. 5*d* to 5*g*, if the auscultatory sound sensor 12, 12$^{1'}$, 12$^{2'}$, 12$^{3'}$, 12$^{1''}$, 12$^{2''}$, 12$^{3''}$ is partially attached to the skin 38 of the thorax 20 of the test-subject 22, and thereby partially decoupled therefrom—i.e., in a condition referred to herein as being debonded therefrom—the resulting auscultatory sound sensor 12, 12$^{1'}$, 12$^{2'}$, 12$^{3'}$, 12$^{1''}$, 12$^{2''}$, 12$^{3''}$ would be only partially responsive to sound signals from within the thorax 20 of the test-subject 22, but not sufficiently responsive to provide for an associated auscultatory sound signal 16 of sufficient amplitude to provide for reliably detecting a prospective associated abnormal cardiovascular condition. More particularly, FIGS. 5*d* and 5*e* respectively illustrate an acoustic/adhesive interface 40, 42 partially detached from skin 38, and an acoustic/adhesive interface 40, 42 partially detached from an auscultatory sound sensor 12, respectively. Furthermore, FIG. 5*f* illustrates an auscultatory sound sensor 12 attached to a wrinkled acoustic/adhesive interface 40, 42, and FIG. 5*g* illustrates an acoustic/adhesive interface 40, 42 attached to wrinkled skin 38. In anticipation of prospective problems with nature of the attachment of the acoustic/adhesive interface 40, 42, the Data Recording Application (DRA) 14 is provided with a means—described more fully hereinbelow— for detecting if one or more auscultatory sound sensors 12, 12$^{1'}$, 12$^{2'}$, 12$^{3'}$, 12$^{1''}$, 12$^{2''}$, 12$^{3''}$ is, or are, either detached or debonded from the skin 38 of the thorax 20 of the test-subject 22, so as to provide for excluding data from auscultatory sound sensors 12, 12$^{1'}$, 12$^{2'}$, 12$^{3'}$, 12$^{1''}$, 12$^{2''}$, 12$^{3''}$ that are either detached or debonded, from the skin 38 of the thorax 20 of the test-subject 22 from being used to diagnose a prospective abnormal cardiovascular condition.

Generally, the adhesive interface 42 could comprise either a hydrogel layer 40', for example, P-DERM® Hydrogel; a silicone material, for example, a P-DERM® Silicone Gel Adhesive; an acrylic material, for example, a P-DERM® Acrylic Adhesive; a rubber material; a synthetic rubber material; a hydrocolloid material; or a double-sided tape, for example, with either rubber, acrylic or silicone adhesives.

Figure 6:
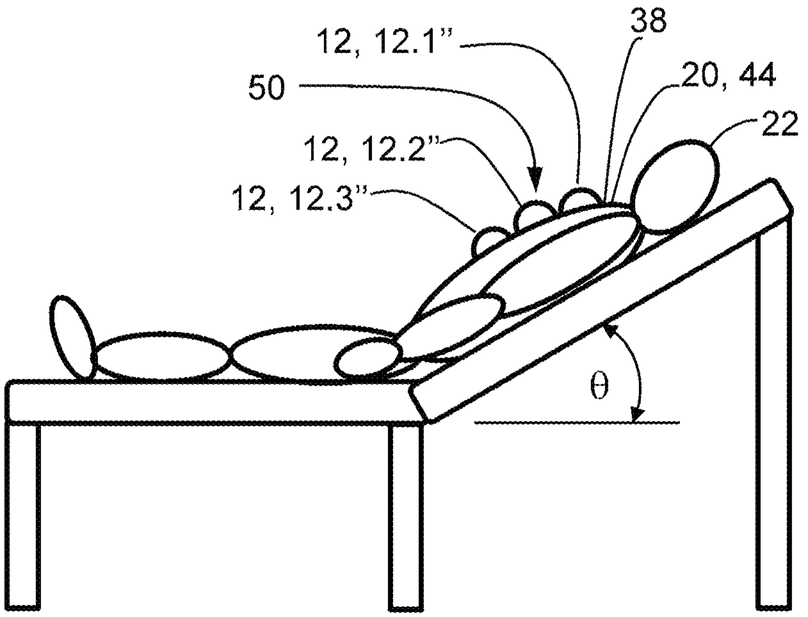
FIG. 6 illustrates a test-subject reclined on a surface, with their torso inclined while capturing auscultatory sound signals from a plurality of auscultatory sound sensors attached to the thorax of the test-subject.

Referring to FIG. 6, it has been found that the quality of the auscultatory sounds acquired from a test-subject 22 can be improved if the torso 44 of the test-subject 22 is inclined, for example, in one set of embodiments, at an inclination angle θ of about 30 degrees above horizontal—but generally, as close to upright (i.e. θ=90 degrees) as can be accommodated by the associated adhesive interface(s) 42 of the associated auscultatory sound sensors 12, 12$^{1'}$, 12$^{2'}$, 12$^{3'}$, 12$^{1''}$, 12$^{2''}$, 12$^{3''}$—which imposes a transverse component of gravitational force on each of the auscultatory sound sensors 12, 12$^{1'}$, 12$^{2'}$, 12$^{3'}$, 12$^{1''}$, 12$^{2''}$, 12$^{3''}$ that is resisted by the associated adhesive interface(s) 42.

Referring to FIGS. 7-15, in accordance with a first aspect 700, an auscultatory-sound-sensing process 700 provides for first determining a scale factor SF from an initially-acquired block of auscultatory-sound-sensor time-series data S, and initially determining from the scale factor SF whether one or more of the auscultatory sound sensors 12, 12$^{1'}$, 12$^{2'}$, 12$^{3'}$, 12$^{1''}$, 12$^{2''}$, 12$^{3''}$ is detached from the skin 38 of the thorax 20 of the test-subject 22, wherein when multiplied by the scale factor SF, the values of the associated auscultatory-sound-sensor time-series data S are nominally within a range that is a predetermined percentage of the dynamic range of the associated data acquisition system (for example, that provides 16-bit signed digital values). If there is no detachment, the first aspect 700, the auscultatory-sound-sensing process 700 provides for acquiring successive blocks of auscultatory-sound-sensor time-series data S while the test-subject 22 is holding their breath, and determining from each block of auscultatory-sound-sensor time-series data S—using an associated predetermined debond-detection threshold—whether or not one or more auscultatory sound sensors 12, 12$^{1'}$, 12$^{2'}$, 12$^{3'}$, 12$^{1''}$, 12$^{2''}$, 12$^{3''}$ is debonded from the skin 38 of the thorax 20 of the test-subject 22, or whether there is excessive noise in the auscultatory-sound-sensor time-series data S. The auscultatory-sensor time-series data S is rejected if excessive noise is detected, and the test is aborted if one or more auscultatory sound sensors 12, 12$^{1'}$, 12$^{2'}$, 12$^{3'}$, 12$^{1''}$, 12$^{2''}$, 12$^{3''}$ has become decoupled from the skin 38 of the thorax 20.

Figure 7:
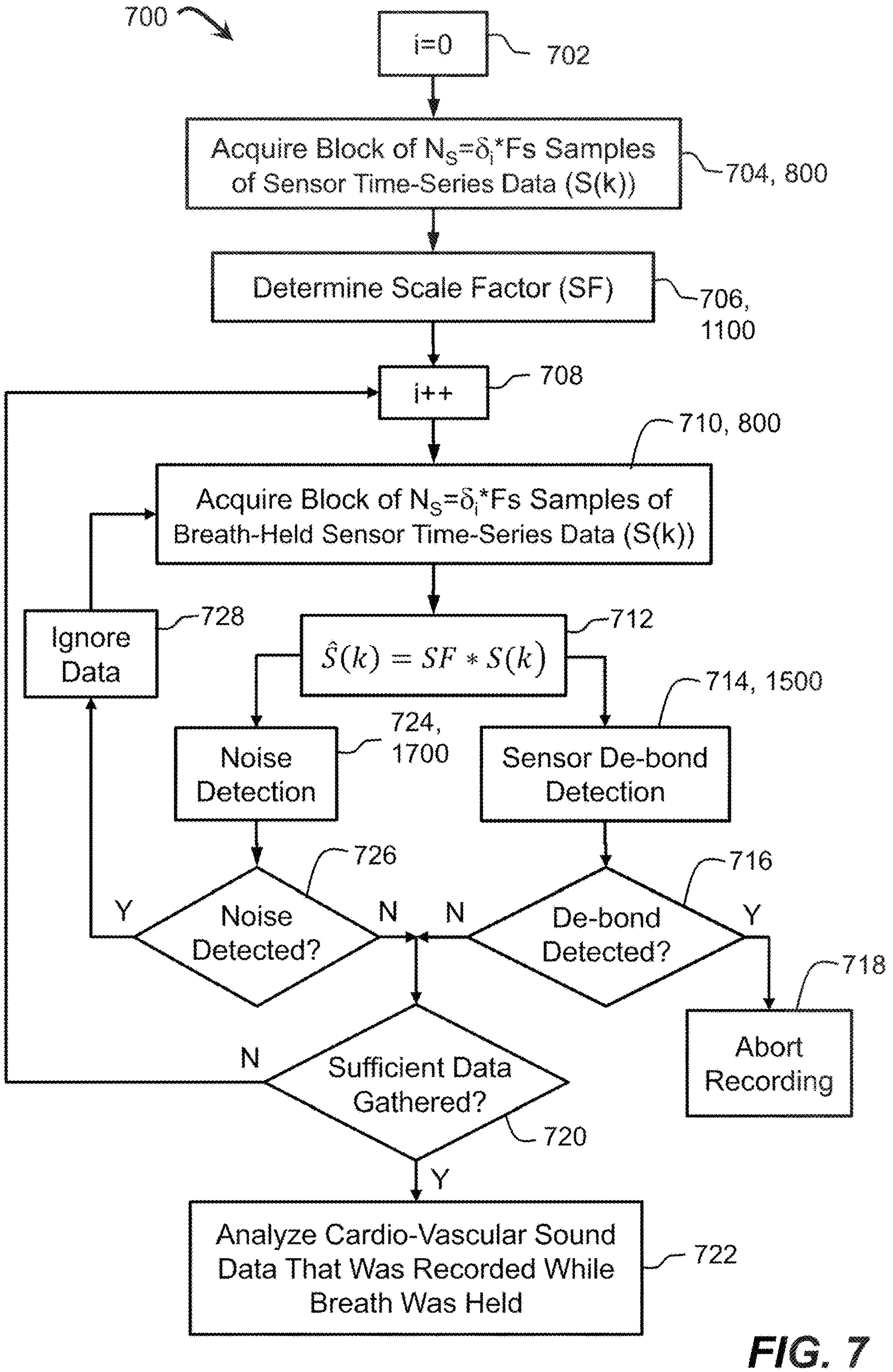
FIG. 7 illustrates a flowchart of a first aspect of an associated auscultatory-sound-sensing process that incorporates a process for detecting a decoupling of the associated auscultatory sound sensors from the skin of the thorax of a test-subject being diagnosed for a prospective abnormal cardiovascular condition, wherein the decoupling-detection process occurs after each block of breath-held auscultatory sound time-series data is acquired, and is based upon scaled time-series data and responsive to an associated pre-determined debond-detection threshold.

More particularly, referring to FIG. 7, the first aspect 700 of the auscultatory-sound-sensing process 700 commences with step (702) by initializing a data-block counter i to a value of zero, and then, in step (704), acquiring a block of $N_S$ contiguous samples of auscultatory-sound-sensor time-series data S in accordance with a first aspect 800 of a data acquisition process 800. This initially-acquired data is then used to determine the scale factor SF that is used to determine whether or not one or more auscultatory sound sensors 12, 12$^{1'}$, 12$^{2'}$, 12$^{3'}$, 12$^{1''}$, 12$^{2''}$, 12$^{3''}$ is/are detached from the skin 38 of the thorax 20 of the test-subject 22, and then subsequently to scale subsequent blocks of time-series data S. The initial block of auscultatory-sound-sensor time-series data S may be acquired either with, or without, the test-subject 22 holding their breath, but typically with the test-subject 22 allowed to breath normally—for their comfort and convenience. The number of samples $N_S$ to be acquired is given by the product of an acquisition period $\delta_i$ in seconds, times a sampling frequency Fs in Hz. For example, in one set of embodiments, in step (704), the initially-acquired block of auscultatory-sound-sensor time-series data S typically contains 10 seconds of data, which at a sampling frequency Fs of 24 KHz, results in $N_S=\delta_i*Fs=240{,}000$ samples.

More particularly, referring to FIG. 8, the data acquisition process 800 commences with step (802) by pre-filtering the electronic signal from the associated auscultatory sound sensor 12, 12$^{1'}$, 12$^{2'}$, 12$^{3'}$, 12$^{1''}$, 12$^{2''}$, 12$^{3''}$ with an analog anti-aliasing filter, for example, an analog second-order band-pass filter having a pass band in the range of 3 Hz to 2.5 KHz, for which the upper-cutoff frequency is sufficiently below the sampling frequency (i.e. no more than half) so as to prevent high frequency components in the signal being sampled from appearing as low frequency components of the sampled signal, i.e. so as to prevent aliasing. Following step (802), if, in step (804), the test-subject 22 need not necessarily hold their breath—as is the case for the initially-acquired block of auscultatory-sound-sensor time-series data S,—then, in step (806), the pre-filtered auscultatory sound signal 16 is sampled at the sampling frequency Fs and converted to digital form by the associated analog-to-digital converter (ADC). Then, from step (808), the auscultatory sound signal 16 continues to be sampled in step (806) until $N_S$ samples of the block of auscultatory-sound-sensor time-series data S have been acquired, after which, in step (810), the $N_S$ samples of auscultatory-sound-sensor time-series data S are returned to step (704) of the auscultatory-sound-sensing process 700. For example, FIGS. 9 and 10*a* each illustrate a first block of auscultatory-sound-sensor time-series data S of duration $\delta_0$ that was recorded from one of the auscultatory sound sensors 12, 12$^{1'}$, 12$^{2'}$, 12$^{3'}$, 12$^{1''}$, 12$^{2''}$, 12$^{3''}$.

Figure 12A:
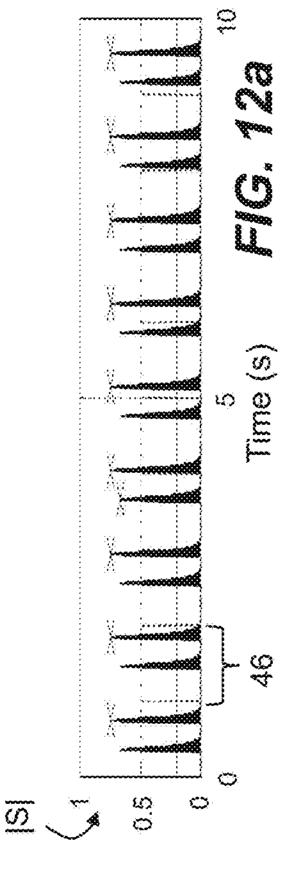
Figure 12F:
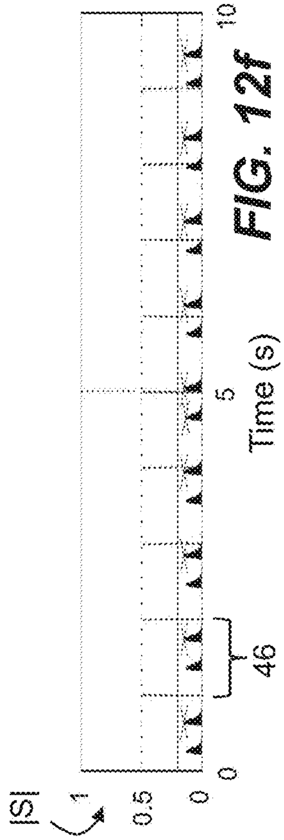
Figure 10B:
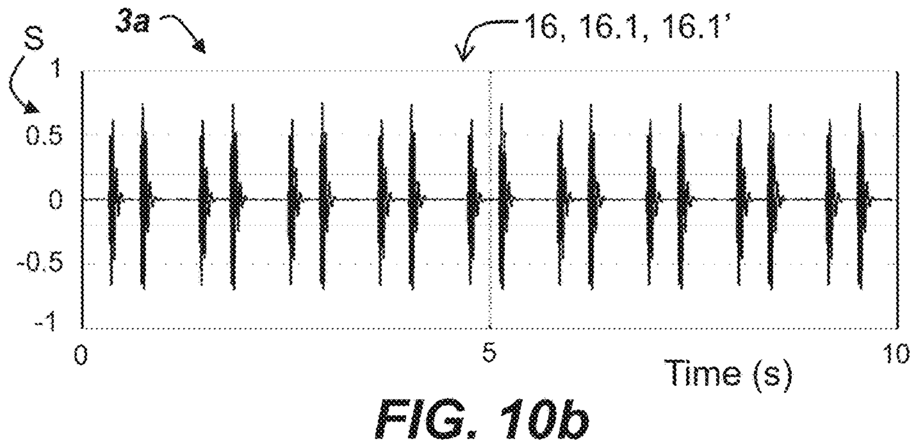
Figure 12B:
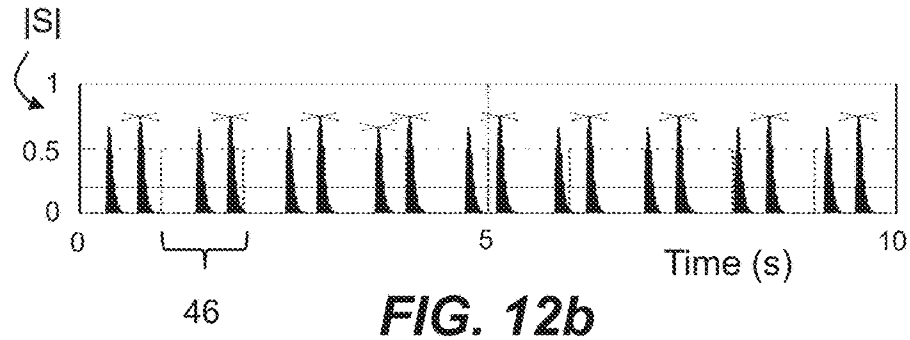
Figure 10C:
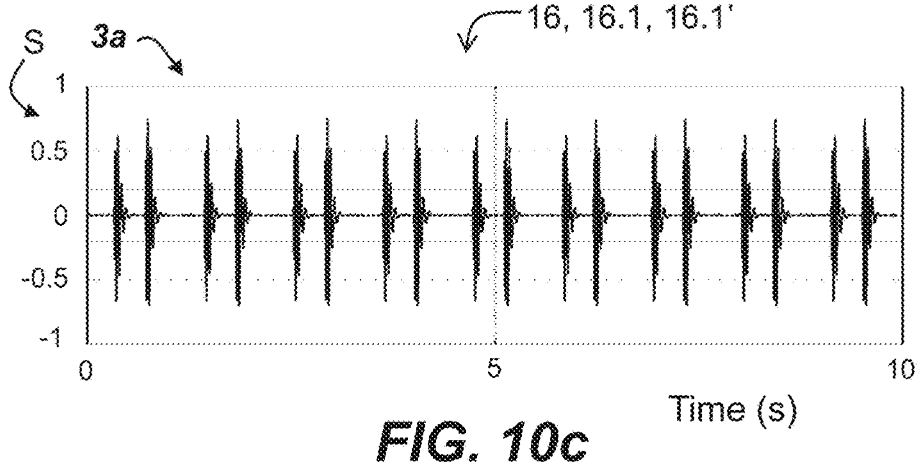
Figure 12C:
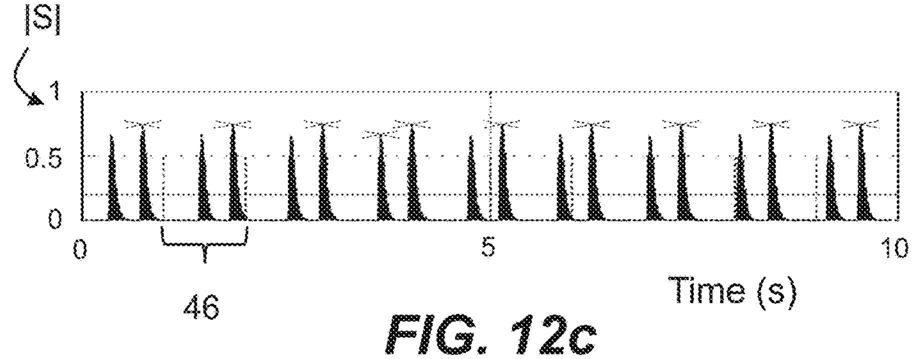
Figure 10D:
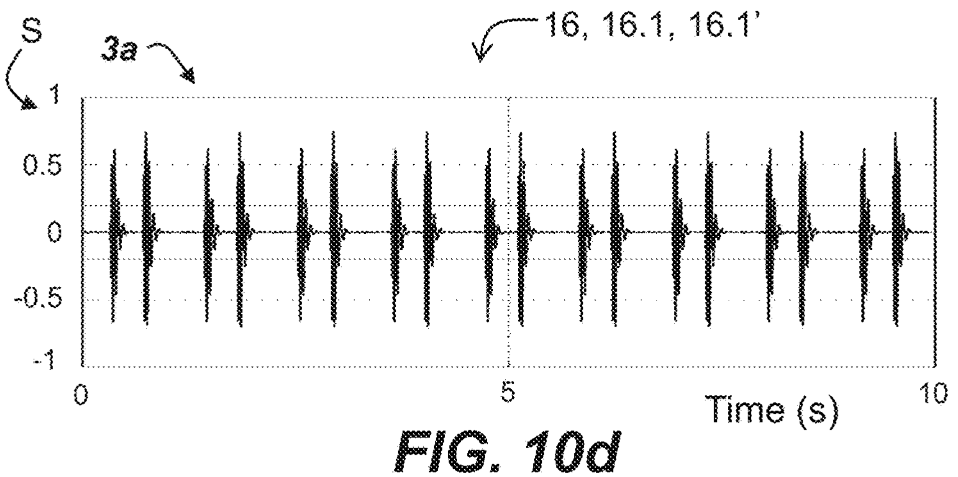
Figure 12D:
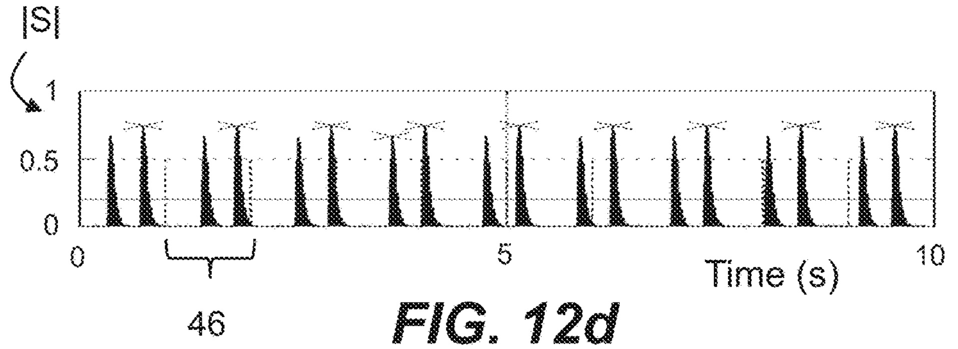
Figure 10E:
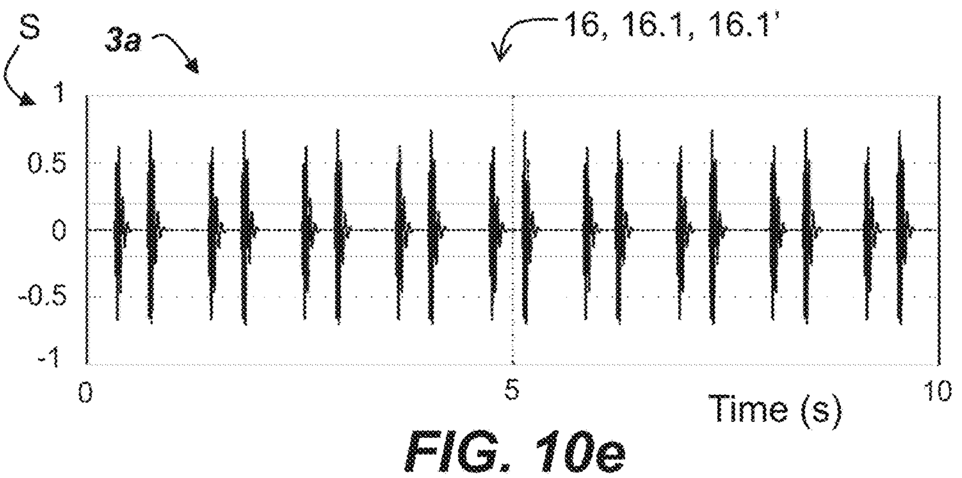
Figure 12E:
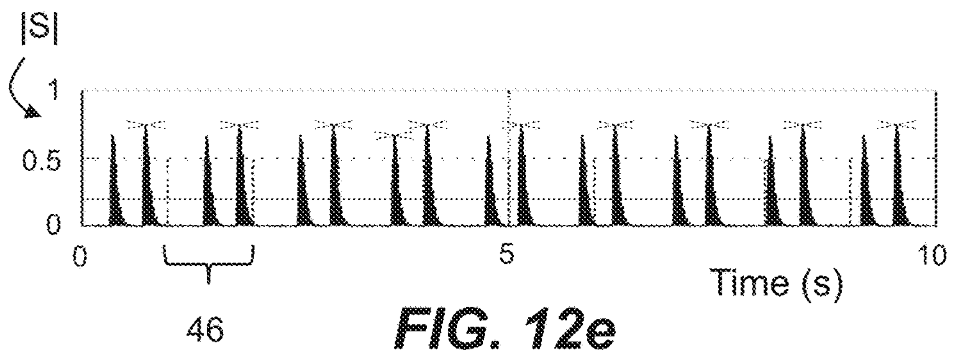
Figure 11:
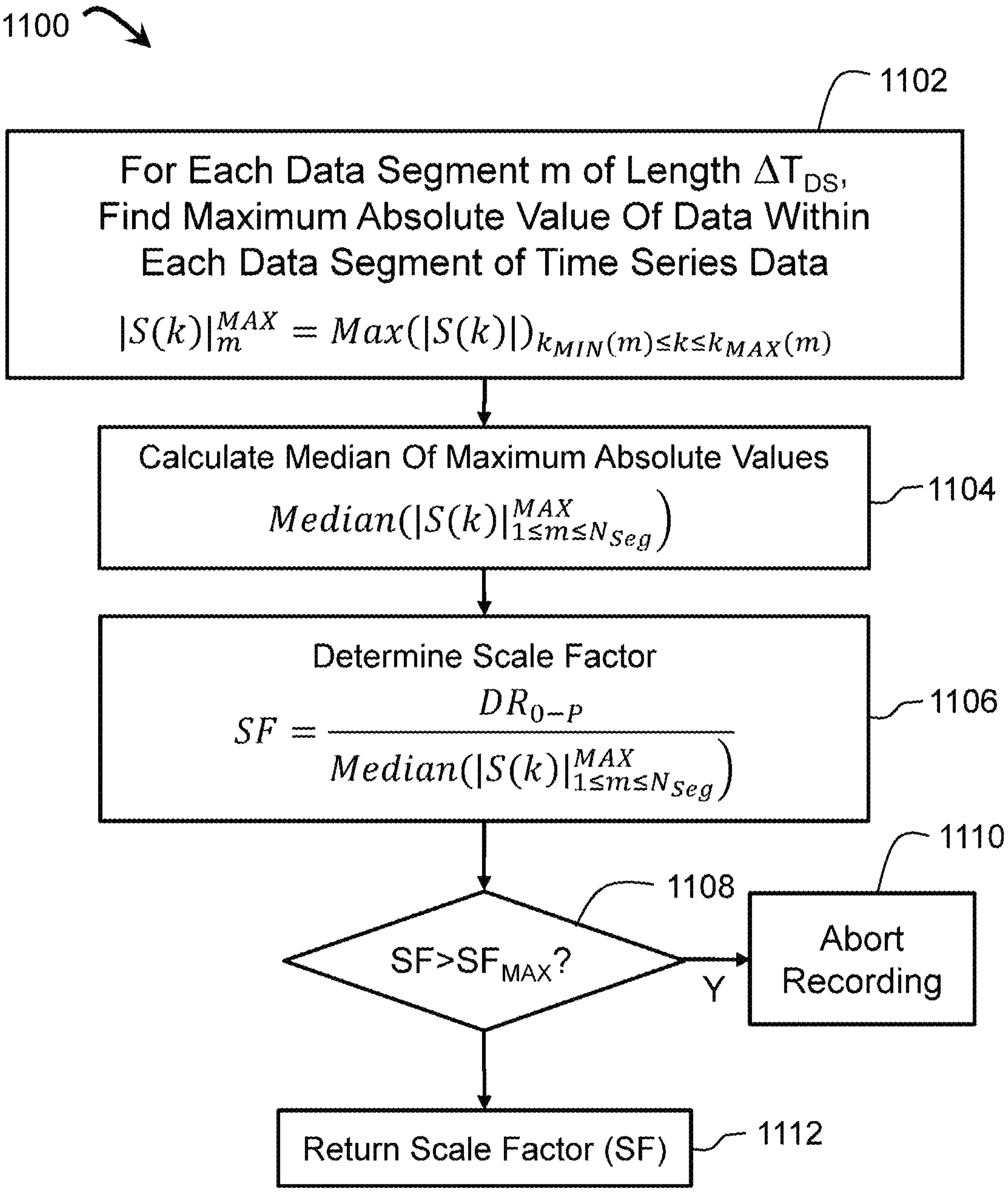
FIG. 11 illustrates a flowchart of a process for determining a scale factor used to scale auscultatory-sound-sensor time-series data, the latter of which is analyzed to detect whether or not the associated auscultatory sound sensor is decoupled from the skin of the test-subject, wherein the scale factor provides for directly determining if the associated auscultatory sound sensor is detached from the skin of the test-subject.

Referring again to FIG. 7, following step (704), in step (706), the scale factor SF is determined from the initially-acquired block of auscultatory-sound-sensor time-series data S, in accordance with an associated scale-factor-determination process 1100. More particularly, referring to FIGS. 11 and 12*a*, the scale-factor-determination process 1100 commences with step (1102), wherein the block of auscultatory-sound-sensor time-series data S is divided into a plurality of data segments 46, for example, each of the same data-segment duration $\delta_D$ that nominally spans a single heartbeat, for example, about one second. For example, in FIG. 12*a*, the $\delta_0$=10 second block of auscultatory-sound-sensor time-series data S is divided into $N_{Seg}$=10 data segments 46, each of $\delta_D$=one second duration. FIG. 12*a* illustrates a time series |S| containing the absolute values of the auscultatory-sound-sensor time-series data S illustrated in FIG. 10*a*. As indicated by X's in FIG. 12*a*, for each data segment 46, m spanning the range k=$k_{MIN}$(m) to k=$k_{MAX}$(m) of the auscultatory-sound-sensor time-series data S(k), the corresponding maximum absolute value of the auscultatory-sound-sensor time-series data S(k) is determined, as given by:

$$S_m^{MAX} = \text{Max}(|S(k)|)_{k_{MIN}(m) \le k \le k_{MAX}(m)} \tag{1}$$

Then, in step (1104), the median of these maximum values is determined, as given by $$\text{median}\left(S_{1 \le m \le N_{Seg}}^{MAX}\right) \tag{2}$$

Finally, in step (1106), the scale factor SF is determined, as given by:

$$SF = \frac{DR_{0-P}}{\text{median}\left(S_{1 \le m \le N_{Seg}}^{MAX}\right)} \tag{3}$$

wherein $DR_{0-P}$ is the nominal zero-to-peak dynamic range of the auscultatory-sound-sensor time-series data S after scaling, i.e. after multiplying the acquired values by the scale factor SF. For example, in one set of embodiments, the nominal zero-to-peak dynamic range is set to be about 80 percent—more broadly, but not limiting, 80 percent plus or minus 15 percent—of the zero-to-peak range of the associated analog-to-digital converter (ADC)—for example, in one set of embodiments, a 16-bit signed analog-to-digital converter (ADC)—used to digitize the auscultatory-sound-sensor time-series data S in step (806). In one set of embodiments, the scale factor SF is integer-valued that, for an attached and bonded auscultatory sound sensor 12, 12$^{1'}$, 12$^{2'}$, 12$^{3'}$, 12$^{1''}$, 12$^{2''}$, 12$^{3''}$, ranges in value between 1 and 28.

If one or more of the associated auscultatory sound sensors 12, 12$^{1'}$, 12$^{2'}$, 12$^{3'}$, 12$^{1''}$, 12$^{2''}$, 12$^{3''}$ is detached from the skin 38 of the thorax 20 of the test-subject 22, then the associated level of the auscultatory sound signals 16 will be low—for example, at a noise level—resulting in a relatively large associated scale factor SF from step (1106). Accordingly, if, in step (1108), the scale factor SF is in excess of an associated threshold $SF_{MAX}$, then the Data Recording Application (DRA) 14 is aborted in step (1110), and the operator 48 is alerted that the one or more auscultatory sound sensors 12, 12$^{1'}$, 12$^{2'}$, 12$^{3'}$, 12$^{1''}$, 12$^{2''}$, 12$^{3''}$ is/are detached, so that this can be remedied. For example, in one set of embodiments, the value of the threshold $SF_{MAX}$ is 28 for the above-described fixed-gain embodiment, i.e. for which the associated amplifier has a fixed gain of 88, feeding a 16-bit analog-to-digital converter (ADC) that provides for converting a +/−5 volt input signal to +/−32,767. Otherwise, from step (1108), if the value of the scale factor SF does not exceed the associated threshold $SF_{MAX}$, then in step (1112), the scale factor SF is returned to step (706) for use in scaling subsequently-recorded breath-held auscultatory sound signals 16.1.

Referring again to FIG. 7, following step (706), in step (708), the value of the data-block counter i is incremented, so as to point to the next block of auscultatory-sound-sensor time-series data S to be recorded. If, while this next block is recorded, the auscultatory sound sensors 12, 12$^{1'}$, 12$^{2'}$, 12$^{3'}$, 12$^{1''}$, 12$^{2''}$, 12$^{3''}$ remain attached and bonded to the skin 38 of the thorax 20 of the test-subject 22, and the associated breath-held auscultatory sound signals 16.1 are not corrupted by excessive noise, then this next block of auscultatory-sound-sensor time-series data S will then be subsequently used to detect a prospective abnormal cardiovascular condition therefrom. The auscultatory sound signals 16 used to detect prospective abnormal cardiovascular conditions are recorded while the test-subject 22 holds their breath, the latter to prevent the resulting cardiovascular-based auscultatory sound signals 16 from being overwhelmed by breathing-related sounds that are substantially louder than cardiovascular-based sounds, thereby providing for improving the associated signal-to-noise ratio of the cardiovascular-based auscultatory sound signals 16.

Accordingly, in step (710), a next block of $N_S$ contiguous samples of auscultatory-sound-sensor time-series data S is acquired over an acquisition period $\delta_i$ in accordance with a first aspect 800 of a data acquisition process 800, during which time the test-subject 22 is instructed to hold their breath. For example, in one set of embodiments, the nominal acquisition period $\delta_i$ is 10 seconds—but at least 5 seconds,—which, at a sampling frequency Fs of 24 KHz, results in $N_S=\delta_i$*Fs=240,000 samples.

More particularly, referring again to FIG. 8, the data acquisition process 800 commences with step (802) by pre-filtering the electronic signal from the associated auscultatory sound sensor 12, 12$^{1'}$, 12$^{2'}$, 12$^{3'}$, 12$^{1''}$, 12$^{2''}$, 12$^{3''}$ with the above-described analog anti-aliasing filter. Then, from step (804), because breath-held data is to be acquired, in step (812), the test-subject 22 is instructed by the operator 48 to hold their breath. In step (814), if the operator 48 observes that the test-subject 22 is compliant in holding their breath, or, additionally or alternatively, if this is confirmed by a below-described breath-hold detection process 1400, then upon manual initiation by the operator 48, in step (816), a sample counter j is initialized to a value of one, and, in step (818), the next sample of pre-filtered auscultatory sound signal 16 is sampled at the sampling frequency Fs and converted to digital form by an associated analog-to-digital converter (ADC). This process continues until either $N_S=\delta_i$*Fs samples have been acquired, or the test-subject 22 resumes breathing. More particularly, in step (820), if one or more addition samples remain to be acquired, and if the operator 48 continues to observe that the test-subject 22 is holding their breath, or, additionally or alternatively, if this is confirmed by a below-described breath-hold detection process 1400, then, in step (822) the sample counter j is incremented, and the next sample is acquired in step (818). Otherwise, from step (820), if either all $N_S=\delta_i*Fs$ samples have been acquired, or if either the operator 48 observes that the test-subject 22 has resumed breathing, or, additionally or alternatively, if this is confirmed by a below-described breath-hold detection process 1400, or, if the test-subject 22 indicates by their own separate manual switch input that they will resume breathing, then, in step (824), the data acquisition process 800 terminates, and the block of breath-held auscultatory-sound-sensor time-series data S containing $N_S=j$ samples is returned to step (710). In one set of embodiments, if, following step (814), the test-subject 22 is not holding their breath, the pre-filtered auscultatory sound signals 16 are also separately-recorded while waiting for the test-subject 22 to hold their breath, or resume doing so. In practice, the auscultatory sound signals 16 typically continue to be recorded between breath-held segments, that latter of which are identified by associated recorded start and stop times with respect to the associated continuous recording.

Figure 13:
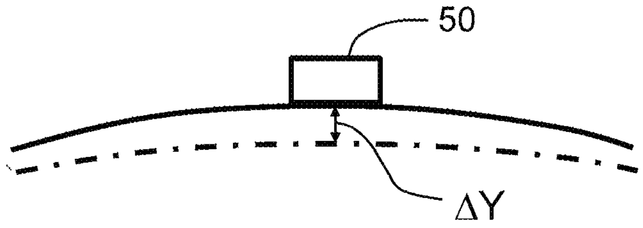
FIG. 13 illustrates an accelerometer on the thorax of a test-subject during a respiration cycle of the test-subject.

Referring also to FIG. 13, alternatively, or additionally, in step (814), the auscultatory coronary-artery-disease detection system 10 may further incorporate an accelerometer 50 operatively coupled to the thorax 20 of the test-subject 22 to provide an associated acceleration signal responsive to the motion of the thorax 20. With the test-subject 22 lying on their back at an inclined angle, for example, at about 30 degrees above horizontal, for example, as illustrated in FIG. 6, the associated acceleration signal—operatively coupled to recording module 13 and possibly transmitted to the docking system 27—may be twice integrated either in recording module 13 or the docking system 27 to generate a measure of the peak-to-peak displacement of the thorax 20, which if greater than a threshold would be indicative of breathing by the test-subject 22.

Figure 8:
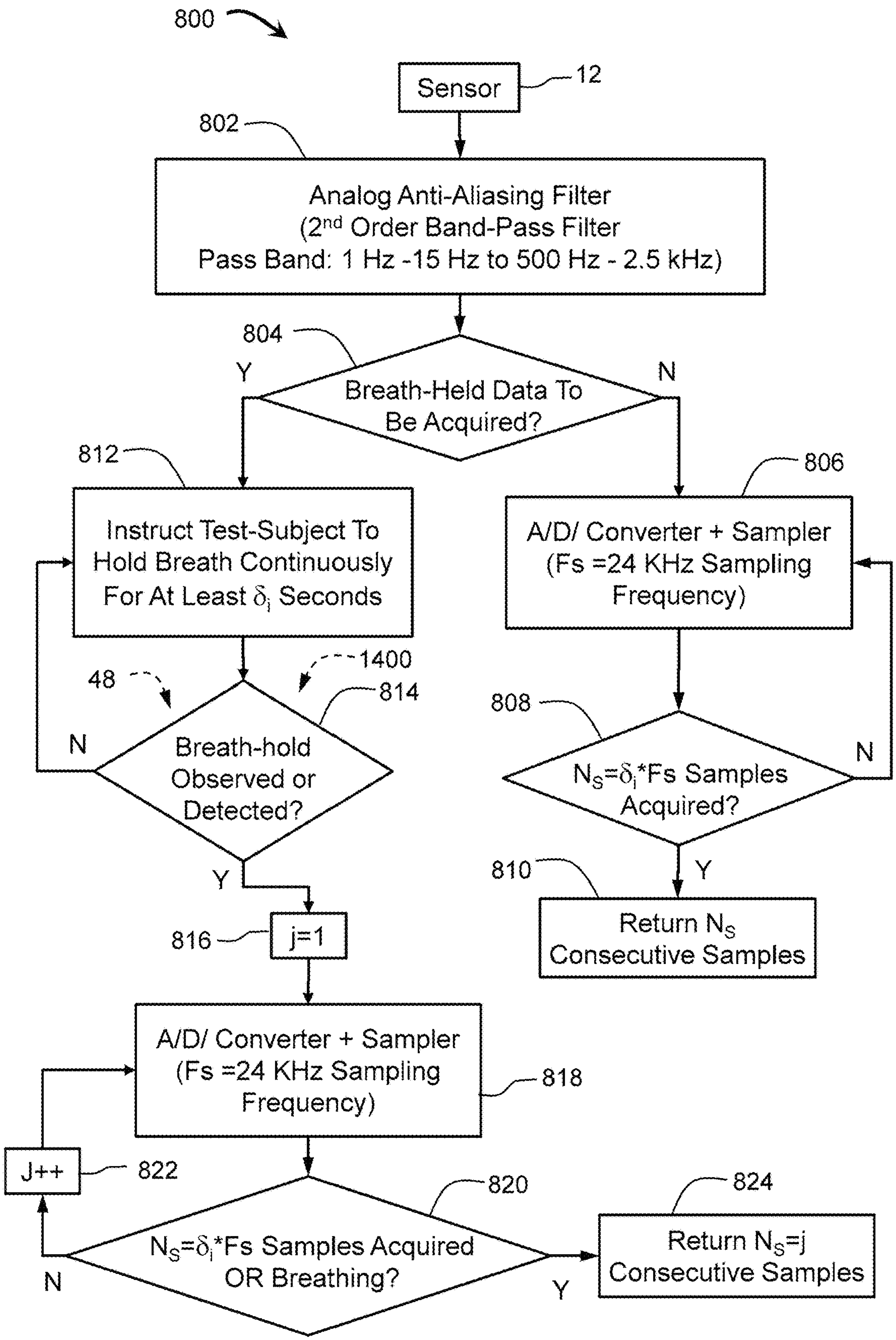
FIG. 8 illustrates a flowchart of a first aspect of a process for acquiring auscultatory sound signals from the associated auscultatory sound sensors coupled to the skin of the thorax of the test-subject being diagnosed for a prospective abnormal cardiovascular condition.
Figure 9:
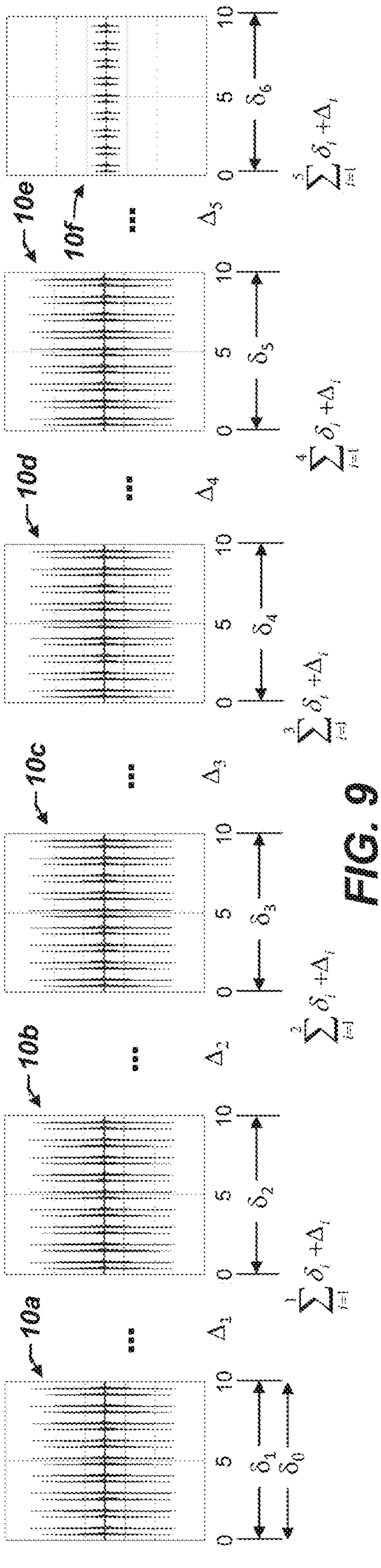
FIG. 9 illustrates a plurality of six blocks of breath-held, auscultatory-sound-sensor time-series data recorded from an auscultatory sound sensor coupled to the skin of the thorax of a test-subject being diagnosed for a prospective abnormal cardiovascular condition.
Figure 14:
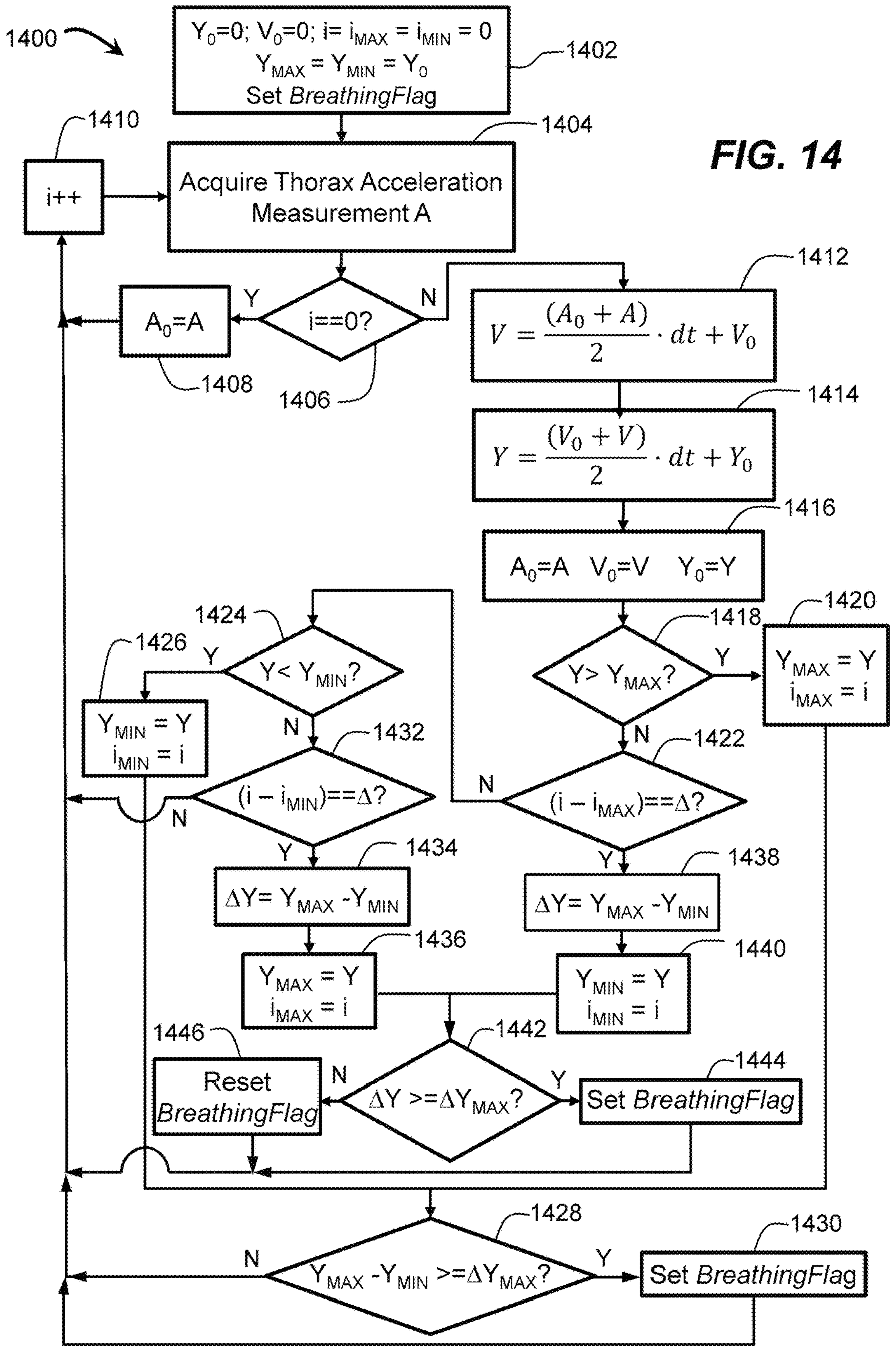
FIG. 14 illustrates a breath-hold detection process.

More particularly, referring also to FIG. 14, for an auscultatory coronary-artery-disease detection system 10 incorporating an accelerometer 50 operatively coupled to the thorax 20 of the test-subject 22, an acceleration signal 52 therefrom may alternatively or additionally be processed by an associated breath-hold detection process 1400 to provide for automatically determining—for example, in step (814) of the data acquisition process 800 illustrated in FIG. 8—whether or not the test-subject 22 is breathing, responsive to the determination, from the acceleration signal 52, of a peak-to-peak displacement of the thorax 20 of the test-subject 22. More particularly, beginning with, and in, step (1402), the respective previous/initial values of thorax displacement $Y_0$ and thorax velocity $V_0$, respectively, are each initialized to values of zero; a sample counter i is initialized to an initial value, for example, zero; the respective minimum $Y_{MIN}$ and maximum $Y_{MAX}$ values of thorax displacement are each set equal to the (initial) value of thorax displacement $Y_0$; the values of the sample counter $i_{MIN}$ and $i_{MAX}$ at which the corresponding minimum $Y_{MIN}$ and maximum $Y_{MAX}$ values of thorax displacement occur are set equal to the initial value of the sample counter i; and a BreathingFlag is set to indicate that the test-subject 22 is breathing. Then, in step (1404), the current sample of thorax acceleration A is acquired. Then, in step (1406), if the sample counter i is equal to the initial value, i.e. i==0, then, in step (1408), the previous value of thorax acceleration $A_0$ (i.e. initially, the initial value thereof) is set equal to the value of the current sample of thorax acceleration A, i.e. $A_0=A$, and then, in step (1410), the sample counter i is incremented, after which the breath-hold detection process 1400 repeats with step (1404).

Otherwise, from step (1406), if the current sample of thorax acceleration A is not the first sample, then, in step (1412), the current value of thorax velocity V is calculated by integrating the previous $A_0$ and current A measurements of thorax acceleration, for example, using a trapezoidal rule, as follows:

$$V = \frac{(A_0 + A)}{2} \cdot dt + V_0 \tag{4}$$

wherein dt is the time period between samples, i.e. dt=1/Fs. Then, in step (1414), the current value of thorax displacement Y is calculated by integrating the above-calculated previous $V_0$ and current V values of thorax velocity, for example, again using a trapezoidal rule, as follows:

$$Y = \frac{(V_0 + V)}{2} \cdot dt + Y_0 \tag{5}$$

Then, in step (1416), the respective previous values of thorax acceleration $A_0$, thorax displacement $Y_0$ and thorax velocity $V_0$ are respectively set equal to the corresponding current values of thorax acceleration A, thorax velocity V and thorax displacement Y, respectively, that will each be used in subsequent iterations of steps (1412) and (1414).

Then, in step (1418), if the current value of thorax displacement Y is greater than then current maximum value of thorax displacement $Y_{MAX}$—for example, as would result during a phase of chest expansion by the test-subject 22,—then, in step (1420), the current maximum value of thorax displacement $Y_{MAX}$ is set equal to the current value of thorax displacement Y and the corresponding value of the sample counter $i_{MAX}$ associated therewith is set to the current value of the sample counter i. Otherwise, from step (1418)—for example, as would result from other than a phase of chest expansion by the test-subject 22,—if, in step (1422), the amount by which the current value of the sample counter i exceeds the value of the sample counter $i_{MAX}$ associated with the maximum value of thorax displacement $Y_{MAX}$ is not equal to a threshold value A (the relevance of which is described more fully hereinbelow), then in step (1424), if the current value of thorax displacement Y is less than then current minimum value of thorax displacement $Y_{MIN}$—for example, as would result during a phase of chest contraction by the test-subject 22,—then, in step (1426), the current minimum value of thorax displacement $Y_{MIN}$ is set equal to the current value of thorax displacement Y and the corresponding value of the sample counter $i_{MIN}$ associated therewith is set to the current value of the sample counter i. From either steps (1420) or (1426), in step (1428), if the amount by which the current maximum value of thorax displacement $Y_{MAX}$ is greater the current minimum value of thorax displacement $Y_{MIN}$ meets or exceeds a displacement threshold $\Delta Y_{MAX}$, then, in step (1430), the BreathingFlag is set to indicate that the test-subject 22 is breathing, after which, in step (1410), the sample counter i is incremented, after which the breath-hold detection process 1400 repeats with step (1404). Similarly, from step (1428), if the displacement threshold $\Delta Y_{MAX}$ is not exceeded, in step (1410), the sample counter i is incremented, after which the breath-hold detection process 1400 repeats with step (1404). Further similarly, from step (1424)—for example, as would result from other than a phase of chest contraction by the test-subject 22,—if, in step (1432), the amount by which the current value of the sample counter i exceeds the value of the sample counter $i_{MIN}$ associated with the minimum value of thorax displacement $Y_{MIN}$ is not equal to the threshold value Δ, in step (1410), the sample counter i is incremented, after which the breath-hold detection process 1400 repeats with step (1404).

If, from step (1432), the amount by which the current value of the sample counter i exceeds the value of the sample counter $i_{MIN}$ associated with the minimum value of thorax displacement $Y_{MIN}$ is equal to the threshold value Δ—following a minimum chest contraction of the test-subject 22, in anticipation of subsequent chest expansion, wherein the threshold value Δ is greater than or equal to one,—then, in step (1434), the peak-to-peak thorax displacement ΔY is calculated as the difference between the current maximum $Y_{MAX}$ and minimum $Y_{MIN}$ values of thorax displacement, and, in step (1436), the maximum value of thorax displacement $Y_{MAX}$ is set equal to the current value of thorax displacement Y, and the value of the sample counter $i_{MAX}$ at which the corresponding maximum value of thorax displacement $Y_{MAX}$ occurred is set equal to the current value of the sample counter i, in anticipation of subsequently increasing magnitudes of the current value of thorax displacement Y to be tracked in steps (1418) and (1420).

Similarly, if, from step (1422), the amount by which the current value of the sample counter i exceeds the value of the sample counter $i_{MAX}$ associated with the maximum value of thorax displacement $Y_{MAX}$ is equal to the threshold value Δ—following a maximum chest expansion of the test-subject 22, in anticipation of subsequent chest contraction, wherein the threshold value Δ is greater than or equal to one,—then, in step (1438), the peak-to-peak thorax displacement ΔY is calculated as the difference between the current maximum $Y_{MAX}$ and minimum $Y_{MIN}$ values of thorax displacement, and, in step (1440), the minimum value of thorax displacement $Y_{MIN}$ is set equal to the current value of thorax displacement Y, and the value of the sample counter $i_{MIN}$ at which the corresponding minimum value of thorax displacement $Y_{MIN}$ occurred is set equal to the current value of the sample counter i, in anticipation of subsequently decreasing magnitudes of the current value of thorax displacement Y to be tracked in steps (1424) and (1426).

Accordingly, the threshold value Δ, provides for a delay to assure that a most-recent extremum of displacement has been reached, either the current maximum $Y_{MAX}$ or minimum $Y_{MIN}$ values of thorax displacement, before calculating the associated peak-to-peak thorax displacement ΔY.

From either steps (1436) or (1440), in step (1442), if the amount of the peak-to-peak thorax displacement ΔY calculated in steps (1434) or (1438), respectively, meets or exceeds the displacement threshold $\Delta Y_{MAX}$, then, in step (1444), the BreathingFlag is set to indicate that the test-subject 22 is breathing. Otherwise, from step (1442), if the amount of the peak-to-peak thorax displacement ΔY calculated in steps (1434) or (1438), respectively, does not exceed the displacement threshold $\Delta Y_{MAX}$, then, in step (1446), the BreathingFlag is reset to indicate that the test-subject 22 is not breathing. Following either steps (1444) or (1446), in step (1410), the sample counter i is incremented, after which the breath-hold detection process 1400 repeats with step (1404).

Referring again to FIG. 7, in step (712), a corresponding block of scaled auscultatory-sound-sensor time-series data $\hat{S}$ is calculated by multiplying the acquired block of auscultatory-sound-sensor time-series data S by the scale factor SF, and in step (714), the scaled auscultatory-sound-sensor time-series data $\hat{S}$ is analyzed by an associated debond detection process 1500 to determine whether or not any of the auscultatory sound sensors 12, $\mathbf{12^{1'}}$, $\mathbf{12^{2'}}$, $\mathbf{12^{3'}}$, $\mathbf{12^{1''}}$, $\mathbf{12^{2''}}$, $\mathbf{12^{3''}}$ was debonded from skin 38 of the thorax 20 of the test-subject 22 during the associated data acquisition process 800.

Figure 15:
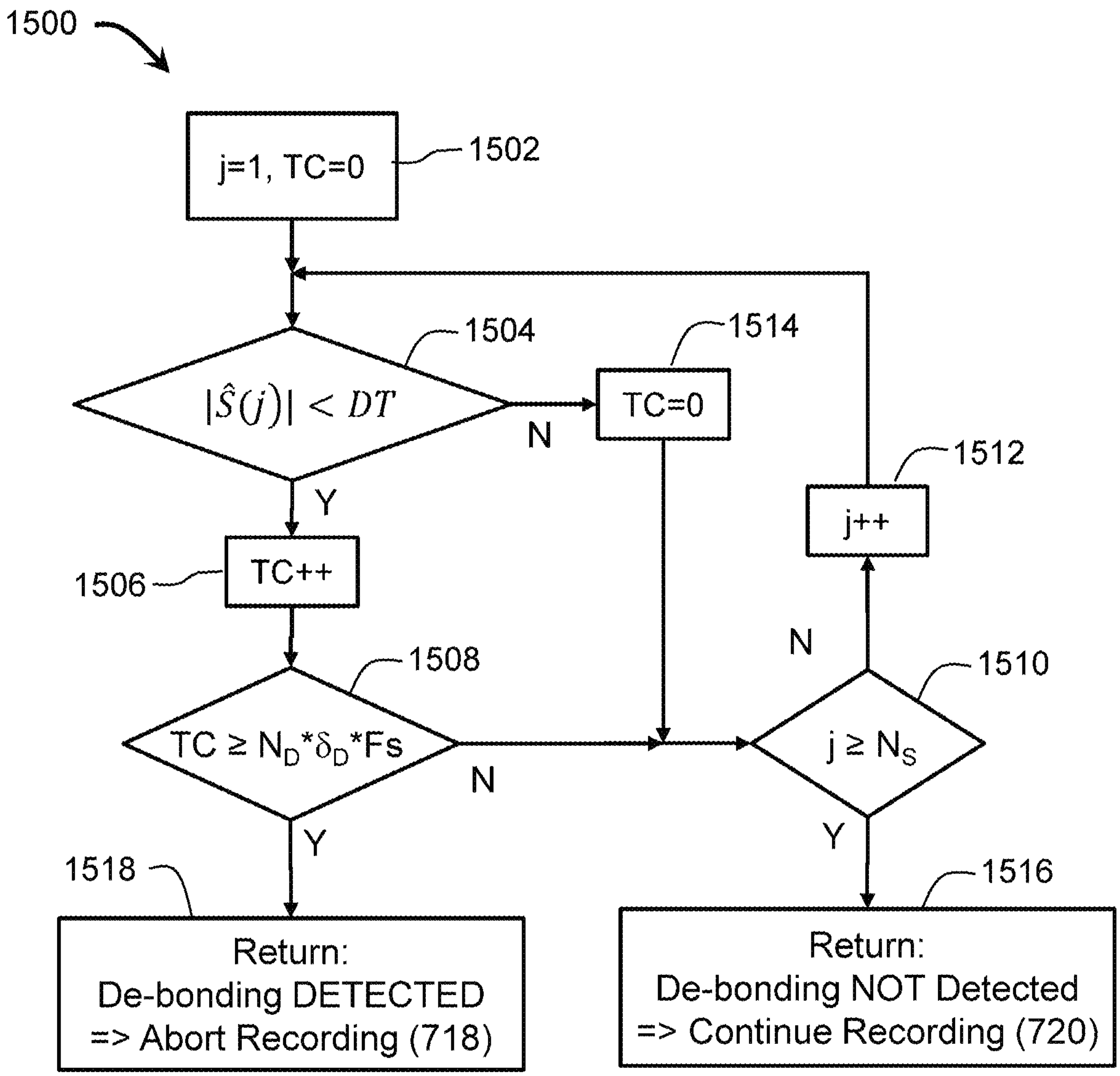
FIG. 15 illustrates a flowchart of a first aspect of a process for detecting whether or not an auscultatory sound sensor is debonded from the skin of a test-subject.

More particularly, referring to FIG. 15, the debond detection process 1500 commences with step (1502) by initializing a sample counter j to a value of one, and initializing a threshold counter TC to a value of zero, wherein the threshold counter TC is a count of the number of contiguous successive samples for which the value of the scaled auscultatory-sound-sensor time-series data $\hat{S}$ is less than an associated predetermined debond-detection threshold DT. For example, in one set of embodiments, the debond-detection threshold DT is set to a value that is about 20% of the achievable maximum value of the output from the analog-to-digital converter (ADC). Then, in step (1504), if the absolute value of the sample of scaled auscultatory-sound-sensor time-series data $\hat{S}$, i.e. $|\hat{S}(j)|$, is less than the predetermined debond-detection threshold DT (or, alternatively, if |SF*S(j)|<DT, thereby precluding a need to separately calculate and store scaled auscultatory-sound-sensor time-series data S), then in step (1506), the threshold counter TC is incremented, after which, in step (1508), if the value of the threshold counter TC does not exceed the number of samples in $N_D$ successive data segments 46, i.e. $TC<N_D*\delta_D*Fs$, and in step (1510), if the sample counter j does not exceed the number of samples $N_S$ in the block of scaled auscultatory-sound-sensor time-series data S, then, in step (1512), the sample counter j is incremented, and the process continues again with step (1504). Otherwise, from step (1504), if the absolute value of the current sample of scaled auscultatory-sound-sensor time-series data $\hat{S}$, i.e. $|\hat{S}(j)|$, is not less than the predetermined debond-detection threshold DT—indicating that the auscultatory sound sensor 12, $\mathbf{12^{1'}}$, $\mathbf{12^{2'}}$, $\mathbf{12^{3'}}$, $\mathbf{12^{1''}}$, $\mathbf{12^{2''}}$, $\mathbf{12^{3''}}$ is not debonded from the skin 38 of the thorax 20 of the test-subject 22,—then, in step (1514), the threshold counter TC is reset to a value of zero and the process continues with step (1510). Otherwise, from step (1510), if the sample counter j exceeds the number of samples $N_S$ in the block of scaled auscultatory-sound-sensor time-series data $\hat{S}$ or auscultatory-sound-sensor time-series data S—indicating that the entire block of scaled auscultatory-sound-sensor time-series data S or auscultatory-sound-sensor time-series data S has been screened,—then the debond detection process 1500 is terminated with step (1516) by returning an indication to step (714) of the auscultatory-sound-sensing process 700 that the associated auscultatory sound sensor 12, $\mathbf{12^{1'}}$, $\mathbf{12^{2'}}$, $\mathbf{12^{3'}}$, $\mathbf{12^{1''}}$, $\mathbf{12^{2''}}$, $\mathbf{12^{3''}}$ is not debonded from the skin 38 of the thorax 20 of the test-subject 22. Otherwise, from step (1508), if the value of the threshold counter TC exceeds the number of samples in $N_D$ successive data segments 46, then the debond detection process 1500 is terminated with step (1518) by returning an indication to step (714) of the auscultatory-sound-sensing process 700 that the associated auscultatory sound sensor 12, $\mathbf{12^{1'}}$, $\mathbf{12^{2'}}$, $\mathbf{12^{3'}}$, $\mathbf{12^{1''}}$, $\mathbf{12^{2''}}$, $\mathbf{12^{3''}}$ is debonded from the skin 38 of the thorax 20 of the test-subject 22. For example, in one set of embodiments, the value of $N_D$ is equal to 4, and the value of $\delta_D$ is equal to 1 second.

Returning to FIG. 7, in step (716), if, from step (714), the debond detection process 1500 detected that the associated auscultatory sound sensor 12, $\mathbf{12^{1'}}$, $\mathbf{12^{2'}}$, $\mathbf{12^{3'}}$, $\mathbf{12^{1''}}$, $\mathbf{12^{2''}}$, $\mathbf{12^{3''}}$ was debonded while acquiring the block of auscultatory-sound-sensor time-series data S, then the Data Recording Application (DRA) 14 is aborted in step (718), and the operator 48 is alerted that one or more auscultatory sound sensors 12, $\mathbf{12^{1'}}$, $\mathbf{12^{2'}}$, $\mathbf{12^{3'}}$, $\mathbf{12^{1''}}$, $\mathbf{12^{2''}}$, $\mathbf{12^{3''}}$ are debonded, so that this can be remedied. Otherwise, if, from step (714), the debond detection process 1500 did not detect that the associated auscultatory sound sensor 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ was debonded while acquiring the block of auscultatory-sound-sensor time-series data S, then, in step (720), if sufficient noise-screened data has not been gathered—for example, in one set of embodiments, a total duration of at least 65 seconds of recorded data,—then the auscultatory-sound-sensing process 700 continues with step (708).

In step (724), an associated noise detection (i.e. noise-screening) process—operating on either the block of scaled auscultatory-sound-sensor time-series data $\hat{S}$, or the block of auscultatory-sensor time-series data S, in parallel with the debond detection process 1500—provides for detecting if the block of auscultatory-sound-sensor time-series data S has been corrupted by excessive noise, and if so, from step (726), that block of auscultatory-sound-sensor time-series data S is ignored, and the auscultatory-sound-sensing process 700 continues by repeating step (710) to acquire a new block of auscultatory-sound-sensor time-series data S. Otherwise, from step (726), if the block auscultatory-sound-sensor time-series data S has not been corrupted by excessive noise, the process continues with the above-described step (720).

From step (720), if sufficient noise-screened data has been gathered for which the associated one or more auscultatory sound sensors 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ were not debonded from the skin 38 of the thorax 20 of the test-subject 22—for example, in one set of embodiments, a total duration of at least 65 seconds of recorded data,—then, in step (722), at least the composite set of blocks of breath-held auscultatory-sound-sensor time-series data S acquired in step (710) are subsequently analyzed by an associated Data Analysis Application (DAA) 54 operative on the docking system 27—as illustrated in FIGS. 2 and 3—so as to provide for detecting an abnormal cardiovascular condition of the test-subject 22. In addition to recording the segments of breath-held data, alternatively, all data may be recorded and provided to the Data Analysis Application (DAA) 54, along with an associated index that provides for identifying the corresponding associated breath-held portions thereof for which the associated auscultatory sound sensors 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ were neither detached nor debonded from the skin 38 of the thorax 20 of the test-subject 22, nor corrupted by noise.

Figure 10A:
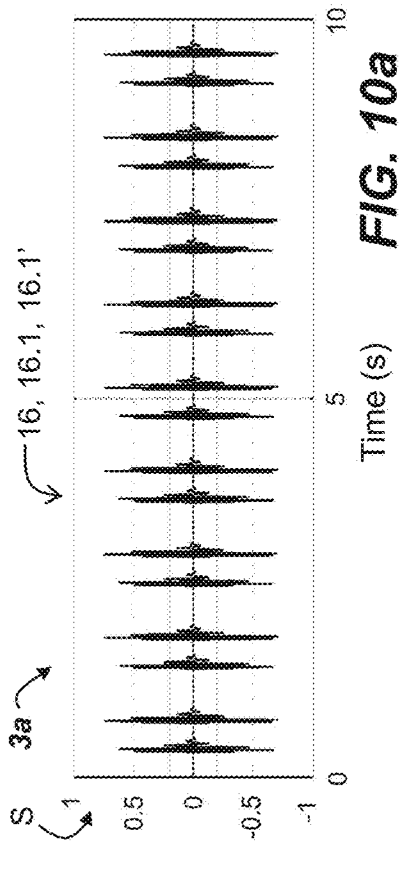
Figure 10F:
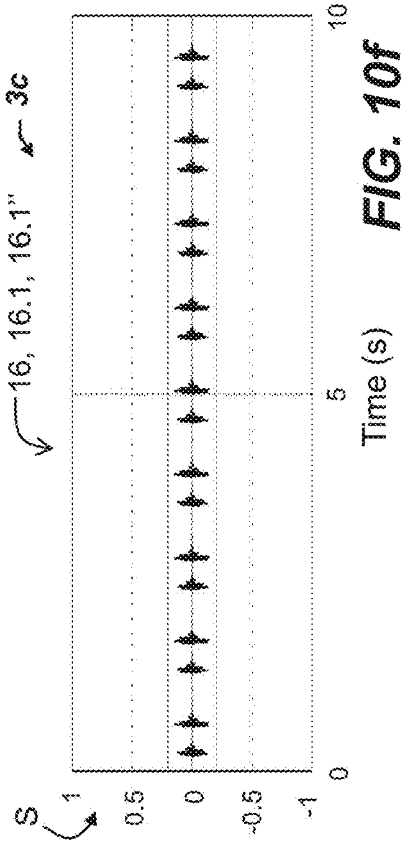

FIGS. 9 and 10*a*-10*f* illustrate a simulation of six blocks of breath-held auscultatory-sound-sensor time-series data S recorded in accordance with the first aspect 700 of auscultatory-sound-sensing process 700, with respective durations of $\delta_1$, $\delta_2$, $\delta_3$, $\delta_4$, $\delta_5$, and $\delta_6$ during which time periods the test-subject 22 was holding their breath, separated by periods $\Delta_1$, $\Delta_2$, $\Delta_3$, $\Delta_4$, and $\Delta_5$ of normal breathing, wherein FIGS. 10*a*-10*e* illustrate breath-held auscultatory sound signals 16.1, 16.1' from a normally-bonded auscultatory sound sensor 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ as illustrated in FIG. 5*a*, and FIG. 10*f* illustrates a breath-held auscultatory sound signal 16.1, 16.1" from a debonded auscultatory sound sensor 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$, for example, as illustrated in any of FIGS. 5*d*-5*g*, for example, as might be caused by excessive hair between the adhesive interface 42 and the auscultatory sound sensor 12, poor placement of the auscultatory sound sensor 12 on the thorax 20 of the test-subject 22, poor angular orientation of the auscultatory sound sensor 12 relative to the surface of the skin 38, or wrinkled adhesive interface 42 between the auscultatory sound sensor 12 and the skin 38, For purposes of simplicity of illustration, FIGS. 10*b*-10*e* are identical to FIG. 10*a*. However, it should be understood that typically the amplitude of the auscultatory sound signals 16, 16.1 varies from heartbeat to heartbeat, and from one breath-held segment to another.

Alternatively, one or more of the auscultatory-sound-sensing process 700, the data acquisition process 800, the scale-factor-determination process 1300, or the de-bond detection process 1500 could be implemented with corresponding alternative processes disclosed in U.S. application Ser. No. 16/136,015 filed on 19 Sep. 2018—with particular reference to FIGS. 16 through 22—which is incorporated by reference herein in its entirety.

Figure 16:
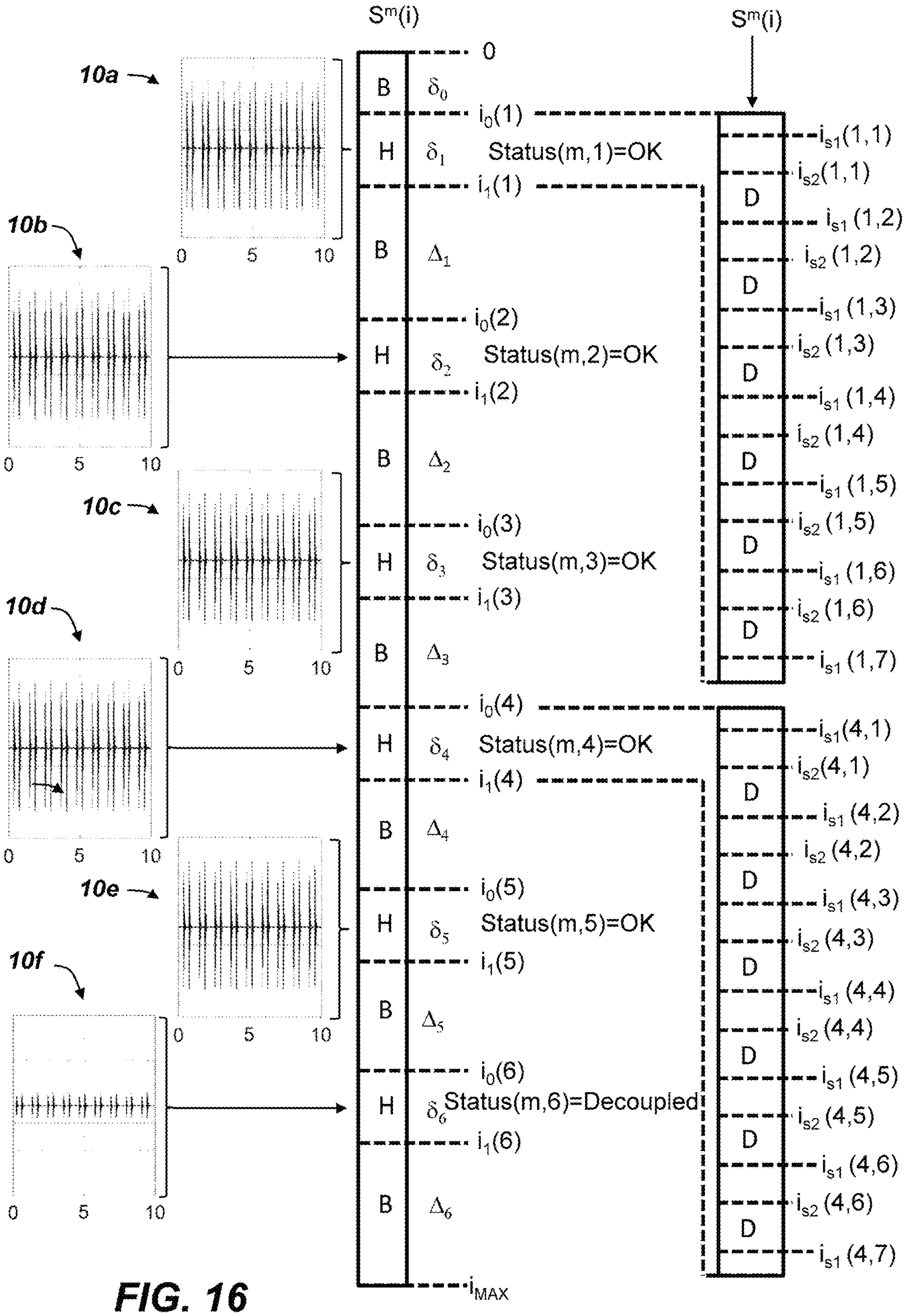
FIG. 16 illustrates an organization of data from an auscultatory sound sensor recorded by an auscultatory coronary-artery-disease detection system from a test-subject.

Referring to FIG. 16, in one set of embodiments, all the data is recorded throughout the duration of the test, including segments both with and without breathing, and a set of index pointers are used to identify locations of associated events, for example, index pointer arrays $i_0$[ ] and $i_1$[ ] to store the sample locations at the beginning and end of breath-held data segments of the corresponding sampled auscultatory sound data $S^m$[ ] from the $m^{th}$ auscultatory sound sensor 12, and later-used index pointer arrays $i_{s1}$[ ] and $i_{s2}$[ ] to store the sample locations of the S1 sound at the beginning of each heart cycle, and the S2 sound at the beginning of diastole respectively, wherein in FIG. 16, the symbol "B" is used to indicate a period of breathing, the symbol "H" is used to indicate a period of breath-holding, and the symbol "D" is used to indicate a period of diastole. A status array Status[m, k] indicates the measurement status of the $k^{th}$ breath-held data segment of the $m^{th}$ auscultatory sound signal 16, i.e. the sampled auscultatory sound data $S^m$[ ] from the $m^{th}$ auscultatory sound sensor 12. Accordingly, step (728)—that provides for ignoring data—may be implemented by setting the corresponding value of the status array Status(m, k) to a value of IGNORE.

Figure 20:
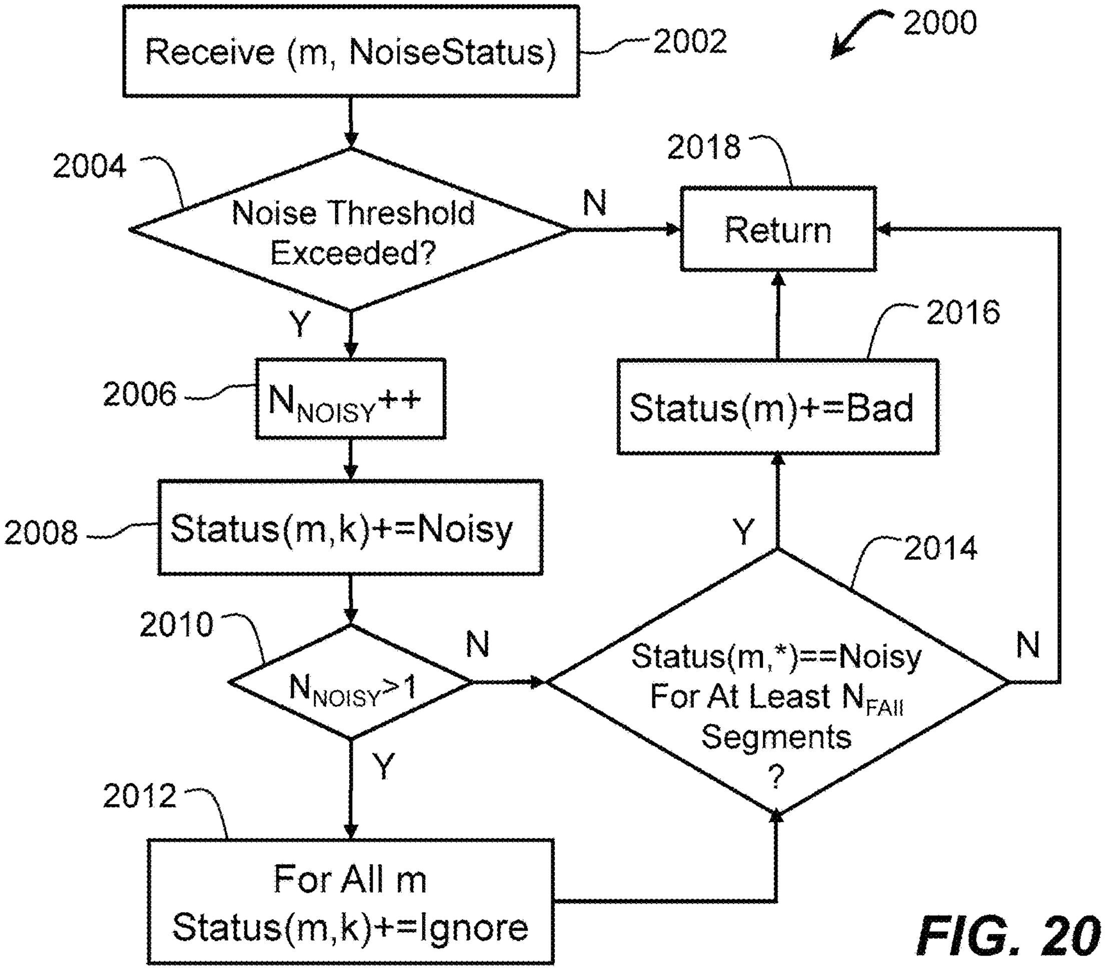
FIG. 20 illustrates a flowchart of a process for logging results from the noise-evaluation process of FIG. 19.

Referring to FIGS. 17-20, a noise detection process 1700 called from step (724) provides for determining whether or not a particular segment of breath-held auscultatory sound signal 16.1 is corrupted by excessive noise, and if so, provides for flagging that segment as being excessively noisy so as to be prospectively excluded from subsequent processing. Generally the noise detection process 1700 generates, in step (1714), frequency-domain noise filters FH[ ] responsive to cross-correlations of frequency spectra of pairs of adjacent auscultatory sound sensors 12. Accordingly, sensor-index pointers m1[*p*] and m2[*p*] provide for identifying the associated auscultatory sound sensors 12, m1[*p*], m2[*p*] of each pair, the latter of which is identified by a pair pointer p. For each pair of adjacent auscultatory sound sensors 12 in a set of adjacent pairs—selected by sensor-index pointers m1[*p*] and m2[*p*] in steps (1706) and (1710), respectively, wherein the pair pointer p is initialized to 1 in step (1704)—the noise detection process 1700 generates, in step (1714), a frequency-domain noise filter FH[ ] by cross-correlating, in step (1802), the frequency spectra $FS^A$[ ] and $FS^B$[ ]—generated in steps (1708) and (1712)—of each associated breath-held auscultatory sound signal 16.1: $S^A$[ ] and $S^B$[ ], wherein the values of the frequency-domain noise filter FH[ ] are generated by normalizing the frequency spectra of the cross-correlation function to a range of 0 to 1 in step (1804), then subtracting these values from unity, and then setting resulting values that are less than a noise floor to the value of the noise floor in step (1806). Accordingly, when used to separately multiply the frequency spectra $FS^A$[ ] and $FS^B$[ ] by the frequency-domain noise filter FH[ ] in step (1904) as called from steps (1716) and (1718) for frequency spectra $FS^A$[ ] and $FS^B$[ ], respectively, the frequency-domain noise filter FH[ ] provides for attenuating the components of the breath-held auscultatory sound signal 16.1: $S^A$[ ] and $S^B$[ ] that are correlated with one another. Accordingly, the operation of step (1904) provides for a matched filtering process to accentuate the underlying noise in the associated breath-held auscultatory sound signal 16.1: $S^A$[ ] or $S^B$[ ] by attenuating frequency-component portions thereof that are correlated with a corresponding breath-held auscultatory sound signal 16.1: $S^B$[ ] or $S^A$[ ] from the other auscultatory sound sensor 12, m1[*p*], m2[*p*] of the pair. Furthermore, in step (1904), the product of the frequency-domain noise filter FH[ ] with either of the frequency spectra $FS^A$[ ] or $FS^B$[ ] is inverse Fourier transformed back to the corresponding time domain noise signal SN[ ]. Then, in steps (1908) through (1918), a plurality of $N_{FFT}$-point short-time Fourier transform (STFT) arrays are generated, for example, with $N_{FFT}$=1024, with each overlapped with respect on one another by a half width, i.e. $N_{FFT}/2$, after which the associated average spectral power array FX[ ] in dB is calculated in step (1920). Then, the average powers $P_{LOW}$, $P_{MID}$, $P_{HIGH}$ in three respective frequency ranges 20 Hz to 200 Hz, 200 Hz to 800 Hz, and 800 Hz to 1,500 Hz, respectively, are calculated in steps (1922), (1924) and (1926), respectively, wherein each average power $P_{LOW}$, $P_{MID}$, $P_{HIGH}$ is compared with a corresponding threshold—for example, in one set of embodiments, −20 dB, −50 dB and −30 dB, respectively—in step (1928). The corresponding breath-held auscultatory sound signal 16.1: $S^A$[ ] or $S^B$[ ] is then flagged in step (1930) as being noisy if any of the associated noise power thresholds are exceeded. Referring to FIG. 20, if an auscultatory sound sensor 12 exceeds the noise threshold in a given $k^{th}$ breath-held segment of breath-held sampled auscultatory sound data $S^m[i_0[k]: i_1[k]]$, that auscultatory sound sensor 12, m is flagged in step (2008) as being noisy so as to later be ignored for that $k^{th}$ breath-held segment. If a particular auscultatory sound sensor 12, m exceeds the noise threshold for more than one breath-held segment of breath-held sampled auscultatory sound data $S^m[i_0[k]: i_1[k]]$, then that auscultatory sound sensor 12, m is flagged in step (2016) as being bad. For each breath-held segment k of data, the process of steps (1706) through (1722) repeats for each of $N_{PAIRS}$ pairs of adjacent auscultatory sound sensors 12. For example, referring to FIG. 3, in one set of embodiments, there are three pairs of adjacent auscultatory sound sensors 12, i.e. $N_{PAIRS}=3$, as follows: for p=1, the auscultatory sound sensors 12 at the left and sternum second intercostal spaces L2, S2; for p=2, the auscultatory sound sensors 12 at the left and sternum third intercostal spaces L3, S3; and for p=3, the auscultatory sound sensors 12 at the left and sternum fourth intercostal spaces L4, S4. The process of steps (1704) through (1726) is repeated until all the breath-held segments k of data have been processed.

Figure 17:
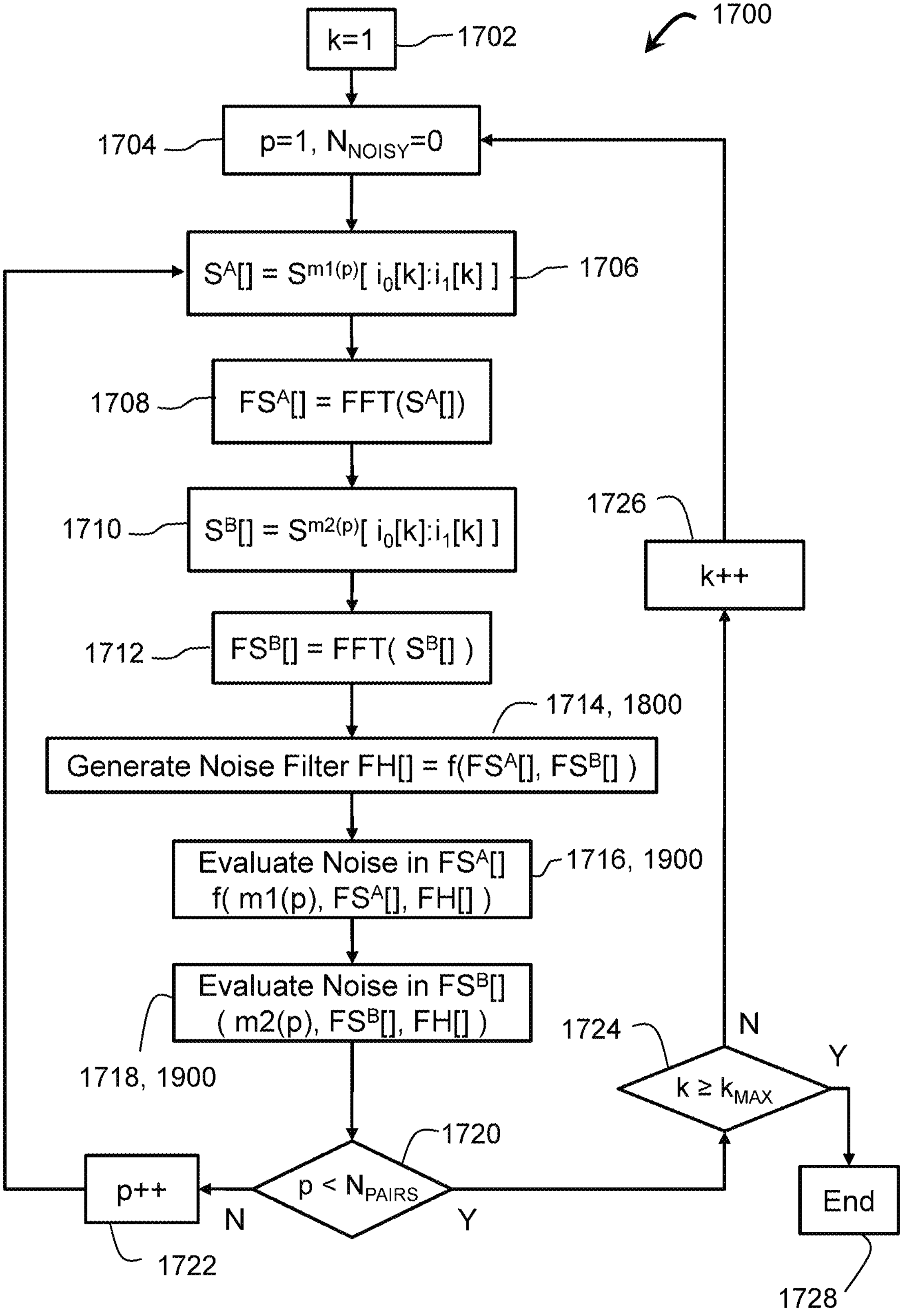
FIG. 17 illustrates a flowchart of a noise detection process.

More particularly, referring to FIG. 17, the noise detection process 1700 commences with step (1702) by initializing a breath-held-segment pointer k to a value of 1, so as to provide for pointing to the first breath-held segment of data. Generally, the breath-held-segment pointer k provides for pointing to the $k^{th}$ breath-held segment of data, of duration $\delta_k$, extending between sample locations $i_0[k]$ and $i_1[k]$, as illustrated in FIG. 16. Then, in step (1704), the pair pointer p is initialized to a value of 1, and a noise counter $N_{NOISY}$ is initialed to a value of 0. Then, in step (1706), the $k^{th}$ breath-held segment of breath-held sampled auscultatory sound data $S^{m1}[p][i_0[k]: i_1[k]]$ is selected as the sampled auscultatory sound data $S^A$[ ] of the first auscultatory sound sensor 12, m1[*p*] of the pair p, and in step (1708) the Fourier Transform of the sampled auscultatory sound data $S^A$[ ] is calculated as $FS^A$[ ]=FFT($S^A$[ ]). Similarly, then, in step (1710), the $k^{th}$ breath-held segment of breath-held sampled auscultatory sound data $S^{m2}[p][i_0[k]: i_1[k]]$ is selected as the sampled auscultatory sound data $S^B$[ ] of the second auscultatory sound sensor 12, m2[*p*] of the pair p, and in step (1712) the Fourier Transform of the sampled auscultatory sound data $S^B$[ ] is calculated as $FS^B$[ ]=FFT($S^B$[ ]).

Figure 18:
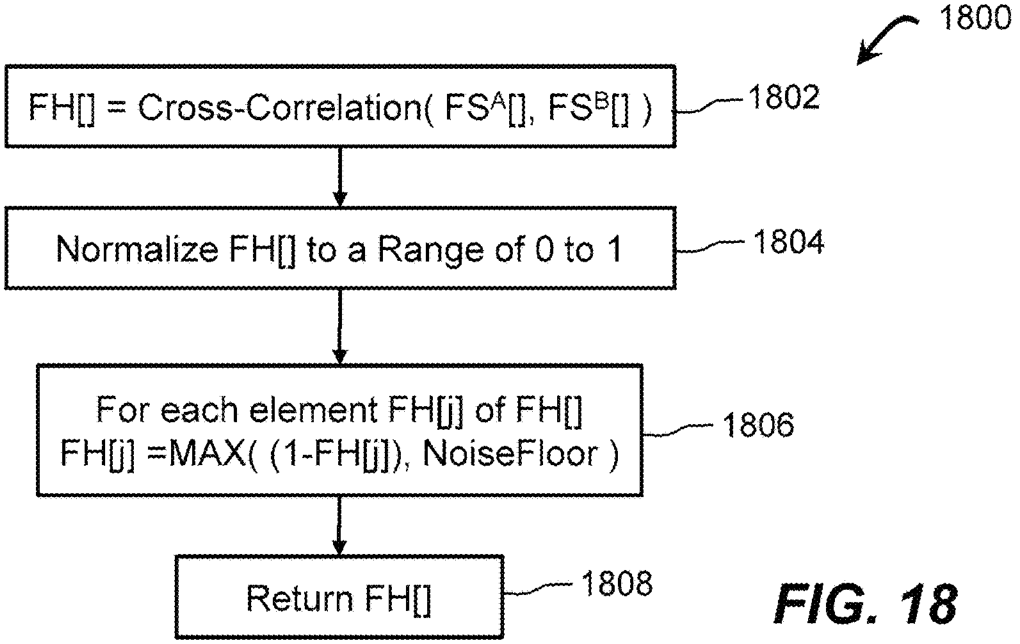
FIG. 18 illustrates a flowchart of a process for generating a matched noise filter.

Then, in step (1714), the frequency-domain noise filter FH[ ] is generated by a matched-noise-filter generation process 1800 that—referring also to FIG. 18—commences in step (1802) with the cross-correlation of the frequency spectra $FS^A$[ ], $FS^B$[ ] of the sampled auscultatory sound data $S^A$[ ], $S^B$[ ] of the first m1[*p*] and second m2[*p*] auscultatory sound sensors 12 of the pair p, wherein the resulting cross-correlation is stored in array FH[ ] and then normalized to a range of 0 to 1 in step (1804), and then inverted in step (1806), wherein each element of the normalized array FH[ ] is subtracted from 1, and if the result is less than a noise floor, is set to the value of the noise floor NoiseFloor. Then, in step (1808), the resulting frequency-domain noise filter FH[ ] is returned and subsequently used in steps (1716) and (1718) of the noise detection process 1700 to evaluate the noise in the frequency spectra $FS^A$[ ], $FS^B$[ ] of the sampled auscultatory sound data $S^A$[ ], $S^B$[ ] of the first m1[*p*] and second m2[*p*] auscultatory sound sensors 12 of the pair p, respectively, in accordance with an associated noise-content-evaluation process 1900, the latter of which is called from step (1716) to evaluate the noise content of the frequency spectrum $FS^A$[ ] of the sampled auscultatory sound data $S^A$[ ] of the first auscultatory sound sensor 12, m1[*p*] of the pair p, and which is called from step (1718) to evaluate the noise content of the frequency spectrum $FS^B$[ ] of the sampled auscultatory sound data $S^B$[ ] of the second auscultatory sound sensor 12, m2[*p*] of the pair p.

Figure 19:
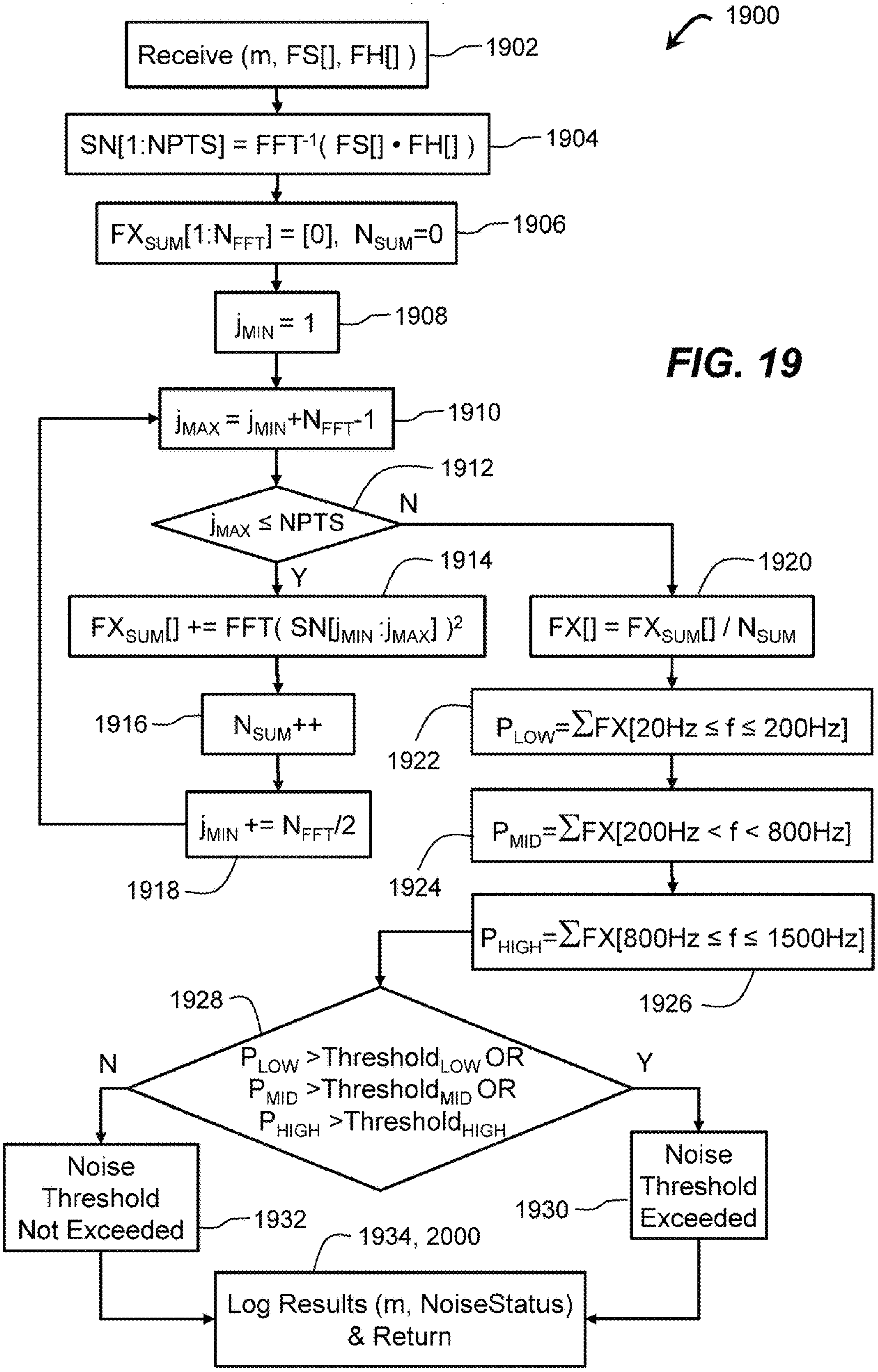
FIG. 19 illustrates a flowchart of a process for evaluating the noise content in a spectral signal of an auscultatory sound signal.

Referring to FIG. 19, the noise-content-evaluation process 1900 commences in step (1902) with receipt of the index m of the associated auscultatory sound sensor 12, *m*, the associated frequency spectrum FS[ ] of the associated auscultatory sound sensor 12, *m*, and the associated frequency-domain noise filter FH[ ]. Then, in step (1904), the time domain noise signal SN[ ]—containing a total of NPTS data points, i.e. the number of data points in the breath-held sampled auscultatory sound data $S^m[i_0[k]: i_1[k]]$—is given by the inverse Fourier Transform of the product of the associated frequency spectrum FS[ ] with the associated frequency-domain noise filter FH[ ], corresponding to a time-domain cross-correlation of the corresponding associated time-domain signals. Then, in step (1906), each of the $N_{FFT}$ summation data points of a frequency-domain summation array FXSUM[ ] is initialized to zero, as is an associated summation counter $N_{SUM}$, wherein the number of summation data points $N_{FFT}$ is a power of 2, for example, 1024, and substantially less than the total number of data points NPTS in the time domain noise signal SN[ ]. Then, in step (1908), an index $j_{MIN}$—to the first sample of an $N_{FFT}$-point window of samples to be analyzed from the time domain noise signal SN[ ]—is initialized to a value of 1. Then, in step (1910), an index $j_{MAX}$—to the last sample of the $N_{FFT}$-point window of samples to be analyzed from the time domain noise signal SN[ ]—is set to the value of $j_{MIN}+N_{FFT}-1$. Then, in step (1912), if the end of the time domain noise signal SN[ ] has not been reached, then, in step (1914), the square of values—i.e. corresponding to noise power—of an $N_{FFT}$-point Fourier Transform of the data from the $N_{FFT}$-point window of samples of the time domain noise signal SN[ ] over the range of samples SN[$j_{MIN}$] to $SN[j_{MAX}]$, is added to the frequency-domain summation array FXSUM[ ]. Then, in step (1916), the summation counter $N_{SUM}$ is incremented, and in step (1918), the index $j_{MIN}$ is incremented by half the width of the $N_{FFT}$-point window, i.e. by a value of $N_{FFT}/2$, so as the provide for the next $N_{FFT}$-point window to be analyzed to overlap the current $N_{FFT}$-point window by half the window width. The above noise-content-evaluation process 1900 repeats beginning with step (1910), until, in step (1912), the index $j_{MAX}$ exceeds the end of the time domain noise signal SN[ ], after which, in step (1920), each of the values of the frequency-domain summation array FXSUM[ ] is divided by the value of the summation counter $N_{SUM}$ so as to calculate an associated average noise power FX [ ]. Then, in steps (1922), (1924) and (1926), respectively, the noise power is summed in three different corresponding respective frequency ranges, for example, 20 Hz to 200 Hz, 200 Hz to 800 Hz, and 800 Hz to 1,500 Hz, respectively, to give three corresponding respective power levels, $P_{LOW}$, $P_{MID}$ and $P_{HIGH}$, respectively. Then, in step (1928), if any of the power levels, $P_{LOW}$, $P_{MID}$ or $P_{HIGH}$ exceeds a corresponding respective power threshold value $Threshold_{LOW}$, $Threshold_{MID}$ or $Threshold_{HIGH}$, then, in step (1930), the noise threshold is considered to have been exceed for the particular auscultatory sound sensor 12, m and the particular associated segment k of breath-held sampled auscultatory sound data $S^m[i_0[k]: i_1[k]]$ is flagged with a corresponding indication of an associated status in an associated NoiseStatus flag. Otherwise, from step (1928), if none of the power levels, $P_{LOW}$, $P_{MID}$ or $P_{HIGH}$ exceeds the corresponding respective power threshold value $Threshold_{LOW}$, $Threshold_{MID}$ or $Threshold_{HIGH}$, then, in step (1932), the noise threshold is considered to have not been exceed for the particular auscultatory sound sensor 12, m and the particular associated segment of breath-held sampled auscultatory sound data $S^m[i_0[k]: i_1[k]]$ is flagged with a corresponding indication of the associated status in the NoiseStatus flag. The results from either steps (1930) or (1932) are then logged by an associated results-logging process 2000, which is called from step (1934).

Referring to FIG. 20, the results-logging process 2000 commences with receipt in step (2002) of the index m of the associated auscultatory sound sensor 12, m and the associated NoiseStatus flag. If, in step (2004), the NoiseStatus flag indicates a noisy auscultatory sound sensor 12, *m*, then, in step (2006), the noise counter $N_{NOISY}$ is incremented, and, in step (2008), the corresponding element of the status array Status [m, k] for the associated auscultatory sound sensor 12, m and breath-held segment k is updated to activate an associated Noisy flag, so as to indicate the associated auscultatory sound sensor 12, m as being noisy for the associated breath-held segment k. Then, in step (2010), if the value of the noise counter $N_{NOISY}$ is greater than 1, then, in step (2012), the corresponding elements of the status array Status [m, k] for each of the auscultatory sound sensors 12, m is updated to activate the Ignore flag, so as to provide for ignoring each of the auscultatory sound sensors 12, m for the associated breath-held segment k. Then, or otherwise from step (2010), in step (2014), if the Noisy flag of the status array Status [m, k] is activated for at least $N_{FAIL}$ breath-held segments k for the associated auscultatory sound sensor 12, *m*, then, in step (2016), status array Status [m] for the associated auscultatory sound sensor 12, m is updated to activate the Bad flag for the associated auscultatory sound sensor 12, *m*, so as to indicate that the associated auscultatory sound sensor 12, m is bad. Then, or otherwise from either step (2004) or step (2014), the results-logging process 2000 terminates by returning to the noise detection process 1700.

More particularly, referring again to FIG. 17, in step (1720), if all of the pairs of adjacent auscultatory sound sensors 12 have not been processed, then, in step (1722), the pair pointer p is incremented, and the noise detection process 1700 is repeated for the next pair of auscultatory sound sensors 12, m1[*p*], m2[*p*], beginning with step (1706) for the same breath-held segment k. Otherwise, from step (1720), if in step (1724), additional segments of breath-held sampled auscultatory sound data $S^m[i_0[k]: i_1[k]]$ remain to be processed, then, in step (1726), the breath-held-segment pointer k is incremented, and the noise detection process 1700 is repeated beginning with step (1704) for the next segment of breath-held sampled auscultatory sound data $S^m[i_0[k]: i_1[k]]$. Otherwise, from step (1724), the noise detection process 1700 terminates with step (1728).

Referring again to FIG. 1, in accordance with one set of embodiments, the results from the docking system 27 may be transferred to a server computer system 56, for example, for subsequent transfer to an external data storage or processing system 58, for example, to provide for either viewing or analyzing the results at a remote location. Referring again to FIGS. 2 and 4, in one set of embodiments, the composite set of blocks of breath-held auscultatory-sound-sensor time-series data S are screened prior to analysis by the associated Data Analysis Application (DAA) 54, for example, by first segmenting the set of blocks of breath-held auscultatory-sound-sensor time-series data S by heart cycle with an associated segmentation process 60, and then validating the associated heart cycle data with an associated heart cycle validation process 62, for example, to provide for additional screening for heart-phase associated noise.

Figure 21:
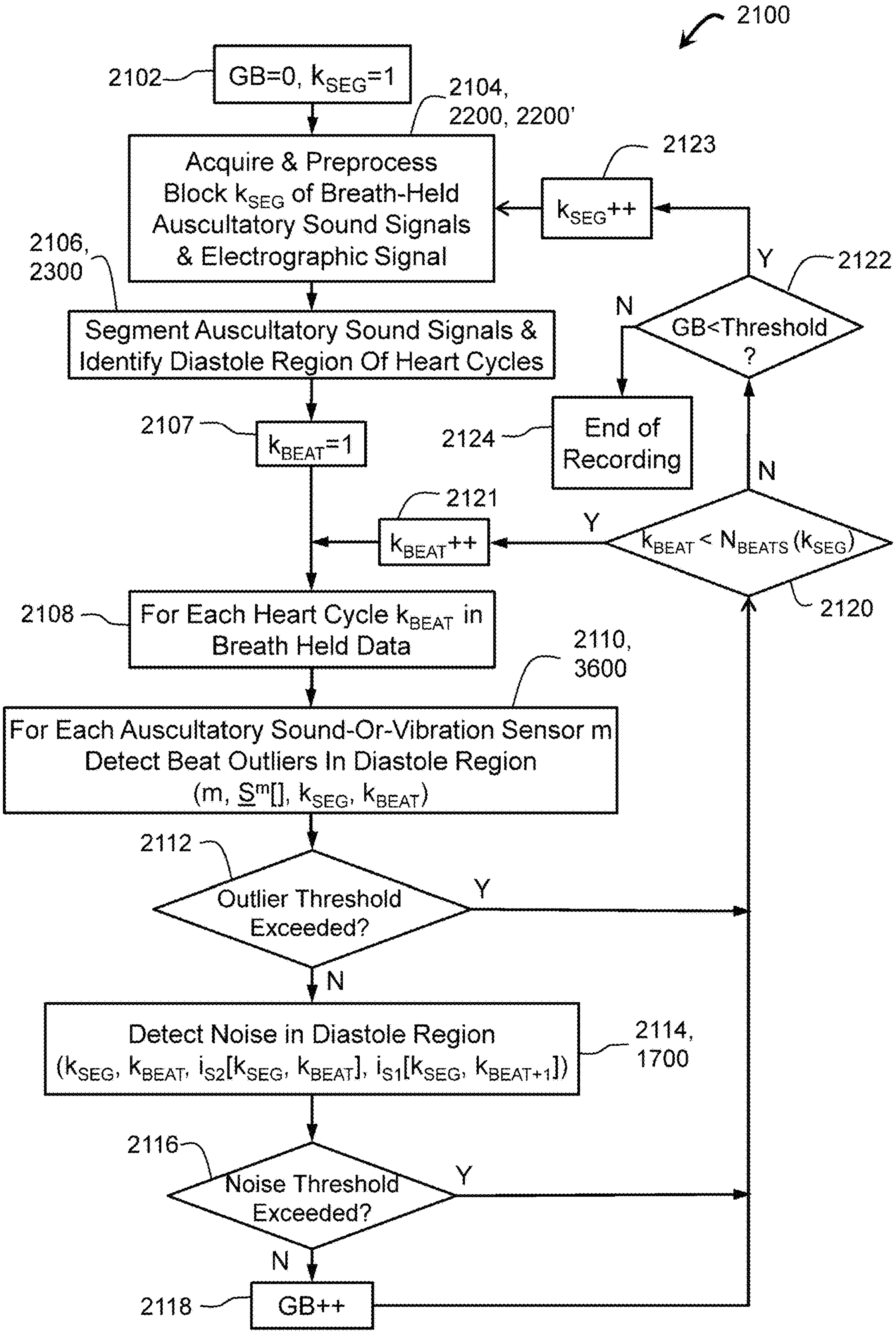
FIG. 21 illustrates a block diagram of a process for preprocessing and screening auscultatory sound signals.

Referring to FIG. 21, an auscultatory sound signal preprocessing and screening process 2100 provides for preprocessing breath-held auscultatory sound signals 16.1 and an associated electrographic signal 37 from an ECG sensor 34, 34', for example, as acquired, for example, in accordance with the above-described auscultatory-sound-sensing process 700, with concurrent recording of an associated electrographic signal 37 from an ECG sensor 34, 34'. In accordance with one embodiment as illustrated, in step (2102) a good beat counter GB is initialized to zero, and a segment counter $k_{SEG}$ is initialized to a value of 1, wherein the good beat counter GB provides a count of the number of heart cycles for which the associated breath-held sampled auscultatory sound data S[ ] is not corrupted by either outliers or noise during diastole, and the segment counter $k_{SEG}$ is the value of the breath-held-segment pointer k for the current block B of breath-held sampled auscultatory sound data S[ ].

Figure 22A:
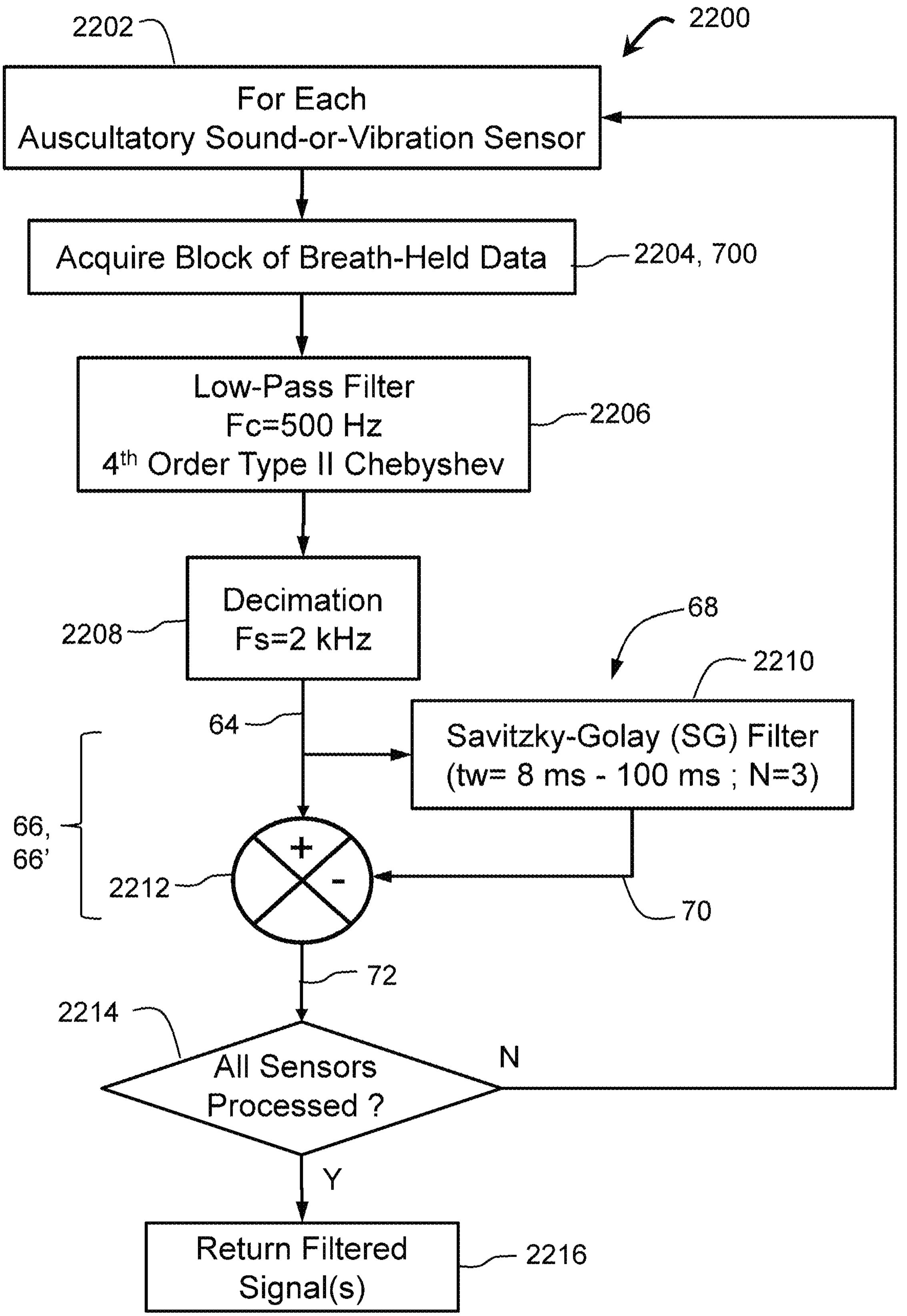
FIG. 22*a* illustrates a process for pre-processing auscultatory sound signals from auscultatory sound-or-vibration sensors.

Then, from step (2104), referring to FIG. 22*a*, a segment of breath-held auscultatory sound signals 16.1 is acquired and preprocessed by an associated auscultatory sound signal acquisition and filtering process 2200, wherein, in step (2202), for each auscultatory sound sensor 12, in step (2204), a block of data of associated breath-held auscultatory sound signals 16.1 is acquired, for example, in accordance with the auscultatory-sound-sensing process 700, or as an associated segment k of a previously acquired and recorded breath-held sampled auscultatory sound data $S^m[i_0[k]: i_1[k]]$ for the $m^{th}$ auscultatory sound sensor 12. With data recorded at a sampling frequency Fs of 24 KHz, and for portions of the spectrum of the breath-held auscultatory sound signals 16.1 of interest related to coronary artery disease limited to a few hundred Hertz—i.e. without significant acoustic energy above 500 Hz—the sampling rate may be reduced to 2 kHz. Accordingly, in step (2206), the breath-held auscultatory sound signal 16.1 is filtered by a fourth order Type II Chebyshev low-pass filter having a cut-off frequency of 500 Hz to avoid aliasing, and then, in step (2208), decimated to a 2 kHz sampling rate using a phase invariant method that also involves low-pass filtering, so as to generate corresponding filtered-decimated breath-held sampled auscultatory sound signal 64.

The breath-held auscultatory sound signal 16.1 in some cases can include very low frequency—for example, around 10 Hz—vibrations that are believed to be associated with movements of the entire auscultatory sound sensor 12 stimulated by chest motion. Considering the sensor housing as an inertial mass under a tangential component of gravitational force attached to an elastic surface, it is possible to initiate sensor vibration by small surface displacements. Such vibrations can be amplified by resonance characteristics of the tissue-sensor interface. Depending on the Q-factor of tissue-sensor system, vibrations may decay very slowly, extending well into the diastolic interval of the heartbeat, contaminating the signal of interest with relatively large amplitude unwanted interference. The net effect of such interference is an unstable signal baseline and distortion of the actual underlying heart sounds. Potential sources of noise relevant to digitized acquisition of acoustic signals include: electric circuit thermal noise, quantization noise from the analog-to-digital converter (ADC), electro-magnetic interference, power line 60 Hz interference and acoustic noises relevant to human physiology and the environment where recording is done (ambient noise). Generally thermal noise power and analog-to-digital converter (ADC) quantization noise are very low for the bandwidth of interest and may be significant only for the signals with amplitudes in the microvolt region. Furthermore, recording artifacts may significantly reduce visibility of the signal of interest since these artifacts may have relatively high amplitude and may overlap in spectral content. These artifacts are due to uncontrolled patient movements, signals related to respiration, and sensor vibrations produced by the associated oscillating mass of the auscultatory sound sensor 12 coupled to the elastic skin tissue surface (cardio seismographic waves). The latter type of artifact may be caused by the inertial mass of the sensor housing and can be relatively high in amplitude due to resonance properties of the sensor-tissue interface. Although the frequency of such vibrations is relatively low (around 10 Hz), the associated relatively high amplitude thereof can result in an unstable signal baseline, which complicates the detection of target signals.

However cardiac activity may also produce low frequency signals—for example, as a result of contraction of heart muscle, or as a result of valvular sounds—that may have valuable diagnostic information. In some situations, the spectrum of the artifacts may overlap with the acoustic spectrum of cardiac signals such as myocardium vibrations. Therefore, it can be beneficial to reduce baseline instability so as to provide for recording primarily acoustic signals originating from the cardiac cycle.

Referring again to FIG. 22*a*, in accordance with one set of embodiments, these very low frequency artifacts may be rejected by using additional signal filtering to suppress the associated characteristic vibration frequencies, for example, using a software-implemented high-pass filter 66 having a 3 dB cut-off frequency above 10 Hz, for example, as provided for by a Savitzky-Golay-based high-pass filter 66', wherein, in step (2210), the filtered-decimated breath-held sampled auscultatory sound signal 64 is smoothed by a Savitzky-Golay (SG) smoothing filter 68 to generate a smoothed breath-held sampled auscultatory sound signal 70, the latter of which, in step (2212), is subtracted from the filtered-decimated breath-held sampled auscultatory sound signal 64 to then generate the corresponding resulting high-pass-filtered breath-held sampled auscultatory sound signal 72 having a relatively-higher signal-to-noise ratio (SNR), but without significant distortion of the original filtered-decimated breath-held sampled auscultatory sound signal 64.

The digital Savitzky-Golay smoothing filter 68 is useful for stabilizing baseline wandering (for example, as may be exhibited in ECG signals) and provides for removing the low-frequency signal components without causing significant ringing artifacts. The Savitzky-Golay smoothing filter 68 employs a least squares approximation of a windowed signal using a polynomial function. The associated parameters of the Savitzky-Golay smoothing filter 68 include the window size M in samples that defines the associated cut-off frequency, and the polynomial degree N used for the approximation. The associated roll-off range is fairly wide and the cut-off frequency is somewhat arbitrary. For example, for the Savitzky-Golay smoothing filter 68 used in step (2210), the associated window size M-expressed in terms of window time duration tw—is in the range of 8 milliseconds to 100 milliseconds, with N=3. For example, a window time duration tw=8 milliseconds provides a cut-off frequency of approximately 100 Hz, and a window time duration tw=25 milliseconds, provides for passing signal frequencies above 40 Hz through the Savitzky-Golay-based high-pass filter 66'.

The Savitzky-Golay smoothing filter 68 is defined by a least-squares fit of windowed original samples, with an $N^{th}$ degree polynomial, $$y(n) = \sum_{k=0}^{N} a_k n^k \tag{6}$$

so as to minimize the associated error function, E:

$$E = \sum_{n=-M}^{M} \left( \sum_{k=0}^{N} a_k n^k - x[n] \right)^2 \tag{7}$$

wherein the total window width is 2M+1 samples. The associated short-time window sliding through entire time series fits the data with a smooth curve. The frequency response of the Savitzky-Golay smoothing filter 68 depends strongly on the window size M and polynomial order N. The normalized effective cut-off frequency of the Savitzky-Golay smoothing filter 68 is empirically given as follows, wherein $f_c=\omega_s/\pi$, for which $\omega_s$, is the radian sampling frequency:

$$f_c = \frac{N+1}{3.2M - 4.6} \tag{8}$$

Following the high-pass filter 66, 66' of steps (2210) and (2212), from step (2214), the auscultatory sound signal acquisition and filtering process 2200 is repeated beginning with step (2202) for each of the auscultatory sound sensors 12, after which, from step (2216), the resulting blocks of high-pass-filtered breath-held sampled auscultatory sound signals 72—for each of the auscultatory sound sensors 12—are returned to step (2104).

Figure 22B:
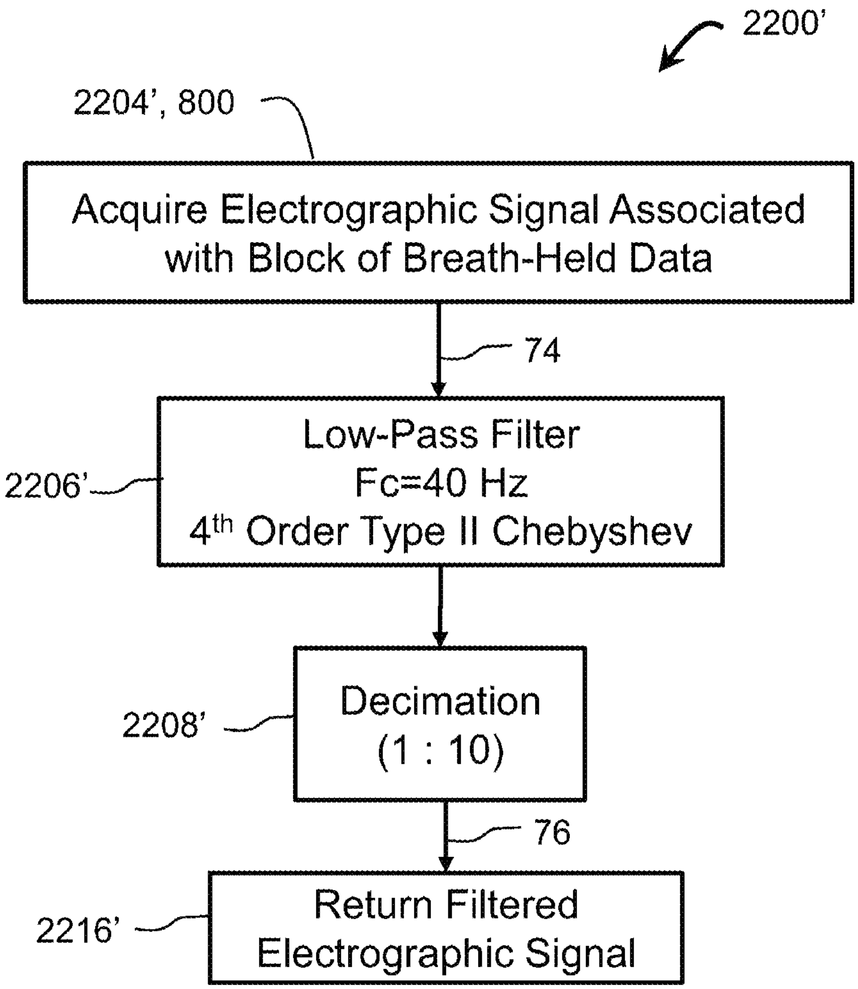
FIG. 22*b* illustrates a process for pre-processing electrographic signals from an ECG sensor.

Then, also from step (2104), referring to FIG. 22*b*, a corresponding segment of a concurrent electrographic signal 37 is acquired and preprocessed by an associated electrographic signal acquisition and filtering process 2200', wherein, in step (2204'), a block of electrographic data 74 of the corresponding electrographic signal 37 from the ECG sensor 34, 34'—in correspondence with the blocks of high-pass-filtered breath-held sampled auscultatory sound signals 72 returned by the above-described auscultatory sound signal acquisition and filtering process 2200—is acquired, for example, in accordance with the above-described data acquisition process 800, or as an associated segment k of previously acquired and recorded electrographic data 74. Then, in step (2206'), and as explained more fully herein below, the electrographic data 74 is filtered by a fourth order Type II Chebyshev low-pass filter having a cut-off frequency of 40 Hz, and then, in step (2208'), is decimated by a factor of ten, so as to generate corresponding filtered-decimated electrographic signal 76, which, in step (2216'), is returned to step (2104).

Referring again to FIG. 21, in step (2106), the high-pass-filtered breath-held sampled auscultatory sound signals 72, or alternatively, the breath-held auscultatory sound signals 16.1, are segmented to identify the starting and ending points of each heart cycle, and to identify the starting and ending points of each associated diastole region or phase, thereof.

In accordance with a first aspect, this may be accomplished using the breath-held auscultatory sound signals 16.1—or the corresponding associated high-pass-filtered breath-held sampled auscultatory sound signals 72—alone, without relying upon the associated electrographic signal 37 from the ECG sensor 34, 34', or upon the corresponding associated filtered-decimated electrographic signal 76, for example, in accordance with the following portions of the disclosure and drawings of U.S. Pat. No. 9,364,184: Abstract, FIGS. 1-50, Col. 1, Line 1 through Col. 3, line 59 (indicated), Col. 5, line 1 through Col. 34, line 55 (indicated), and the claims, which are incorporated herein by reference.

However, in accordance with a second aspect, the electrographic signal 37 from the ECG sensor 34, 34', and particularly, the corresponding associated filtered-decimated electrographic signal 76 responsive thereto, provides an effective basis for segmenting the breath-held auscultatory sound signals 16.1, 72 by heart cycle, after which the high-pass-filtered breath-held sampled auscultatory sound signal 72 may then be used to locate the associated dominant S1 and S2 heart sounds that provide for locating the associated heart phases of systole and diastole, data from the latter of which provides for detecting coronary artery disease responsive to information in the breath-held auscultatory sound signals 16.1, 72.

Figure 23:
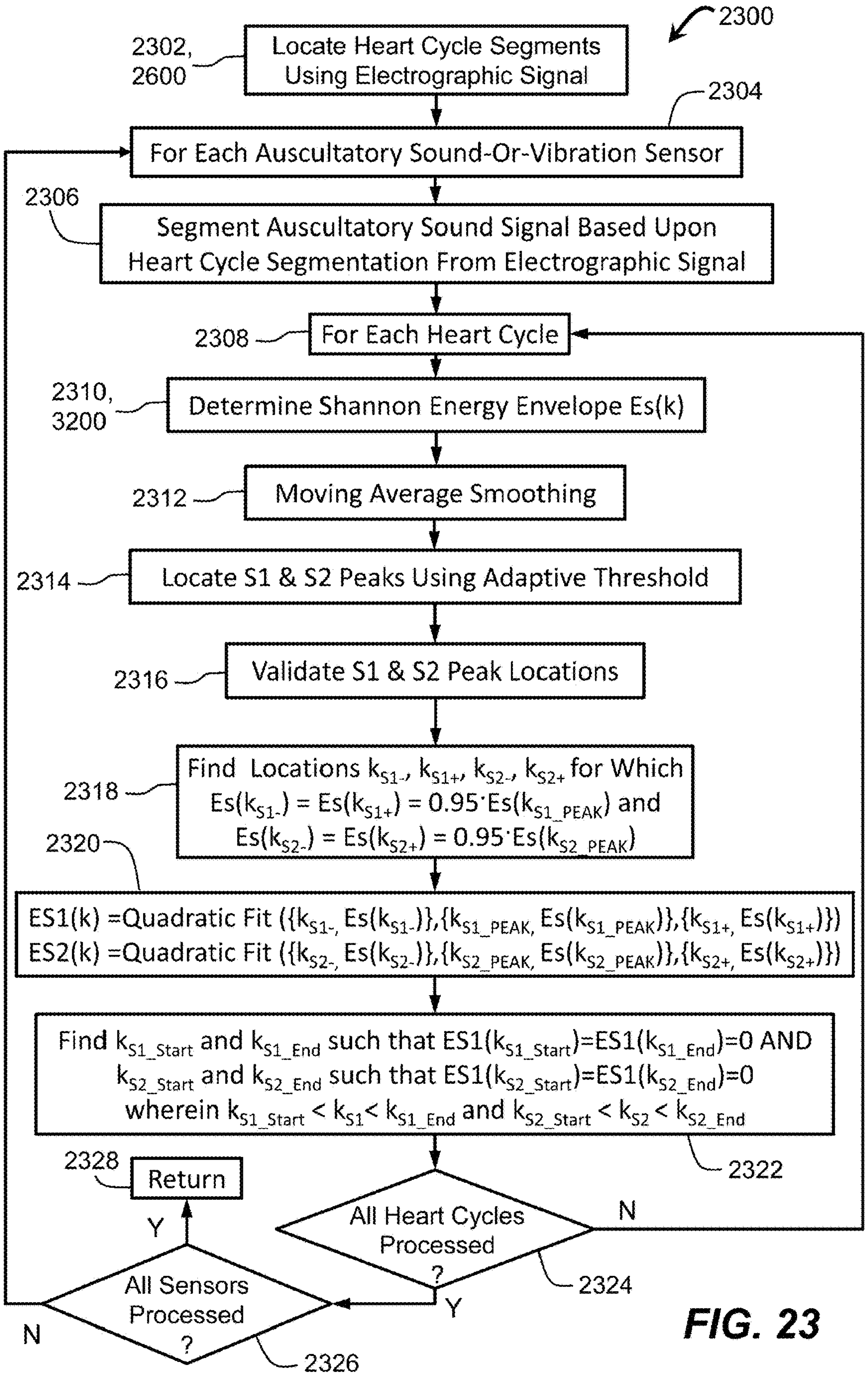
FIG. 23 illustrates a process for segmenting auscultatory sound signals from auscultatory sound-or-vibration sensors, by heart cycle based upon an electrographic signal from an ECG sensor, and by heart phase based upon the auscultatory sound signals.

Referring also to FIG. 23, in accordance with the second aspect, a heart-cycle segmentation and heart-phase identification process 2300 is called from step (2106) of the auscultatory sound signal preprocessing and screening process 2100 to locate the heart cycles responsive to the filtered-decimated electrographic signal 76, to then segment the high-pass-filtered breath-held sampled auscultatory sound signal 72 by heart cycle responsive thereto, and to then identify the region of diastole within each heart cycle (and implicitly, to therefor also identify the remaining region of systole) from an analysis of the high-pass-filtered breath-held sampled auscultatory sound signal 72 alone.

The normal human cardiac cycle consists of four major intervals associated with different phases of heart dynamics that generate associated audible sounds: 1) the first sound (S1) is produced by closing of mitral and tricuspid valves at the beginning of heart contraction, 2) during the following systolic interval, the heart contracts and pushes blood from ventricle to the rest of the body, 3) the second sound (S2) is produced by the closing of aortic and pulmonary valves and 4) during the following diastolic interval, the heart is relaxed and the ventricles are filled with oxygenated blood.

Figure 24:
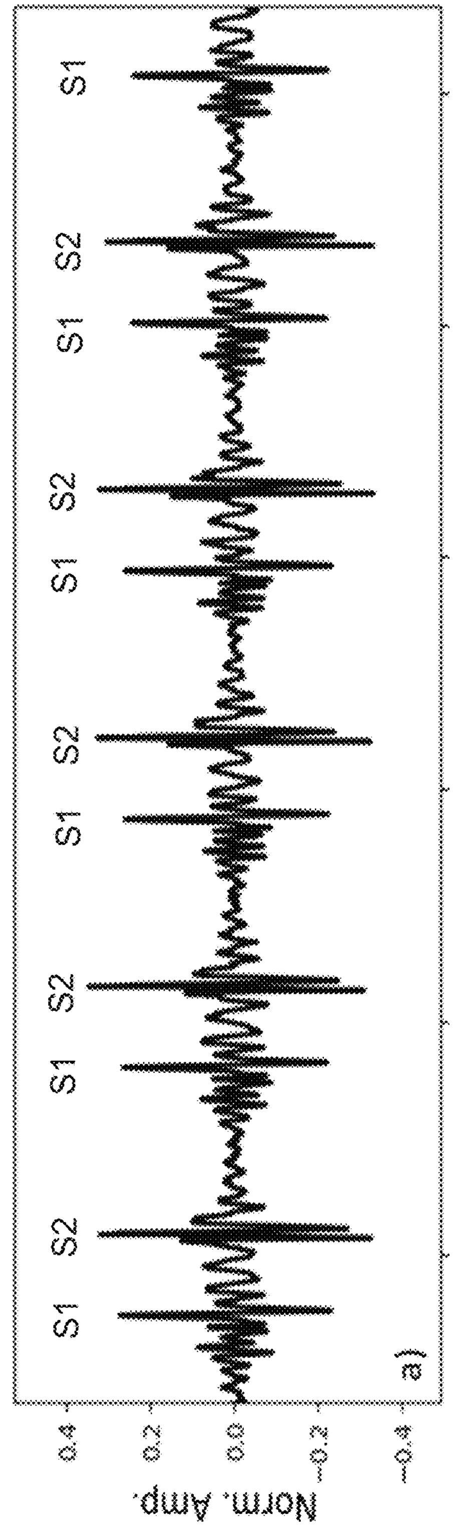
FIG. 24 illustrates an auscultatory sound signal from an auscultatory sound-or-vibration sensor.
Figure 25:
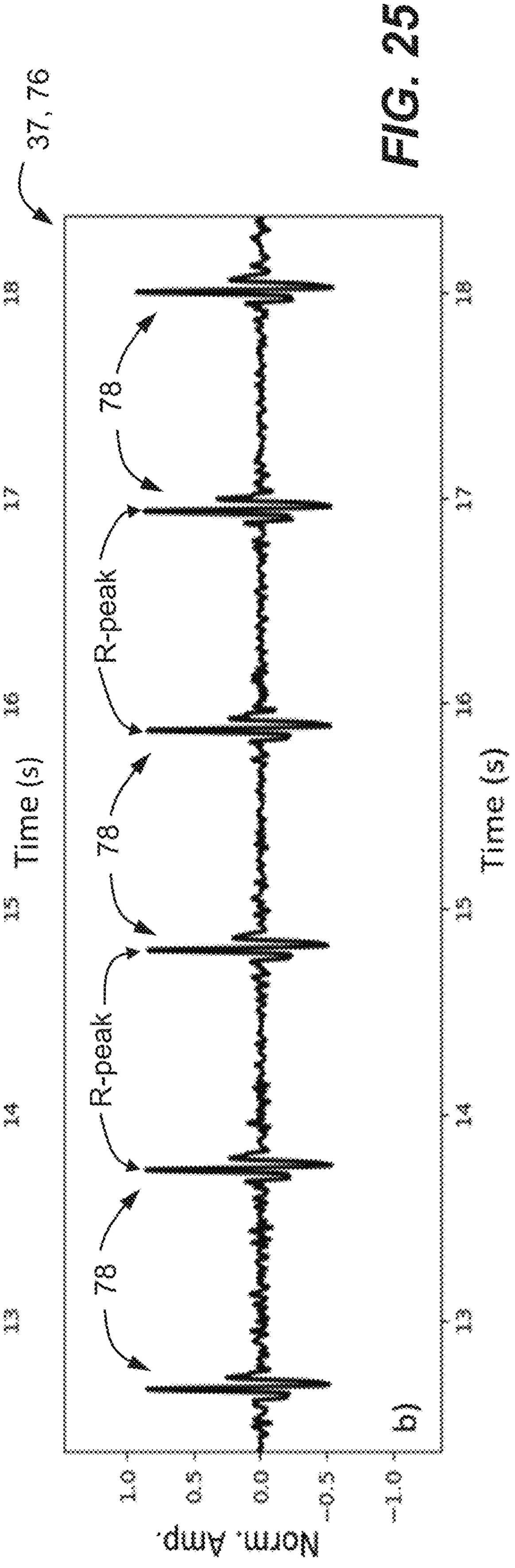
FIG. 25 illustrates a corresponding electrographic signal from an ECG sensor, in correspondence with the auscultatory sound signal illustrated in FIG. 24.

Referring to FIGS. 24 and 25, respectively illustrating a breath-held auscultatory sound signal 16.1, 72 and a corresponding electrographic signal 37, 76 associated with six heartbeats, each QRS complex 78 illustrated in FIG. 25 is generated by an associated ventricular depolarization that precedes cardiac contraction. The S1 heart sound resulting from the closing of mitral and tricuspid valves is observed immediately after R-peak, and the S2 heart sound resulting from the closing of aortic and pulmonary valves is observed at the end of T-wave of the ECG cycle. This relative timing of the heart sounds S1, S2 and the QRS complex 78 of the associated electrographic signal 37, 76 provides for using the electrographic signal 37 to locate the beginning and end of each heart cycle without relying upon the breath-held auscultatory sound signal 16.1, 72 to do so. For each heartbeat, the S1 heart sound—marking the start of systole—follows shortly after the R-peak, and the S2 heart sound—marking the end of systole and the beginning of diastole—follows thereafter, with diastole continuing until the next R-peak.

Although the QRS complex 78 is the most prominent feature, the electrographic signal 37, 76 may be distorted by low frequency baseline wandering, motion artefacts and power line interference. To stabilize the baseline, a Savitzky-Golay-based high-pass filter 66'-similar to that used in steps (2210/2212) when filtering the breath-held auscultatory sound signal 16.1—may be used to cancel low-frequency drift, for example, prior to the subsequent low-pass filtering, in step (2206'), by the fourth order Type II Chebyshev low-pass filter, for example, having a 40 Hz cut-off frequency, and/or prior to decimation of the sampling by a factor of 10 in step (2208'), which together provide for both reducing high frequency noise and emphasizing QRS complexes 78.

Figure 26:
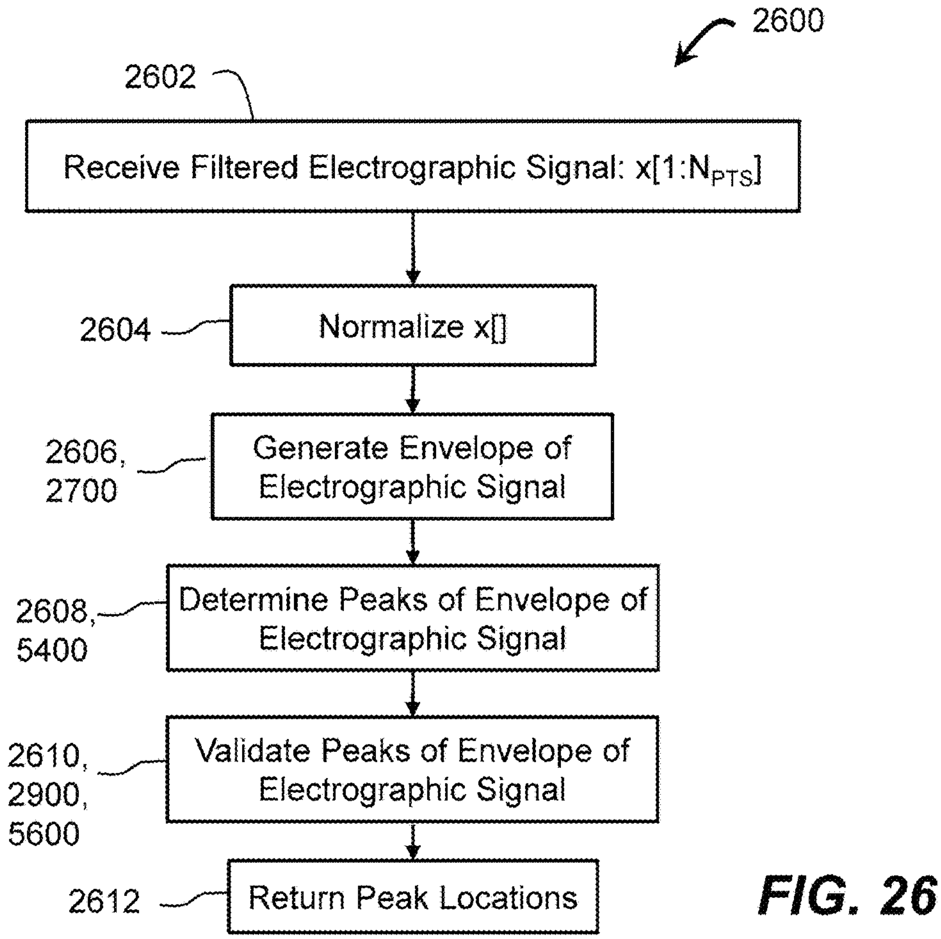
FIG. 26 illustrates a process for identifying heart-cycle boundaries in an electrographic signal from an ECG sensor.

More particularly, referring again to FIG. 23, and also referring to FIG. 26, the heart-cycle segmentation and heart-phase identification process 2300 commences in step (2302) by calling an electrographic segmentation process 2600 that provides for identifying the locations of the R-peaks. More particularly, in step (2602), a block of electrographic data x[ ] is received, and, in step (2604), normalized so as to have a maximum absolute value of unity. Then, referring also to FIGS. 27 and 28, from step (2606), beginning with step (2702) of an associated first envelope generation process 2700, the block of filtered-normalized electrographic data x[ ] is used to generate an associated electrographic envelope waveform 80, $F_S$[ ] that emphasizes the R-peaks of the filtered-normalized electrographic data x[ ], wherein, for each value of index k—set in step (2702)—the corresponding value of the electrographic envelope waveform 80, $F_S[k]$ is set in step (2704) responsive to a sum of values within a sliding window containing a subset of $N_W$ points, as follows:

$$F_S(t(k)) = -\frac{1}{N_W}\sum_{i=1}^{N_W}(x(k+i))^4\ln\left((x(k+i))^4\right) \tag{9}$$

Equation (9) is similar to a Shannon energy function, but with the associated discrete signal values raised to the fourth power—rather than a second power—to emphasize difference between R-peaks 80' and baseline noise. The value of the electrographic envelope waveform 80, $F_S[\ ]$ is calculated for each of the $N_{PTS}$ values of index k until, in step (2706), all points have been calculated, after which, in step (2708), the electrographic envelope waveform 80, $F_S[\ ]$ is returned to step (2606) of the electrographic segmentation process 2600.

Figure 28:
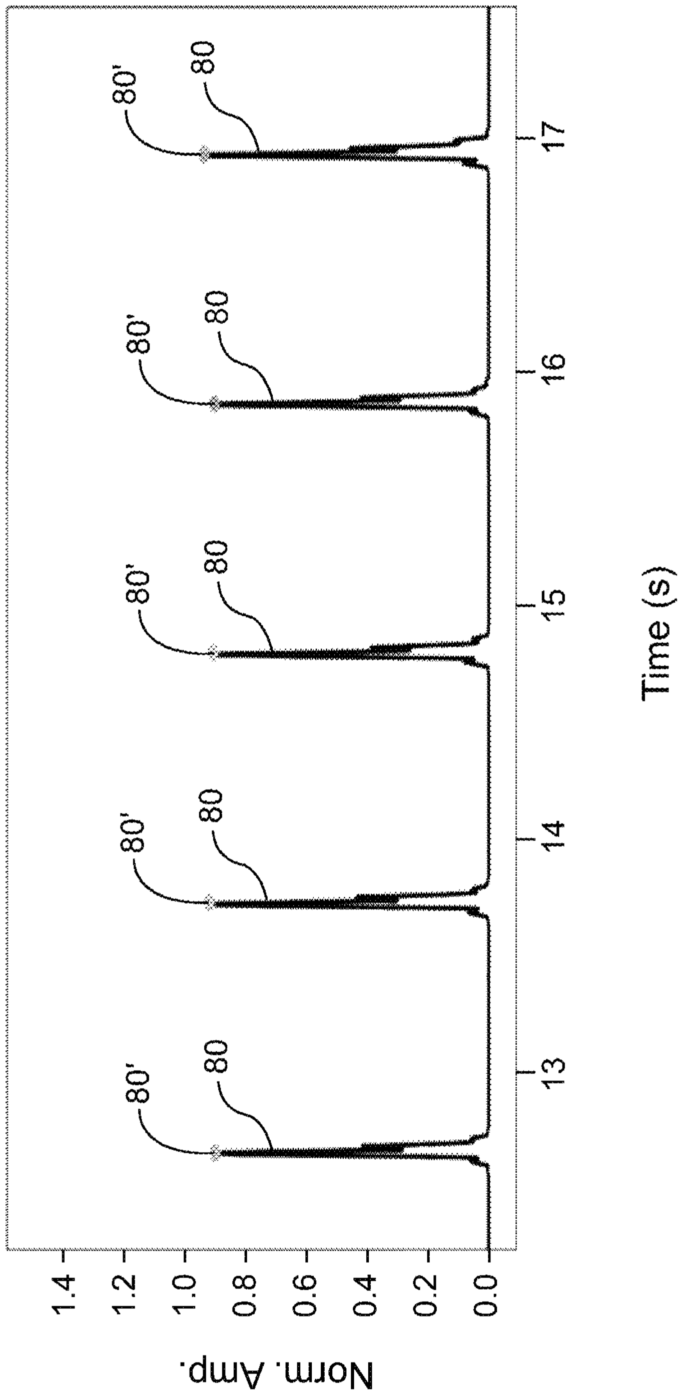
FIG. 28 illustrates an envelope, and associated peaks, of a portion of the electrographic signal illustrated in FIG. 25, generated in accordance with the process illustrated in FIGS. 26 and 27.

Returning to FIG. 26, in step (2608), in accordance with a first aspect, the peaks of the electrographic envelope waveform 80, $F_S[\ ]$ are located, for example, by finding indices k for which the associated value of the electrographic envelope waveform 80, $F_S[k]$ is a local maximum exceeding a fixed, predetermined threshold. For example, FIG. 28 illustrates the electrographic envelope waveform 80, $F_S[\ ]$ and associated R-peaks 80' thereof, for a portion of a 10-second recording of a filtered-decimated electrographic signal 76.

The electrographic segmentation process 2600 for finding R-peaks is quite simple and stable when signal-to-noise ratio (SNR) of recording is sufficiently high. Otherwise, when the electrographic data 74 is excessively noisy, additional signal processing such as discrete wavelet decomposition may be used to further enhance R-peaks and facilitate QRS detection. Occasional relatively high amplitude transients due to patient movements or ambient interference may produce false peaks unrelated to the QRS complex and therefore complicate segmentation.

Figure 29:
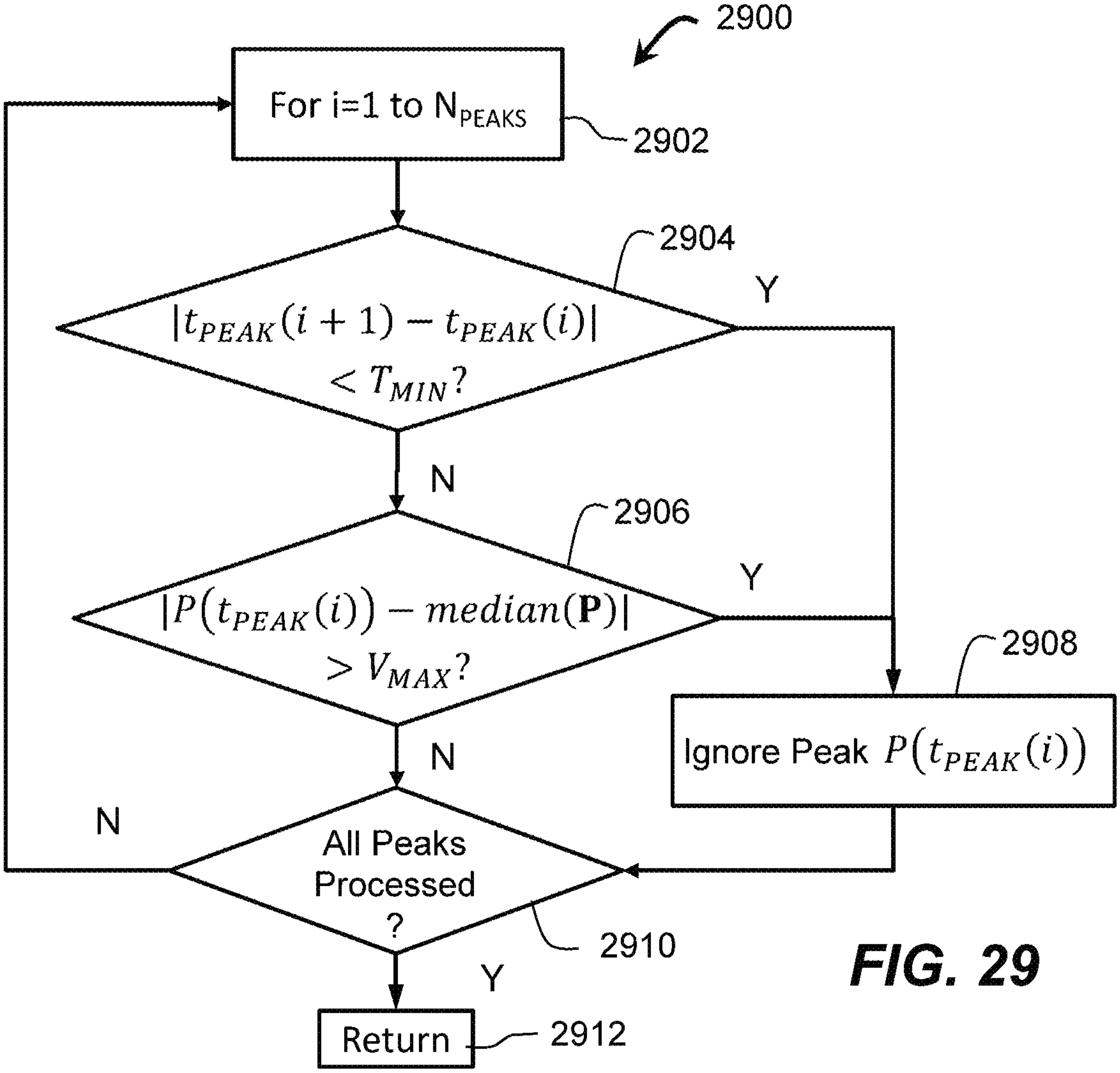
FIG. 29 illustrates a first aspect of a process for validating the peaks of an electrographic signal, which is called from the process illustrated in FIG. 26.

Referring to FIG. 29, in step (2610), the R-peaks 80' of the electrographic envelope waveform 80, $F_S[\ ]$ are then validated by a peak validation process 2900, both with respect to temporal location—i.e. relative spacing—and magnitude—i.e. deviation from a median value,—so as to verify that the detected R-peaks 80' correspond to R-peaks 80' rather than noise. More particularly, in step (2902), for each of the detected R-peaks 80', in step (2904), if the difference in temporal locations of each pair of R-peaks 80' is less than a time threshold $T_{MIN}$, or if, in step (2906), the difference between the magnitude $P(t_{PEAK}(i))$ of each R-peak 80' and the median value of the magnitudes of all R-peaks 80' is greater than a magnitude threshold $V_{MAX}$, then, in step (2908), a status indicator associated with the R-peak 80' being tested is set to IGNORE, in order to prevent the associated R-peak 80' from being used for subsequent segmentation of the breath-held auscultatory sound signal 16.1, 72. Otherwise, from step (2910), the peak validation process 2900 terminates in step (2912) and returns to step (2612) of the electrographic segmentation process 2600, which, in turn, returns the peak locations $t_{PEAK}[\ ]$ to step (2302) of the heart-cycle segmentation and heart-phase identification process 2300, wherein valid R-peaks 80' satisfy both of the following conditions:

$$|t_{PEAK}(i+1) - t_{PEAK}(i)| \geq T_{MIN} \text{ and} \tag{10}$$

$$|P(t_{PEAK}(i)) - \text{median}(P)| \leq V_{MAX} \tag{11}$$

wherein $t_{PEAK}(i)$ is the time of the $i^{th}$ R-peak 80' and $P(t_{PEAK}(i))$ is the corresponding magnitude of the R-peak 80'.

Figure 54:
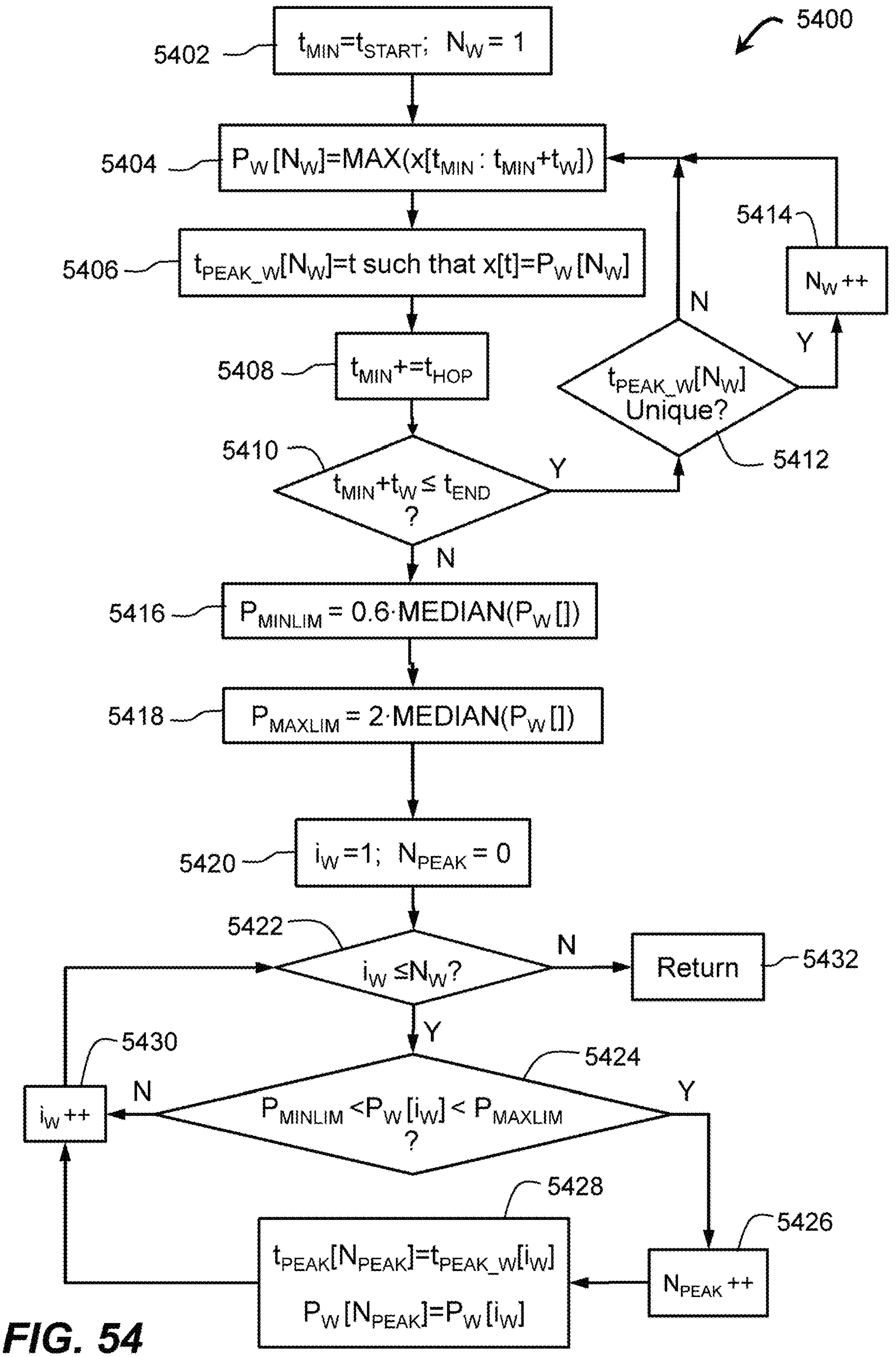
FIG. 54 illustrates a second aspect of a process for detecting R-peaks in an electrographic signal.
Figure 55:
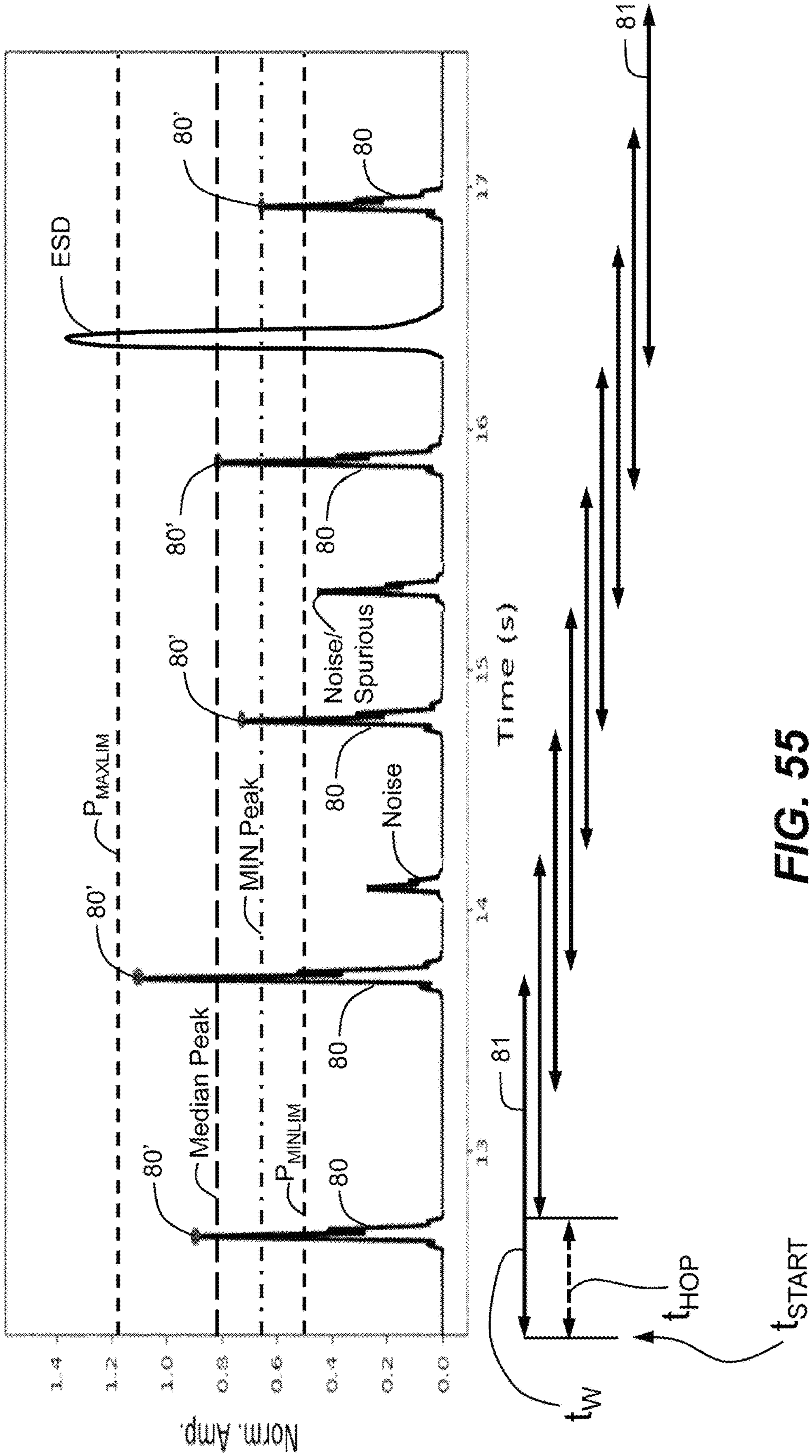
FIG. 55 illustrates an envelope, and associated peaks, of a portion of the electrographic signal that includes noise and other signal components to be ignored.

Referring again to FIG. 26, alternatively, in accordance with a second aspect, the R-peaks 80' of the electrographic envelope waveform 80, $F_S[\ ]$ are located in step (2608) by an associated R-peak detection process 5400 that provides for discriminating valid R-peaks 80' from noise or other anomalies. Referring to FIGS. 54 and 55, the R-peak detection process 5400 determines the peak values and associated samples times of the electrographic envelope waveform 80, $F_S[\ ]$ within a plurality of sample windows 81, each of window width $t_W$, and each offset from one another with an associated hop period trop. More particularly, the R-peak detection process 5400 commences with step (5402) by setting a window start time $t_{MIN}$ to point to the beginning of the electrographic envelope waveform 80, $F_S[\ ]$, and by initializing a window counter $N_W$ to a value of 1. Then, in step (5404), the maximum value of the electrographic envelope waveform 80, $F_S[\ ]$ is determined within the sample window 81 extending between sample times $t_{MIN}$ and $t_{MIN}+t_W$, and stored in element $P_W[N_W]$ of window-peak array $P_W[\ ]$, wherein, for example, the window width $t_W$ is sufficiently wide to span a single heart cycle, for example, with $t_W$ equal to about 1.5 seconds. Then, in step (5406), the corresponding sample time at which the associated peak value occurred is stored as a corresponding element $t_{PEAK\_W}[N_W]$ of an associated window-peak-time array $t_{PEAK\_W}[\ ]$. Then, in step (5408), the window start time $t_{MIN}$ is incremented by the hop size $t_{HOP}$, and, in step (5410), if the prospective end $t_{MIN}+t_W$ of the prospective next sample window 81 is before the end $t_{END}$ of the electrographic envelope waveform 80, $F_S[\ ]$, then, in step (5412), if the most-recently detected R-peak 80' is unique, then, in step (5414), the window counter $N_W$ is incremented. Then, or otherwise directly from step (5412), the R-peak detection process 5400 repeats beginning with step (5404). For example, in one set of embodiments, the hop size $t_{HOP}$ is set to half the shortest heart cycle, but no less than 0.3 second, or a corresponding fraction of the window width $t_W$, although it should be understood that the particular values of the window width $t_W$ and hop size $t_{HOP}$ are not limiting. Although depending upon the window width $t_W$ and hop size $t_{HOP}$, different sample windows 81 may potentially span the same R-peak 80', step (5412) provides for ensuring that each of the R-peaks 80' in the window-peak array $P_W[\ ]$ are unique, and that the associated sample times in the window-peak array $P_W[\ ]$ are in monotonically increasing order.

Then, from step (5410) following R-peak detection within the last sample window 81, in step (5416), a minimum peak-threshold $P_{MINLIM}$ is set equal to about 60 percent of the median amplitude of the R-peaks 80' within the window-peak array $P_W[\ ]$, and, in step (5418), a maximum peak-threshold $P_{MAXLIM}$ is set equal to twice the median amplitude of the R-peaks 80' within the window-peak array $P_W[\ ]$. Then, in steps (5420) through (5430), R-peaks 80' that are outside those limits are ignored, so as to provide for ignoring noise or other spurious signal components. More particularly, beginning in step (5420), a second window counter $i_W$—that provides pointing to the above-detected unique R-peaks 80'—is initialized to a value of 1, and a peak counter $N_{PEAK}$—that provides for counting the number of R-peak 80' within the above-determined amplitude thresholds—is initialized to a value of 0. Then, in step (5422), if the value of the second window counter $i_W$ is less than the number of windows $N_W$ determined above in steps (5402) through (5414), then, in step (5424), if the magnitude of the currently-pointed-to R-peaks 80', i.e. $P_W[i_W]$, is greater than the minimum peak-threshold $P_{MINLIM}$ and less than the maximum peak-threshold $P_{MAXLIM}$-indicating a potentially valid R-peak 80'-then, in step (5226), the peak counter $N_{PEAK}$ is incremented, and the corresponding magnitude and time of the associated R-peak 80', i.e. $P_W[i_W]$ and $t_{PEAK}$ w $[i_W]$, are stored as respective values in in a corresponding peak array $P[N_{PEAK}]$ and peak-time array $t_{PEAK}[N_{PEAK}]$ (alternatively, the window-peak array $P_W[\ ]$ and the window-peak-time array $t_{PEAK\_W}[\ ]$ could be reused in place for storing these values). For example, referring also to FIG. 55, step (5424) provides for ignoring occurrences of noise, or a noise or spurious signal—the magnitudes of each of which would be less than the minimum peak-threshold $P_{MINLIM}$,—and, for example, provides for ignoring a false R-peak 80' resulting from electro-static discharge (ESD) that exceeds the maximum peak-threshold $P_{MAXLIM}$. Then, in step (5430), the second window counter $i_W$ is incremented to point to the next entry of the window-peak-time array $t_{PEAK\_W}[\ ]$, and the R-peak detection process 5400 repeats with step (5422). If, from step (5422), all entries of the have been processed, then, in step (5432), the process returns control to step (2608) of the electrographic segmentation process 2600.

Figure 56:
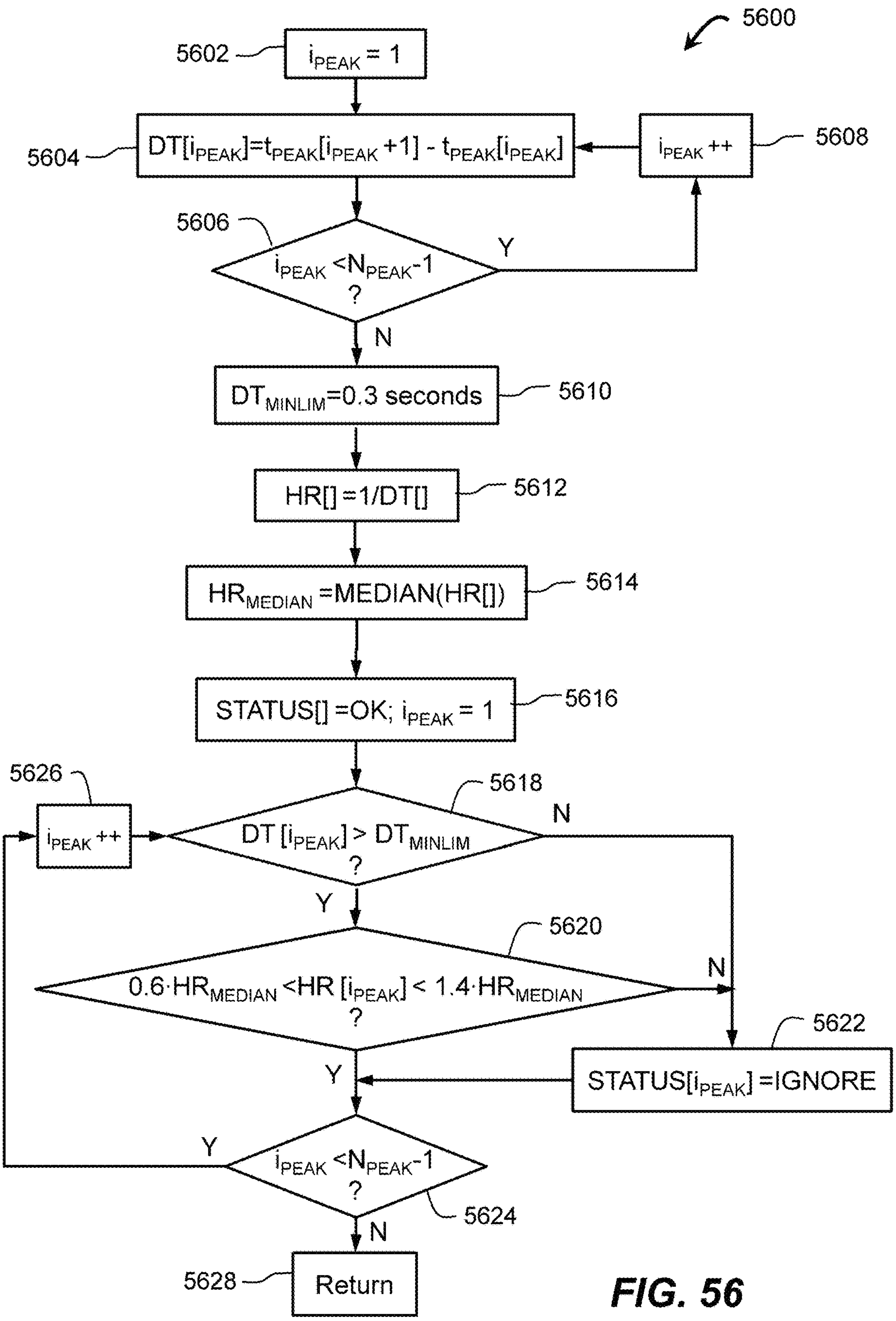
FIG. 56 illustrates a second aspect of a process for validating the peaks of an electrographic signal, which is called from the process illustrated in FIG. 26, following the second-aspect process for detecting R-peaks in an electrographic signal illustrated in FIG. 54.

Referring again to FIG. 26, following step (2608) and completion of the associated second-aspect R-peak detection process 5400, a second aspect of a peak validation process 5600 provides for validating the R-peaks 80' detected by the second-aspect R-peak detection process 5400. More particularly, referring also to FIG. 56, in steps (5602) through (5608), the associated heart-cycle period $DT[i_{PEAK}]$ between each pair of temporally-adjacent R-peaks 80' is calculated in step (5604), indexed by a second peak counter $i_{PEAK}$ that is initialized to a value of 1 in step (5602) and incremented in step (5608) so long as, in step (5606), the value thereof is less than $N_{PEAK}-1$ that had been determined in steps (5424) and (5426) of the second-aspect R-peak detection process 5400. Then, in step (5610), a minimum heart-cycle-period-threshold $DT_{MINLIM}$ is set to 0.3 seconds (corresponding to a heart rate of 200 BPM). Then, in step (5612), a corresponding heart-rate HR[ ] array is calculated from the heart-cycle period DT[ ] array, wherein each element of the former is given by the inverse of the corresponding element of the latter, after which, in step (5614), the median heart-rate $HR_{MEDIAN}$ is determined as the median of the values of the elements of the heart-rate array HR[ ]. Then, in step (5616), a status STATUS[ ] array is initialized to indicate that each R-peak 80' associated with the heart-rate array HR[ ] is "OK", and the second peak counter $i_{PEAK}$ is initialized to a value of 1. Then, if, in step (5618), the heart-cycle period $DT[i_{PEAK}]$ is not greater than the minimum heart-cycle-period-threshold $DT_{MINLIM}$, or, in following step (5620), if the heart-rate HR[ ] is not both greater than 60 percent of the median heart-rate $HR_{MEDIAN}$ AND less than 140 percent of the median heart-rate $HR_{MEDIAN}$, then, in step (5622), the $STATUS[i_{PEAK}]$ of the corresponding R-peak 80' is set to "IGNORE". Then, or otherwise from steps (5618) and (5620), if, in step (5624), all R-peaks 80' have not been processed, then, in step (5626), the second peak counter $i_{PEAK}$ is incremented, and the second-aspect peak validation process 5600 repeats with step (5618). Otherwise, from step (5628), the process returns control to step (2610) of the electrographic segmentation process 2600.

Figure 30:
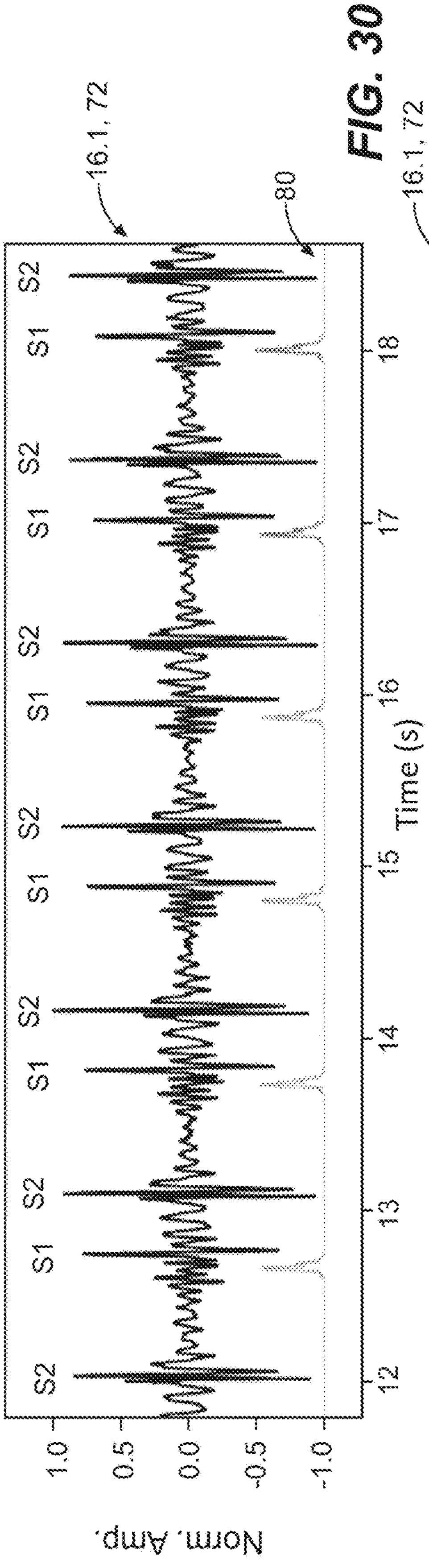
FIG. 30 illustrates a plot of the auscultatory sound signal illustrated in FIG. 24 together with plot of an envelope of the corresponding electrographic signal illustrated in FIG. 28.
Figure 31:
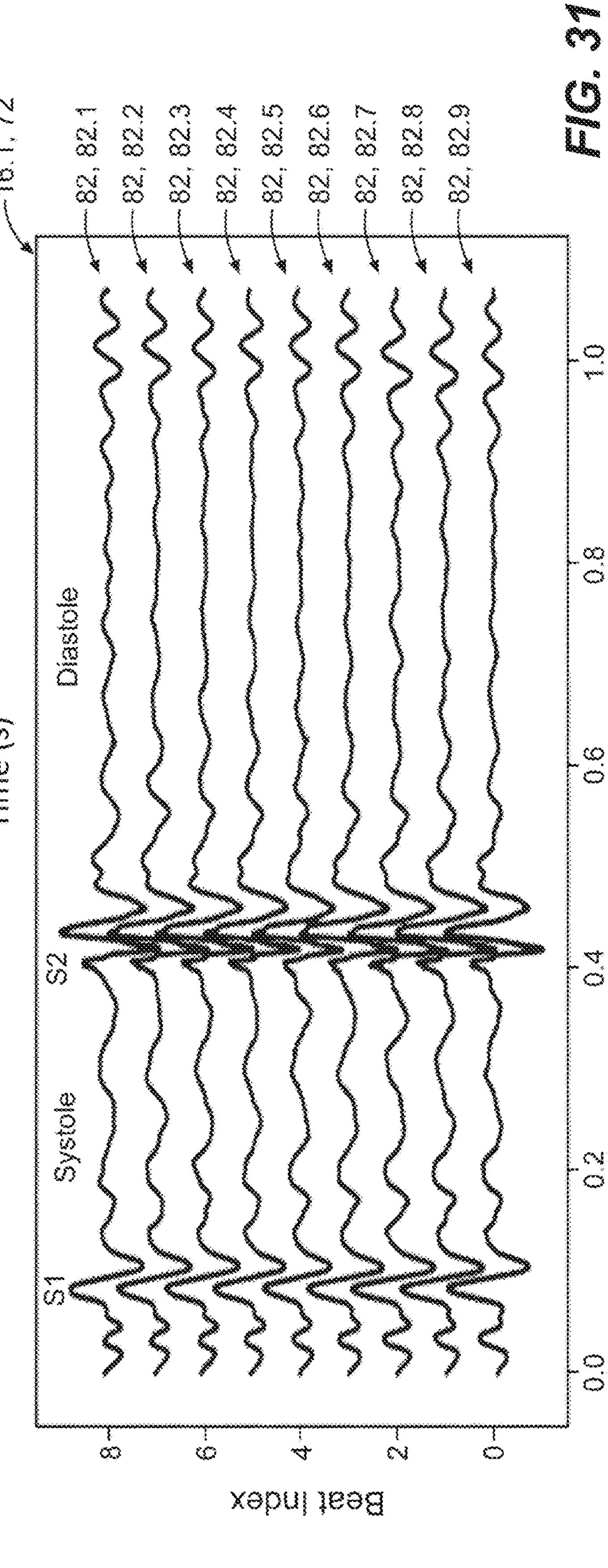
FIG. 31 illustrates a plot of the auscultatory sound signal illustrated in FIG. 24, but over a relatively greater total period of time, with the auscultatory sound signal segmented based upon the peaks of the envelope of the associated electrographic signal, and presented as a beat stack, each illustrating a corresponding associated heartbeat.

Referring again to FIG. 23, in step (2304), for each auscultatory sound sensor 12, in step (2306), the associated high-pass-filtered breath-held sampled auscultatory sound signal 72 thereof is segmented based upon the locations of the associated R-peaks 80' in the corresponding filtered-decimated electrographic signal 76. For example, FIG. 30 illustrates a correspondence between the breath-held auscultatory sound signal 16.1, 72 and the corresponding electrographic envelope waveform 80, $F_S[\ ]$, wherein the locations of the R-peaks 80' in the latter are used to segment the former by heart cycle. Furthermore, FIG. 31 illustrates a stack of segments of the high-pass-filtered breath-held sampled auscultatory sound signal 72, each segment corresponding to a different corresponding heart cycle 82, 82.1, 82.2, 82.3, 82.4, 82.5, 82.6, 82.7, 82.8, 82.9—each resulting from a single corresponding heartbeat—within the corresponding continuous high-pass-filtered breath-held sampled auscultatory sound signal 72 illustrated in FIG. 30.

The exact location of the first S1 and second S2 heart sounds produced by the respective closing of atrioventricular and semilunar valves is somewhat ambiguous, and can be particularly difficult to locate in situations when the associated breath-held auscultatory sound signals 16.1 are recorded in an environment with relatively high level ambient noise, or if there are associated heart murmurs resulting from turbulent blood flow. However, even under relatively-poor recording conditions, the first S1 and second S2 heart sounds of the cardiac cycle remain the most prominent acoustic features.

Referring again to FIG. 23, following segmentation of the high-pass-filtered breath-held sampled auscultatory sound signal 72 into corresponding resulting associated heart-cycle segments in step (2306)—each comprising one heart cycle 82, resulting from a single corresponding heartbeat,—beginning with step (2308), for each of the heart cycles 82 located in step (2306), in step (2310) a Shannon energy envelope is generated from the corresponding associated portion of the high-pass-filtered breath-held sampled auscultatory sound signal 72 in accordance with a corresponding second envelope generation process 3200, which is similar to the above-described first envelope generation process 2700 except for the associated envelope function. More particularly, referring to FIG. 32, beginning with step (3202) of the second envelope generation process 3200, for the $k^{th}$ of $N_{SAMPLES}$ samples of a block of high-pass-filtered breath-held sampled auscultatory sound data 72, s[ ] of the corresponding associated heart cycles 82, a corresponding value of an associated acoustic envelope waveform 84, $E_S[k]$ is generated in step (3204), responsive to a sum of values within a short-time sliding window—with different windows overlapping one another—containing a subset of $N_W$ points, as follows in accordance with a canonical Shannon energy function $E_S[k]$ that provides a measure of the energy of the underlying high-pass-filtered breath-held sampled auscultatory sound signal 72, s[ ]:

$$E_S(t(k)) = -\frac{1}{N_W}\sum_{i=1}^{N_W}(s(k+i))^2\ln\left((s(k+i))^2\right) \tag{12}$$

The values of the acoustic envelope waveform 84, $E_S[k]$ are calculated for each of the $N_{SAMPLES}$ values of index k until, in step (3206), all points have been calculated, after which, in step (3208), the acoustic envelope waveform 84, $E_S[k]$ is returned to step (2310) of the heart-cycle segmentation and heart-phase identification process 2300.

Figure 27:
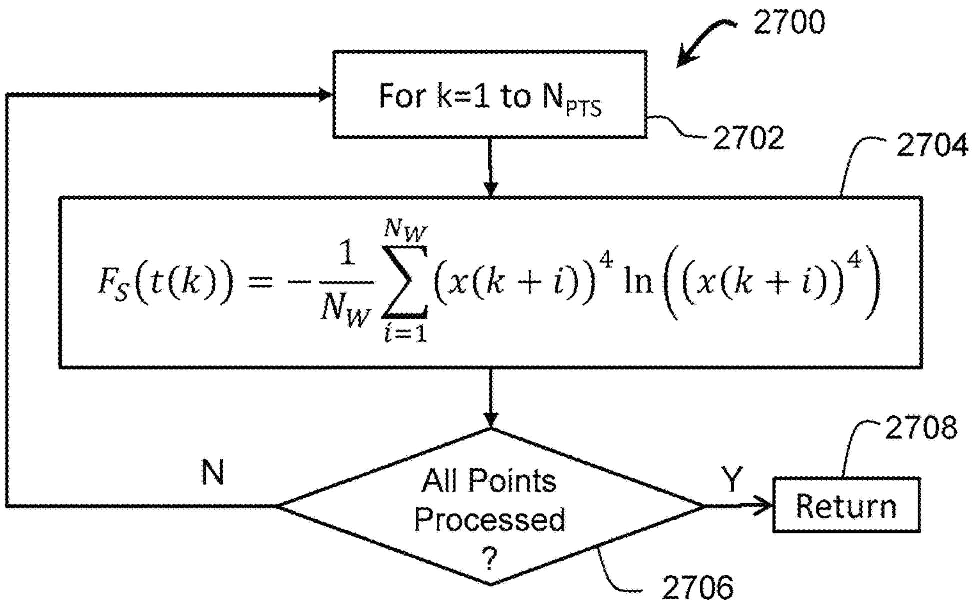
FIG. 27 illustrates a first process for generating an envelope of a signal, which is called from the process illustrated in FIG. 26.
Figure 32:
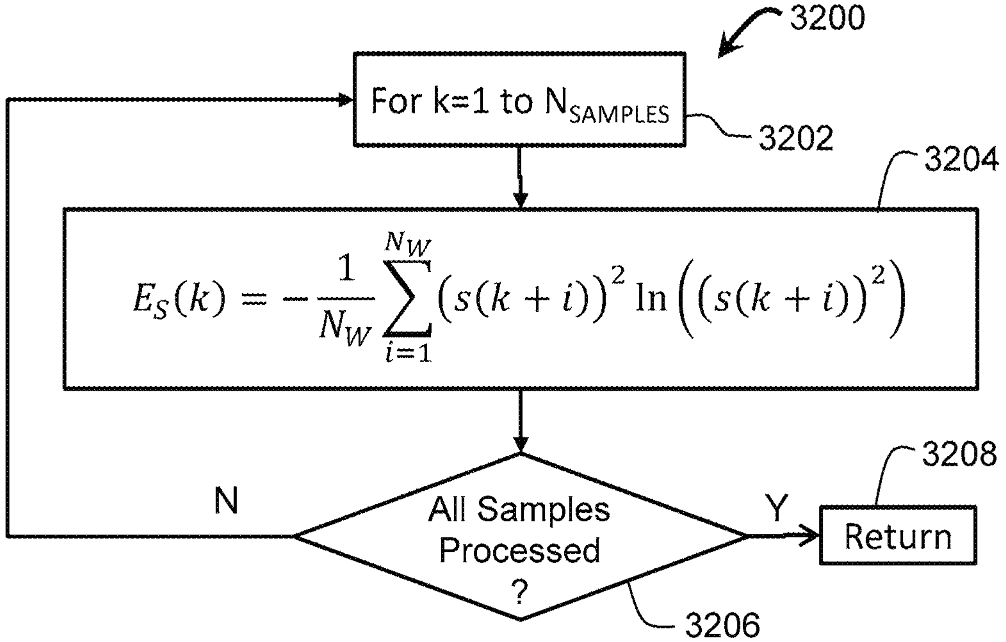
FIG. 32 illustrates a second process for generating an envelope of a signal, which is called from the process illustrated in FIG. 23.

For envelope generation by each of the first 2700 and second 3200 envelope generation processes illustrated in FIGS. 27 and 32, the associated signal x[ ], s[ ], from which the corresponding envelope $F_S[\ ]$, $E_S[\ ]$ is generated, is zero-padded at the beginning and at the end with (Nw−1)/2 zeros, assuming Nw is an odd integer, wherein the first data point in the padded signal x[ ], s[ ] would then begin at index 1+ (Nw−1)/2. After that, sliding window with size Nw and stride=1 is used to compute windowed values of the associated envelope function, so as to provide for generating a time-series of the same length as the associated signal x[ ], s[ ], without a time shift relative thereto.

Referring again to FIG. 23, in step (2312), the acoustic envelope waveform 84, $E_S[k]$ generated in step (2310) is smoothed to reduce local fluctuations therein, for example using either a moving average filter, or a Savitzky-Golay smoothing filter 68, for example, with an associated window size of tw=8.3 milliseconds.

Figure 33:
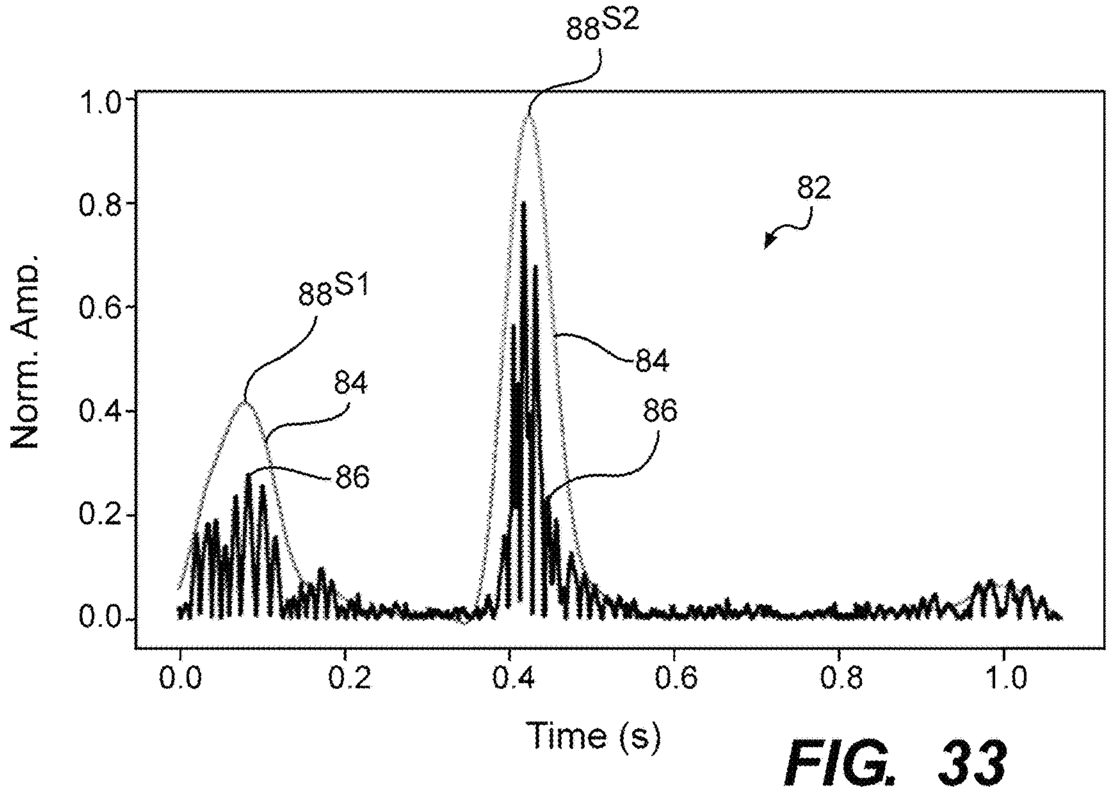
FIG. 33 illustrates a rectified auscultatory sound signal and an associated envelope thereof determined in accordance with the process illustrated in FIG. 32.

FIG. 33 illustrates an example of an acoustic envelope waveform 84, $E_S[\ ]$ in correspondence with a rectified version 86 (i.e. containing an absolute value) of the associated high-pass-filtered breath-held sampled auscultatory sound data 72, s[ ] from which the acoustic envelope waveform 84, $E_S[k]$ was generated, wherein the respective envelope peaks $\mathbf{88}^{S1}$, $\mathbf{88}^{S2}$ associated with the corresponding S1 and S2 heart sounds can be readily identified in the acoustic envelope waveform 84, $E_S[\ ]$.

Figure 34:
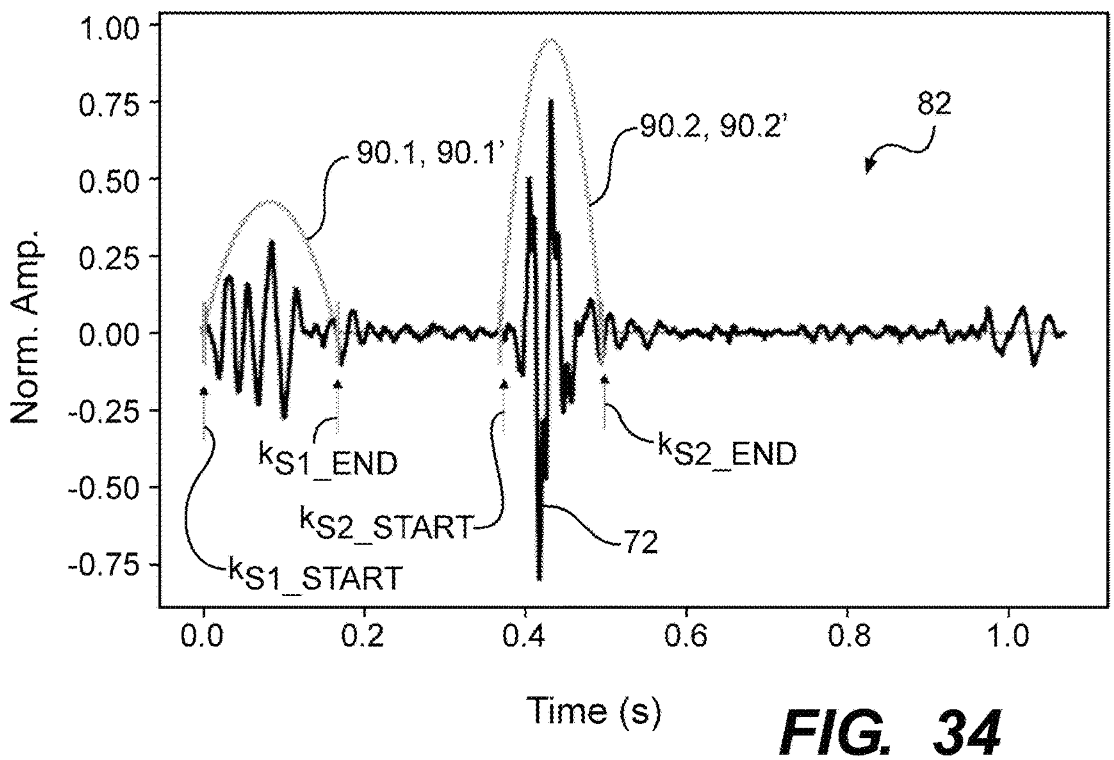
FIG. 34 illustrates a plot of the auscultatory sound signal that is shown rectified in FIG. 33, together with plots of the associated quadratic models of the associated envelopes in proximity to the associated S1 and S2 heart sounds, illustrating time-points associated with zero-amplitude roots of the associated quadratic models that are used to locate associated heart phases.

Referring again to FIG. 23, in step (2314), the locations of the envelope peaks $\mathbf{88}^{S1}$, $\mathbf{88}^{S2}$ associated with the corresponding S1 and S2 heart sounds are identified using an adaptive threshold method that iteratively adjusts an associated threshold value down from a maximum value until the two most prominent envelope peaks $\mathbf{88}^{S1}$, $\mathbf{88}^{S2}$ emerge within the associated heart cycle 82, above a particular threshold limit. Referring also to FIG. 34, the final positions of envelope peaks $\mathbf{88}^{S1}$, $\mathbf{88}^{S2}$ associated with the corresponding S1 and S2 heart sounds is found as the corresponding apexes of corresponding associated local quadratic models 90.1, 90.2 of the acoustic envelope waveform 84, $E_S[\ ]$, as described more fully hereinbelow. Adaptive thresholding provides for accommodating substantial variation in the relative magnitude of the envelope peaks $\mathbf{88}^{S1}$, $\mathbf{88}^{S2}$ that might occur either from one heartbeat to another, from one patient to another, or from one recording site to another.

Then, in step (2316), the locations of the envelope peaks $\mathbf{88}^{S1}$, $\mathbf{88}^{S2}$ associated with the corresponding S1 and S2 heart sounds are validated using a normalized acoustic envelope waveform 84, $E_S[\ ]$, i.e. normalized to a range of 0 and 1, and the associated local quadratic models 90.1, 90.2 thereof, in accordance with a minimum-time-spacing criteria used to remove or ignore spurious transient peaks unrelated to heart sounds, similar to equation (10) above that is associated with step (2904) of the above-described peak validation process 2900 used to validate the electrographic envelope waveform 80, $F_S[\ ]$.

Then, in step (2318), the acoustic envelope waveform 84, $E_S[\ ]$ is searched relative to the associated indices $k_{S1\_PEAK}$, $k_{S2\_PEAK}$—respectively associated with the corresponding respective envelope peaks $\mathbf{88}^{S1}$, $\mathbf{88}^{S2}$—to find adjacent data points therein,—i.e. having associated indices $k_{S1-}$, $k_{S1+}$, $k_{S2-}$, $k_{S2+}$—for which the corresponding values of the acoustic envelope waveform 84, $Es(k_{S1-})$, $Es(k_{S1+})$, $Es(k_{S2-})$, $Es(k_{S2+})$ are each about 5 percent down, i.e. 95 percent of, the corresponding values $Es(k_{S1\_PEAK})$, $Es(k_{S2\_PEAK})$ of the associated envelope peaks $\mathbf{88}^{S1}$, $\mathbf{88}^{S2}$.

Then, in step (2320), respective local quadratic models ES1($k$), 90.1' and ES2($k$), 90.2' are fitted—for example, by least-squares approximation—to the three points associated with each of the corresponding respective envelope peaks $\mathbf{88}^{S1}$, $\mathbf{88}^{S2}$ as follows:

$$ES1(k) = \text{Quadratic Fit}\left(\{k_{S1-}, Es(k_{S1-})\}, \{k_{S1\_PEAK}, Es(k_{S1\_PEAK})\}, \{k_{S1+}, Es(k_{S1+})\}\right) \quad (13a)$$

-continued $$ES2(k) = \text{Quadratic Fit}\left(\{k_{S2-}, Es(k_{S2-})\}, \{k_{S2\_PEAK}, Es(k_{S2\_PEAK})\}, \{k_{S2+}, Es(k_{S2+})\}\right) \quad (13b)$$

Then, referring again to FIG. 34, in step (2322), the respective pairs of roots ($k_{S1\_START}$, $k_{S1\_END}$) and ($k_{S2\_START}$, $k_{S2\_END}$) of the local quadratic models ES1($k$), 90.1' and ES2($k$), 90.2' are solved, such that ES1($k_{S1\_START}$)=ES1($k_{S1\_END}$)=0 and ES2($k_{S2\_START}$)=ES2($k_{S2\_END}$)=0, wherein $k_{S1\_START}<k_{S1\_PEAK}<k_{S1\_END}$ and $k_{S2\_START}<k_{S2\_PEAK}<k_{S2\_END}$.

Figure 70:
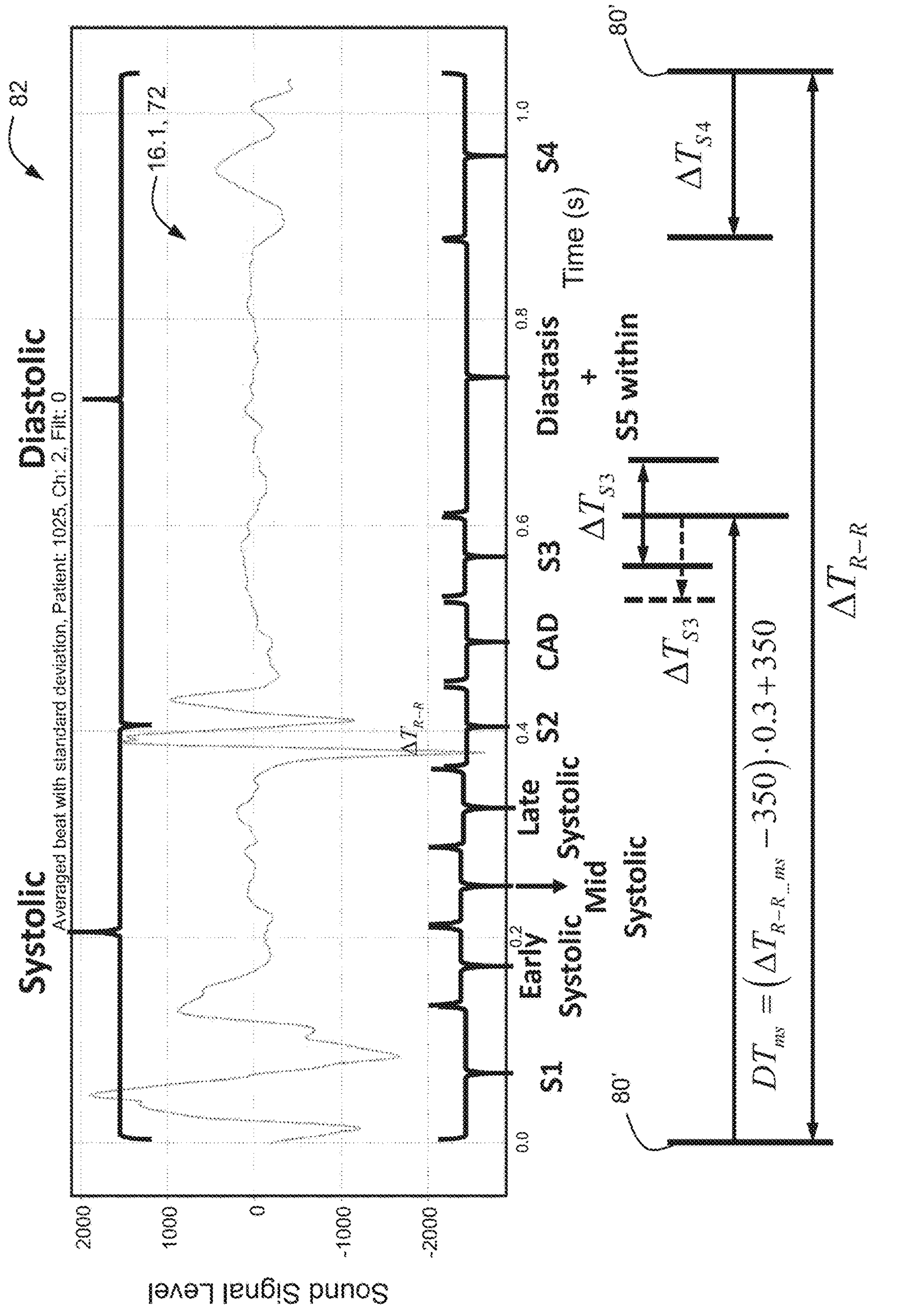
FIG. 70 illustrates various phases of a heart cycle in relation to an electrographic signal.
Figure 71:
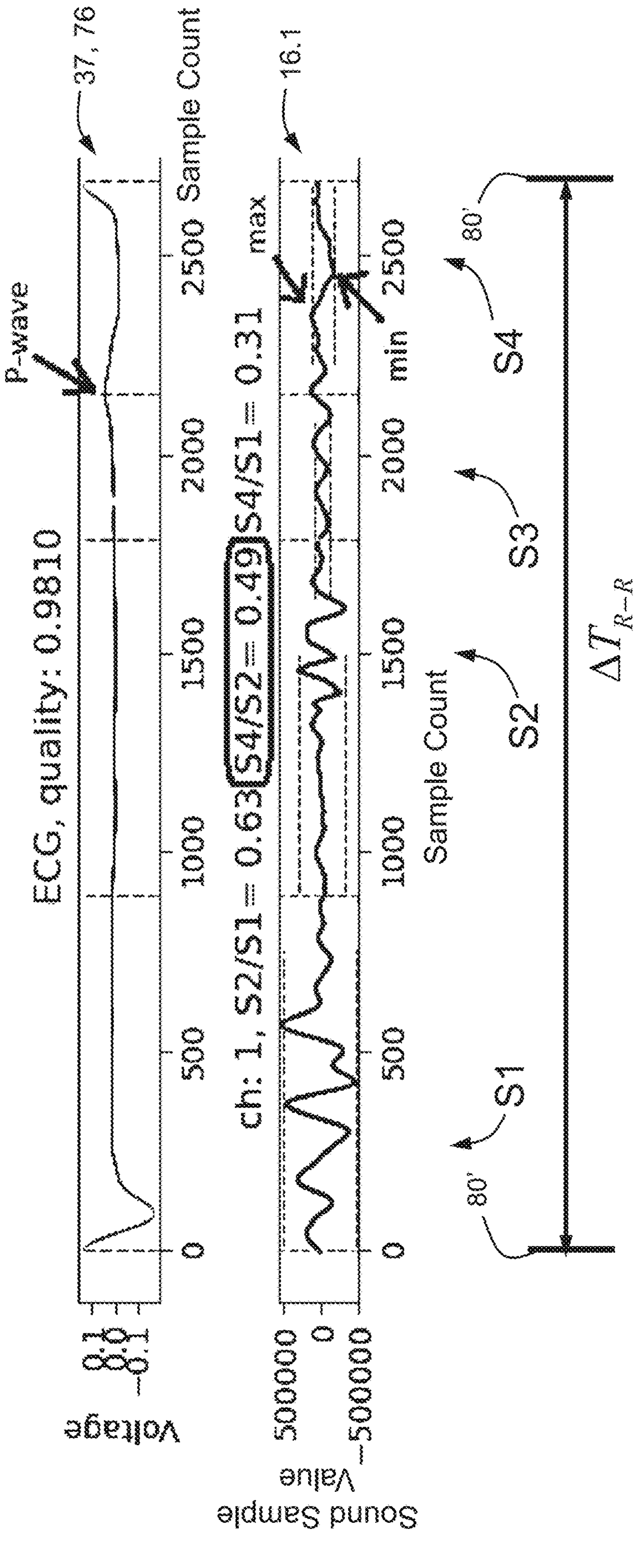
FIG. 71 illustrates the S1, S2, S3 and S4 phases of a heart cycle in relation to an electrographic signal.

Referring to FIGS. 70 and 71, in addition to the S1 and S2 sounds, S3, S4 or S5 sounds may be present in the heart cycles 82 for some test-subjects 22. The purpose of identifying S1, S2, S3, S4, and S5 regions is to help extract or derive useful features (such as Indicators that correlate highly with the existence of coronary artery disease (CAD)) from heart sounds. In turn, these features can be used in direct detection and machine learning for discriminating CAD patients from non-CAD patients. The prerequisite of many feature extractions is to correctly identify the S1 and S2 sounds.

The S3, S4, and S5 sounds do not appear for every patient. But each may indicate one or more cardiac conditions, such as, coronary artery disease (CAD), Aortic Insufficiency, Aortic Stenosis, Luminal Irregularities, and Mitral Regurgitation. The regions within diastole during which the S3 and S5 sounds may occur are located relative to the diastasis region of diastole, which is a relative rest period of the heart during mid-to-late diastole, during which period the heart motion is minimal. The region during which the S4 sound may occur is located relative to the R-peak 80' at the end of the heart cycle 82 and the beginning of the next heart cycle 82.

The starting point of the diastasis region is determined using what is referred to as the Weissler or Stuber formula for the period of delay DT—in milliseconds—from an R-peak 80' to the starting point of the diastasis region, given by the following:

$$DT_{ms} = (\Delta T_{R-R\_ms} - 350)\cdot 0.3 + 350 \quad (14)$$

wherein $\Delta T_{R-R}$ is the time interval in milliseconds between R-peaks 80'. In one set of embodiments, this is approximately the ending point for the region most likely to include S3, i.e. the S3 region. Accordingly, the starting point for the S3 region is determined by advancing relative to the starting point of diastasis—or, equivalently, the end point of the S3 region—by a time interval $\Delta T_{S3}$. For example, in this set of embodiments, the time interval commences at about 100 milliseconds prior to the starting point of diastasis and ends at the starting point of diastasis. In another set of embodiments, the time interval of the S3 region is taken to extend from about 60 milliseconds prior, to 60 milliseconds after, the starting point of diastasis. The S3 swing is calculated by subdividing the S3 region of the associated breath-held auscultatory sound signal 16.1, for example, band-pass-filtered breath-held sampled auscultatory sound data s[ ] having a pass-band in the range of 20, 25, or 30 Hz to 40 or 50 Hz, into a series of—i.e. one or more—time intervals, and calculating or determining one or more of the difference between the maximum and minimum amplitude values—i.e.

maximum amplitude-minimum amplitude,—the minimum amplitude, and the maximum amplitude, for each interval in the S3 region.

In addition to the above time-domain analysis, the associated breath-held auscultatory sound signal 16.1 is also analyzed in the frequency domain using a Short-Time Fourier Transform (STFT), for example, in one set of embodiments, having a 1 Hz frequency resolution and a 0.0025 second time resolution—but generally, using frequency and time resolutions that may be empirically adjusted to improve detection and discrimination—in cooperation with an associated windowing method, for example, using Chebyshev windowing on a sliding window that is moved along the S3 region of the breath-held auscultatory sound signal 16.1. The frequency-domain features for each heartbeat are generated by calculating the mean and median of each of the windows of the STFT.

The S3 swing values and frequency-domain features are saved for further calculations and/or for use as an input to one or more of the below-described classification processes. In view of there being relatively few patients that clearly exhibit an S3 sound, an unsupervised clustering method is applied on all the generated features to classify heartbeats into two clusters that respectively include "with S3" and "without S3" heartbeats. S3 is analyzed on a beat-by-beat basis. Given that S3 is not an intermittent signal, one strategy is to analyze all heartbeats from a given patient, and if S3 appears in more than one third of all the heartbeats, that patient would be identified as having S3. There are some patients who exhibit a low-ejection fraction ratio (e.g. an ejection fraction (E. F.) lower than 35%) that are highly likely to have S3. However some of these patients have coronary artery disease (CAD), and some have other types of cardiac arrhythmia. Once the unsupervised clustering is applied followed by voting among all heartbeats belonging to one patient, if those patients are found in the cluster "with S3", this would provide for validating that the clustering matches reality.

The S4 region is located in a final portion of diastole, starting at the P wave on the ECG signal. However, in anticipation of a prospective absence of the P wave in some ECG recordings, an approximate starting point for the S4 region may be used, for example, a time interval of $\Delta T_{S4}$, for example, from 10 to 20 percent of the period of the heart cycle 82, for example, about 100 to 200 milliseconds in a 1 second duration heart cycle 82, in advance of the R-peak 80' at the end of the heart cycle 82, or equivalently, in advance of the beginning of the S1 sound of the next heart cycle 82. The S4 region of the associated breath-held auscultatory sound signal 16.1, e.g. the band-pass-filtered breath-held sampled auscultatory sound data s[ ] having a pass-band in the range of 20, 25, or 30 Hz to 40 or 50 Hz, is subdivided into a series of intervals and the associated S4 swing within each interval is calculated as the absolute value of the difference between maximum and minimum amplitude magnitudes of the raw or high-pass-filtered data within that interval in the S4 region. The S4 swing is calculated separately for audible (above 20 Hz) and inaudible (below 20 Hz) frequency ranges, for which the configurations of the associated signal filters are specific to the particular frequency range. Generally, the minimum and maximum values of the signal will depend upon the associated frequency range of the associated signal, and the type of filter used to generate the filtered signal.

The S2 swing is also similarly calculated over the associated S2 region, in addition to calculating the S4 swing as described hereinabove. The ratio of the S4 swing to S2 swing provides a measure of the likelihood that a patient exhibits an S4 sound, with that likelihood increasing with increasing value of the associated S4-to-S2 swing ratio. For example, FIG. 71 illustrates a heartbeat for which the S4-to-S2 swing ratio has a value of 0.49 for the illustrated channel 1 of the band-pass-filtered breath-held sampled auscultatory sound data s[ ].

The S2 and S4 swing values, and/or the S4-to-S2 swing ratio, are saved for further calculations and/or for use as an input to one or more of the below-described classification processes. In accordance with one approach, the mean value of the S4-to-S2 swing ratio is calculated for an entire population of patients, beat by beat, and then the median of S4-to-S2 swing ratio is taken across all heartbeats of each patient. Those those patients for which the S4-to-S2 swing ratio is greater than the associated mean value of the S4-to-S2 swing ratio are identified as having an S4 sound for purposes of training the associated below-described classifier, from which an associated threshold value is determined that—in combination with other factors—provides for discriminating patients with coronary artery disease (CAD) from patients without coronary artery disease (CAD), after which the threshold value of the S4-to-S2 swing ratio is then applied to the associated test set.

The S5 region is identified as the end of the S3 region to the start of the S4 region. Accordingly, the starting point is determined using the above-described Weissler or Stuber formula. As mentioned, this is approximately the ending point for the S3 region. The ending point of the S5 region is located at the beginning of a time interval of $\Delta T_{S4}$, for example, about 100 milliseconds, in advance of the R-peak 80' at the end of the heart cycle 82, or equivalently, in advance of the beginning of the S1 sound of the next heart cycle 82. The S5 swing is calculated by subdividing the S5 region of the associated breath-held auscultatory sound signal 16.1, e.g. the band-pass-filtered breath-held sampled auscultatory sound data s[ ] having a pass-band in the range of 20, 25, or 30 Hz to 40 or 50 Hz, into a series of intervals and calculating the absolute value of maximum amplitude-minimum amplitude for each interval in the S5 region. The S5 swing values may be saved for further calculations and/or for use as an input to one or more of the below-described classification processes.

If, in step (2324), all heart cycles 82 in the high-pass-filtered breath-held sampled auscultatory sound signal 72 have not been processed, then the heart-cycle segmentation and heart-phase identification process 2300 is repeated beginning with step (2308) for the next heart cycle 82. Otherwise, from step (2326), if all auscultatory sound sensors 12 have not been processed, then the heart-cycle segmentation and heart-phase identification process 2300 is repeated beginning with step (2304) for the next auscultatory sound sensor 12. Otherwise, from step (2326), in step (2328), the heart-cycle segmentation and heart-phase identification process 2300 returns either the mean values $k_{S1}$, $k_{S2}$ of the corresponding root locations $\{k_{S1\_START}, k_{S1\_END}\}$, $\{k_{S2\_START}, k_{S2\_END}\}$ associated with the corresponding S1 and S2 heart sounds, or the corresponding mean values $t_{S1}$, $t_{S2}$ of the associated times, i.e. $\{t(k_{S1\_START}), t(k_{S1\_END})\}$, $\{t(k_{S2\_START}), t(k_{S2\_END})\}$, for each of the heart cycles 82 in each of the high-pass-filtered breath-held sampled auscultatory sound signals 72 from each of the associated auscultatory sound sensors 12.

Figure 35:
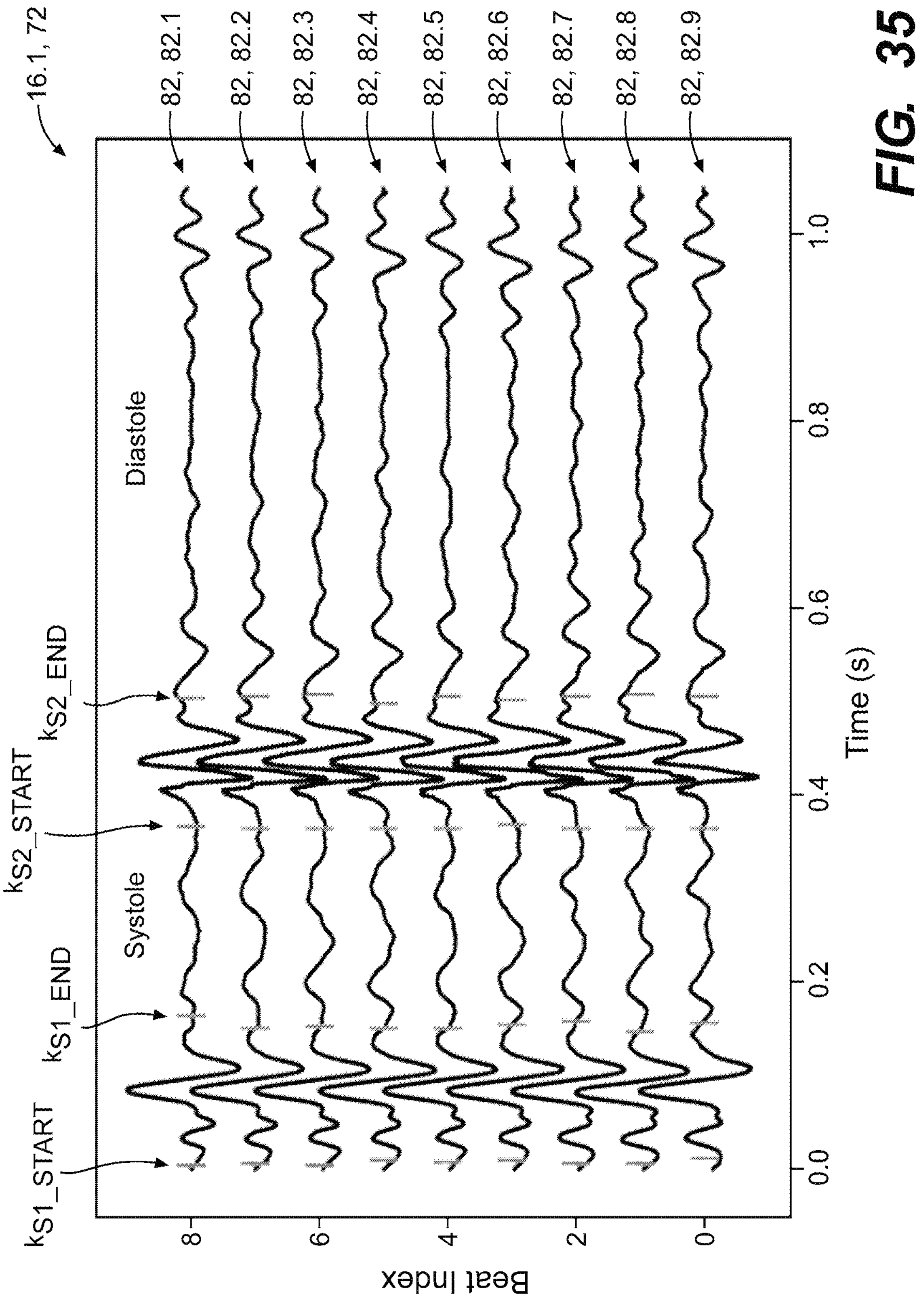
FIG. 35 illustrates the auscultatory sound signal beat stack illustrated in FIG. 31, together with indicia showing the locations of the roots of the quadratic models associated with the S1 and S2 heart sounds that are used to locate associated heart phases, with the auscultatory sound signals of the beat stack aligned with one another based upon the mean values of the roots of the S2 heart sounds.

Referring to FIG. 35, segmented high-pass-filtered breath-held sampled auscultatory sound data 72, s[ ] from each of the heart cycles 82, 82.1, 82.2, 82.3, 82.4, 82.5, 82.6, 82.7, 82.8, 82.9 may be synchronized with respect to the mean time $t_{S2}$ associated with the S2 heart sound of each heart cycle 82, 82.1, 82.2, 82.3, 82.4, 82.5, 82.6, 82.7, 82.8, 82.9, as illustrated in FIG. 35, or alternatively, may be synchronized with respect to the mean time $t_{S1}$ associated with the S1 heart sound of each heart cycle 82, 82.1, 82.2, 82.3, 82.4, 82.5, 82.6, 82.7, 82.8, 82.9, wherein the region of diastole extends from the time associated with the second root $k_{S2\_END}$, i.e. $t(k_{S2\_END})$, associated with the S2 heart sound, to the end of the associated heart cycle 82, 82.1, 82.2, 82.3, 82.4, 82.5, 82.6, 82.7, 82.8, 82.9.

Figure 36:
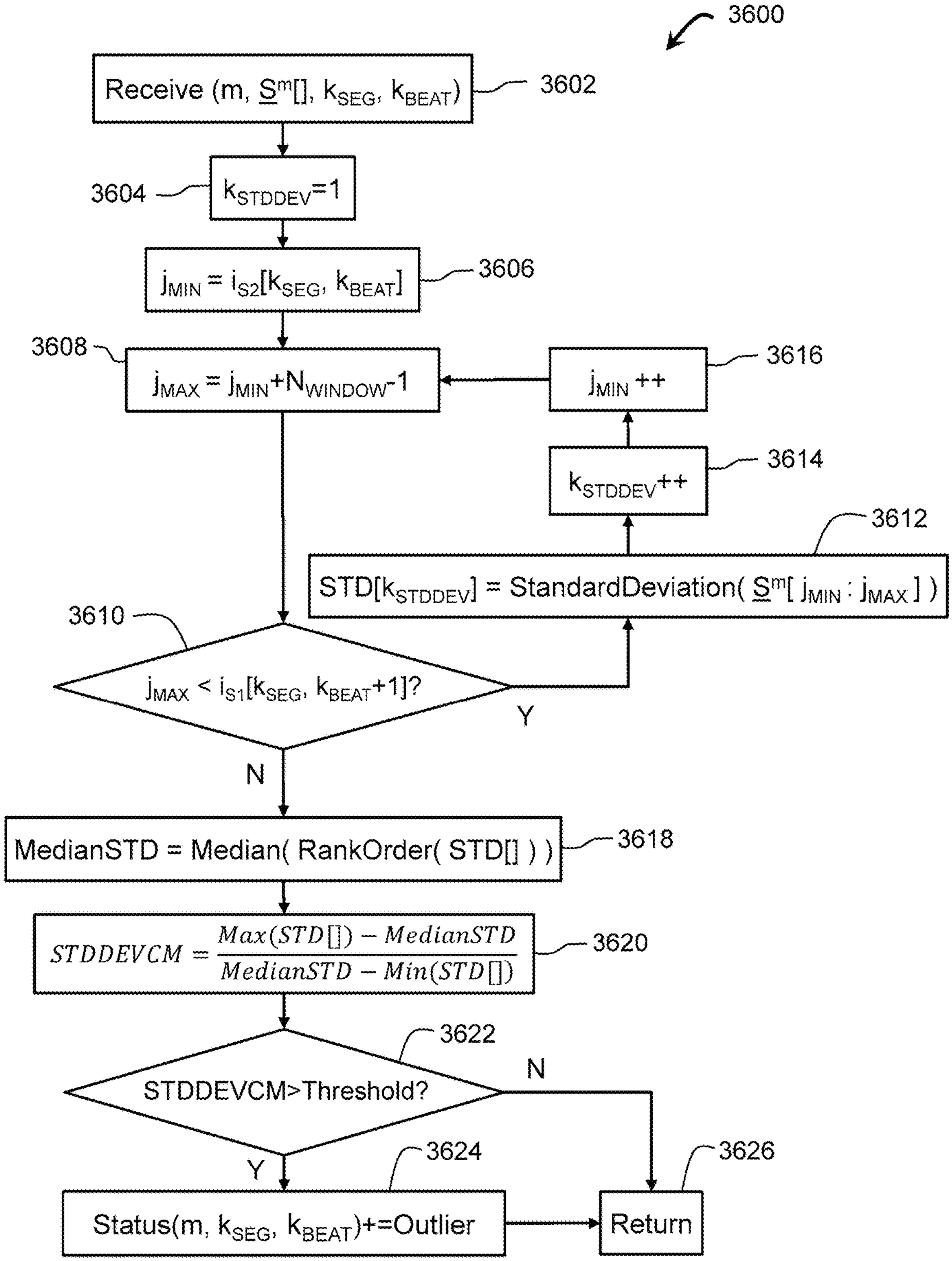
FIG. 36 illustrates a process for identifying outliers in a diastole region of an auscultatory sound signal.

Referring again to FIG. 21, either the breath-held auscultatory sound signal 16.1, or the corresponding high-pass-filtered breath-held sampled auscultatory sound signal 72, is first analyzed within each region of diastole for each heart cycle 82 identified in step (2106/2300), and for auscultatory sound sensor 12, m to identify any outliers, and to detect, for selected pairs of auscultatory sound sensor 12, excessive noise. More particularly, beginning with step (2107), a heart-cycle pointer $k_{BEAT}$ is first initialized to a value of 1, after which, via step (2108), for each heart cycle 82 and for each auscultatory sound sensor 12, *m*, in step (2110), each region of diastole of either the breath-held auscultatory sound signal 16.1, or the corresponding high-pass-filtered breath-held sampled auscultatory sound signal 72, i.e. extending between samples $i_{S2}[k_{SEG}, k_{BEAT}]$ and $i_{S1}[k_{SEG}, k_{BEAT}+1]$ is checked for outliers, e.g. random spikes, using a beat outlier detection process 3600, wherein the heart-cycle pointer $k_{BEAT}$ points to the particular heart cycle 82 within the selected breath-held segment $k_{SEG}$, $i_{S2}[k_{SEG}, k_{BEAT}]$ that corresponds to the $k_{S2\_END}$ of the associated heart cycle 82 at the beginning of diastole, and $i_{S1}[k_{SEG}, k_{BEAT}+1]$ corresponds to the end of diastole of that heart cycle 82 and the beginning of the systole for the next heart cycle 82. Referring to FIG. 36, the beat outlier detection process 3600 commences in step (3602) with receipt of the identifier m of the auscultatory sound sensor 12, the associated sampled auscultatory sound data $S'''[\ ]$, the segment counter $k_{SEG}$, and the heart-cycle pointer $k_{BEAT}$. Then, in steps (3604) and (3606), a standard-deviation counter $k_{STDDEV}$ is initialized to a value of 1, and an index $j_{MIN}$ is set equal to $i_{S2}[k_{SEG}, k_{BEAT}]$ associated with the location of the beginning of diastole in the sampled auscultatory sound data $S'''[\ ]$, respectively. Then, steps (3608) through (3616) provides for repetitively calculating, in step (3612), a standard deviation $STD[k_{STDDEV}]$ of the sample values $S'''[j_{MIN}: j_{MAX}]$ in a plurality of windows of $N_{WINDOW}$ samples, each window shifted by one sample with respect to the next in steps (3614) and (3616)—that increment $k_{STDDEV}$ and $j_{MIN}$, respectively,—resulting in a standard deviation array STD[ ] containing $k_{STDDEV}$ standard deviation values, wherein, in step (3608), $j_{MAX}=j_{MIN}+N_{WINDOW}-1$. For example, in one set of embodiments, $N_{WINDOW}$ is equal to 128. Then, in step (3618), the standard deviation array STD[ ] is rank ordered, and the median value thereof, MedianSTD, is used in step (3620) to calculate a standard deviation compactness metric STDDEVCM, as follows:

$$STDDEVCM = \frac{\text{Max}(D[\ ]) - medianStd}{medianStd - \text{Min}(D[\ ])} \tag{15}$$

Then, in step (3622), if the standard deviation compactness metric STDDEVCM exceeds a threshold, for example, in one set of embodiments, equal to 6, but generally between 1 and 10, the particular region of diastole for the particular breath-held segment from the particular auscultatory sound sensor 12, *m*, is flagged as an outlier in step (3624). Then, or otherwise from step (3622), in step (3626), the process returns to step (2110) of the auscultatory sound signal preprocessing and screening process 2100.

Referring again to FIG. 21, then, in step (2112) of the auscultatory sound signal screening process 2100, if an outlier was detected in step (3622) and flagged in step (3624) of the beat outlier detection process 3600, then in step (2120), if the end of the breath-held segment has not been reached, i.e. if $k_{BEAT}<N_{BEATS}(k_{SEG})$, then the auscultatory sound signal preprocessing and screening process 2100 repeats beginning with step (2108) for the next heart cycle 82.

Otherwise, from step (2112), referring again to FIGS. 17-20, the above-described noise detection process 1700 may be called from step (2114) to provide for determining whether or not a particular region of diastole for a particular heart cycle 82 of either the breath-held auscultatory sound signal 16.1, or the corresponding high-pass-filtered breath-held sampled auscultatory sound signal 72, is corrupted by excessive noise, and if so, provides for flagging that region of diastole as being excessively noisy so as to be prospectively excluded from subsequent processing, wherein above references to breath-held auscultatory sound signal 16.1 in the description of the associated noise detection process 1700 should be interpreted as referring to the corresponding region of diastole, i.e. between samples $i_{S2}[k_{SEG}, k_{BEAT}]$ and $i_{S1}[k_{SEG}, k_{BEAT}+1]$ for the $k_{BEAT}{}^{th}$ heart cycle 82 of segment $k_{SEG}$ of either the breath-held auscultatory sound signal 16.1, or the corresponding high-pass-filtered breath-held sampled auscultatory sound signal 72, and references to the breath-held segment k in the associated noise detection process 1700—which in this case would not be incremented in step (1726), with $k_{MAX}$=k in step (1724),—should be interpreted as referring to a corresponding particular heart cycle 82 associated with the particular region of diastole, wherein the noise detection process 1700 would terminate with step (1934) of the associated noise-content-evaluation process 1900.

Then, returning to the step (2116) of the auscultatory sound signal screening process 2100, if a noise threshold was exceeded in step (1930) of the noise-content-evaluation process 1900, in step (2120), if the end of the breath-held segment has not been reached, i.e. if $k_{BEAT}<N_{BEATS}(k_{SEG})$, then the process repeats beginning with step (2108) for the next heart cycle. Otherwise, from step (2116), the good beat counter GB is incremented in step (2118) before continuing with step (2120) and proceeding therefrom as described hereinabove. Otherwise, from step (2120) if the end of the breath-held segment has been reached, in step (2122), if a threshold number of valid heart cycles has not been recorded, the process repeats with step (2104) after incrementing the segment counter $k_{SEG}$ in step (2123). Otherwise, the recording process ends with step (2124).

Accordingly, each breath-holding interval B, $k_{SEG}$ of either the breath-held auscultatory sound signal 16.1, or the corresponding high-pass-filtered breath-held sampled auscultatory sound signal 72 is segmented into individual heartbeats 82 (i.e. heart cycles 82, wherein reference to heart cycles 82 is also intended as a short-hand reference to the associated breath-held sampled auscultatory sound data S[ ], and each heartbeat 82 is associated with a corresponding heart cycle 82, the latter of which comprises a plurality of heart phases associated with the pumping action of the heart and the actions of the associated heart valves) and the diastolic interval D is analyzed to determine the associated noise level so as to provide for quality control of the associated breath-held sampled auscultatory sound data S[ ], so as to provide for signal components thereof associated with coronary artery disease (CAD) to be detectable therefrom. Quality control of the recorded signals provides for detecting weak signals that may indicate health problems but can otherwise be blocked by strong noise or unwanted interference. The present method is developed for quantitative control of signal quality and can be deployed in the recording module 13 for real-time quality monitoring, or can be used at the post recording stage to extract only low-noise heartbeats 82 that satisfy specific quality conditions.

Figure 37:
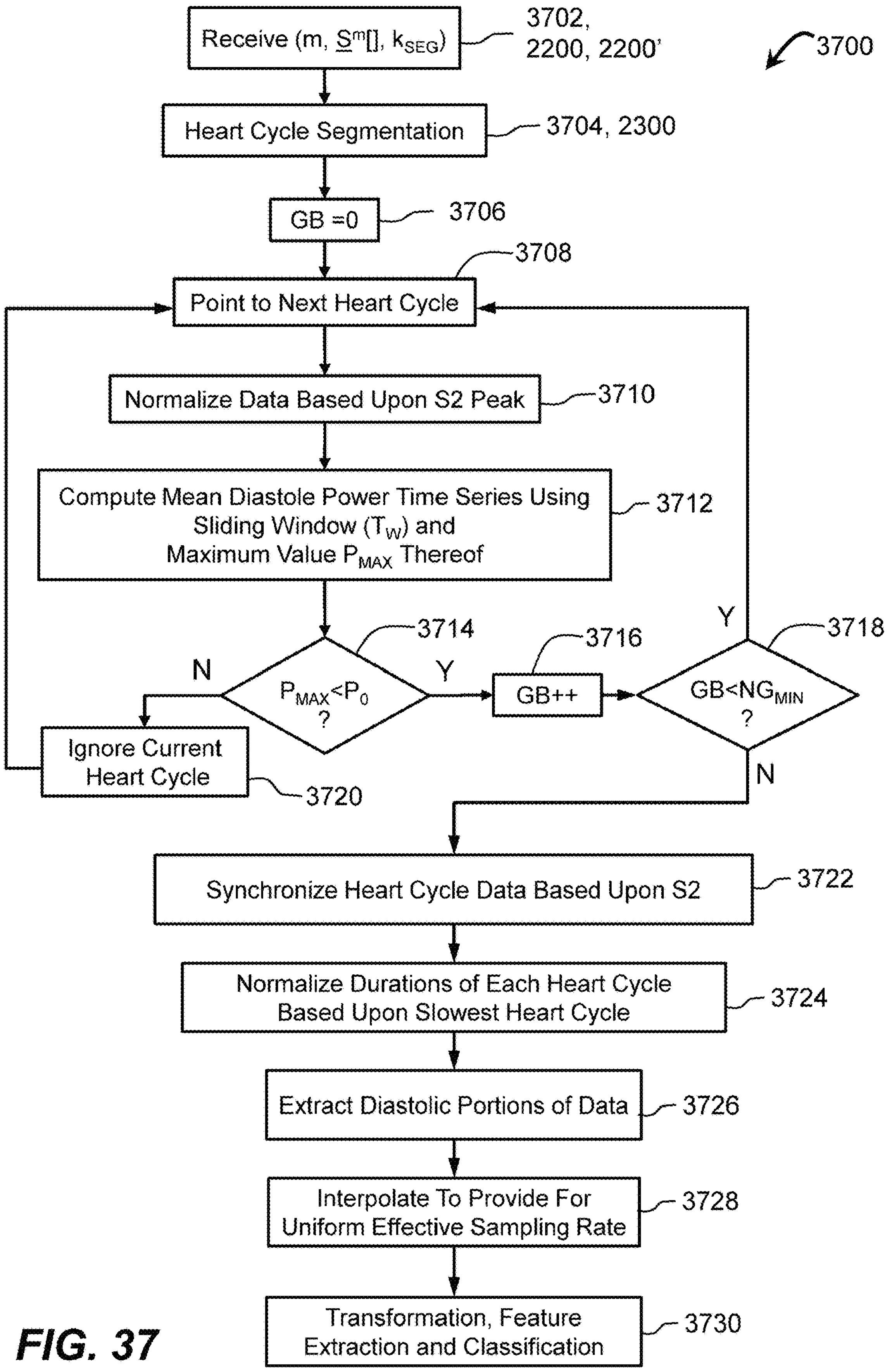
FIG. 37 illustrates a flow chart of a process for selecting valid heart cycles and analyzing the results therefrom.

Referring to FIG. 37, a second aspect of an auscultatory sound signal preprocessing and screening process 3700—also referred to as a beat selection algorithm, as was the first-aspect auscultatory sound signal preprocessing and screening process 2100—provides for collecting heartbeats 82 that have a diastolic noise level below the specific mean noise power level threshold $P_0$. As described hereinabove, the associated auscultatory-sound-sensing process 700 proceeds through sequential acquisition of heart sound intervals with durations between 5 and 15 sec (for example, breath-holding intervals B). In step (3702), the sampled auscultatory sound data $S^m$[ ], the identifier m of the associated auscultatory sound sensor 12, and the associated segment counter $k_{SEG}$ are received, and, in step (3704), the corresponding recorded data block is passed through the heart-cycle segmentation and heart-phase identification process 2300 that identifies the beginning and the end of each heartbeat 82 using synchronized ECG recording or another signal processing code that identifies timing of the first (S1) and second (S2) heart sounds, as described hereinabove. The second-aspect auscultatory sound signal preprocessing and screening process 3700 input parameters also include the mean noise power level threshold $P_0$ and the required number $NG_{MIN}$ of high quality heartbeats 82. In step (3706), a good beat counter GB is initialized to a value of 0. Following the heart-cycle segmentation and heart-phase identification process 2300, a two-dimensional array of heartbeats 82 is created, for example, as illustrated in FIGS. 31 and 35. The heart-cycle segmentation and heart-phase identification process 2300 also identifies timing of a diastolic interval D of each heartbeat 82. Beginning with the selection of the first heart cycle 82 in step (3708), in step (3710), the breath-held sampled auscultatory sound data S[ ] is normalized with respect to absolute value of the S2 peak, and, in accordance with a first aspect, in step (3712), the mean noise power P is computed within a time window $T_w$. The time-window $T_w$ is slid along the diastolic interval D with a 50% overlap to compute an array of localized signal power P[ ]. After the power P[$i_W$] of the sampled auscultatory sound data $S^m$[ ] is calculated within each time-window $T_w$ indexed by index $i_W$, the maximum power $P_{MAX}$ of diastole D is determined i.e. as given by the maximum of the array of localized signal power P[ ], and, in step (3714), is compared against the mean noise power level threshold $P_0$, the latter of which in one set of embodiments, for example, has a value of −20 dB. A noise power level P[$i_W$] in one of the time-windows $T_w$ greater than the mean noise power level threshold $P_0$ may indicate either excessive noise or presence of a large amplitude transient outlier.

Figure 38:
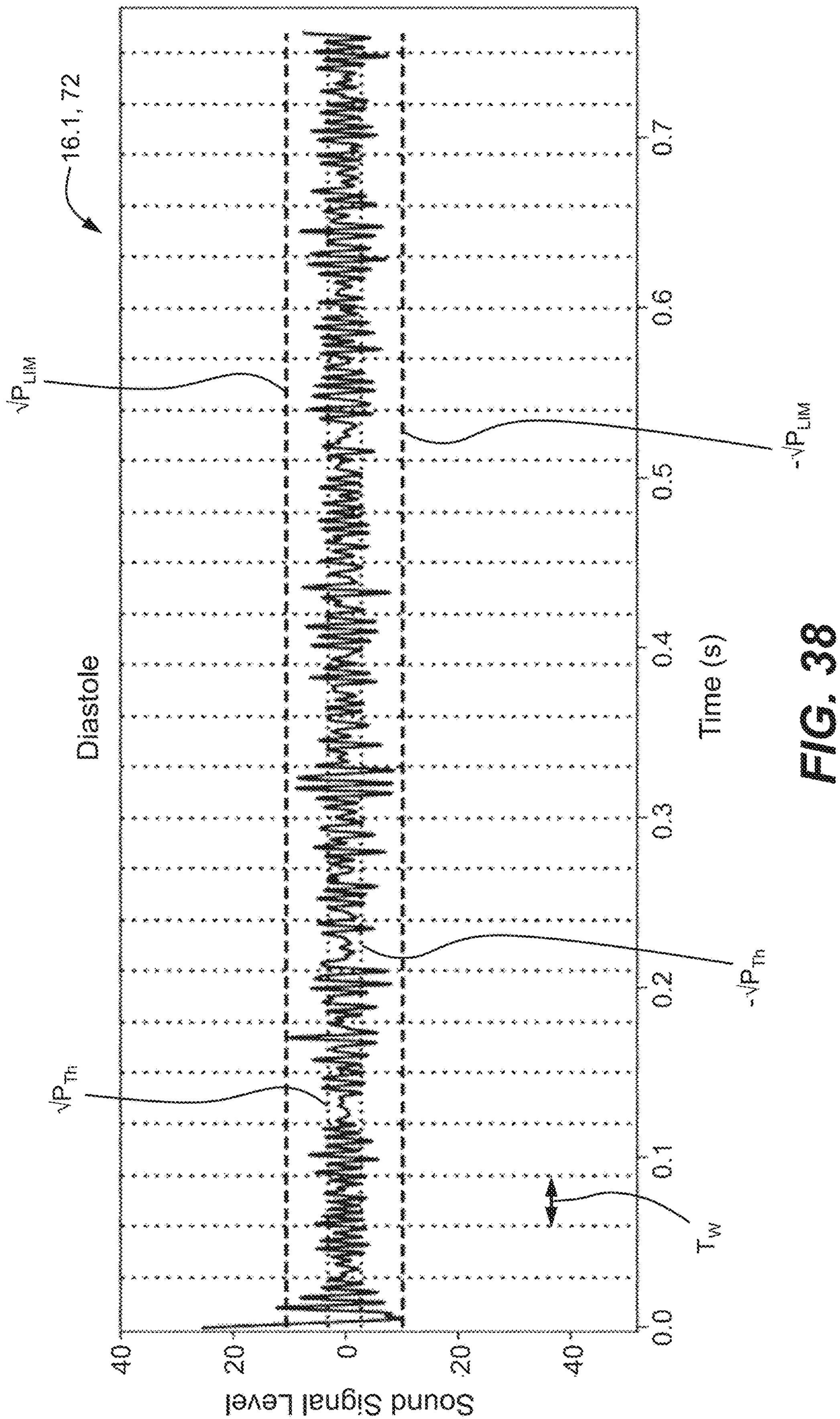
FIG. 38 illustrates a portion of an auscultatory sound signal during diastole, and also illustrates associated noise power thresholds.

Referring to FIG. 38, in accordance with a second-aspect heartbeat quality assessment procedure, the associated quality test consists of two stages designed to detect high amplitude transient spikes and noisy heartbeats with a broad-band spectrum. The quality tests are performed on the diastolic portion of the heart cycle 82, which is the region of primary interest for coronary artery disease (CAD) detection. Nonstationary signals can be analyzed using a relatively short time sliding time-window $T_w$, for example, in one set of embodiments, with $T_w$=30 ms ($N_w$=120 samples at $f_s$=4 kHz), which is slid across diastole, with each time-window $T_w$ advanced in time with respect to the previous time-window $T_w$ by a stride period. In one set of embodiments, the stride period is equal to the duration of the time-window $T_w$, so that adjacent time-windows $T_w$ abut one another without overlap. The total number of time-windows $T_w$ (i.e. sub-segments) in diastole, without overlap, is given by $Ns=N/N_w$, where N is the total number of samples during diastolic, and $N_w$ is the number of samples in each time-window $T_w$.

The variance within each time-window $T_w$—used to detect any outliers therein—is computed as:

$$\sigma_i^2 = \frac{1}{N_w}\sum_{k=1}^{N_w}(x_{ik} - \mu_x)^2 \tag{16}$$

wherein $x_{ik}$ and $\mu_x$ are respectively the $k^{th}$ sample and the mean value, of the $i^{th}$ time-window $T_w$, respectively. The local signal power of the $i^{th}$ time-window $T_w$, is given by:

$$P_i = \sigma_i^2 \tag{17}$$

An outlier power threshold PLIM is determined by adding 6 dB to the median value of $P_i$ for all time-windows $T_w$, and in step (3714), if the value of $P_i$ exceeds PLIM for any time-window $T_w$, then, in step (3720), the current heart cycle 82 is ignored.

If none of the time-windows $T_w$ include an outlier, then the mean power of diastole is given by:

$$P_m = \frac{1}{N_S}\sum_{i=1}^{N_S} P_i \tag{18}$$

The associated noise power threshold $P_{Th}$ is defined with respect to the 2-byte analog-to-digital converter (ADC) range, so that:

$$P_{Th} = P_{ADC}\cdot 10^{\left(\frac{Th}{10}\right)} \tag{19}$$

wherein Th is a predetermined threshold, for example, −50 dB, and $P_{ADC}$ is the power associated with the maximum signed range of a 2-byte analog-to-digital converter (ADC), i.e. $(32767)^2$. Accordingly, if, in step (3714), the mean diastole power Pm exceeds the noise power threshold $P_{Th}$, then, in step (3720), the current heart cycle 82 is ignored.

If, from step (3714), the diastolic signal power exceeds the mean noise power level threshold $P_0$, then, in step (3720), the associated heartbeat 82 is labeled as noisy beat and is not counted in the overall tally of heartbeats 82. Otherwise, from step (3714), the good beat counter GB is incremented in step (3716), and if, in step (3718), if the number of good heartbeats 82, i.e. the value of the good beat counter GB, is less than the required number $NG_{MIN}$ of high quality heartbeats 82, then the second-aspect auscultatory sound signal preprocessing and screening process 3700 repeats with step (3708) for the next heart cycle 82. In one set of embodiments, if the required number of high quality heartbeats 82 is not reached within a reasonable period of time, then the user is informed that recording is excessively noisy so that additional actions can be performed to improve signal quality.

Figure 73:
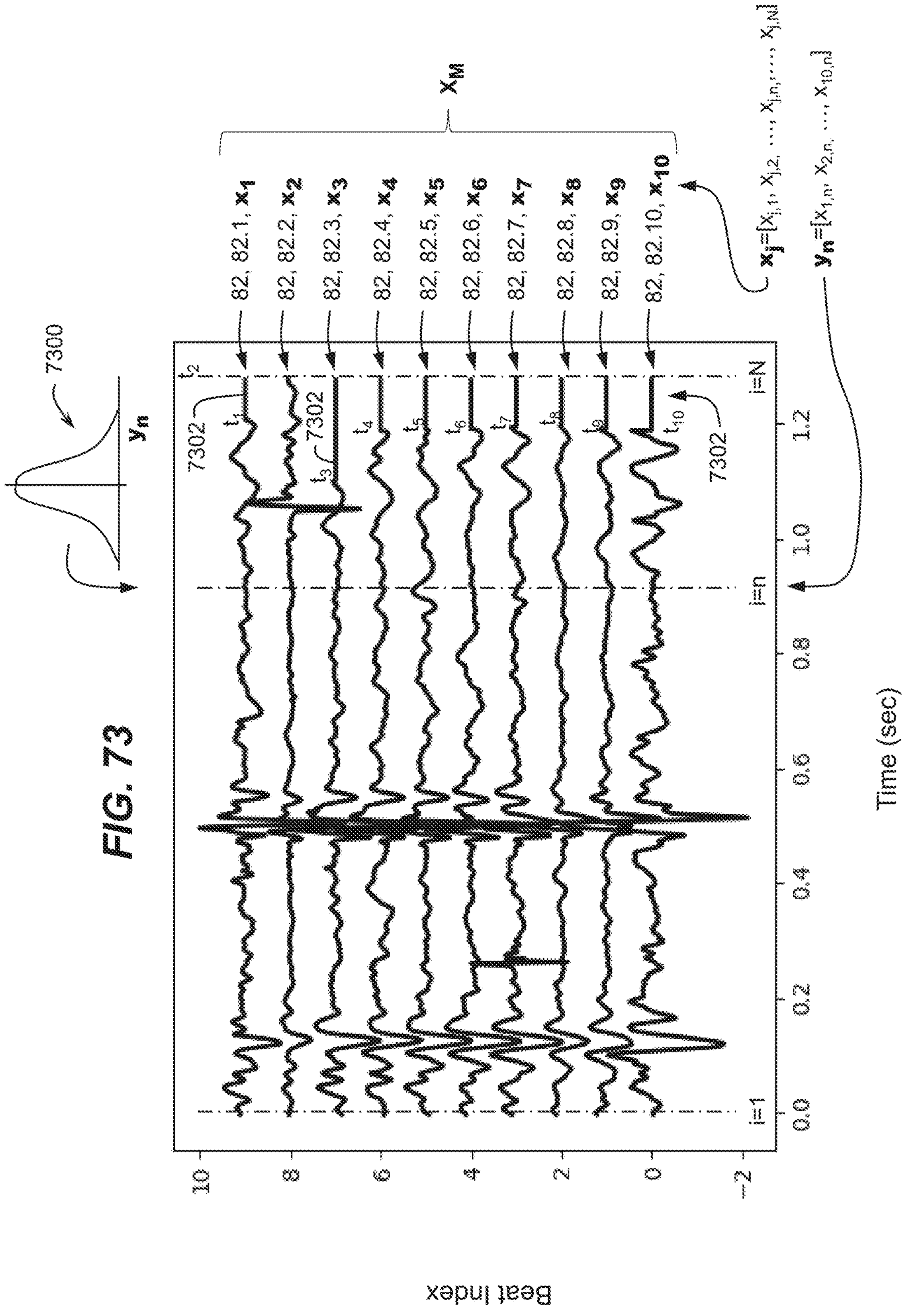
FIG. 73 illustrates a stack of heartbeats prior to processing by a third-aspect quality assessment procedure.

Referring to FIGS. 73-76, as another example, either as an alternative to, or in addition to, the above-described second-aspect heartbeat quality assessment procedure implemented in steps (3712) and (3714) of the second-aspect auscultatory sound signal preprocessing and screening process 3700, a third aspect of a heartbeat quality assessment process 7400 is responsive to the statistical properties of heartbeat signals treated as a random time-series process within an ensemble of heartbeats acquired during the recording time, generally in accordance with the following two steps: 1) segmentation of the recorded breath-held sampled auscultatory sound data S[ ] into individual heartbeats 82 as described hereinabove, and 2) estimating statistical parameters of each heartbeat 82 relative to an associated ensemble average, wherein the discrete signal value of a particular heartbeat 82, 82.*j* at a specific time $t_n$ is considered as a normally distributed random variable $x_n$, and the entire heartbeat 82, j can be considered as a random vector in the multidimensional space with dimensionality defined by the signal duration and the sampling rate. For example, referring to FIG. 73, using a stack of segmented heartbeats 82, the third-aspect heartbeat quality assessment process 7400 identifies those heartbeats 82, 82.*j* that significantly deviate from an associated ensemble median with respect to one or more of an associated vector magnitude, an associated vector hyper-angle, and a duration of the associated heartbeat 82, *j*. Such deviations can result from either significant noise, motion artifacts or acoustic interference signals irrelevant to heart function. For example, a stack of segmented heartbeats 82, 82.1, 82.2, 82.3, 82.4, 82.5, 82.6, 82.7. 82.8. 82.9. 82.10—which include noisy heartbeats 82—is illustrated in FIG. 73.

Figure 74:
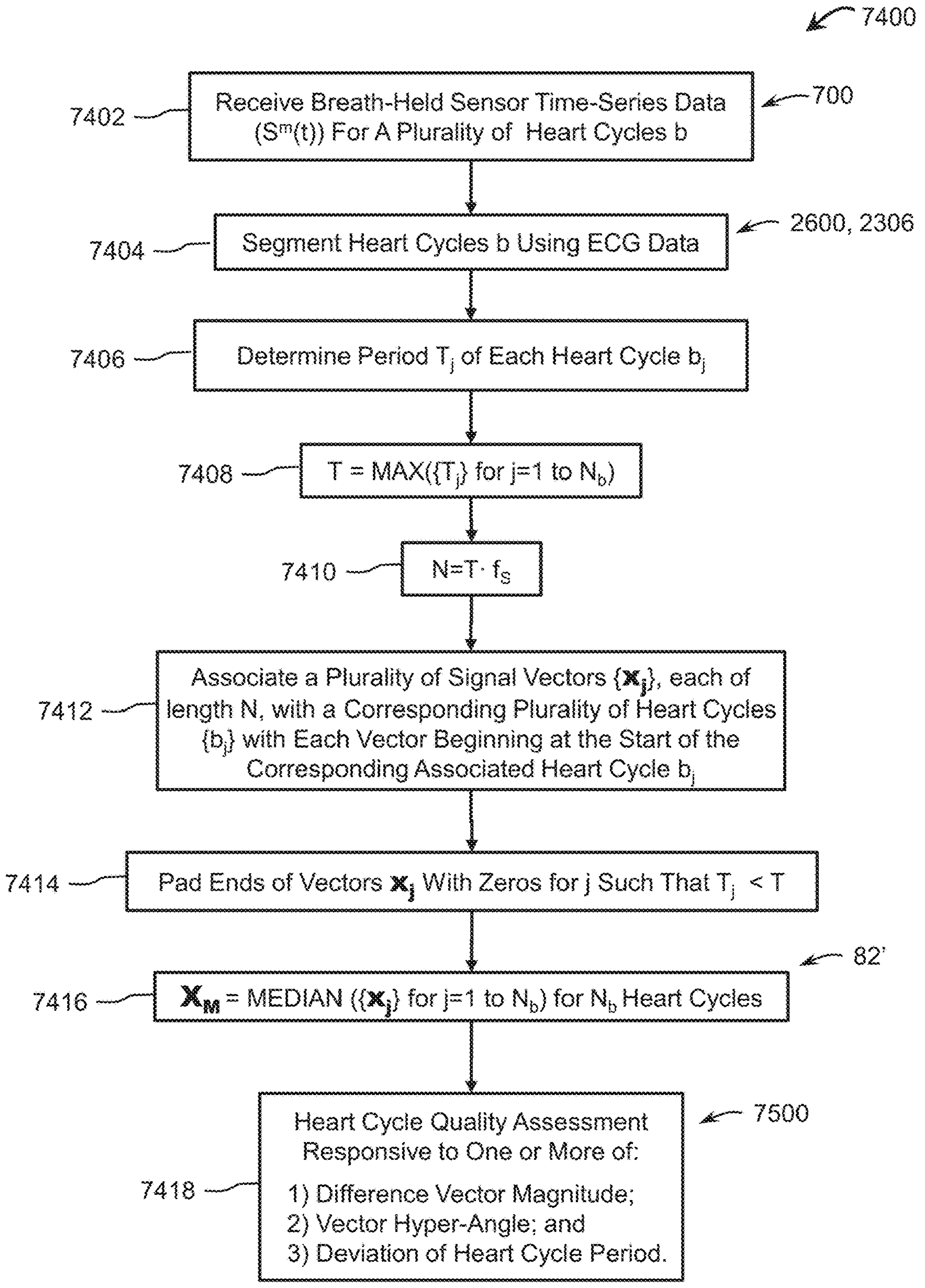
FIG. 74 illustrates a third aspect of a quality assessment process that provides for assessing the quality of an auscultatory sound signal.

More particularly, referring to FIG. 74, the third-aspect heartbeat quality assessment process 7400 commences in step (7402) with receipt of the breath-held sampled auscultatory sound data $S^m[t]$ for a plurality of heart cycles 82, 82.*j, b*, followed by segmentation of the heart cycles 82, 82.*j, b* in step (7404), so as to generate a plurality of signals $x_j$, each of which is associated with a different heart cycle 82, 82.*j, b*, with the heart-cycle period $T_j$ of each heart cycle 82, 82.*j, b* determined in step (7406). Each signal $x_j$ associated with each—i.e. the $j^{th}$—heartbeat 82, 82.*j* can be considered as a random vector $x_j = x_{j,1}, x_{j,2}, \ldots, x_{j,n}, \ldots, x_{j,N}$, with the total number of samples N of each random vector $x_j$ given by the number of samples N of the longest duration heartbeat 82, 82.*j* sampled at a sampling rate $f_s$ over the duration of the longest beat period T, the latter of which is determined in step (7408) as the maximum of the heart-cycle periods $T_j$ of the associated $N_b$ heart cycles 82, 82.*j, b*, i.e. j=1 to $N_b$, with N then being determined in step (7410) as the product of the longest beat period T and the sampling rate $f_s$, i.e. as given by $N=T*f_s$. Then, in step (7412), each of the resulting $N_b$ random vectors $x_j=[x_{j,1}, x_{j,2}, \ldots, x_{j,n}, \ldots, x_{j,N}]$ is associated with a corresponding heartbeat 82, 82.1, 82.2, 82.3, 82.4, 82.5, 82.6, 82.7. 82.8. 82.9. 82.10, and the set of random vectors $x_j=[x_{j,1}, x_{j,2}, \ldots, x_{j,n}, \ldots, x_{j,N}]$ are synchronized with respect to one another at time zero corresponding to the start of each heart cycles 82, 82.*j, b*, as illustrated in FIG. 73, wherein the collection of samples $y_n=[x_{1,n}, x_{2,n}, \ldots, x_{10,n}]$ from each of the heartbeats 82, 82.1, 82.2, 82.3, 82.4, 82.5, 82.6, 82.7. 82.8. 82.9. 82.10 associated with a particular sample n at a particular sample time $t_n$ relative to the start of each of the associated heartbeats 82, 82.1, 82.2, 82.3, 82.4, 82.5, 82.6, 82.7. 82.8. 82.9. 82.10 are considered to be normally distributed, as illustrated by the normal distribution 7300 in FIG. 73. Then, in step (7414), signals $x_j$ associated with heartbeats 82, 82.*j* that are shorter in duration than the longest beat period T in the stack are sufficiently padded with zeros 7302 so as to provide for a total of N samples in each signal/random vector $x_j$.

As a vector object, each signal $x_j$ can be characterized by an associated difference-vector magnitude $d_j$ and an associated vector hyper-angle $\alpha_j$ (or, for example, the cosine thereof) with respect to a reference direction. Accordingly, in step (7416), the median signal $X_M$ associated with a median heartbeat 82' of the ensemble of segmented heartbeats 82, 82.1, 82.2, 82.3, 82.4, 82.5, 82.6, 82.7. 82.8. 82.9. 82.10 is determined by computing the median value of each corresponding random variable $x_{j,n}$, for n=1, . . . N of the ensemble, wherein the value of each sample $x_M(n)$ of the median vector $x_M$ associated with a corresponding median heartbeat 82' is given by $x_M(n)=\text{Median}(x_{j,n})$ for j=1 to $N_b$). Following the determination the median heartbeat 82', then, as a counterpart to steps (3712) through (3720) of the auscultatory sound signal preprocessing and screening process 3700, supra, in step (7418), a heart-cycle pruning process 7500 provides for assessing the quality of each heartbeat 82, 82.*j* responsive to one or more of 1) a difference-vector magnitude $d_j$, 2) a vector hyper-angle $\alpha_j$ (or the cosine thereof), and 3) a deviation of the heart-cycle period $T_j$, and for pruning relatively-lower-quality heart cycles 82, 82.*j, b*, if any, responsive thereto.

Figure 75:
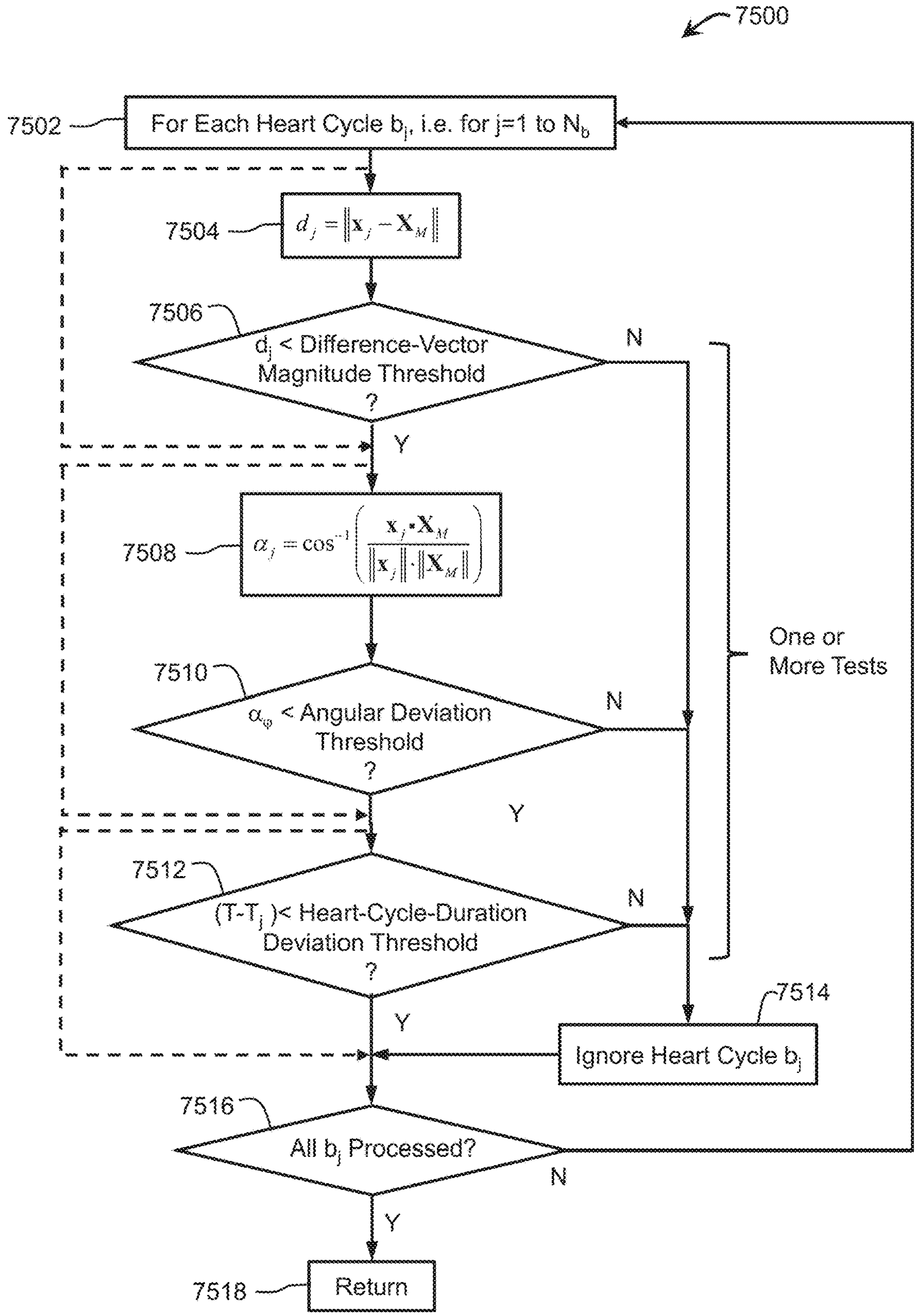
FIG. 75 illustrates a process for pruning an auscultatory sound signal of heart cycles that do not satisfy one or more associated quality assessment tests, in association with the third aspect of a quality assessment process illustrated in FIG. 74.

More particularly, referring to FIG. 75, the heart-cycle pruning process 7500 commences, in step (7502), for each of the plurality of heart cycles 82, 82.*j, b* associated with the heartbeats 82, 82.1, 82.2, 82.3, 82.4, 82.5, 82.6, 82.7. 82.8. 82.9. 82.10 associated with the median heartbeat 82' determined in step (7416), supra. Then, in step (7504), a scaler difference-vector magnitude $d_j$ is determined from the vector distance between the random vector $x_j$ associated with the particular heart cycles 82, 82.*j, b*, and the corresponding associated median vector $x_M$, as follows:

$$d_j = \|x_j - X_M\| = \left(\sum_{i=1}^{N}((x_j)_i - (X_M)_i)^2\right)^{\frac{1}{2}} \tag{20}$$

Then, in step (7506), if the difference-vector magnitude $d_j$ does not exceed a corresponding difference-vector magnitude threshold, then, or if step (7504) had been bypassed, in step (7508), a scaler vector hyper-angle $\alpha_j$ (or the cosine thereof) associated with the selected heartbeat 82, j is calculated as follows:

$$\alpha_j = \cos^{-1}\left(\frac{x_j \cdot X_M}{\|x_j\| \cdot \|X_M\|}\right) = \cos^{-1}\left(\frac{\sum_{i=1}^{N}(x_j)_i \cdot (X_M)_i}{\left(\sum_{i=1}^{N}(x_j)_i^2\right)^{\frac{1}{2}} \cdot \left(\sum_{i=1}^{N}(X_M)_i^2\right)^{\frac{1}{2}}}\right) \tag{21}$$

wherein $x_j \cdot X_M$ is the dot product of vectors $x_j$ and $X_M$. Then, in step (7510), if the vector hyper-angle $\alpha_j$ (or the cosine thereof) does not exceed a corresponding angular deviation threshold, then, or if step (7508) had been bypassed, in step (7512), a heart-cycle-duration deviation of the selected heartbeat 82, j is compared with an associated heart-cycle-duration deviation threshold, wherein, for example, the heart-cycle-duration deviation is given by the difference between the longest beat period T and the heart-cycle period $T_j$, or by the difference between the heart-cycle period $T_j$ and a median value thereof. Otherwise, from step (7506), if the difference-vector magnitude $d_j$ exceeds the corresponding difference-vector magnitude threshold, or from step (7510), if the vector hyper-angle $\alpha_j$ (or the cosine thereof) exceeds the corresponding angular deviation threshold, or, from step (7512), if the heart-cycle-duration deviation exceeds the heart-cycle-duration deviation threshold, then, in step (7514), the selected heart cycle 82, 82.*j, b* is ignored (or flagged to be ignored). Then, from either steps (7514) or (7512), or if step (7512) had been bypassed, then, from step (7516), if all of the heart cycles 82, 82.*j, b* have not been processed, then the heart-cycle pruning process 7500 is repeated beginning with step (7502) for the next heart cycle 82, 82.*j, b*. Otherwise, from step (7516), after all of the heart cycles 82, 82.*j, b* have been processed, from step (7518), the heart-cycle pruning process 7500 returns to the point of invocation.

Figure 76:
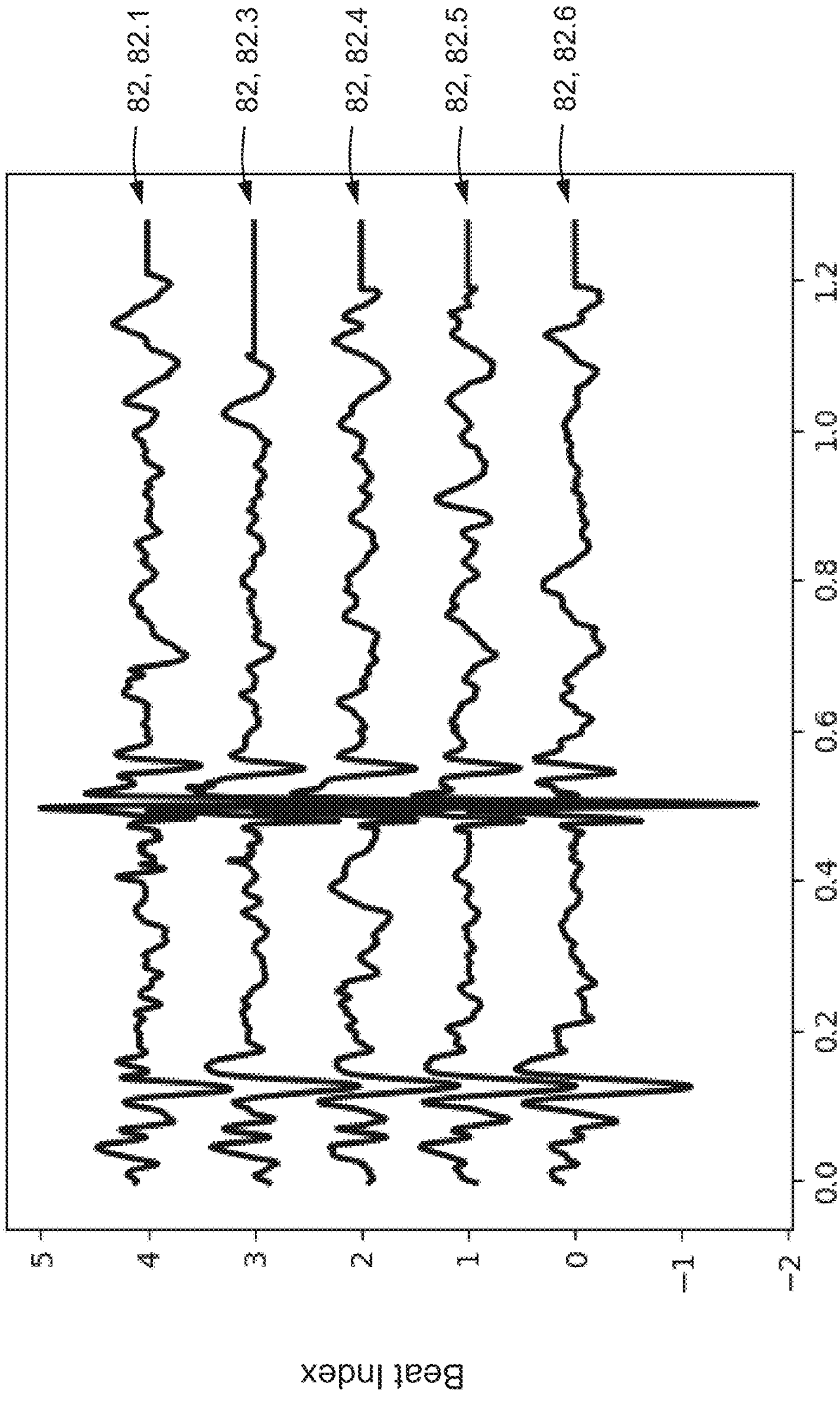
FIG. 76 illustrates a stack of heartbeats following processing by the third-aspect quality assessment procedure, corresponding to the stack of heartbeats illustrated in FIG. 73.

Accordingly, the quality of the segmented heartbeats 82, 82.*j* can then be assessed in a counterpart to step (3714) by comparison of the associated vector magnitude $d_j$, the associated vector hyper-angle $\alpha_j$ (or the cosine thereof), and/or the associated fluctuation in the length of the heartbeat 82, j in relation to that of the ensemble, with corresponding upper bound threshold values, for example, the maximum difference-vector magnitude $d_{max}$, the maximum angular deviation $\alpha_{max}$ (or cosine thereof cos $\alpha_{max}$) and/or the maximum tolerable deviation in the length of the heartbeat 82, j, respectively. For example, FIG. 76 illustrates the results of screening and pruning the stack of heartbeats 82, 82.1, 82.2, 82.3, 82.4, 82.5, 82.6, 82.7. 82.8. 82.9. 82.10 illustrated in FIG. 73, using the third-aspect heartbeat quality assessment process 7400 with associated thresholds of $\alpha_{max}$=50 degrees, and with the maximum deviation in the heartbeat length of dt/mean($t_i$)<20%, resulting in the rejection of noisy heartbeats 82.2, 82.7. 82.8. 82.9. 82.10. The associated threshold values can be defined empirically considering reproducibility of heartbeats 82, j during the recording interval, noise conditions and number of heartbeats labelled as being of insufficient quality. A resulting fraction of rejected heartbeats that appears to be too high may indicate a serious problem with recording procedure or ambient room conditions less than optimal for the test.

More generally, in accordance with another set of embodiments, instead of determining and using the median vector $x_M$, the heartbeat quality assessment process 7400 could determine an use a composite vector that is responsive to the ensemble of random vectors, $x_j=[x_{j,1}, x_{j,2}, \ldots, x_{j,n}, \ldots, x_{j,N}]$ for example, an average vector or a vector responsive to a different ranking than that used to generate a median. Furthermore, the deviation in heartbeat length could be determined relative to the length of any of the heartbeats from the longest to the shortest, or relative to a composite heartbeat length measure, for example, a mean length or a median length of the plurality of heartbeats 82, 82.1, 82.2, 82.3, 82.4, 82.5, 82.6, 82.7. 82.8. 82.9. 82.10.

Figure 39A:
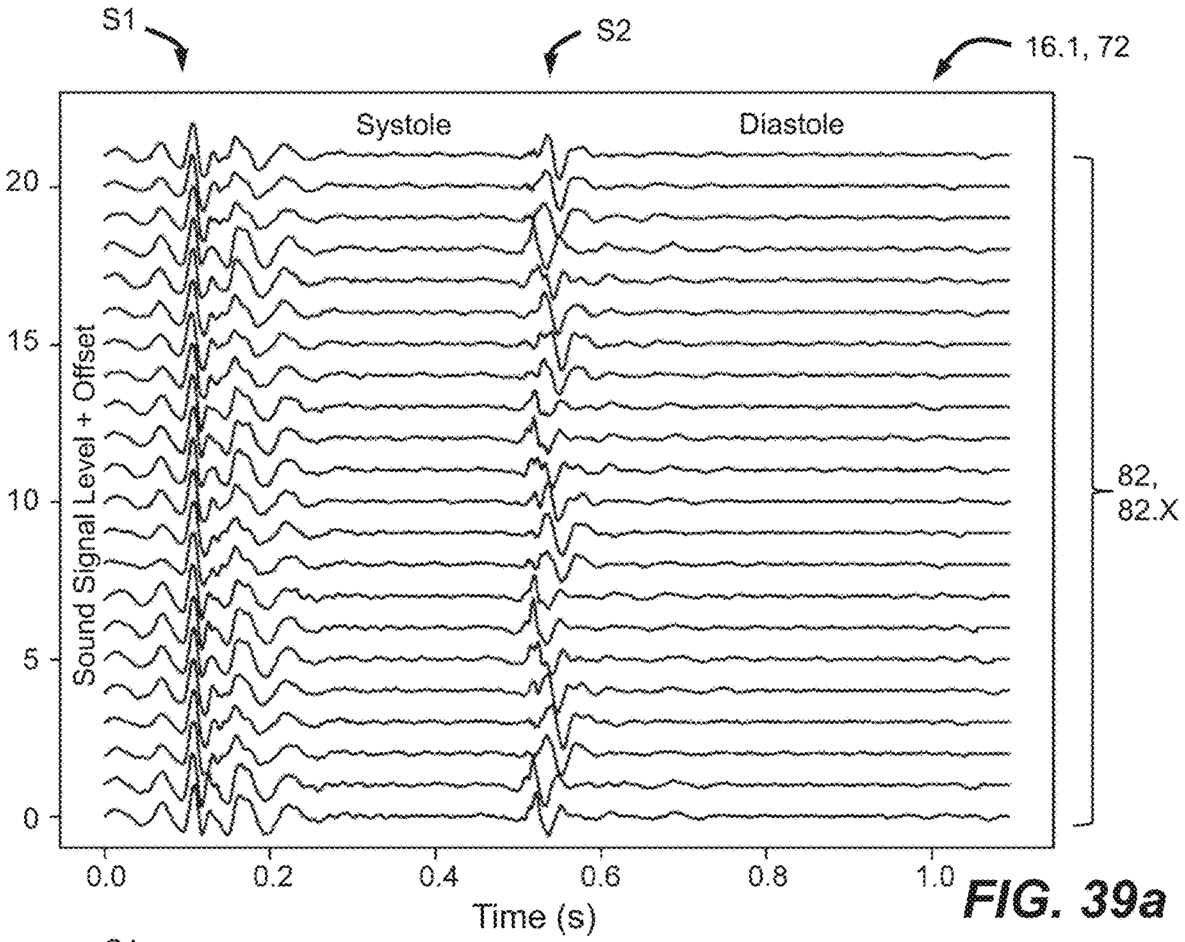
FIG. 39*a* illustrates auscultatory sound signals for a plurality of heart cycles.
Figure 39B:
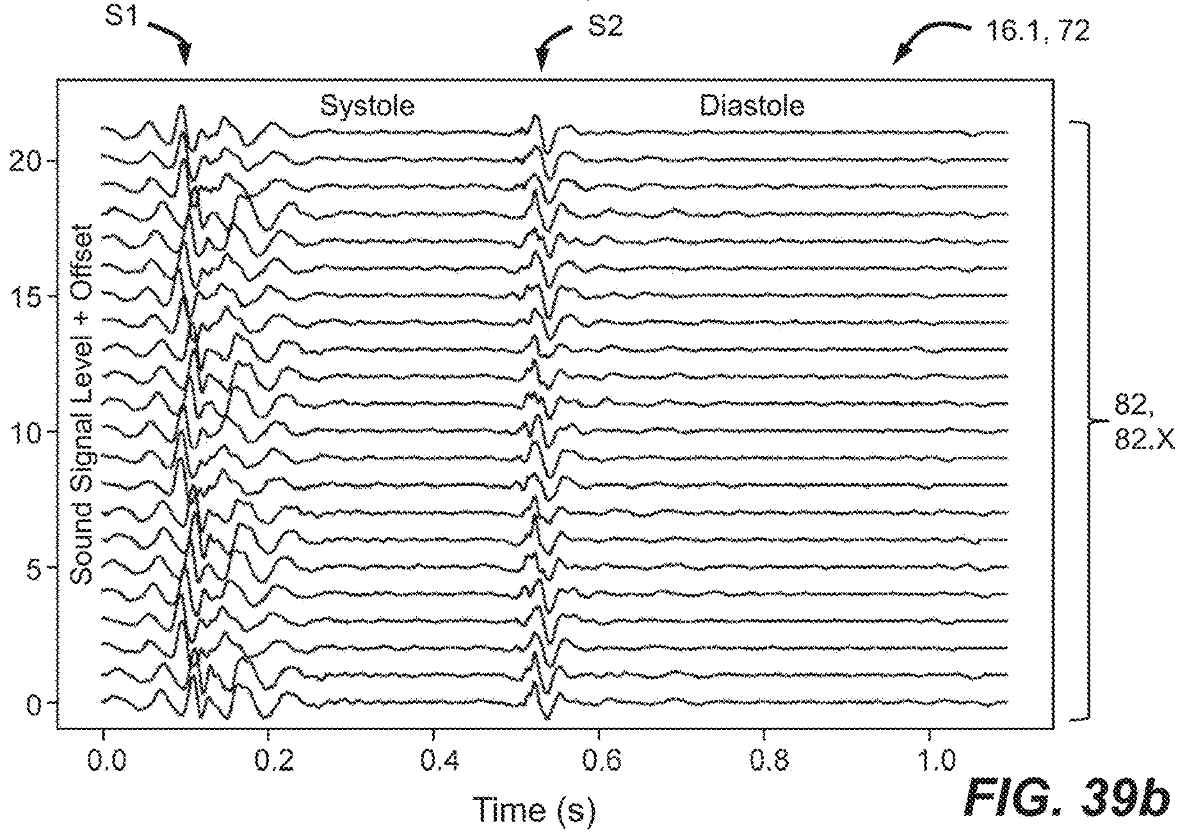
FIG. 39*b* illustrates the auscultatory sound signals for the plurality of heart cycles illustrated in FIG. 39*a*, with the heart cycles aligned with respect to the mean times of the S2 heart sound.

Returning to FIG. 37, following the acquisition of a sufficient number of sufficiently-low-noise heartbeats 82, following step (3718), the sampled auscultatory sound data $S^m$[ ] is further preprocessed to emphasize acoustic signals in diastole D and extract signal specific features that can be used for disease classification. For example, in step (3722), the mean position of the peak of the S2 heart sound—for example, the above-described mean value $t_{S2}$—is determined for each heartbeat 82, after which the heartbeats 82 are synchronized with respect thereto, for example, as illustrated in FIGS. 39*a* and 39*b*, which respectively illustrate a stack of heartbeats 82 before and after this S2 alignment, wherein the synchronization of the heartbeats 82 with respect to the S2 heart sound helps to locate an acoustic signature that might be present in a majority of the heartbeats 82 and that is coherent between or amongst different heartbeats 82.

Figure 40A:
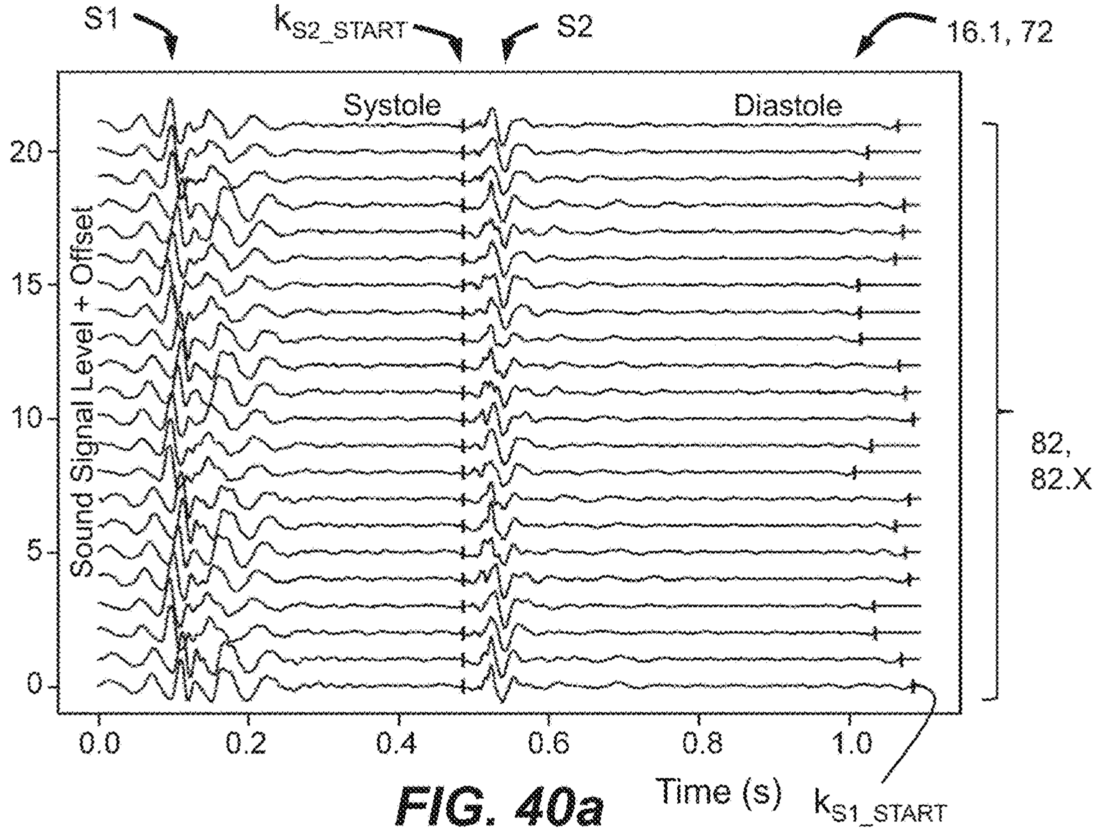
FIG. 40*a* illustrates the auscultatory sound signals for a plurality of heart cycles illustrated in FIG. 39*b*, including indications of the start of the S2 heart sound and the end of diastole.
Figure 40B:
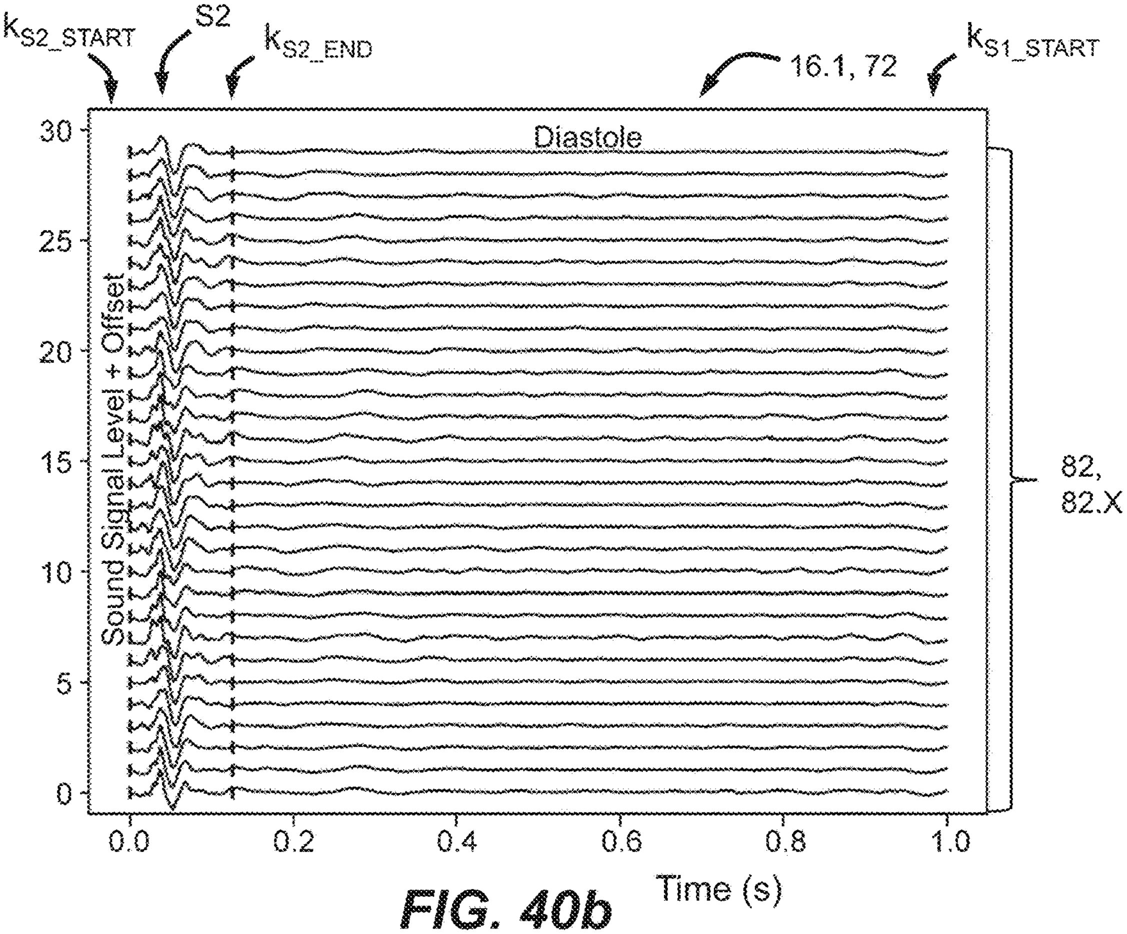
FIG. 40*b* illustrates portions of the auscultatory sound signals during diastole for the plurality of heart cycles illustrated in FIG. 40*a*, with the heart cycles temporally normalized and resampled.

Then, in step (3724), the heartbeats 82 are normalized with respect to time so as to compensate for a variation in heartbeat rate amongst the heartbeats 82, and to compensate for a resulting associated variation in the temporal length of the associated diastolic intervals. Generally, heartbeat rate is always changing and typically never remains the same over a recording period of several minutes, which if not compensated, can interfere with the identification of specific signal features in diastole D, for example, when using the below-described cross-correlation method. Although heartbeat segmentation alone provides for aligning heartbeat starting points, variations in the heartbeat rate can cause remaining features of the heart cycle 82 to become shifted and out of sync—i.e. offset—with respect to each other. However, such offsets can be removed if the associated heartbeats 82 are first transformed to common normalized time scale t/T*, where T* is the fixed time interval, for example, the duration of the slowest heartbeat 82, followed by heartbeat resampling and interpolation so as to provide for normalizing the original signal at a new sampling rate, for example, as illustrated in FIGS. 40*a* and 40*b* that respectively illustrate stacks of heartbeats 82 before and after such a time normalization, wherein FIG. 40*a* illustrates complete heart cycles 82, and FIG. 40*b* illustrates only the temporally-normalized diastolic portions D thereof.

Referring again to FIG. 37, in step (3730), a final stage of signal pre-processing provides for extracting acoustic features from the recorded heartbeats 82. There are numerous options that can be applied to feature extraction which typically involves certain transformation of raw data to low-dimensional or sparse representation that uniquely characterizes the given recording. Alternatively, the raw data can be transformed in a set of images and some image recognition algorithm like convolutional neural net can be employed for automatic feature selection. For example, in accordance with one set of embodiments, referring to FIG. 41, a local cross-correlation (CC) of multiple heartbeats 82 provides for identifying a relatively high-pitch signal component in the diastolic phase of the heart cycle 82 occurring in multiple heartbeats 82, which can be result from turbulent blood flow, wherein pairs of heartbeats 82 of a 2-D stack of heartbeats 82—each segmented from the above-described high-pass-filtered breath-held sampled auscultatory sound data 72, s[ ]—are cross-correlated with one another by computing an associated set of cross-correlation functions $R_{xixj}$ for each pair of heartbeats 82, $x_i$[ ], $x_j$[ ]. This computation is made using a sliding short-time window with Nw samples (for example, typically 128) which is advanced in time one sample per each iteration of the cross-correlation computation. The cross-correlation is computed without time lag, resulting in an array—of the same size as that of the original signals—that is given by:

$$R_{x_i x_j}(n) = \frac{1}{N_w}\sum_{k=1}^{N_w} x_i(n+k)\cdot x_j(n+k) \tag{22}$$

Figure 42:
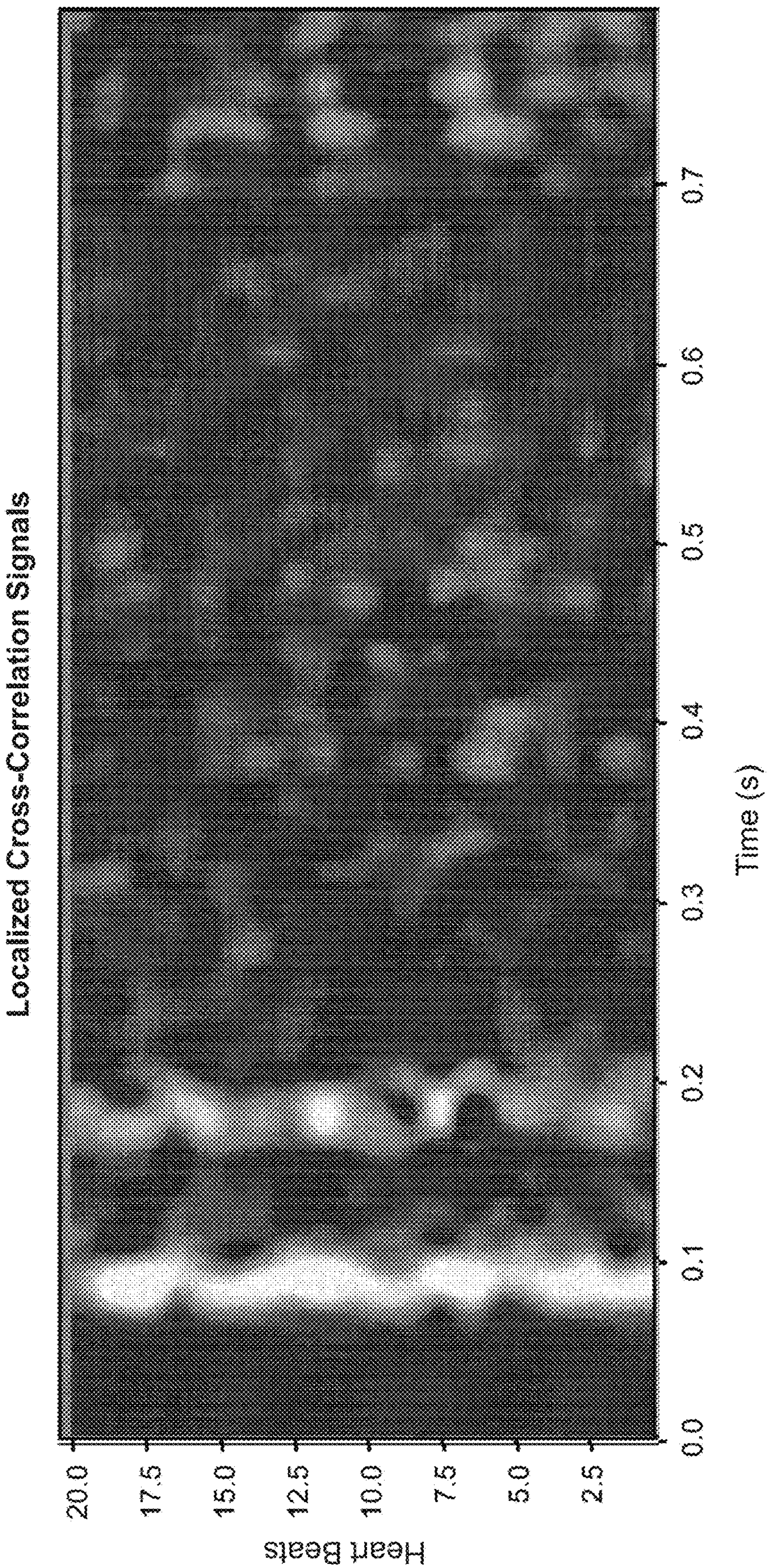
FIG. 42 illustrates a image of a plurality of localized cross-correlation signals associated with auscultatory sound signals from a plurality of heart cycles.

The cross-correlation value assigned to each heartbeat is given by an average of cross-correlations thereof with the remaining $N_b-1$ heartbeats 82:

$$R_{x_i}(n) = \frac{1}{(N_b - 1)} \sum_{j=1}^{N_b-1} R_{x_i x_j}(n) \tag{23}$$

wherein $x_i$ and $x_j$ are the diastolic high-pass-filtered breath-held sampled auscultatory sound data 72, s[ ] of two distinct heartbeats 82, and $N_b$ is the total number of heartbeats 82 in the 2-D stack. Following computation of all possible pairs of heartbeats 82, an $N_b \times N_t$ cross-correlation matrix is obtained and displayed as a 2D image, wherein $N_t$ is the number of time samples in each heartbeat 82. A similar signal pattern during diastole that is present in majority of heartbeats 82 will produce a localized cross-correlation peak in diastole D. Accordingly, cross-correlation peaks associated with a micro-bruit signal occurring at approximately at the same temporal location within the diastolic interval D from one heartbeat 82 to another will produce distinct bands across the image within the same temporal region of each heartbeat 82, for example, as illustrated in FIG. 42, which illustrates an image of the cross-correlation function $R_{xi}$ as a function of n (corresponding to time) for each heartbeat 82, with different heartbeats 82 at different ordinate positions, wherein the value of the cross-correlation function is indicated by the color of the associated pixels. The cross-correlation operation provides for emphasizing signal features that are coherent within the current time window, and provides for suppressing uncorrelated noise, thereby providing for increasing the associated signal-to-noise ratio.

Figure 43:
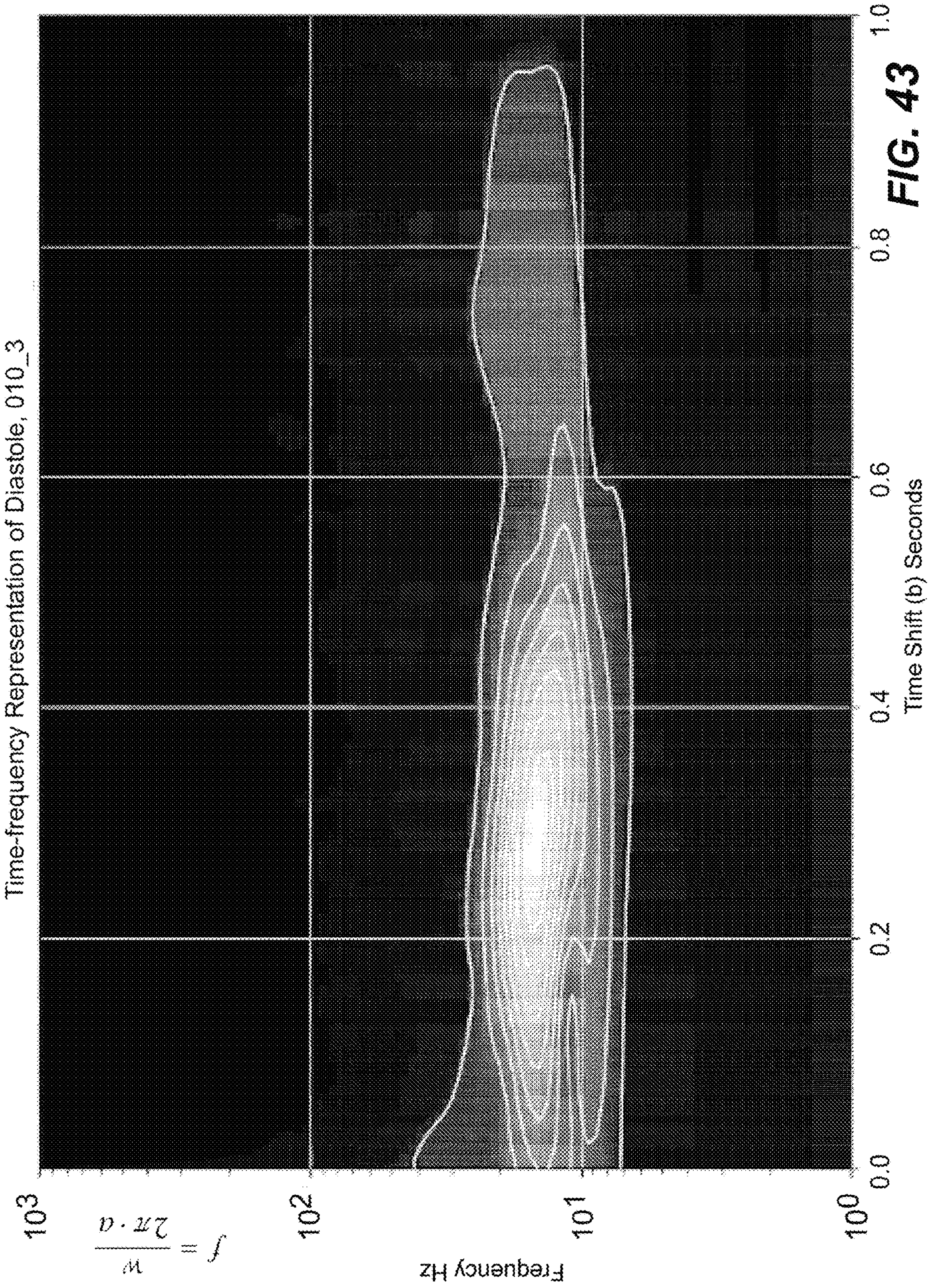
FIG. 43 illustrates a time-frequency analysis based on a continuous wavelet transform of an auscultatory sound signal during diastole.

Alternatively, or additionally, acoustic features in the diastolic interval D of a heartbeat 82 can be visualized using a continuous wavelet transform (CWT). The wavelet transform processing is similar to the short-time cross-correlation, but instead of cross-correlating signals from different heartbeats 82, the signal of interest is correlated using a wavelet function with limited support to facilitate temporal selectivity.

$$X(a, b) = \frac{1}{|a|^{1/2}} \int_{-\infty}^{\infty} x(t)\psi\left(\frac{t-b}{a}\right)dt \tag{24}$$

wherein the associated mother wavelet $\psi$ is a continuous function in time and frequency domains. The wavelet family is typically chosen empirically using specifics of the signal under consideration. The family of Morlet wavelets appears as an appropriate choice for analysis of heart sounds. Output of the wavelet transform is a two-dimensional time-frequency representation of signal power $|X(a,b)|^2$ defined in terms of scaling and shift parameters. An example of a wavelet transform—using a 6th order Morlet wavelet—is illustrated in FIG. 43, where the associated corresponding original color map represents distribution of the signal power in a time-frequency plane, with normalized time-shift—as a function of b—as the abscissa, and frequency as the ordinate, with frequency f in Hertz given as follows:

$$f = \frac{w}{2\pi \cdot a} \tag{25}$$

wherein w is the wavelet order, for example, w=6 for a 6th order Morlet wavelet, and the results plotted in FIG. 43 are the result of a cumulative processing of the diastolic portions of a plurality of heart cycles. For the purpose of signal classification, the wavelet representation can be reduced further by dividing the time axis into discrete intervals and computing overall signal power within such interval and specific frequency bandwidth. For example, in one embodiment, the wavelet image may be subdivided in time intervals of 200 milliseconds and two frequency bands of 10 Hz-40 Hz and 40 Hz-100 Hz. The resulting output vector of the signal power within the associated intervals of time and frequency can be used as an input to a neural network classifier.

Generally, step (3730) of the second-aspect auscultatory sound signal preprocessing and screening process 3700—which may also be used in cooperation with the above-described first-aspect auscultatory sound signal preprocessing and screening process 2100—incorporates one or more feature extraction algorithms which identify significant signal parameters that can be linked to coronary artery disease (CAD) and which can be used for training a machine learning algorithm for automatic coronary artery disease (CAD) detection. Furthermore, if auscultatory sound signals 16 are recorded at a relatively high sampling rate (for example, at a 4 kHz sampling rate), each heartbeat 82 might contain over 4000 samples per each of six channels. Such large amount of highly correlated variables makes the usage of the raw waveform for classification very difficult without additional signal processing to reduce the dimensionality of the problem. Such dimensionality reduction can be achieved by use of an appropriate feature extraction algorithm that identifies a reduced set of parameters that are related to coronary artery disease (CAD). Mathematically, the feature extraction procedure provides a mapping of the high-dimensional raw data into the low-dimensional feature space with adequate inter-class separation. For example, standard dimensionality reduction routines such as singular value decomposition (SVD) or principal component analysis (PCA) may be used to decompose raw data onto orthonormal basis and to provide for selecting relevant features with minimal loss of information. The time domain signal itself can be transformed prior to feature extraction to emphasize unique features thereof. For example, frequency domain representation by Fourier transform can be advantageous for feature extraction if the signal contains discrete set of characteristic frequencies. The performance of a signal classifier can be dramatically improved by excluding a large number of irrelevant features from analysis. In accordance with one aspect, the signal classification problem begins with a mapping from the original high-dimensional space (size N) to a feature space (size $p \ll N$), followed by a mapping of the feature space to an m-dimensional space, wherein the dimension m is equal to the number of classes. For example, for a binary classification problem—e.g. CAD or no CAD,—m=2.

In accordance with one set of embodiments, step (3730) of the second-aspect auscultatory sound signal preprocessing and screening process 3700 employs a wavelet packet transformation (WPT) for sparse representation of heart sounds in time-frequency domain, followed by a custom designed binary classifier. Several standard classifier algorithms can be trained using reduced feature set, and to provide for binary classification of the associated heart sounds—useable either individually or in combination,—including, but not limited to, a support vector machine (SVM), a fully-connected artificial neural network (ANN), or a convolution neural network (CNN) applied to two-dimensional time-frequency images.

Referring to FIGS. 57-66, a wavelet packet transformation (WPT) processing stage provides for reducing dimensionality by converting raw time-domain auscultatory sound signals 16 into a time-frequency basis using discrete wavelet transform (DWT), followed by elimination of associated components that do not provide significant contribution to the original signal or do not provide substantial contrast between two classes of interest. For example, referring to FIG. 57, in one set of embodiments of discrete wavelet decomposition, an initial (input) signal x[n] is passed through a series of stages at which low-pass and high-pass filter functions (quadrature mirror filters) are applied to obtain approximation $a_j(k)$ and detail $d_j(k)$ coefficients at the $j^{th}$ level of decomposition. This procedure is repeated recursively at the subsequent steps with the only approximation coefficients used as an input, The coefficients generated at each indicated level of filtering provide the corresponding amplitude of the initial signal x[n] after filtering by a filter having a corresponding bandpass filter response characteristic illustrated in FIG. 58.

Referring to FIGS. 59 and 60, In accordance with one set of embodiments, the discrete wavelet transform (DWT) is implemented using a Daubechies wavelet family, for example, a Daubechies 4 (db4) wavelet family, for which the associated scaling function φ—having low-pass filter coefficients $h_0$ through $h_7$—is illustrated in FIG. 59, and for which the associated wavelet function Ψ—having high-pass filter coefficients $g_0$ through $g_7$—is illustrated in FIG. 60.

Figure 57:
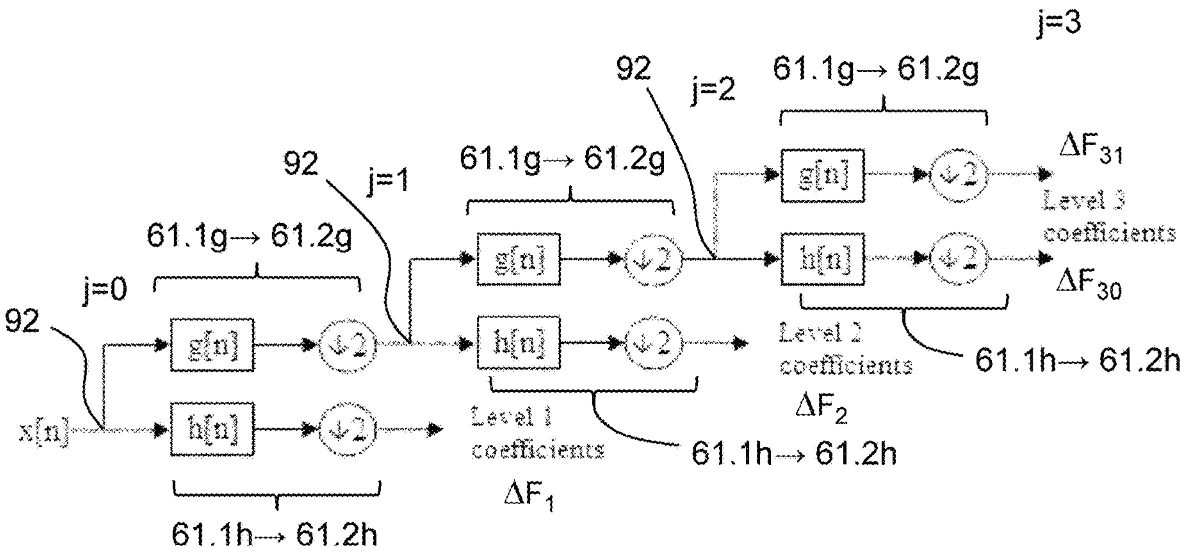
FIG. 57 illustrates a three-level Discrete Wavelet Transformation (DWT) process.
Figure 58:
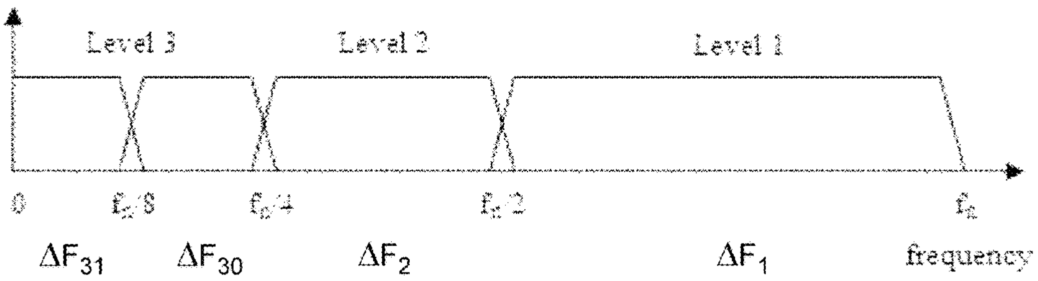
FIG. 58 illustrates the effective filter spectra associated with the outputs of the three-level Discrete Wavelet Transformation process illustrated in FIG. 57.

Referring to FIGS. 57 and 61, at each node 92 of the discrete wavelet transform (DWT), an input time series $w_{j,k}[l]$ from decomposition level j is transformed into two output time series at decomposition level j+1, i.e. $w_{j+1,2k}[l]$ and $w_{j+1,2k+1}[l]$, each containing half the number of samples as in the input time series, and mutually-exclusive halves of the frequency content of the input time series, wherein the transformation to generate the $w_{j+1,2k+1}[l]$ lower-half bin of frequency content is given by the transformation 61.1*g*→61.2*g* illustrated in FIG. 61 and in equation (26) below, and the transformation to generate the $w_{j+1,2k}[l]$ upper-half bin of frequency content is given by the transformation 61.1*h*→61.2*h* illustrated in FIG. 61 and equation (27) below, wherein k designates an associated frequency bin for the associated decomposition level j.

The filter functions are designed to provide for energy conservation and lossless reconstruction of the original signal from the set of transformed time series $w_{j,k}[l]$ from a particular decomposition level j. These properties along with smoothness requirements define the family of scaling and wavelet functions used for decomposition. The resulting set of $K=2^j$ distinct frequency bands at each decomposition level j, together with the corresponding associated transformed time series $w_{j,k}[l]$. can be used for analysis and feature extraction, instead of relying upon the corresponding original raw signal x[n].

Figure 62:
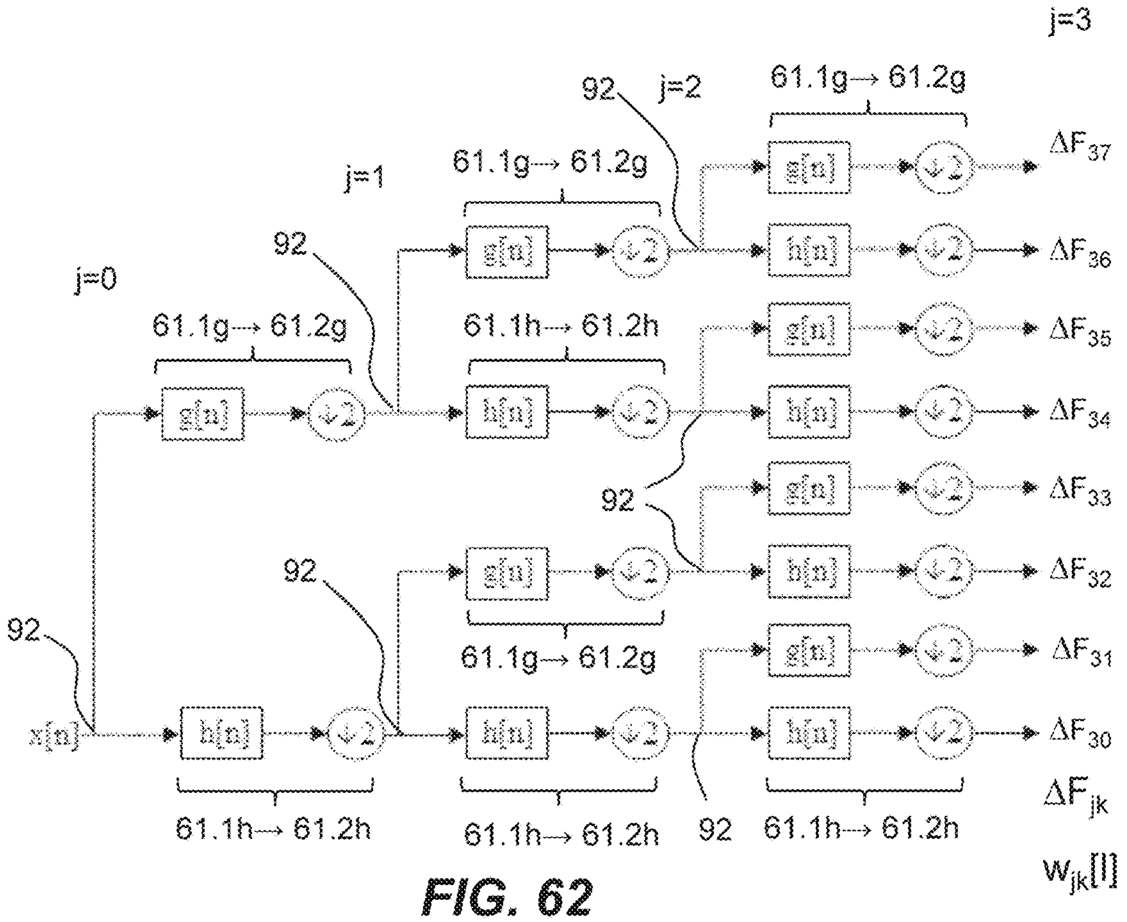
FIG. 62 illustrates a three-level Wavelet Packet Transformation (WPT) process.
Figure 63:
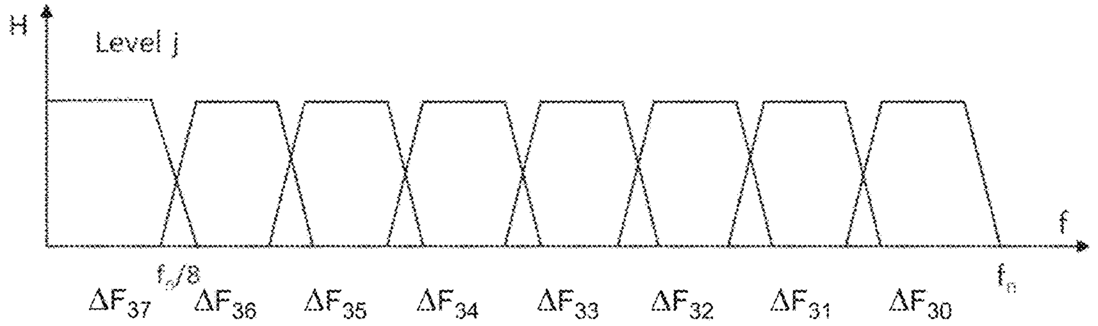
FIG. 63 illustrates the effective filter spectra associated with the outputs of the three-level Discrete Wavelet Transformation process illustrated in FIG. 62.
Figure 64:
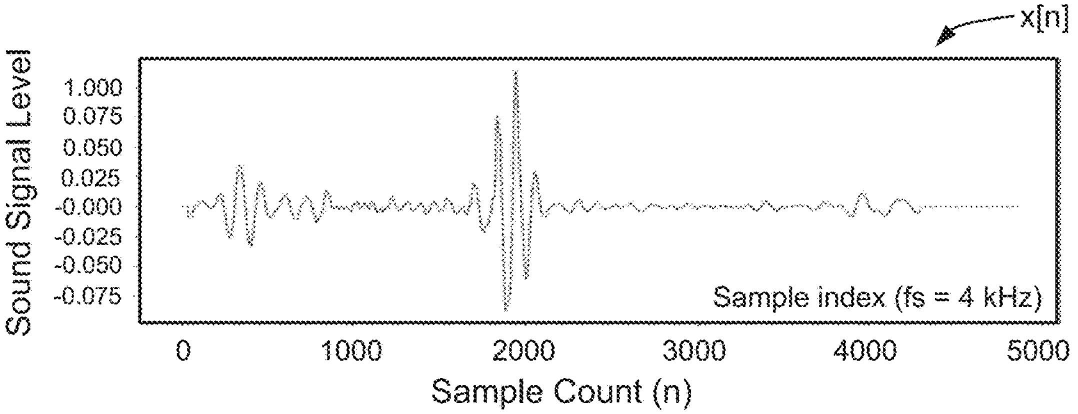
FIG. 64 illustrates a high-pass-filtered auscultatory sound signal for a single heart cycle from a high-pass filter having a 30 Hz cut-off frequency.

The wavelet packet transformation (WPT) is a generalization of the standard multi-level DWT decomposition, wherein both approximation and detail coefficients are decomposed using quadrature mirror filters, for example, as described in M. Wickerhauser, "Lectures on Wavelet Packet Algorithms", http://citeseerx.ist.psu.edu, which is incorporated herein by reference. FIG. 62 illustrates a wavelet packet transformation (WPT) at decomposition level j=3, and FIG. 63 illustrates the bandpass frequency responses associated with each of the outputs thereof. Analytically, the wavelet packet transformation (WPT) decomposition can be described by the following recursive expressions:

$$w_{j+1,2k+1}[l] = \sqrt{2}\cdot\sum_{m=1}^{M} g_m w_{j,k}[2\cdot l - m] \tag{26}$$

$$w_{j+1,2k}[l] = \sqrt{2}\cdot\sum_{m=1}^{M} h_m w_{j,k}[2\cdot l - m] \tag{27}$$

where $g_m$ is the coefficient of the scaling function and $h_m$ is the coefficient of the wavelet function, k is the index of the associated frequency bin at decomposition level j, and l is the index of the associated time series array associated with the particular frequency bin k.

Figure 65:
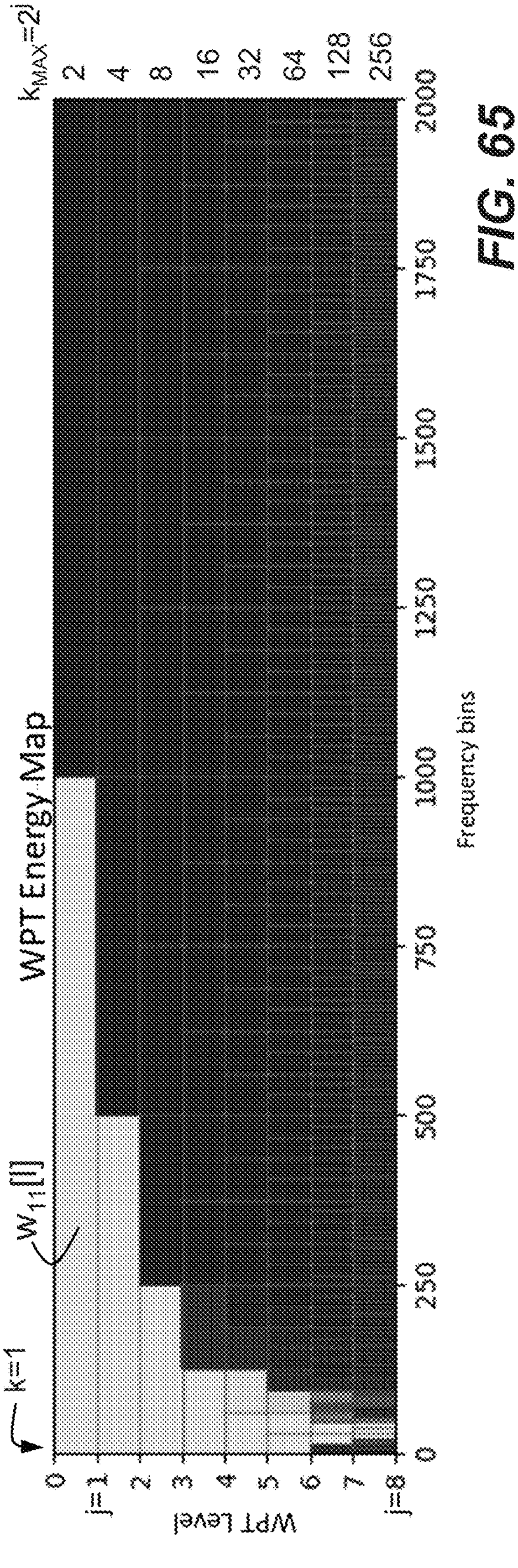
FIG. 65 illustrates a Wavelet Packet Transformation energy map for the high-pass filtered auscultatory sound signal illustrated in FIG. 64, with eight decomposition levels.

The wavelet packet transformation (WPT) provides a benefit of sparse signal representation similar to the discrete wavelet transformation (DWT), but also provides better resolution of frequency components by decomposing the detail part of discrete wavelet transformation (DWT), which results in the sub-band structure illustrated in FIG. 63. The maximum decomposition level j for a given signal depends on the signal length and the trade-off between desired time and frequency resolutions. The resulting tree-like structure of wavelet packet transformation (WPT) bases—each base corresponding to a particular frequency bin k at a particular decomposition level j—provides a highly redundant representation of the original signal x[n], which limits the amount of dimensionality reduction. However, heart sounds have characteristic properties that can be well described by a relatively small number of wavelet packet transformation (WPT) bases and a substantial amount of irrelevant information can be discarded. For example, in one set of embodiments, the WPT tree nodes with highest energy concentration are retained for further analysis and classification. For example, FIG. 65 illustrates a wavelet packet transformation (WPT) energy map of the high-pass-filtered breath-held sampled auscultatory sound signal 72 for the heart cycle 82 illustrated in FIG. 64, generated by an 8-level wavelet packet transformation (WPT) using a Daubechies 4 (db4) wavelet family, wherein the individual nodes 92—or associate bases or frequency bins—are outlined with rectangular boundaries in the image, and each frequency bin is color coded to indicated the total energy $E_{jk}$ of the $k^{th}$ node at the $j^{th}$ decomposition level, which is computed using wavelet packet transformation (WPT) coefficients $w_{jk}[l]$ as follows:

$$E_{j,k} = \sum_{l} w_{j,k}{}^{2}[l] \tag{28}$$

For each decomposition level j, the total energy from all frequency bins is the same, i.e.

$$E_{Total} = \sum_{k} E_{j,k} \text{ is the same value regardless of decomposition level } j. \tag{29}$$

Figure 66:
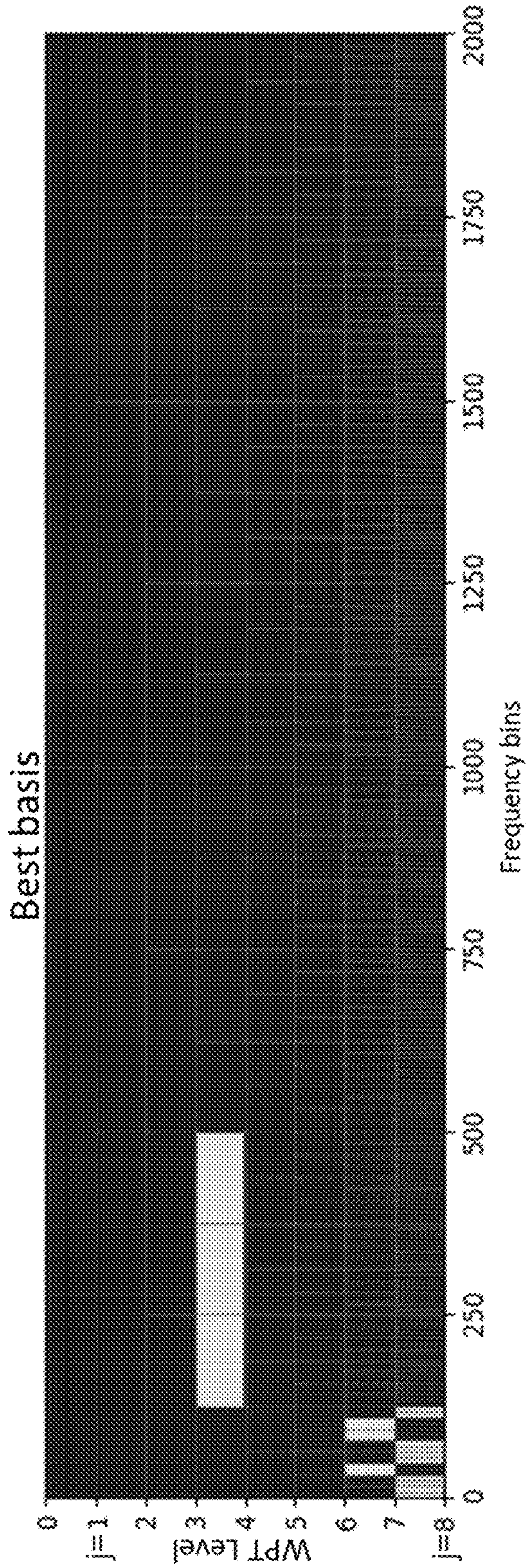
FIG. 66 illustrates a selected basis of frequency bins from the Wavelet Packet Transformation energy map illustrated in FIG. 64, selected using Shannon entropy as a cost function.

The wavelet packet transformation (WPT) energy map of FIG. 65 illustrates that most of the signal energy is concentrated in the relatively low frequency bands, and that only the levels 7 and 8 of decomposition show the fine structure of the energy distribution. Accordingly, this example shows that most of the wavelet packet transformation (WPT) nodes 92 can be ignored without significant loss of information. A formal approach to the selection of the best bases—that relies on Shannon entropy as a cost function computed for each node in the tree—is described by H. Saito and R. Coifman in the following documents that are incorporated herein by reference: N. Saito, R. R. Coifman, "On local feature extraction for signal classification", https://www.math.ucdavis.edu/~saito/publications/saito_iciam95.pdf, and N. Saito, R. R. Coifman, "Local discriminant bases and their applications", J. Math. Imaging and Vision, 5, 337-358 (1995). For example, traversing the wavelet packet transformation (WPT) tree from the leaf level up (i.e. highest to lowest decomposition level j), children nodes with the combined entropy lower than that of the parent node will be retained as the most relevant for a given signal, for example, as illustrated in FIG. 66 for the wavelet packet transformation (WPT) energy map illustrated in FIG. 65, wherein the Shannon entropy is given by:

$$I_{j,k} = \sum_{l} p_{j,k}[l] \cdot \log(p_{j,k}[l]) \quad (30)$$

$$\text{and } p_{j,k}[l] = \frac{w_{j,k}^2[l]}{\sum_{l} w_{j,k}^2[l]}. \quad (31)$$

The Wavelet Packet Transform (WPT) provides a redundant representation of the actual signal using the discrete wavelet transform with various decomposition levels that provide higher frequency resolution (in terms of filter banks) at the expense of reduced time resolution. The WPT of the signal can be described by a set of coefficient wj(k, l), where j is the decomposition level, k is the filter bank index and l is the coefficient index within the filter bank. An example of WPT decomposition is shown in FIG. 65, where each cell outlines positions of the filter bank for each level, and intensity is related to the signal energy from equation (28). It can be seen that the energy distribution within specific frequency bands becomes apparent at high decomposition levels (j> 6). Although, the color of the high frequency cells is dark blue, the values of the associated WPT coefficients is not zero.

The entire WPT energy map is highly redundant and not well suited in its raw form for signal classification. Instead, only those cells that uniquely characterize a given signal are kept while ignoring remaining cells. This can be accomplished using the best WPT basis selection algorithm which employs entropy WPT coefficients as a metric of the filter bank (cell) importance. This algorithm runs from leaf cells up along the decomposition tree and selects parent cell whose entropy is less compared to the sum of the two child cells. An example of best basis selection applied to the WPT map in FIG. 65 is shown in FIG. 66. Values of the best basis would generally not coincide with the energy map shown in FIG. 65 because entropy and energy differ from one another.

In FIG. 65, the total energy of a particular cell is represented by the intensity thereof. FIG. 65 illustrates that most of the energy is concentrated in the relatively-lower frequency bands. The cells of FIG. 66—for which intensity is inversely related to entropy—are considered to be a signature of a given signal, and do not overlap with the corresponding cells of FIG. 65, the latter of which is representative of energy. None of the cells below the highlighted (children) cells in FIG. 66 are selected because they exhibit high entropy.

The wavelet packet transformation (WPT) energy map and the associated best basis selection can be used to reduce dimensionality of the heartbeat classification problem by analyzing the signal represented by transformed time series $w_{j,k}[l]$ and rejecting information irrelevant for the classification task. The wavelet packet transformation (WPT) is one of a variety of signal processing techniques that can be used for extraction of important parameters or features suitable for prediction of coronary artery disease (CAD). The very basic set of features may include typical metrics of raw signals (amplitude, timing, spectral power and other) that can be derived from segmented heartbeats. However, such hand-crafted feature set may not be optimal for current problem of coronary artery disease (CAD) classification. Regardless of which method is used for feature extraction, the output of this data processing stage is a vector of p elements with p<<N, where N is the size of raw signals. The feature vector can be represented either as a 1-D array of p elements or as a 2-D matrix for a classification algorithm operating on image information. There are several powerful classification algorithms that can be trained for disease detection using recorded heart sounds and the extracted feature vector. These algorithms include support vector machine (SVM), feed-forward artificial neural network (ANN) and convolutional neural network (CNN), which is particularly suitable for 2-D image classification.

Figure 67:
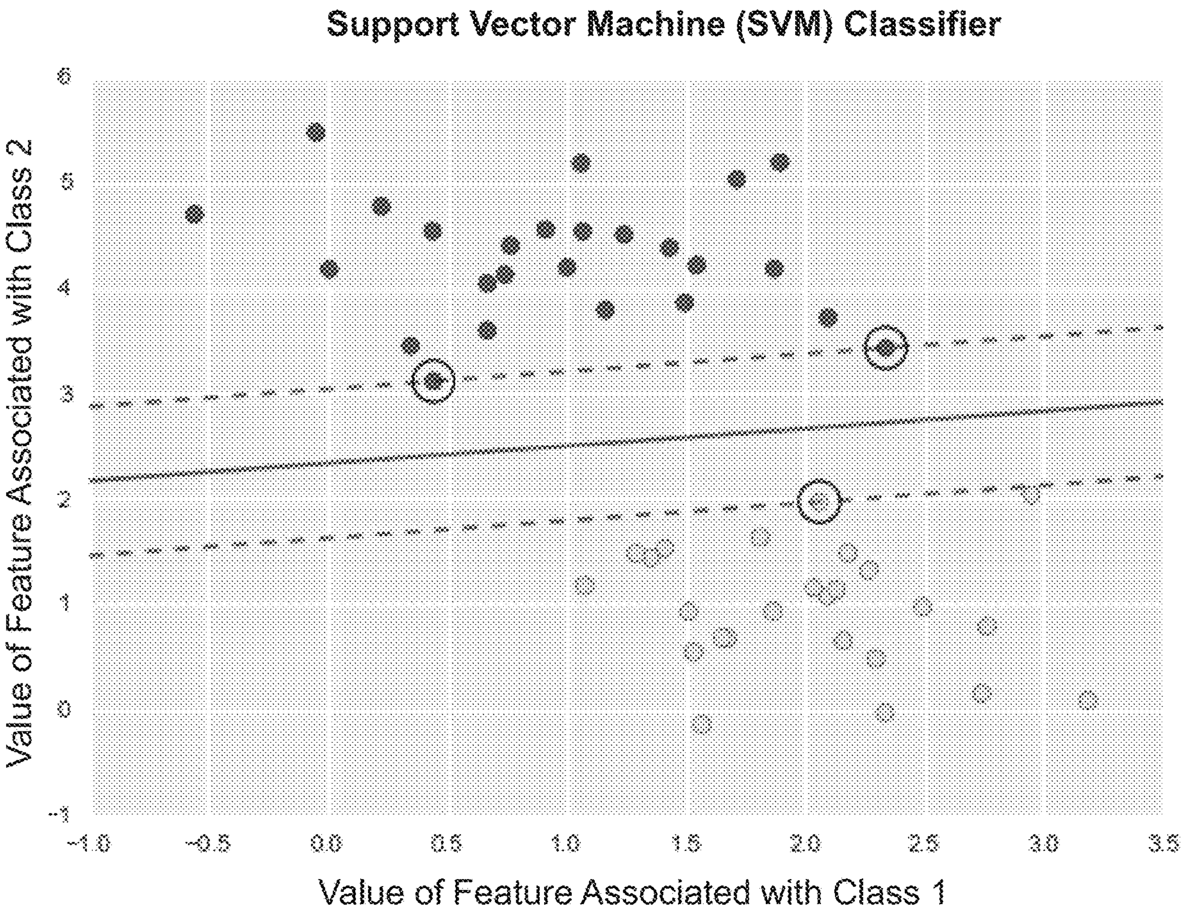
FIG. 67 illustrates a Support Vector Machine (SVM) classifier trained to distinguish two-class data samples with respect to an associated highest-margin hyperplane.

Referring to FIG. 67, a support vector machine (SVM) is a powerful supervised machine leaning algorithm frequently used for data classification problems, which has several useful properties and can operate reliably on a small data sets with poor class separation. In case of linearly separable data, the Support Vector Machine (SVM) classifier will create decision hyperplane in feature space with highest separation between two classes using training data set. For example, FIG. 67 illustrates a trained Support Vector Machine (SVM) classifier and decision boundary for a two-dimensional feature space with two classes. The support vectors are circled, and the highest margin hyperplane is shown by the solid straight line. When separation between classes is less than perfect, the tolerance of the Support Vector Machine (SVM) algorithm to data misclassification can be tuned by adjusting an associated C parameter during training. In more complicated situations, a nonlinear decision boundary can be created using a kernel function to project data into higher dimensions, with the Support Vector Machine (SVM) algorithm then applied to the modified data.

The Support Vector Machine (SVM) algorithm can be used as a coronary artery disease (CAD) classifier of data recorded by the Data Recording Application (DRA) 14, 14.1. Prior to sending data to the Support Vector Machine (SVM) algorithm, recordings are processed by beat segmentation and feature extraction stages to produce a feature vector for each test-subject 22, by preprocessing available recordings and extracting p features, with each channel of data then transformed into an n×p feature matrix. The feature vector extracted from the segmented heartbeats can be either a set of custom selected metrics (amplitude, timing of specific segment, energy, statistic parameters, sample entropy and others) or a subset of wavelet packet transformation (WPT) coefficients associated with the signal region of interest. If the resulting number of features p is still relatively high, a principal component analysis (PCA) procedure can be applied to identify a subset of features with highest variance, and then eliminate correlating features. After all preprocessing steps and data normalization, the feature matrix is split into testing and training sets with ratio 1 to 4 respectively. The training set is used to train the Support Vector Machine (SVM) and to optimize classifier hyper-parameters, while the testing set is used to evaluate classifier performance with unseen data. Computer code that provides for implementing a Support Vector Machine (SVM) classifier is available in several open source packages for Python and R programming languages, for example, the sklearn machine learning package in Python.

Figure 68:
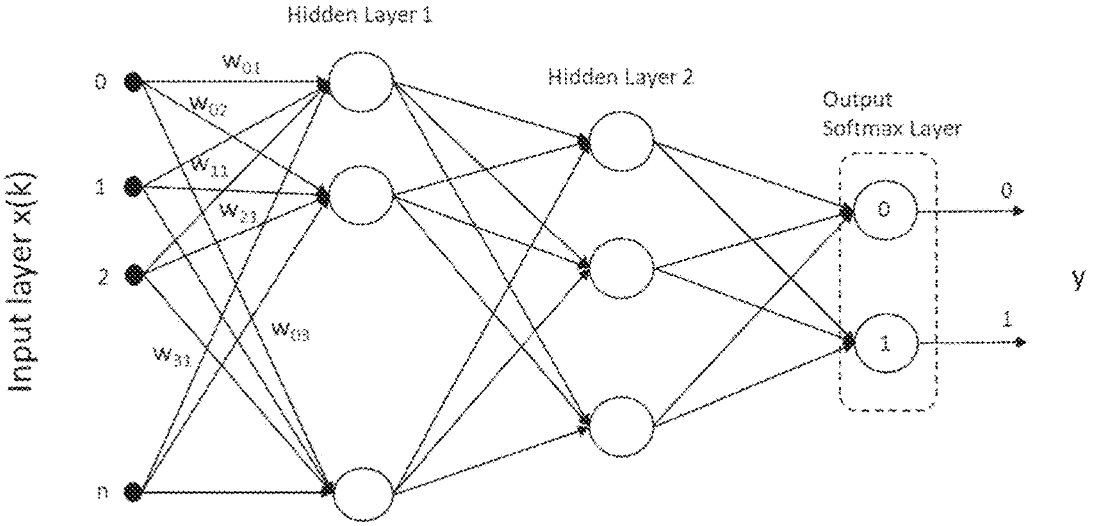
FIG. 68 illustrates a feed-forward artificial neural network for binary classification.

Referring to FIG. 68, a feed-forward artificial neural network (ANN) provides an alternative option for classification of auscultatory sound signals 16 following preprocessing and feature extraction stages. An artificial neuron is a nonlinear processing element with p inputs and a nonlinear activation function that generates an activation output. Assuming x(p) is a feature vector which is sent to the p inputs of each neuron, then the associated activation output of $i^{th}$ neuron is computed as:

$$a_i = g\left(\sum_j w_{i,j} \cdot x_j + b_i\right) \tag{32}$$

wherein $w_{ij}$ is the weight matrix that defines connection strength of $i^{th}$ neuron to $j^{th}$ input, $b_i$ is the neuron bias and $g(z=w^T x+b)$ is the associated nonlinear activation function. The specific form of the activation function g is chosen at the design stage, wherein commonly used functions include sigmoid, hyperbolic tan and rectified linear unit (ReLu). The network of interconnected neurons constitutes the artificial neural network (ANN), which can be capable of modeling relatively complicated relationships between the input vector and target class variables by adjusting weights and biases during training stage.

Properties of a specific artificial neural network (ANN) implementation are defined at the design stage and include: 1) number of hidden layers, 2) number of neurons per hidden layer, 2) type of activation function, 3) learning rate and 4) regularization method to prevent overfitting. For example, in one set of embodiments, the artificial neural network (ANN) is implemented using the open source TensorFlow deep learning framework, which provides for setting each of these parameters. The neuron connection strength is defined by the weight matrix $w_{ij}$ for each layer which is adjusted during network training, and a cost function is evaluated at each training epoch using available truth labels. The artificial neural network (ANN) training is accomplished by a standard back-propagation algorithm using a cross-entropy cost function. The network design specifics are determined by the available data, because a network with multiple hidden layers (deep ANN) can be very powerful, but also is prone to overfitting when a small data set is used. Therefore, the specific artificial neural network (ANN) architecture is developed on a trail-and-error basis, dependent upon the available data and the size of feature vector. In one set of embodiments, the output layer of the artificial neural network (ANN) for a binary classifier is implemented as a softmax function with a two-element vector, with [1, 0] for a CAD positive case and [0, 1] for a CAD negative case.

For example, in one set of embodiments, the features used as inputs to either an artificial neural network (ANN) classifier or a Support Vector Machine (SVM) classifier are selected from the following: length (time duration) of: S1, systole, S2, and diastole; ECG RR peak duration; amplitudes of S1, systole, S2, and diastole; ratios of corresponding amplitudes; and energy of spectral bands associated with S1, systole, S2 and diastole. Other features such statistics (mean, variance, skewness and kurtosis) of the parameter distributions can also be used as features for input to either an artificial neural network (ANN) classifier or a Support Vector Machine (SVM) classifier.

Figure 44:
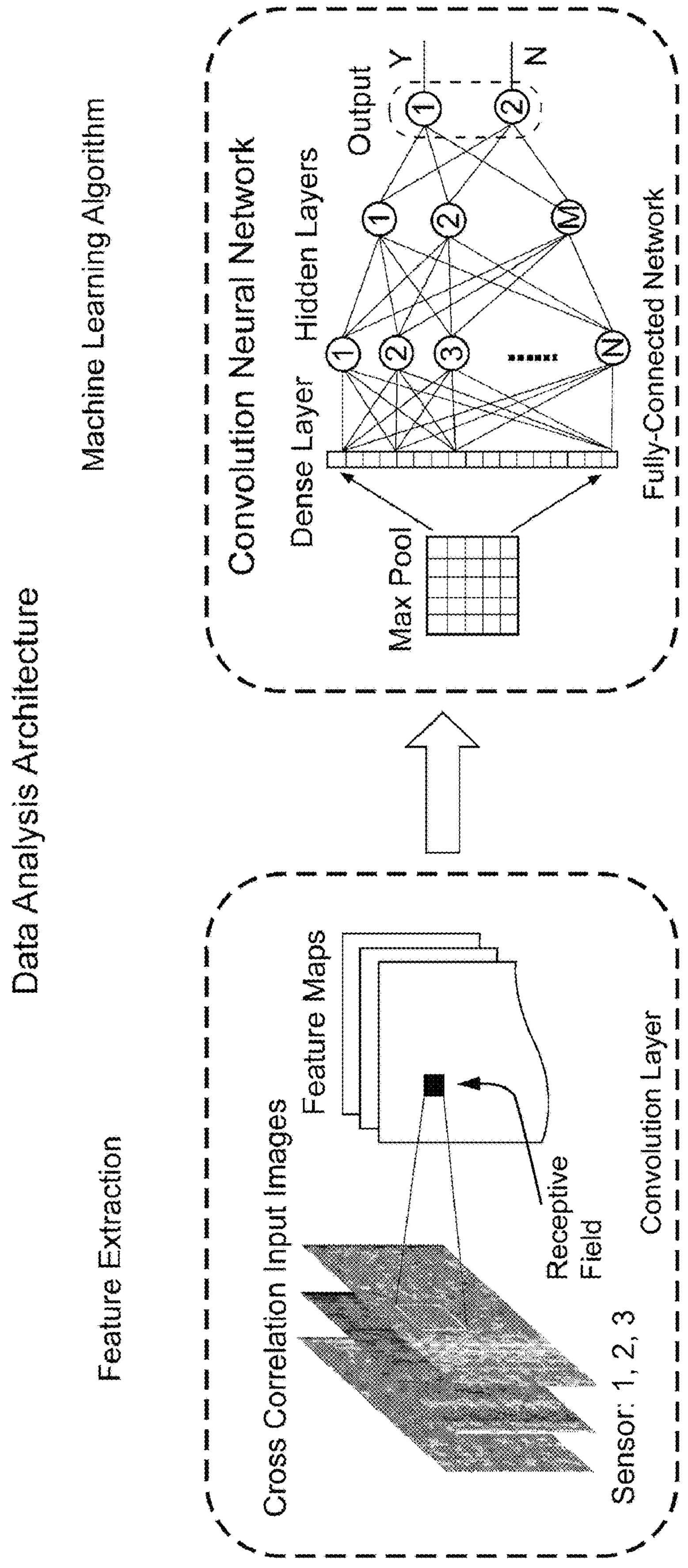
FIG. 44 illustrates a process for detecting coronary artery disease from features of cross-correlation images generated from analysis of auscultatory sound signals during diastole for a plurality of heart cycles, incorporating a Convolution Neural Network (CNN) classifier with a single convolution layer.

Referring to FIG. 44, in one set of embodiments, a convolutional neural network (CNN) is employed to analyze cross-correlation images of acoustic signals in order to provide for automating the process of acoustic feature extraction. The network input consists of the three-dimensional array of cross-correlation data recorded from the left or right positions on the thorax 20 of the test-subject 22, and combined into a single array, for example, representing three individual channels associated with three different auscultatory sound sensors 12. The convolutional neural network (CNN) comprises several convolutional layers that each use a 5×5 kernel array to scan input data to build a structure of acoustic features with increasing complexity. Neuron activation uses rectified linear unit (ReLU) nonlinearity to produce output data. The final stage of the network classifier is a fully connected neural net with an additional clinical information (age, gender, blood pressure, etc.) merged with the acoustic features identified by the convolutional neural network (CNN). The network output is a two-node layer implementing binary classification via a softmax function applied to the incoming data. The convolutional neural network (CNN) classifier is trained using 80% of all available data with binary coronary artery disease (CAD) labels (Yes=1 and No=0). The remaining 20% of the data is randomly selected to test the classifier performance. Reported performance metrics include prediction accuracy, sensitivity, specificity, negative prediction value and positive prediction value. New patient data are classified by passing through the same pre-processing stages and feeding the computed cross-correlation image to the convolutional neural network (CNN) classifier.

Convolutional neural networks (CNN) have proved to be very efficient for prediction and classification problems especially with large scale problems involving images. The typical size of input image data can be quite large, which makes application of standard feed forward networks either impractical or even impossible due to huge number of parameters to be trained. Convolutional neural networks (CNN) accommodate the size of the problem by weight sharing within small number of neurons comprising a receptive field that is scanned over the 2-D input. One benefit of using a convolutional neural network (CNN) for machine learning problems is the ability thereof to learn important features directly from data, so as to provide for bypassing the feature extraction stage that is used by support vector machine (SVM) and feed-forward artificial neural network (ANN) classifiers. A typical convolutional neural network (CNN) structure consists of one or more convolution and pooling layers that build a hierarchical structure of features with increasing complexity. Following convolution and max pooling, the extracted features are fed to a fully connected network at the final stage of convolutional neural network (CNN) classifier. For example, FIG. 44 illustrates a convolutional neural network (CNN) architecture incorporating a single convolution layer. Each cell of the max pool contains the maximum value of a corresponding array of cells in the corresponding convolution layer.

The receptive field is a relatively small 2-D array of neurons (for example, 5×5) that is scanned across the input image while performing an associated cross-correlation operation. A relatively small number of connected neurons provides for a relatively small number of corresponding weights to be adjusted. The max polling operation provides for reducing the size of the input to the associated fully-connected neural network by selecting pixels with maximum intensity from the associated convolution layer. Similar convolution and max polling operations can be performed multiple times to extract the most significant features before being submitted to an associated fully-connected neural network for classification. Although a convolutional neural network (CNN) can be trained to recognize complicated patterns in 2-D data sets, this typically requires large amount of data for efficient generalization and to avoid overfitting. The convolutional neural network (CNN) classifier can be applied either directly to the auscultatory sound signals 16 (or filtered versions thereof), or to corresponding 2-D images generated therefrom, for example, using either a continuous wavelet transform or an associated decomposition thereof by wavelet packet transformation (WPT). For example, in cooperation with the extraction of features using wavelet packet transformation (WPT), the coefficients of a $J^{th}$ level of decomposition can be transformed into a matrix with dimensions $(N/2^J)\times 2^J$, where N is the size of the time domain signal. Such 2-D data can be used to train the convolutional neural network (CNN) classifier in order to find any patterns associated with coronary artery disease (CAD). This type of network is more complicated than a standard feed-forward artificial neural network (ANN), and utilizes more hyperparameters to be tuned to achieve optimal performance. In addition to parameters applicable to an artificial neural network (ANN), the convolutional neural network (CNN) design includes specification of the number of convolution layers, the size of receptive fields (kernel size), the number of channels processed simultaneously, filter properties, and regularization. After finalization of its design, the convolutional neural network (CNN) can be trained using a training data set and then evaluated using an unseen test data set. For example, for one set of embodiments, the open-source TensorFlow flexible deep learning toolkit and API—which provide for building high-performance neural networks for variety of applications—have been used to design and train the convolutional neural network (CNN) for detecting coronary artery disease (CAD).

Figure 72:
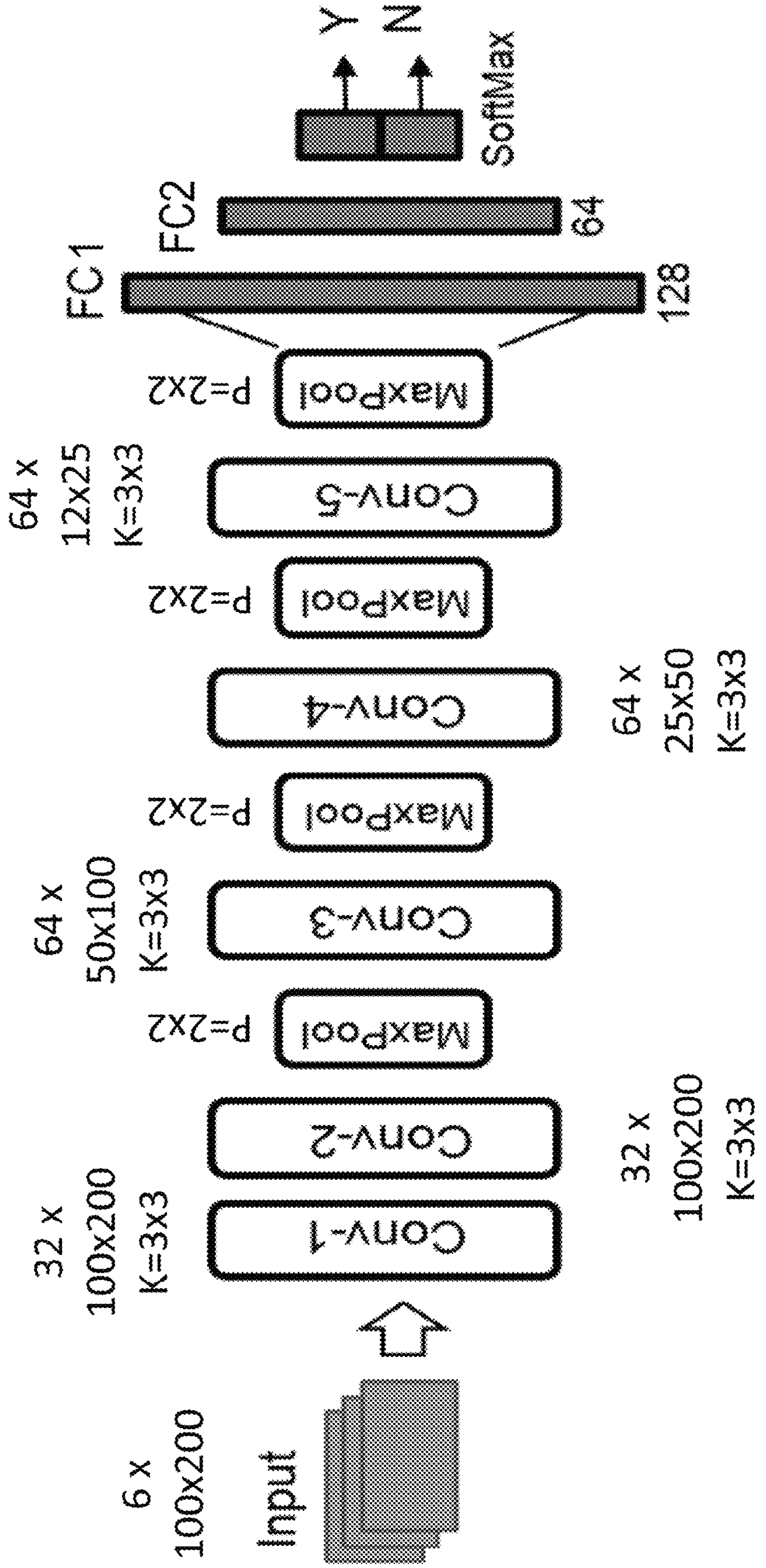
FIG. 72 illustrates a second embodiment of a Convolution Neural Network (CNN)

Referring to FIG. 72, a second embodiment of a convolutional neural network (CNN) incorporates a plurality of convolution stages (Conv-1, Conv-2, Conv-3, Conv-4 and Conv-5) that are interspersed with corresponding associated MaxPool stages, wherein the output of the final max pooling stage is fed into a first fully-connected neural network (FC1) with 128 neurons, the output of which is fed into a second fully-connected neural network (FC2) with 64 neurons, the output of which is processed by a SoftMax output operation given by:

$$\text{out}_i = \frac{e^{z_i}}{e^{z_1} + e^{z_2}} \qquad (33)$$

where $z_i = w_{ij}x_j + b_i$, $b_i$ is a bias term, and repeated indexes imply summation. The result of the classification (CAD/No CAD) is defined by the highest value of output $\text{out}_i$.

Figure 41:
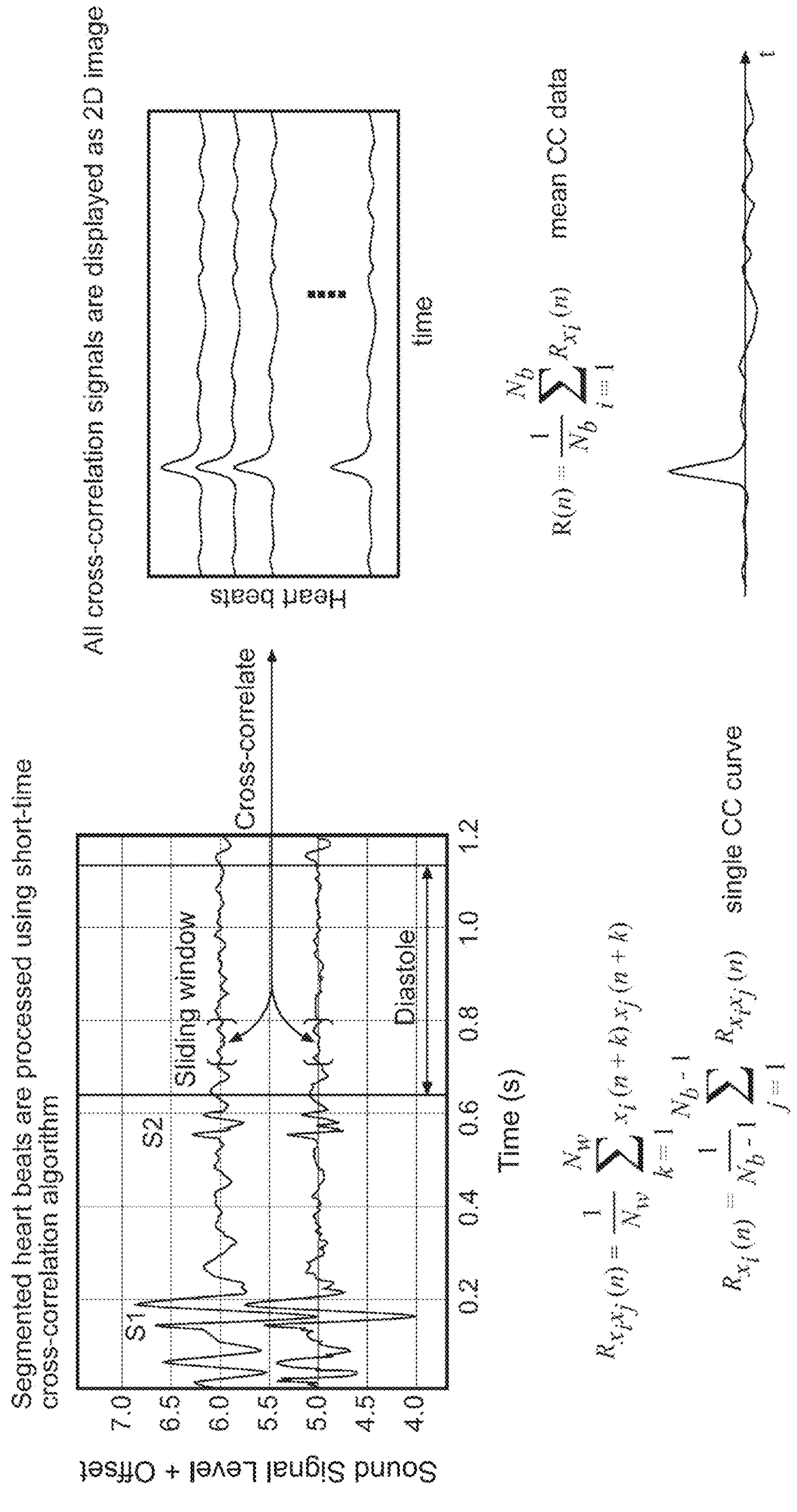
FIG. 41 illustrates a cross-correlation process.

The input to the convolutional neural network (CNN) is a series of either FIGS. 41/42-style convolution images, or a series of FIG. 43-style CWT transform images, with one image for each of the six different auscultatory sound sensors 12, with each image, for example, given by a 100 by 200 array of pixels.

Each of the convolution stages (Conv-1, Conv-2, Conv-3, Conv-4 and Conv-5) provides for convolving the array of input elements (or pixels) with an either 3×3 or 5×5 kernel or weight array, which is scanned across the input image with a stride of one pixel. If zero padding is used a single kernel generates one feature map with the same size as the original image, but with 2D convolution applied as follows:

$$y(n_1, n_1) = \sum_{k_1}\sum_{k_2} x(k_1, k_2)\cdot w(n_1 - k_1, n_2 - k_2) \qquad (34)$$

where x(k1, k2) is the input image, and w is the kernel matrix. To extract a variety of features, each convolution layer has multiple kernels that are applied to the input image. For example, in FIG. 72, each of the convolution stages (Conv-1, Conv-2, Conv-3, Conv-4 and Conv-5) is designated as P×M×N and K=L×L, wherein P is the number of different kernels that are applied, M×N is the dimension of the associated image, and L×L is the dimension of the associated kernel matrix. If zero padding is not used, the dimension of the output from the convolution stages (Conv-1, Conv-2, Conv-3, Conv-4 and Conv-5) is reduced by (L−1). Following convolution, the max pooling layer is applied, which is a simple 2×2 mask scanned across feature maps. At each position, only one pixel with the highest magnitude is selected, which is essentially a decimation operation that reduces the size of the feature map by 2 while selecting brightest pixels.

It should be understood that the convolutional neural network (CNN), artificial neural network (ANN) and Support Vector Machine (SVM) classifiers each provide an independent means of classifying the associated input features in order to determine whether or not coronary artery disease (CAD) is likely. These are alternative classification algorithms and a decision as to which one to use is typically based on their respective performances, for example, prediction accuracy. Alternatively, the different algorithms could be combined to make a single prediction, for example, using either a voting scheme or a weighted sum of likelihoods.

The auscultatory coronary-artery-disease detection system 10 can present various views of the acoustic data (both unprocessed and processed) that was captured during the test for review by a clinician. By reviewing different visualizations of the test results, the clinician may strengthen their case for a particular diagnosis, either in agreement with, or disagreement with, the result produced by the system. Additionally, particular visualizations may help reassure the patient that the diagnosis is the correct one.

Figure 45:
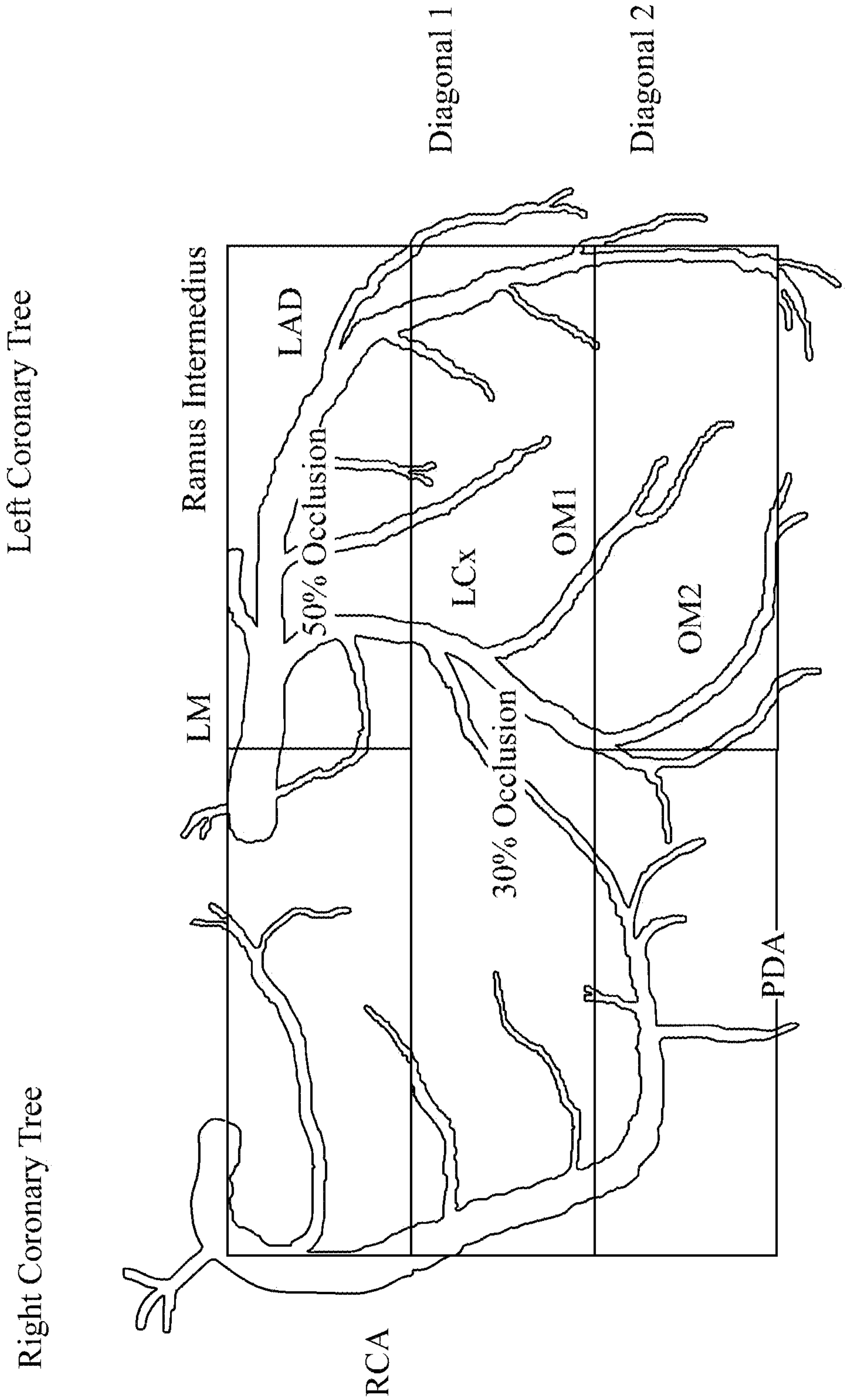
FIG. 45 illustrates a display of results in a heart/arteries view and textual view.

Referring to FIG. 45, the system presents a heart/arteries view comprising a graphical representation of the heart and coronary artery tree, highlighting the data in accordance with a Textual View. By selecting any of the occlusions, the clinician is presented with the option to highlight the blockage in either: a Stacked Heartbeat View; a Bruit Identification View (either mode); a Bruit Analysis View; or a Receiver Operating Characteristic Curve. For example, FIG. 45 illustrates test results showing severity of obstructions and zonal location of each obstruction within coronary artery tree. The tree diagram also indicates which arteries are critical, and which are not, with associated color coding in accordance with the amount of occlusion, for example, with the illustrated region of 50% occlusion highlighted in a reddish hue, and the region of 30% occlusion highlighted in a yellowish hue.

In accordance with the Textual View, the system presents, in a textual manner, the system's interpretation of the acoustic data, including: whether or not the patient has a clinical level of coronary artery disease (CAD); the count of obstructions detected, for each obstruction: the location (zone) of the obstruction; the percentage occlusion of the obstruction; or the type of blockage (soft plaque, hard plaque). For each of the items in the view listed above, the system provides for presenting an associated confidence level, which indicates how confident the system is of each specific element of information presented, or, based on the patient's demographic data (age, sex, BMI, medical and family history), the percentage of other patients who have a similar count, severity, and position of obstructions. From this view, the clinician may switch to any other view listed in this document for more information.

Figure 46A:
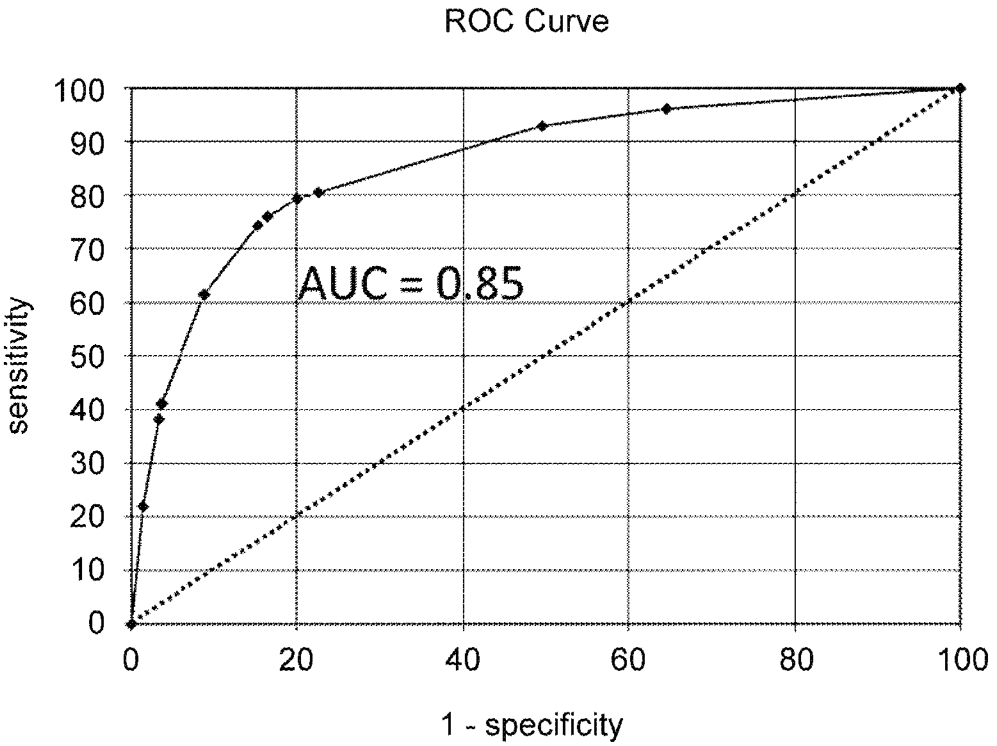
FIG. 46*a* illustrates a display of a Receiver Operating Characteristic (ROC) curve.

Referring to FIG. 46*a*, the system presents a Receiver Operating Characteristic (ROC) curve to highlight the system's coronary artery disease (CAD) detection algorithm sensitivity as a function of its false positive rate (1-specificity). The graph's attributes will be as is standard for ROC curves-vertical axis representing sensitivity, horizontal axis representing the false positive rate, with a 45-degree dotted line representing a "coin flip" test (AUC=0.5).

On this graph, the system will plot the ROC curve and calculate the Area Under the Curve (AUC) based on the patient's demographics, and the system's clinical trial results. The coordinate that corresponds to the current positivity criterion will be highlighted. The clinician will be able to display a modified graph if they command the system to exclude specific parts of the patient's demographic data. The graph may, or may not, contain gridlines and/or data points defining the ROC curve, and it may or may not fill in the AUC.

Figure 46B:
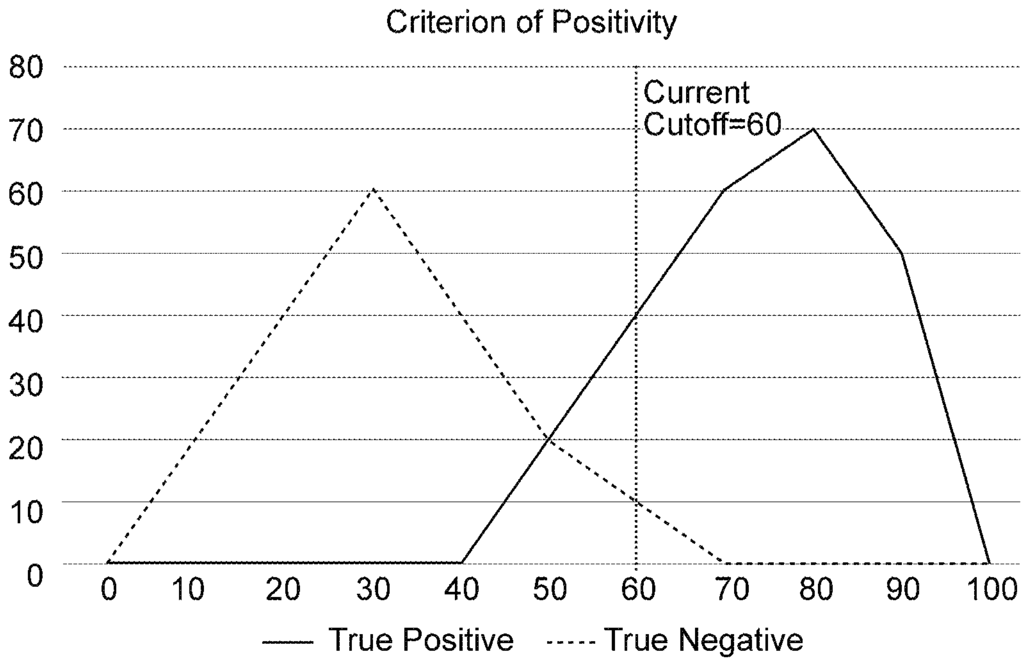
FIG. 46*b* illustrates line graph display of true positives, true negatives, false negatives, and false positives.

Alternatively, referring to FIG. 46*b*, the data may be visualized as a line graph (with or without underfill), where true positives, true negatives, false negatives, and false positives are displayed, with a line indicating the currently-used cutoff value.

Referring to FIGS. 47 through 53, the system provides for visualizing the acoustic data resulting from an analysis of the breath-held auscultatory sound signals 16.1 from the auscultatory sound sensors 12.

Figure 47:
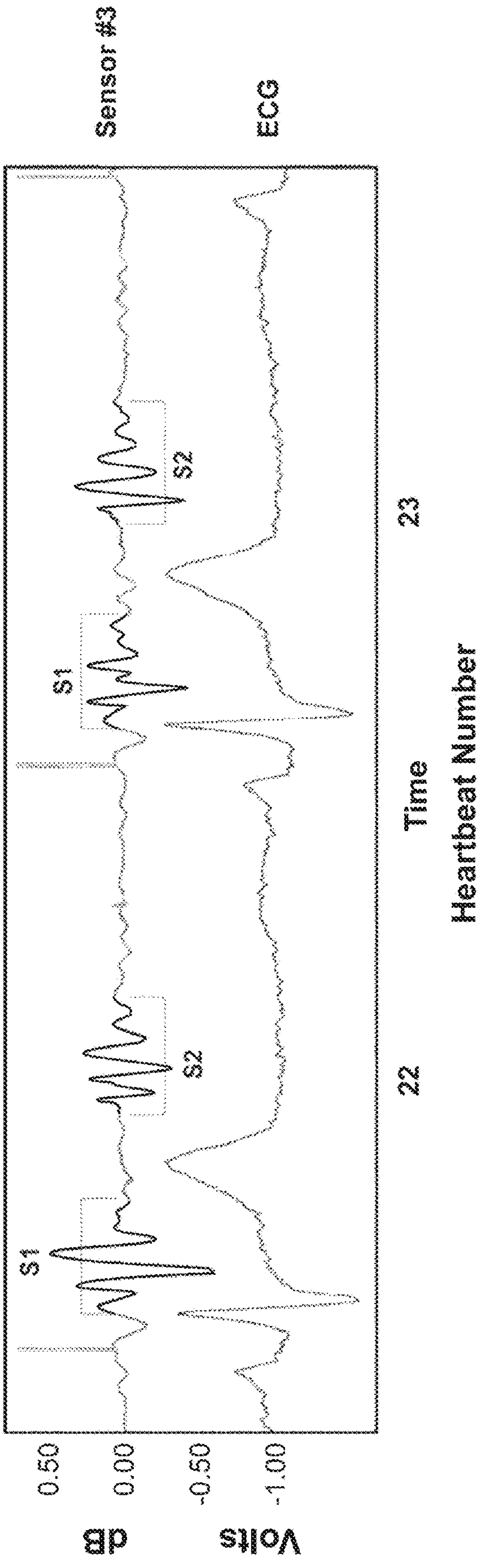
FIG. 47 illustrates a display of a Heartbeat View comprising a graphical plot of the systolic and diastolic intervals of each heartbeat captured.

Referring to FIG. 47, the system presents a heartbeat view comprising a graphical plot of the systolic and diastolic intervals of each heartbeat captured. The horizontal axis of the graph represents captured heartbeats. This representation is a subset of the acoustic capture time, as some acoustic data acquired is discarded (poor quality, etc.) during the system's analysis process. The duration of the S1 and S2 sounds are also highlighted on this axis.

Generally the vertical axis may comprise acoustic data captured from each of the system's sensors—both acoustic and ECG. A correlation procedure is performed to ensure that the data captured from each of the system's sensors is aligned to one another. Because the initial display of this view may contain many dozens of heartbeats, the clinician has the option to highlight a subset of the data on the horizontal axis, and command the system to zoom into the selected section. In this way, the clinician can perform a deeper analysis on one or more sections of the acoustic capture data as they so choose, and explore any discrepancies between the data captured by the ECG and acoustic sensors for any particular heartbeat. For example, FIG. 47 illustrates an example of the Heartbeat View wherein the acoustic view has been limited by the clinician to Sensor #3 only, and zoomed in to see only 2 heartbeats, with the ECG data also displayed.

Figure 48:
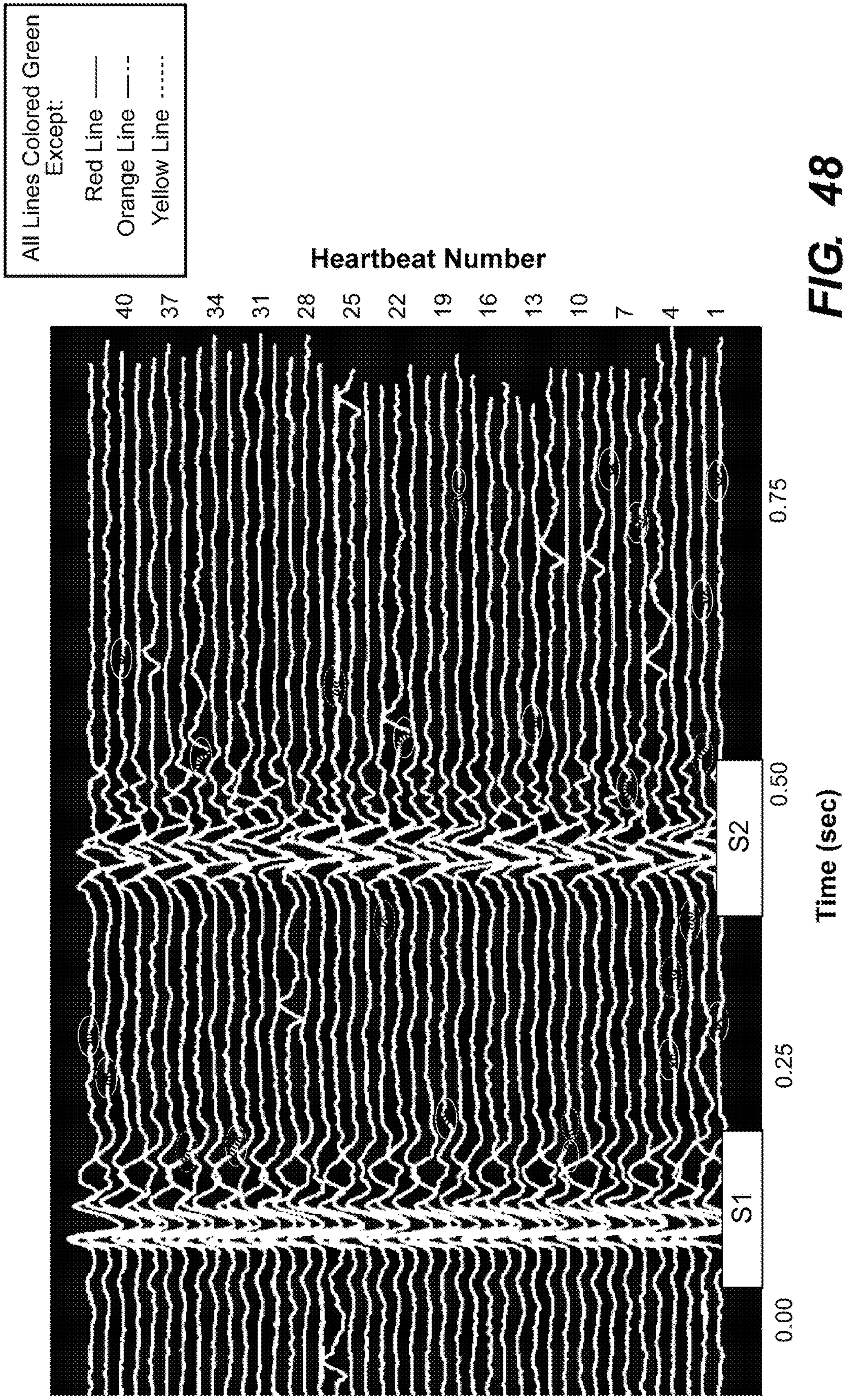
FIG. 48 illustrates a display of a Stacked Heartbeat View.

Referring to FIG. 48, in accordance with a Stacked Heartbeat View, the system presents a graphical plot of the systolic and diastolic intervals of each heartbeat captured. The horizontal axis of the graph represents time (in seconds or milliseconds) from the beginning of the systolic interval to the end of the diastolic interval. The duration of the S1 and S2 sounds are highlighted on this axis. The vertical axis is comprised of the acoustic data captured for each of the heartbeats, in either ascending or descending order of capture, where each heartbeat is itself a graph, with a vertical axis representing intensity. A correlation procedure is performed to ensure that the start of the systolic interval for each heartbeat is aligned on x-axis=0. For each heartbeat, the system highlights any unexpected acoustic signals captured, as such signals may be an indication of an obstruction or other cardiac condition. For example, in FIG. 48, unexpected acoustic signals are highlighted in red. The clinician has the option to highlight a subset of the data on the horizontal axis, and command the system to zoom into the selected section. In this way, the clinician can perform a deeper analysis on one or more sections of the acoustic capture data as they so choose, especially so that they may explore more deeply any unexpected acoustic signals.

Figure 49:
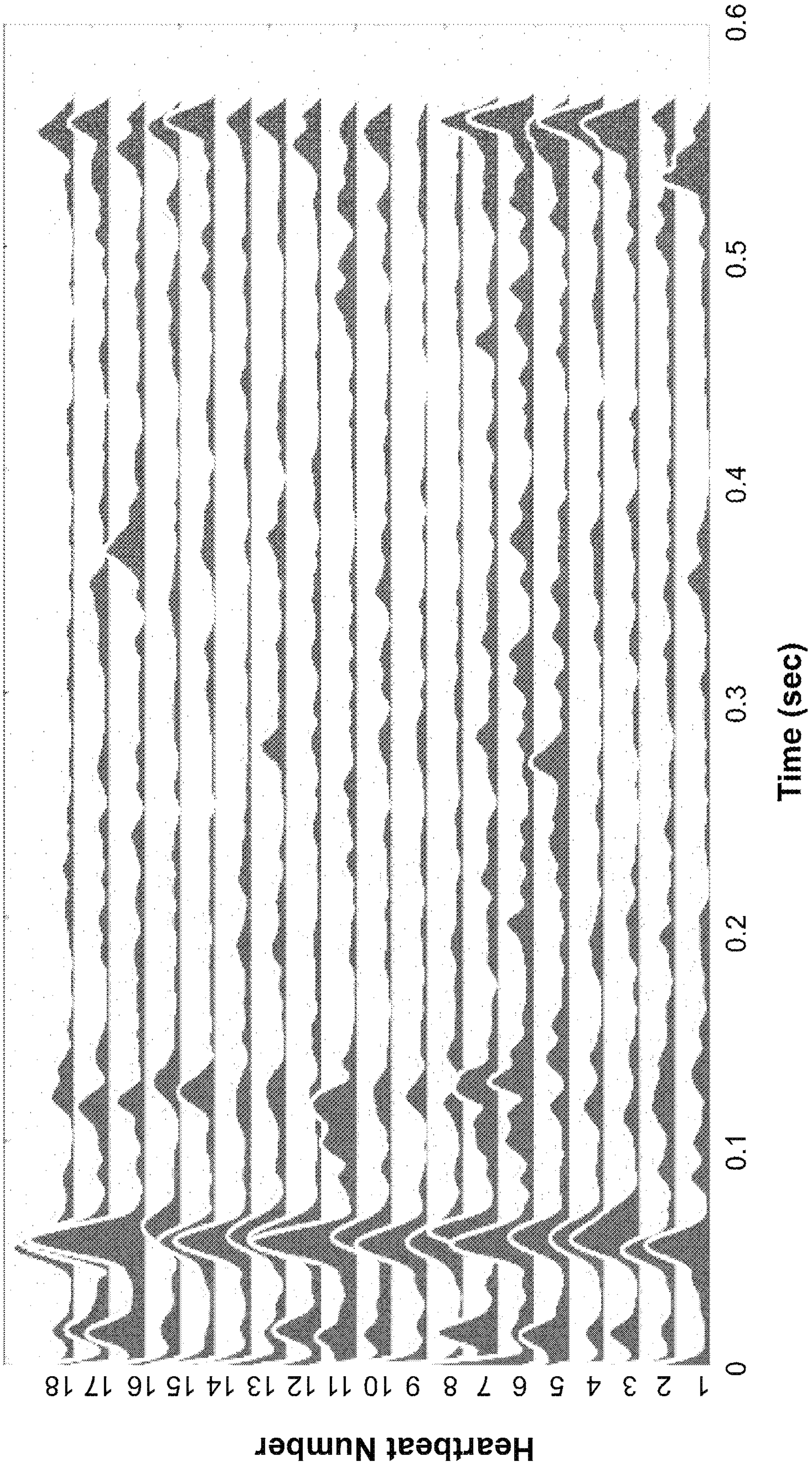
FIG. 49 illustrates a Bruit Identification View in a Line Graphs with Underfill mode.

Referring to FIG. 49, in accordance with a Bruit Identification View in a Line Graphs with Underfill mode, the system presents a graphical plot of unexpected acoustic signals captured during the diastolic interval by means of a line graph with underfill. The horizontal axis of the graph represents time (in seconds or milliseconds) from the beginning of the diastolic interval to the end of the diastolic interval. The duration of the S2 sound is also highlighted on this axis. The vertical axis is comprised of the acoustic data captured for each of the heartbeats, in either ascending or descending order of capture, where each heartbeat is itself a graph, with a vertical axis representing intensity. A correlation procedure is performed to ensure that the start of the diastolic interval for each heartbeat is aligned on x-axis=0. An underfill is used to visually highlight deviation from the baseline.

For each heartbeat diastole displayed, the system highlights any unexpected acoustic signals captured, as such signals may be an indication of an obstruction or other cardiac condition. Such signals are highlighted by the height of the line graph, which represents intensity. These highlighted areas on the graph allow a clinician to distinguish low-energy noise (which may or may not be a sign of non-obstructive coronary artery disease (CAD)) from high-energy noise (which is a likely indicator of obstructive coronary artery disease (CAD)). In this view, it is also easy for a clinician to understand the correlation (across heartbeats) of noise, as well as the number and timing of correlated instances of noise (which may indicate the number and location of blockages, respectively). For example, the data illustrated in FIG. 49 exhibits relatively high intensity noise in many heartbeats at approximately t=0.05 seconds into diastole.

The clinician has the option to highlight a subset of the data on the horizontal axis, and command the system to zoom into the selected section. In this way, the clinician can perform a deeper analysis on one or more sections of the acoustic capture data as they so choose, especially so that they may explore more deeply any unexpected acoustic signals.

Figure 50:
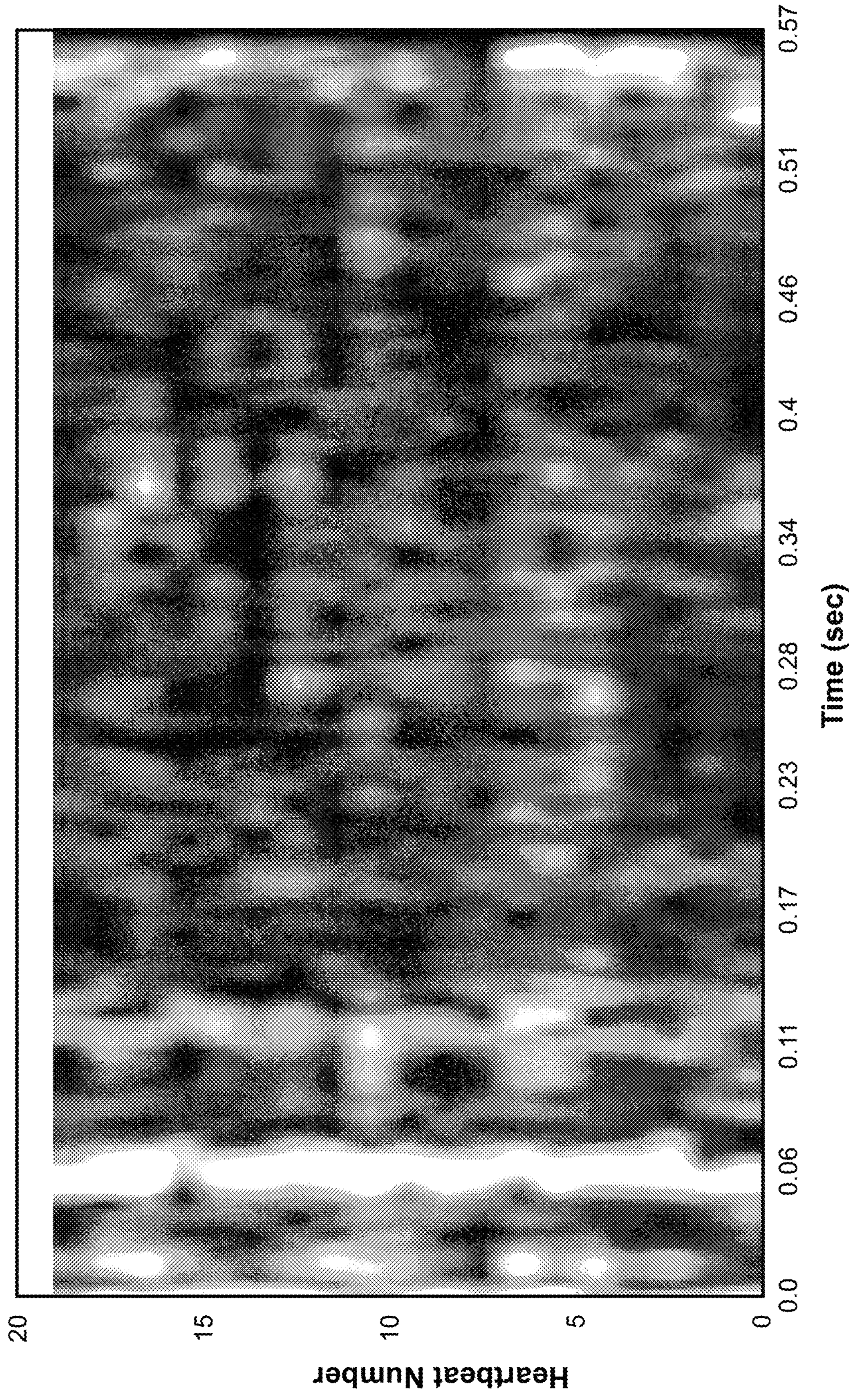
FIG. 50 illustrates a display of a Bruit Identification View in a Spectrogram mode.

Referring to FIG. 50, in accordance with a Bruit Identification View in a Spectrogram mode, the system presents a graphical plot of unexpected acoustic signals captured during the diastolic interval by means of a spectrogram. The horizontal axis of the graph represents time (in seconds or milliseconds) from the beginning of the diastolic interval to the end of the diastolic interval. The duration of the S2 sound is also highlighted on this axis. The vertical axis is comprised of the acoustic data captured for each of the heartbeats, in either ascending or descending order of capture. A correlation procedure is performed to ensure that the start of the diastolic interval for each heartbeat is aligned on x-axis=0.

For each heartbeat diastole displayed, the system highlights any unexpected acoustic signals captured, as such signals may be an indication of an obstruction or other cardiac condition. Such highlighted areas indicate the intensity of the unexpected signal. Highlights are in the form of color, which indicate varying intensity of the signal. This view could alternatively be represented in monochrome as a contour plot. For example, the data illustrated in FIG. 50 exhibits relatively high intensity noise in many heartbeats at approximately t=0.05 seconds into diastole.

These highlighted areas on the graph allow a clinician to distinguish low-energy noise (which may or may not be a sign of non-obstructive coronary artery disease (CAD)) from high-energy noise (which is a likely indicator of obstructive coronary artery disease (CAD)). In this view, it is also easy for a clinician to understand the correlation (across heartbeats) of noise, as well as the number and timing of correlated instances of noise (which may indicate the number and location of blockages, respectively).

The clinician has the option to highlight a subset of the data on the horizontal axis, and command the system to zoom into the selected section. In this way, the clinician can perform a deeper analysis on one or more sections of the acoustic capture data as they so choose, especially so that they may explore more deeply any unexpected acoustic signals.

Figure 51:
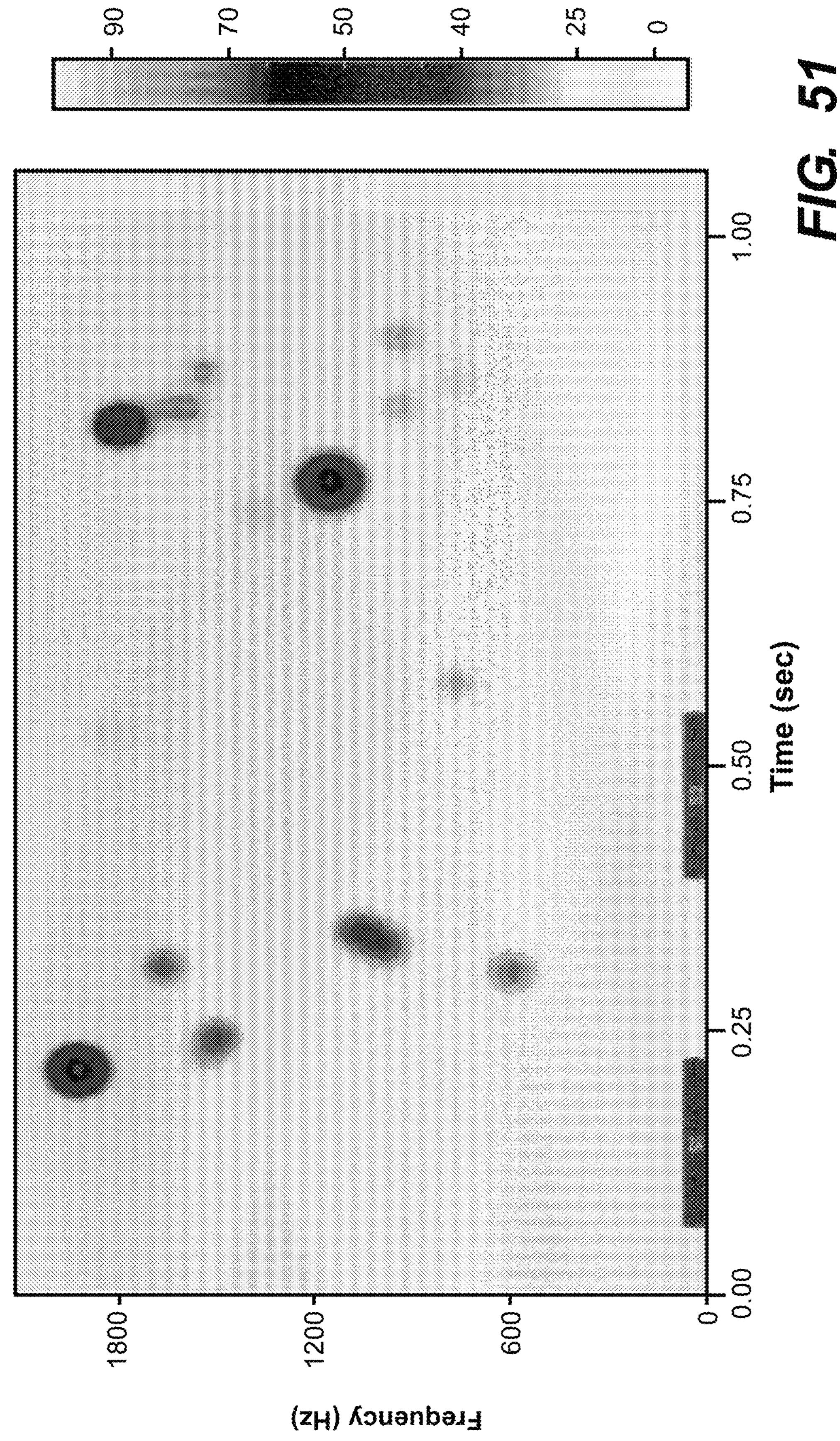
FIG. 51 illustrates a display of a Bruit Analysis View.

Referring to FIG. 51, in accordance with a Bruit Analysis View, the system presents a graphical time/frequency plot of unexpected acoustic signals captured. The horizontal axis of the graph represents time (in seconds or milliseconds) from the beginning of the systolic interval to the end of the diastolic interval. The duration of the S1 and S2 sounds are highlighted on this axis. The vertical axis represents the frequency (in Hz or kHz) of any unexpected acoustic signals, averaged from all captured data. For each unexpected acoustic signal captured, the color on the graph represents the intensity of that signal. Alternatively, the graph could be represented in monochrome as a contour plot.

These highlighted areas on the graph allow a clinician to distinguish low-energy noise (which may or may not be a sign of non-obstructive coronary artery disease (CAD)) from high-energy noise (which is a likely indicator of obstructive coronary artery disease (CAD)). It is also easy for a clinician to understand the frequency of high-energy noise, as well as the timing of this noise—this is important as different cardiac conditions may be defined by specific frequencies and timings of noise. For example, the data illustrated in FIG. 51 exhibits relatively high intensity noises at approximately t=0.25, 0.75 and 0.8 seconds into the heartbeat.

The system provides a User Interface, and associated navigation, is designed for use on tablets and smartphones, and thus uses common touch-screen user interface paradigms. For example, two fingers moving apart from one another can be used to zoom in to any area on any graph, and two fingers moving together can be used to zoom out. A single finger can be used to highlight any areas on the horizontal axis, and the graph can be zoomed in to that highlighted area by touching a button.

Touching any area of the graph provides information to the user (either in a pop-up window or beside/below the graph) on the values of the horizontal and vertical axes at that point, as well as the "height" information of that point if available (e.g. in the Matrix View). For example, in Stacked Heartbeat View, touching on an individual heartbeat would cause the system to provide the heartbeat number, the maximum intensity of that heartbeat (and the time on the horizontal axis at which the maximum intensity occurs), and the time on the horizontal axis corresponding to the touch. In the case of the Matrix View, touching on any area of the graph would cause the system to provide the frequency, time, and intensity corresponding to the coordinate on the graph that was touched.

For use with a mouse, the user interface paradigms are similar, except with zoom. In this case, zoom can be accomplished through a common desktop/laptop user interface paradigm, such as dedicated zoom in/out buttons in the UI, or mouse wheel scrolling.

For some of these graphs, it is possible to restrict the display of data to some subset of the acoustic sensors (for example, as illustrated in FIG. 47), to combine acoustic data from all sensors (the default mode), or to display data from each sensor individually. This may be helpful to clinicians who want to spatially localize any unexpected acoustic signals. This capability is relevant to the Stacked Heartbeat View, the Bruit Identification View (both modes), and the Bruit Analysis View.

The following features of sound propagation within the body provide for the localization of acoustic sources based upon the relative strengths of the associated acoustic signals from different auscultatory sound sensors 12. First, any sound feature that originates from the heart, acts as a single source for all auscultatory sound sensors 12. For example, the characteristic sound that the heart makes, dub-blub, acts like two sounds coming from two separate locations. Second, for practical purposes, sound travels fast enough in the body that all auscultatory sound sensors 12 would effectively receive each sound individually at substantially the same time. Third, the farther a sound's origin is from an auscultatory sound sensor 12, the weaker that sound will be when received by that auscultatory sound sensor 12. This is due to the sound energy being dissipated as it travels through the body. In view of these features, using the relative signal strengths from different auscultatory sound sensors 12, the location of the sound source can be triangulated from the locations of the auscultatory sound sensors 12 with the three largest signal strengths, weighted by the relative strengths of those signals, with the resulting calculated location of the sound source being relatively closer to auscultatory sound sensors 12 with relatively stronger signals than to auscultatory sound sensors 12 with relatively weaker signals.

Figure 69:
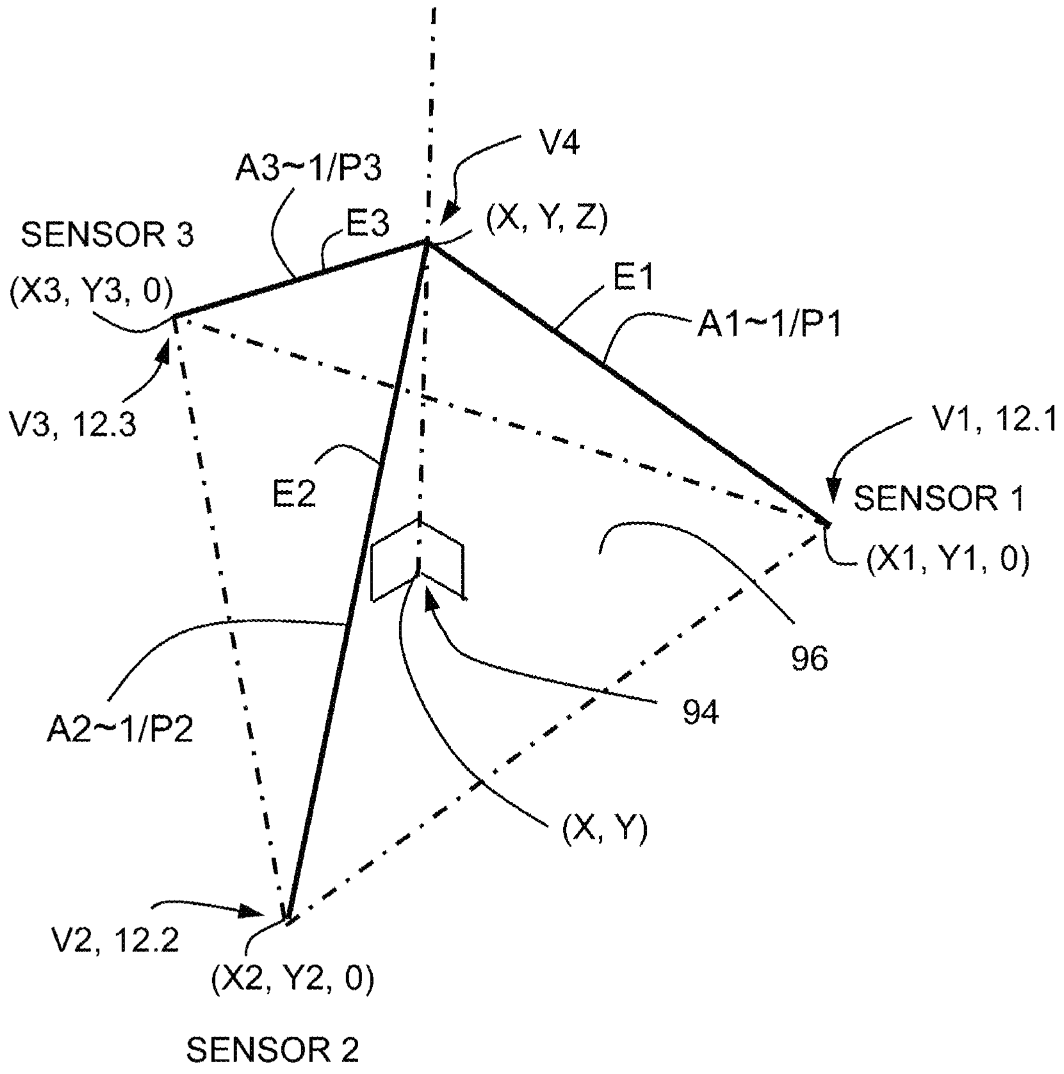
FIG. 69 illustrates a geometric construction that provides for determining a projected transverse location of an acoustic source with respect to a plane containing three auscultatory sound sensors.

More particularly, referring to FIG. 69, in accordance with one method of localizing the sound source 94 of an auscultatory sound signal 16 based upon associated respective signal strengths P1, P2 and P3 of respective first 12.1, second 12.2 and third 12.3 auscultatory sound sensors that are assumed to be located in Cartesian space on an X-Y plane 96 at respective predetermined sensor locations (X1, Y1), (X2, Y2) and (X3, Y3), at Z=0. Assuming that the distance from each of the auscultatory sound sensors 12.1, 12.2, 12.3 is inversely related to the corresponding associated signal strengths P1, P2 and P3, the corresponding lengths A1, A2, A3 of corresponding edges E1, E2, E3 of an associated tetrahedral solid 98 are assumed to be inversely related to the corresponding associated signal strength P1, P2, P3 of the auscultatory sound sensors 12.1, 12.2, 12.3 located at a corresponding vertices V1, V2, V3 of the tetrahedral solid 98 to which the corresponding edge E1, E2, E3 is connected. Other than being sufficiently long to meet at a fourth vertex V4 of the tetrahedral solid 98 at location (X, Y, Z), the lengths A1, A2, A3 of the edges E1, E2, E3 are otherwise arbitrary, although relatively shorter lengths provide for less geometric dilution of precision (GDOP) of the ultimate determination of the lateral, (X, Y) location of the fourth vertex V4 than to relatively longer lengths. In view of the lateral (X, Y) location of the sound source 94 on the X-Y plane 96 being the same as the lateral (X, Y) location of the fourth vertex V4, the lateral (X, Y) location of the sound source 94 may be determined by solving the following system of three equations in three unknowns (X, Y, Z) for the location (X, Y, Z) of the fourth vertex V4:

$$(X-X1)^2+(Y-Y1)^2+Z^2=A1^2 \tag{35}$$

$$(X-X2)^2+(Y-Y2)^2+Z^2=A2^2 \tag{36}$$

$$(X-X3)^2+(Y-Y3)^2+Z^2=A3^2 \tag{37}$$

Following the solution of equations (35-37), the resulting lateral (X, Y) location of the sound source 94 may then be displayed, for example, as a location on a silhouette of a torso, or transformed to a corresponding location on the image of the heart illustrated in FIG. 45.

Figure 52:
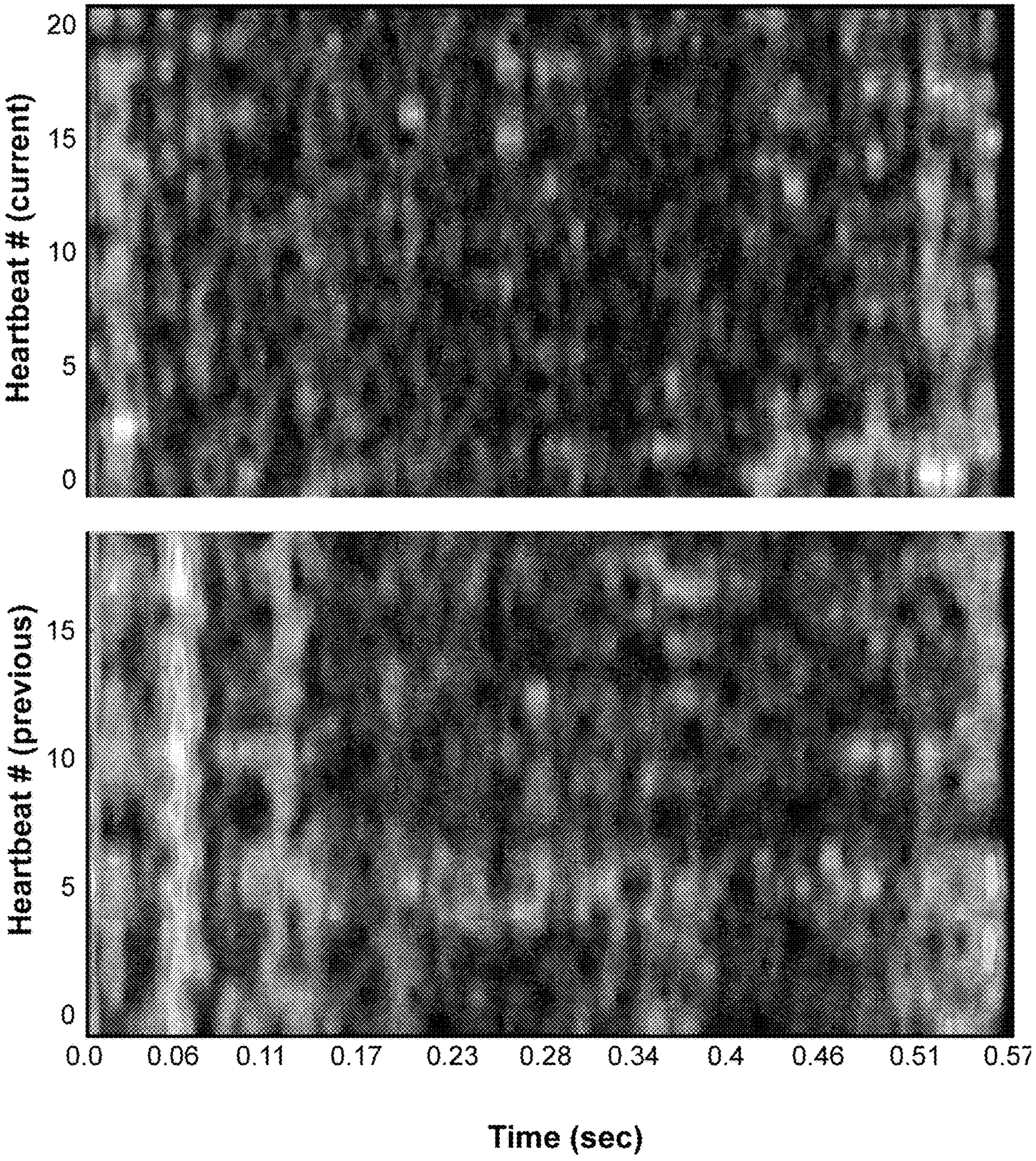
FIG. 52 illustrates a comparison of a current test with a previous test, using the Bruit Identification View, Spectrogram mode, to confirm success of PCI.
Figure 53:
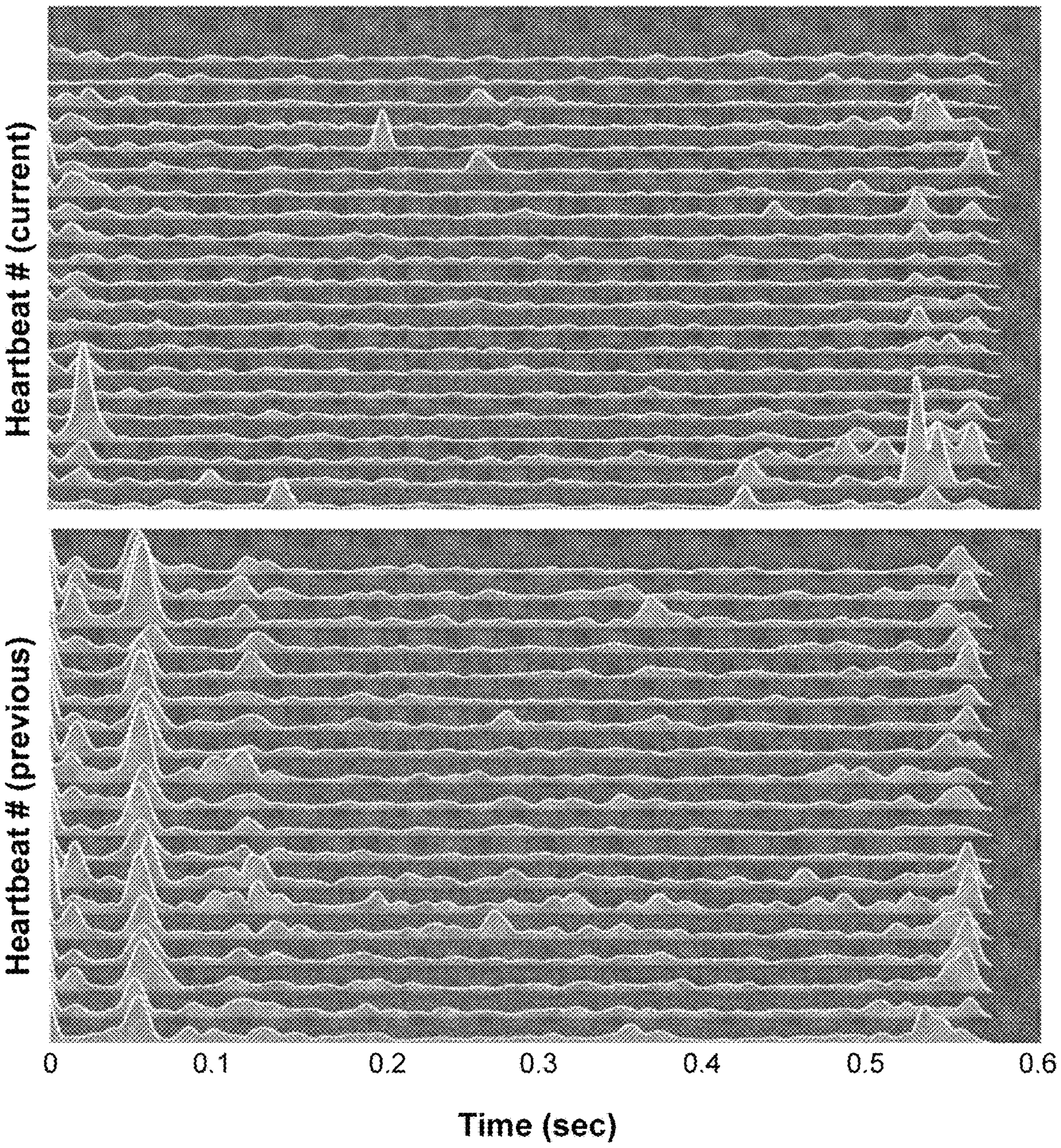
FIG. 53 illustrates a comparison of a current test with a previous test, using the Bruit Identification View, Line Graph with Underfill mode, to confirm success of PCI.

For some of these graphs, it is possible for the user to directly compare the results of the current test with one or more previous tests. This can be done by simply placing the graphs side-by-side (for example, as illustrated in FIGS. 52 and 53), or by overlaying them on-top of one other, with some variable transparency or color variation so that the clinician can distinguish data from one test versus another. In the case where the graphs are placed on top of one another, the system could fade in to one graph and out from the other slowly, repeatedly in a loop (almost like a video file), so that the clinician can easily see the differences in the processed data between one test and the other. Alternatively, if the graphs are placed on top of one another, a subtraction operation could be performed to highlight only the differences between the two graphs (e.g. red for increase in noise from previous test result, green for decrease). For example, FIG. 52 illustrates a comparison of a current test with a previous test, using the Bruit Identification View, Spectrogram mode, to confirm success of PCI. Similarly, as another example, FIG. 53 illustrates a comparison of a current test with a previous test, using the Bruit Identification View, Line Graph with Underfill mode, to confirm success of PCI.

The ability to compare the current test with a previous test is critical to the clinicians understanding of the progression of a particular cardiovascular condition (either worsening, or improved as in the case of a PCI procedure). This capability is relevant to the Stacked Heartbeat View, the Bruit Identification View (both modes), and the Bruit Analysis View.

The graphs may be rendered locally or remotely (server-based) or both, depending on the capabilities desired by the clinician and the organization to which they belong. In most use cases (tablet, phone, desktop, or laptop), the graph rendering will be done locally, either through a web-browser (full or embedded) on the client, or through a graphics library optimized for each specific supported client platform.

In other cases, the rendering may be done on the server side-graphs may be generated and exported to JPEG (or other similar) format so that they can be emailed or sent via instant message to interested parties.

Figure 77:
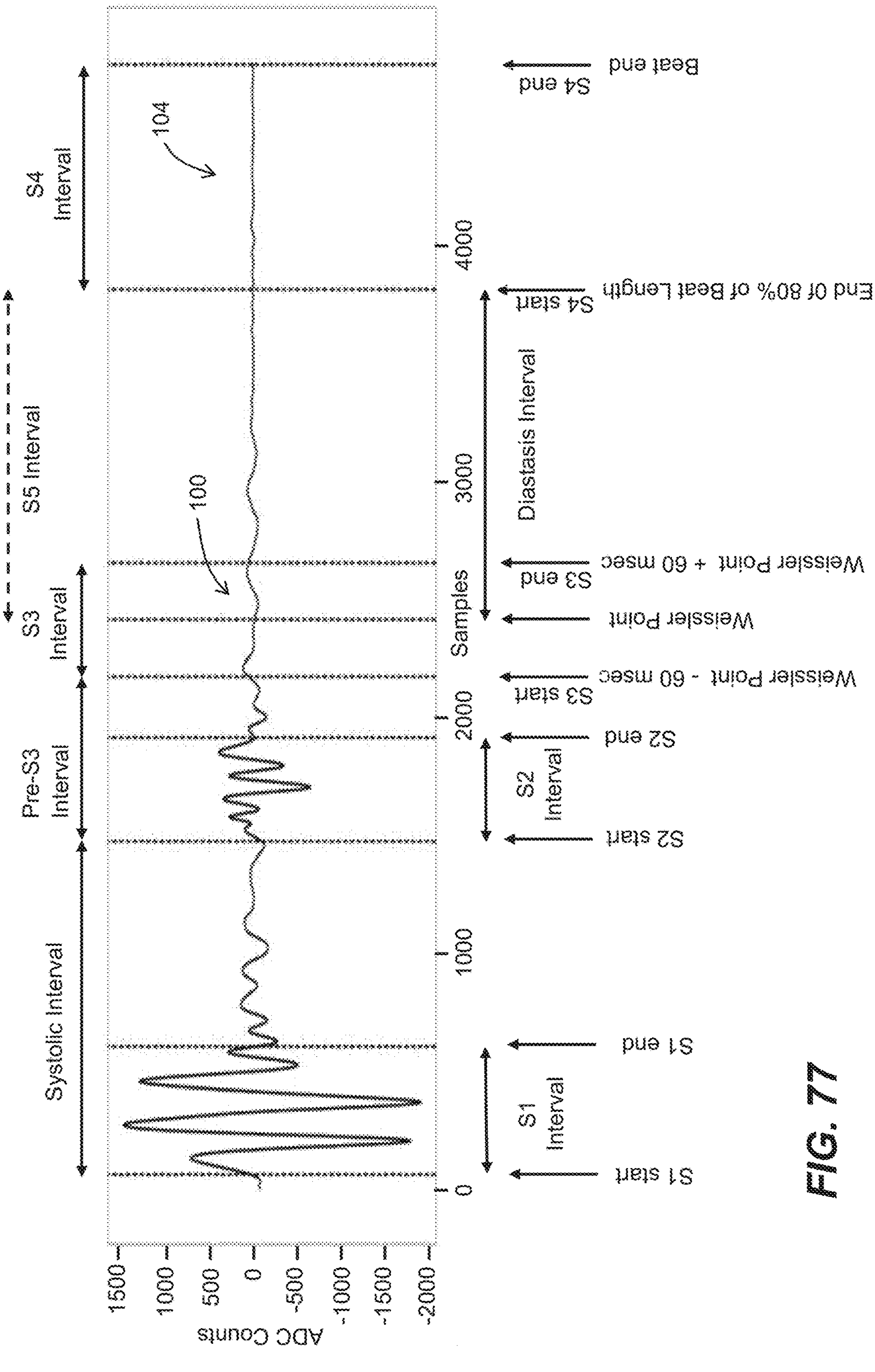
FIG. 77 illustrates an auscultatory sound signal associated with heart sounds of a single heart cycle, further illustrating locations of associated S1, S2, S3, S4 and S5 sounds, the Weissler point used as a basis for identifying an associate region of diastasis, and associated intervals.

Referring to FIG. 77, an auscultatory sound signal 16 associated with a heart sound from a single heart cycle may be subdivided into intervals associated with the S1, S2, S3 and S4 heart sounds, and other intervals, as follows:

1) The S1 interval is associated with the first heart sound, S1, resulting from the closure of the mitral and tricuspid valves, extends between S1_start and S1_end, wherein S1_start is assumed to be proximally coincident with the peak of the ECG R-wave at time 0 of the heart cycle, and S1_end is assumed to be in accordance with the above-described heart-cycle segmentation and heart-phase identification process 2300 illustrated in FIG. 23 et seq, i.e. $t(k_{S1\_END})$;
2) The S2 interval is associated with the second heart sound, S2, resulting from the closure of the aortic and pulmonary valves, extends between S2_start and S2_end, wherein S2_start and S2_end are assumed to be in accordance with the above-described heart-cycle segmentation and heart-phase identification process 2300 illustrated in FIG. 23 et seq, i.e. $t(k_{S2\_START})$ and $t(k_{S2\_END})$;
3) The S3 interval is associated with a third heart sound, S3—an extra heart sound present in some people, but rarely,—that extends between S3_start and S3_end, wherein, in accordance with one set of embodiments, S3_start is assumed to be 60 milliseconds prior to the Weissler point defined hereinabove by equation (14), and S3_end is assumed to be 60 milliseconds after the Weissler point;
4) The S4 interval is associated with a fourth heart sound, S4—an extra heart sound present in some people, but rarely,—that extends between S4_start and S4_end, wherein, in accordance with one set of embodiments, S4_start is assumed to be at 80% of the beat length, and S4_end is assumed to be at the beginning of the next heart cycle 82;
5) The systolic interval is associated with the contraction of the myocardium of the left and right atria after refilling with blood, that extends between S1_start and S2_start;
6) The pre-S3 interval that extends between S2_start to S3_start; and
7) The diastasis interval that extends between the Weissler point and S4_start.

Figure 78:
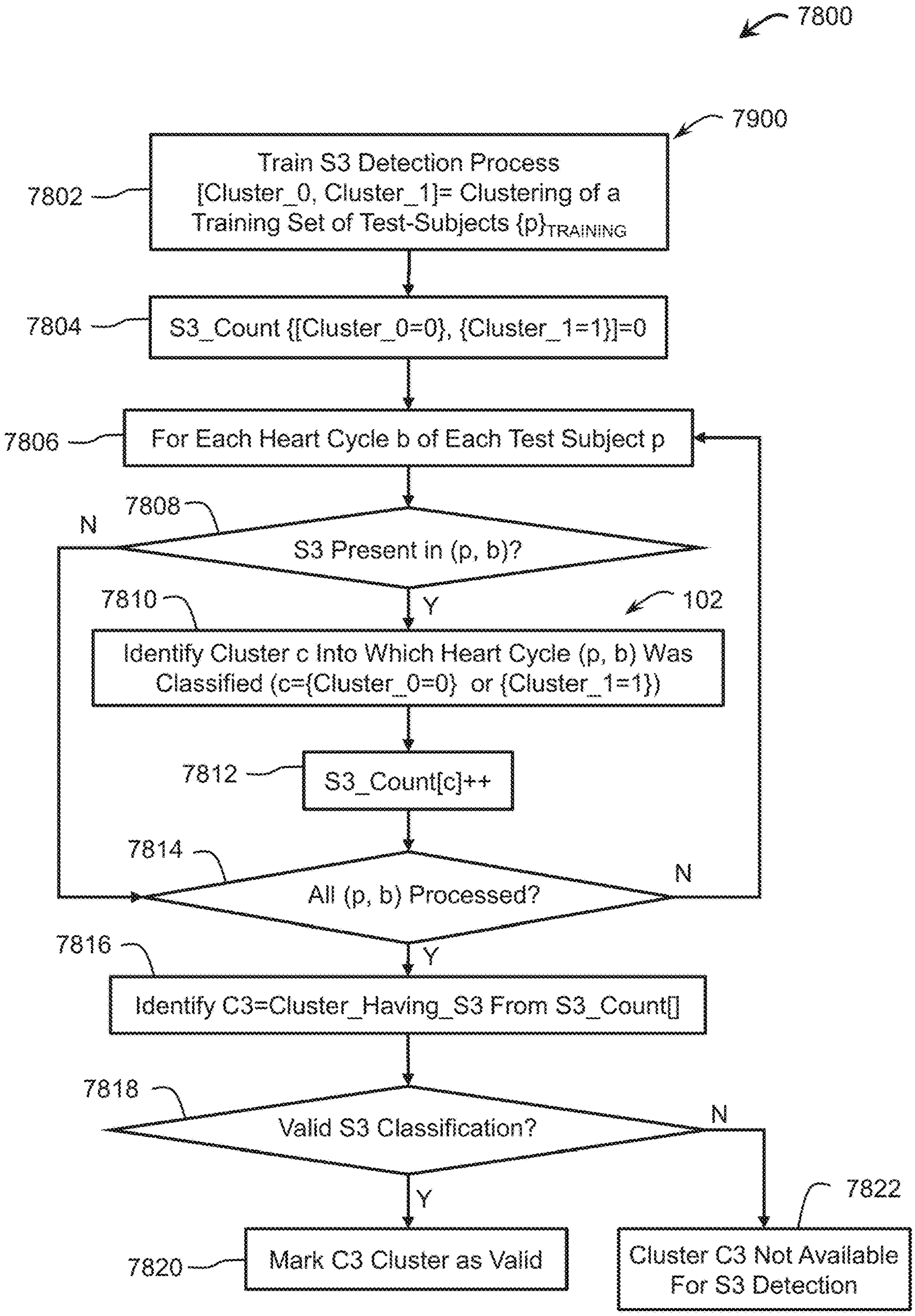
FIG. 78 illustrates an S3-detection-training process for training a third heart sound (S3) detection process based upon a training set of a plurality of test-subjects, so as to provide for an unsupervised classification of auscultatory sound signals into two different classes that provide for the detection of a third heart sound (S3) in an auscultatory sound signal.
Figure 83:
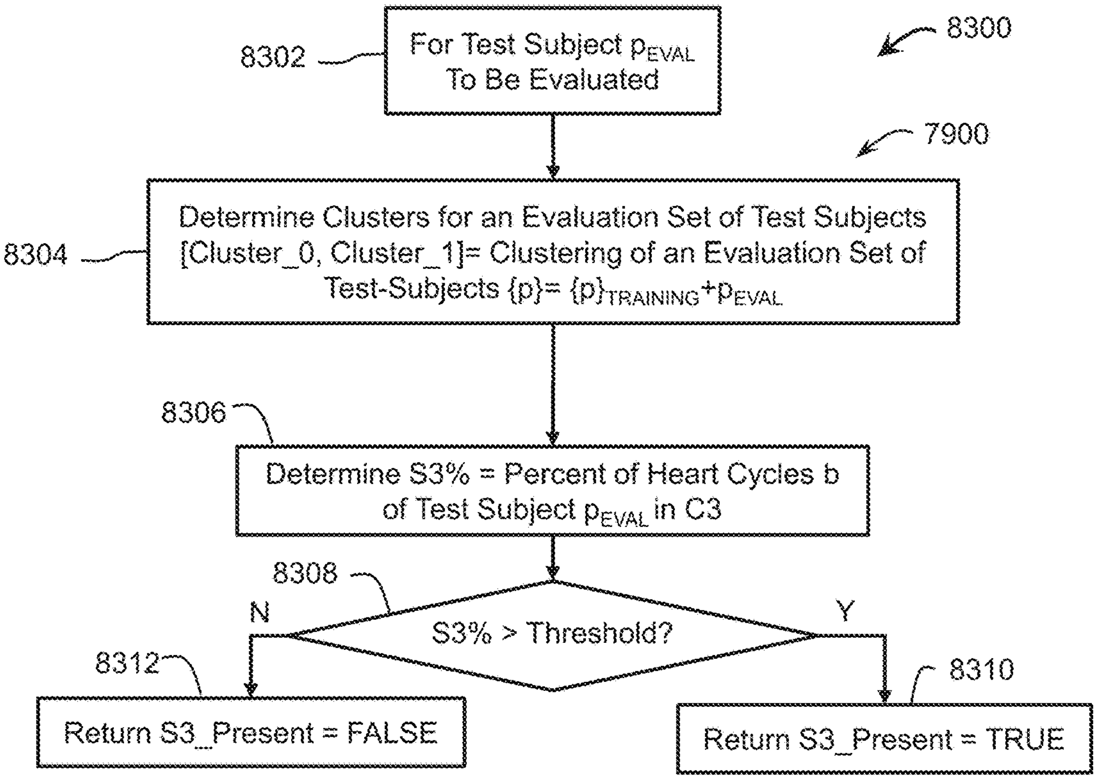
FIG. 83 illustrates a flow chart of a process for detecting the presence of a third heart sound (S3) in an auscultatory sound signal.

Referring to FIGS. 78-83, an S3-detection process 8300 illustrated in FIG. 83 provides for detecting the presence of an S3 heart sound 100 using a k-means clustering model 102 that is trained in accordance with the S3-detection-training process 7800 illustrated in FIG. 78. An unsupervised classification method is used to detect the S3 heart sound 100 because there are typically relatively few test-subjects 22 that exhibit the S3 heart sound 100—i.e. relatively few labeled cases—that could otherwise be used to train a supervised classification model. For example, k-means clustering—for example, as described in https://en.wikipedia.org/wiki/K-means clustering, which is incorporated herein by reference—is an unsupervised classification method which, when trained in accordance with the S3-detection-training process 7800, has been found to be useful for detecting an S3 heart sound 100 in accordance with the below-described S3-detection process 8300.

Referring to FIG. 78, the S3-detection-training process 7800 commences in step (7802) with execution of a k-means-clustering training process 7900 that provides for segregating heart-cycle data—from a plurality of heart cycle 82, *b* recorded by one or more auscultatory sound sensor 12, *m*, for each of a plurality of test-subjects 22, *p* exclusively of an associated training set of test-subjects 22, $\{p\}_{TRAINING}$—into two different clusters, i.e. Cluster_0 and Cluster_1, neither of which is known a priori to be associated with an S3-sound.

Figure 79:
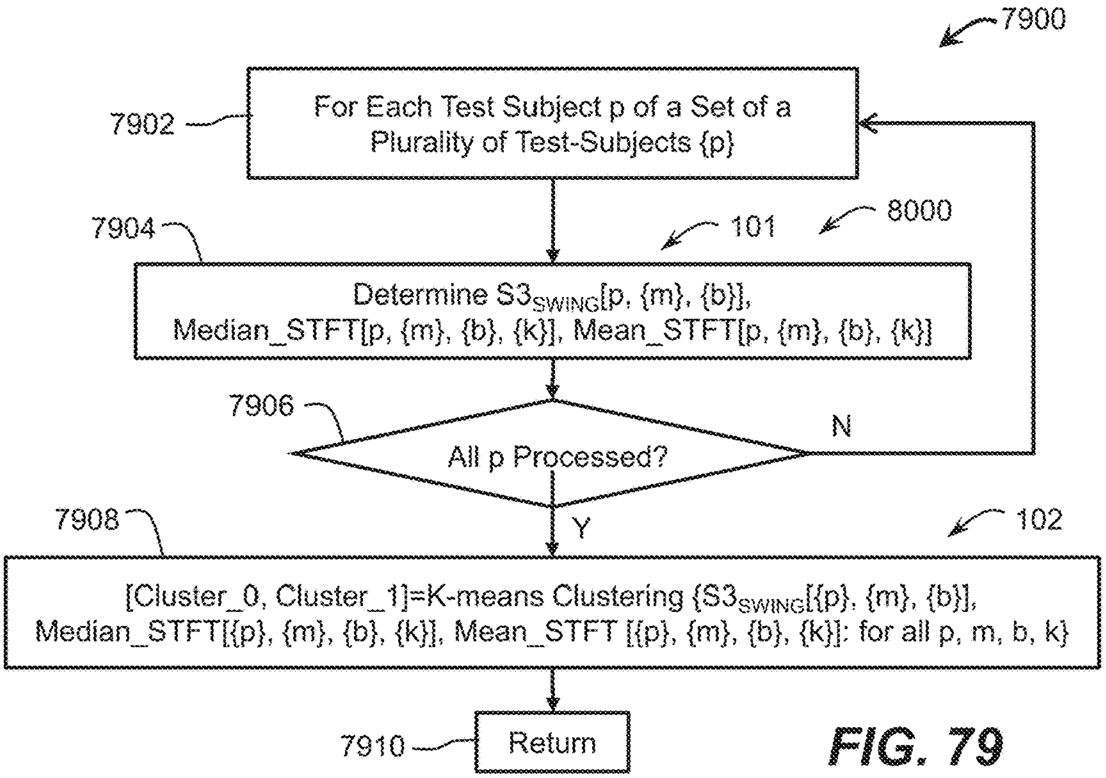
FIG. 79 illustrates a flow chart of a k-means-clustering training process that is called both from the process illustrated in FIG. 78 for exclusively a training set of test-subjects, and from the third heart sound (S3) detection process illustrated in FIG. 83 for a different set of test-subjects, and that provides for processing a plurality of test-subjects to determine associated features from associated auscultatory sound signals to be used in an associated k-means clustering unsupervised classification process, and for then clustering the heartbeats from the set of test-subjects into two clusters using the k-means clustering process.

Referring to FIG. 79, the k-means-clustering training process 7900 commences with step (7902), for each of a plurality of test-subjects 22, *p*, with the determination from step (7904), by an associated S3-clustering feature determination process 8000, of a set of features 101 responsive to which the heart-cycle data will be clustered, for example, in one set of embodiments, features including an $S3_{SWING}$ value, and, for each of a plurality of frequency intervals k, a median value of a Short Time Fourier Transform (STFT), Median_STFT[ ], and a mean value of the Short Time Fourier Transform (STFT), Mean_STFT[ ].

Figure 80:
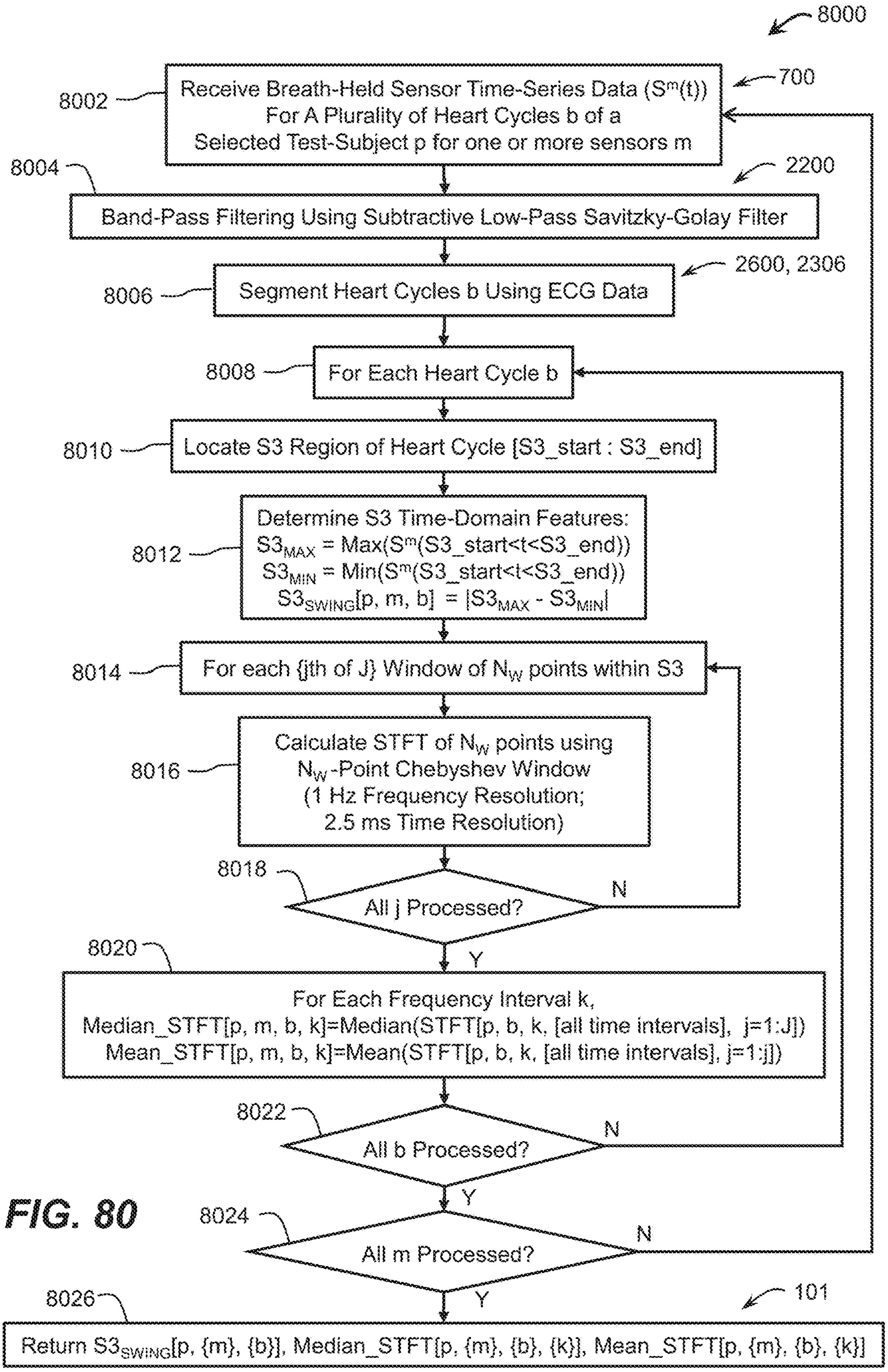
FIG. 80 illustrates an S3-clustering feature determination process that is called from the process illustrated in FIG. 79, and that provides for determining, from an auscultatory sound signal of a particular test-subject, the associated features to be used in the k-means clustering unsupervised classification process called from the process illustrated in FIG. 79.

Referring to FIG. 80, the S3-clustering feature determination process 8000 commences, in step (8002), with receipt of a breath-held sampled auscultatory sound data S‴[ ] containing a plurality of heart cycles 82 (counted by index b) for one of a plurality of test-subjects 22 (counted by index p) from one or more auscultatory sound sensors 12, $12^{1'}$, $12^{2'}$, $12^{3'}$, $12^{1''}$, $12^{2''}$, $12^{3''}$ (counted by index m). Then, in step (8004), breath-held sampled auscultatory sound data S‴[ ] is preprocessed with a band pass filter—for example, in accordance with the auscultatory sound signal acquisition and filtering process 2200 illustrated in FIG. 22*a*—which uses aa Savitzky-Golay (SG) smoothing filter 68 to extract low-frequency content, and then removes that low-frequency content by subtraction after low-pass filtering using a $4^{th}$ order type II Chebyshev filer. The resulting band-pass filtered signal is then segmented in step (8006) using the above-described heart-cycle segmentation and heart-phase identification process 2300 illustrated in FIG. 23 et seq, for example, responsive to R-peaks 80' of an associated electrographic signal 37. Beginning with step (8008), for each heart cycle 82, *b*, in step (8010), the S3 region is located within the S3 interval in accordance with the above-defined S3_start and S3_end time/sample locations within the heart cycle 82, *b*, after which, in step (8012), the maximum $S3_{MAX}$ and minimum $S3_{MIN}$ values of the band-pass-filtered breath-held sampled auscultatory sound data S‴[ ] within the S3 interval are determined, after which an associated swing value $S3_{SWING}$ is determined as the absolute value of the difference between the maximum $S3_{MAX}$ and minimum $S3_{MIN}$ values, and stored as a value $S3_{SWING}$ [p, m, b] in an associated array. Then, beginning with step (8014), for each $j^{th}$ window of $N_W$ samples—for example, 400 samples sampled at 4 KHz,—of a total of J sliding, Chebyshev windows, a Short-Time Fourier Transform (STFT) is calculated in step (8016), for example, having a 1 Hz frequency resolution and a 2.5 millisecond time resolution, after which, from step (8018), step (8016) is repeated until all J windows of the S3 interval have been processed. Then, in step (8020), for each frequency interval k, both the median and mean value of the STFT results from step (8018) are calculated with respect to a combination of time windows and STFT sliding windows, resulting a value for each of the median and mean for the test-subject 22, *p*, auscultatory sound sensor 12, *m*, heart cycle 82, *b*, and frequency interval k. Then, from step (8022), the processes of steps (8008) through (8020) are repeated for each heart cycle 82, *b*, and then, from step (8024), the processes of steps (8002) through (8022) are repeated for each auscultatory sound sensor 12, *m*, after which, in step (8026), the resulting set of features 101 is returned to step (7904) of the k-means-clustering training process 7900, after which, in step (7906), if additional test-subject 22, p remain to be processed, steps (7902) and (7904) are repeated for the next test-subject 22, *p*. Otherwise, from step (7906), in step (7908), normalized values of the sets of features 101 from step (7904), i.e. $S3_{SWING}$ [p, m, b], Median_STFT[p, m, b, k], Mean_STFT [p, m, b, k]: for all p, m, b, k, are clustered with respect to $S3_{SWING}$, Median_STFT, Mean_STFT, with the resulting k-means clustering model 102 having two clusters, i.e. Cluster_0 and Cluster_1, wherein the normalization is given by subtracting an associated mean value and dividing by an associated standard deviation, after which, in step (7910), the k-means-clustering training process 7900 returns to step (7802) of the S3-detection-training process 7800.

Referring again to FIG. 78, the S3-detection-training process 7800 then continues with the characterization in steps (7804) through (7818) of the two clusters, Cluster_0 and Cluster_1 of the k-means clustering model 102, with respect to the S3 sound. More particularly, in step (7804), the elements of a counter array, i.e. S3_Count[0] and S3_Count[1], are each initialized to a value of zero. Then, beginning with step (7806), for each heart cycle 82, *b* of each test-subject 22, *p*, if, in step (7808), that particular heart cycle 82, *b* is known a priori by other means to include an S3 sound, then, in step (7810), the cluster c (i.e. c=0 or 1) into which that heart cycle 82, *b* for that test-subject 22, *p* had been classified in the k-means clustering model 102 is identified, and, in step (7812), the corresponding associated counter, i.e. S3_Count[c], is incremented. Then, or otherwise from step (7808), from step (7814), the process of steps (7806) though (7812) is repeated for each heart cycle 82, *b* and each test-subject 22, *p*. Then, in step (7816), the cluster, Cluster_0 and Cluster_1, for which the corresponding associated counter S3_Count[0] and S3_Count[1] has a substantially larger value is identified as the S3 cluster C3 associated with the S3 sound. If, in step (7818), the values of the counters S3_Count[0] and S3_Count[1] are substantially different-indicating a strong association of the S3 cluster C3 with the S3 sound, then, in step (7820), the S3 cluster C3 is marked as being valid for use by the S3-detection process 8300. Otherwise, from step (7818), in step (7822), the S3 cluster C3 is indicated either as being invalid or otherwise not available for S3 detection.

Figure 81A:
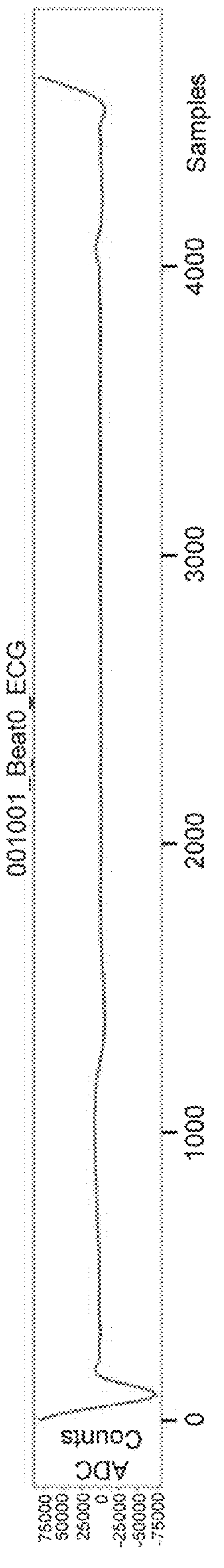
FIG. 81*a* illustrates an ECG signal associated with a single heart cycle.
Figure 81B:
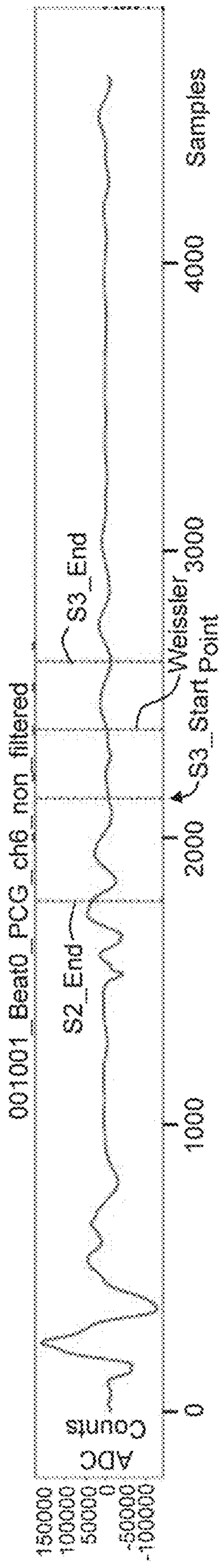
FIG. 81*b* illustrates a non-filtered auscultatory sound signal associated with a heart sound associated with the same single heart cycle associated with the ECG signal illustrated in FIG. 81*a*
Figure 81C:
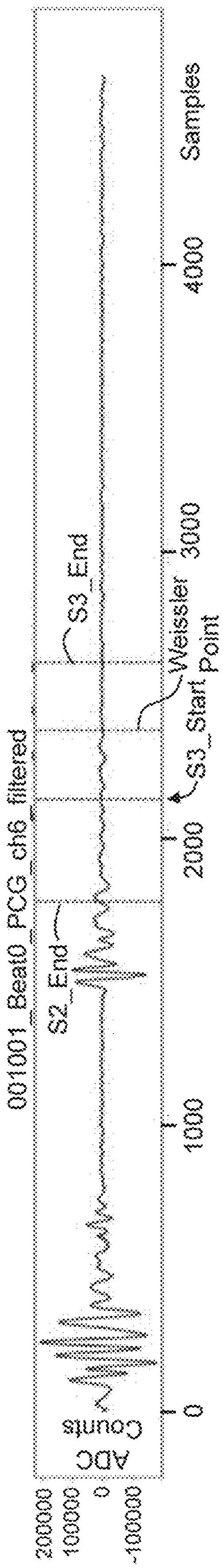
FIG. 81*c* illustrates a band-pass-filtered version of the auscultatory sound signal illustrated in FIG. 81*b*, for purposes of illustrating the process illustrated in FIGS. 79,80 and 83 for detecting the presence of a third heart sound (S3)
Figure 81D:
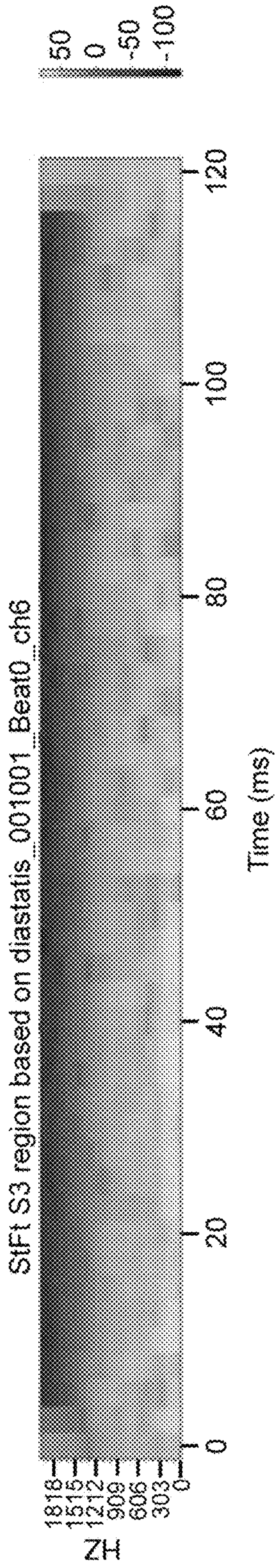
FIG. 81*d* illustrates the results of Short Time Fourier Transform (STFT) of the band-pass-filtered auscultatory sound signal illustrated in FIG. 81*c*, for purposes of illustrating the process illustrated in FIGS. 79, 80 and 83 for detecting the presence of a third heart sound (S3)
Figure 82:
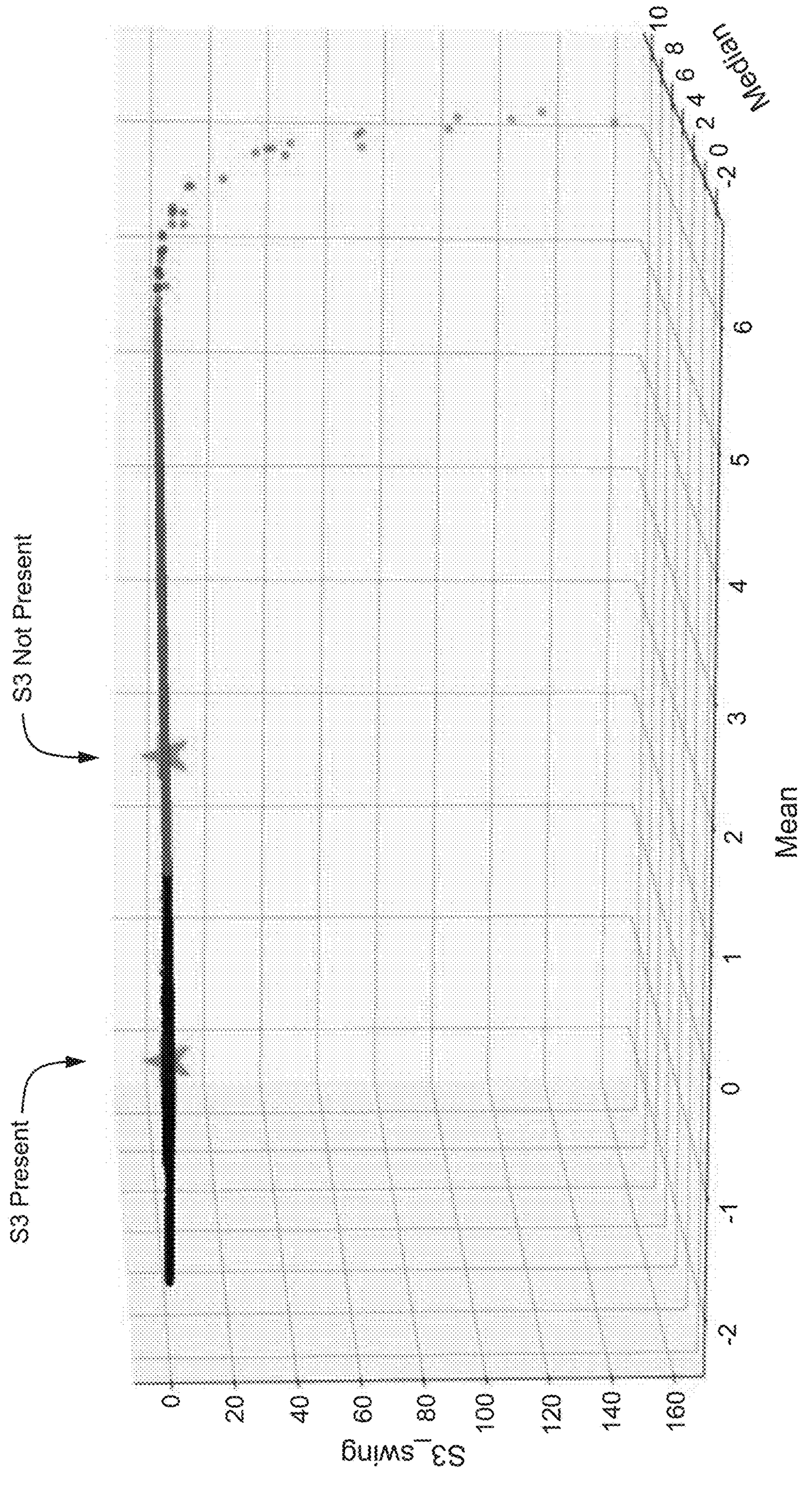
FIG. 82 illustrates the outcome of a k-Means clustering process used by the process illustrated in FIGS. 79, 80 and 83 for detecting the presence of a third heart sound (S3)

For example, for a particular heart cycle 82, *b*, FIG. 81*a* illustrates the associated electrographic data 74 of the associated electrographic signal 37, FIGS. 81*b* and 81*c* illustrates a breath-held sampled auscultatory sound data S‴[ ] prior to and following, respectively, removal of the low-frequency content extracted by the associated Savitzky-Golay (SG) smoothing filter 68, and FIG. 81*d* illustrates an example of an associated Short Time Fourier Transform (STFT) of the band-pass-filtered auscultatory sound signal illustrated in FIG. 81*c*. Furthermore, FIG. 82 illustrates the results of the k-means clustering of a set of breath-held sampled auscultatory sound data S‴[ ] for which some of the associated test-subjects 22 exhibited an S3 sound.

Referring to FIG. 83, following the identification of an S3 cluster C3 by the S3-detection-training process 7800, the S3-detection process 8300 provides for detecting whether or not a particular test-subject 22, $p_{EVAL}$ exhibits an S3 sound. Following identification or input of the test-subject 22, $p_{EVAL}$ in step (8302), in step (8304), the k-means-clustering training process 7900 is repeated for an augmented set of test-subject 22, $p_{EVAL}$ comprising the test-subject 22, $p_{EVAL}$ to be evaluated in combination with the training set of test-subjects 22, $\{p\}_{TRAINING}$ that had been used to identify the S3 cluster C3, so as to provide for associating the data from the test-subject 22, $p_{EVAL}$ with the clusters, i.e. Cluster_0 and Cluster_1 with which the S3 cluster C3 is associated. Then, for each of the heart cycles 82, *b* of the test-subject 22, $p_{EVAL}$ to be evaluated, the percentage S3% of heart cycles 82, *b* that are associated with the S3 cluster C3 is determined in step (8306), and if, in step (8308), that percentage exceeds a corresponding threshold, for example, 33%, then, in step (8310), an associated flag S3_Present[p] for that test-subject 22, *p* is set to TRUE. Otherwise, in step (8312), the associated flag S3_Present[p] for that test-subject 22, *p* is set to FALSE. Alternatively, the test-subject 22, $p_{EVAL}$ to be evaluated could be embedded within the training set of test-subjects 22, $\{p\}_{TRAINING}$, thereby precluding the need for step (8304) of the S3-detection-training process 7800 because heart data of the test-subject 22, $p_{EVAL}$ will already have been clustered, so that the presence, or not, of an S3 sound in the test-subject 22, $p_{EVAL}$,—or of any other test-subject 22, *p* of the training set of test-subjects 22, $\{p\}_{TRAINING}$,—can be ascertained directly from steps (8306) and (8308) without reprocessing the data in step (8304).

Figure 84:
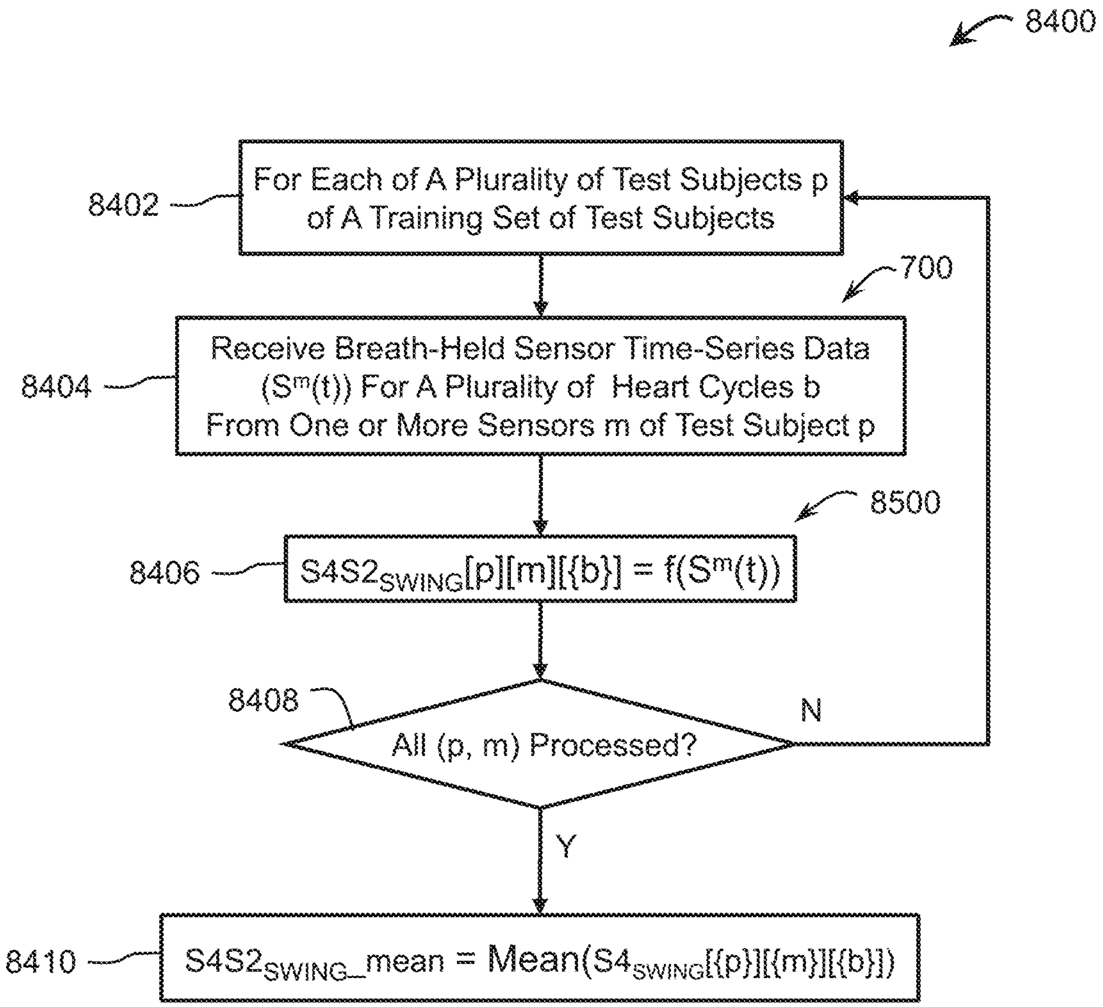
FIG. 84 illustrates a flow chart of a process for determining a mean value of a S4S2$_{SWING}$ metric from a training set of test-subjects, wherein the mean value of the S4S2$_{SWING}$ metric is used by the process illustrated in FIG. 87 for detecting the presences of a fourth heart sound (S4) in an auscultatory sound signal.
Figure 85:
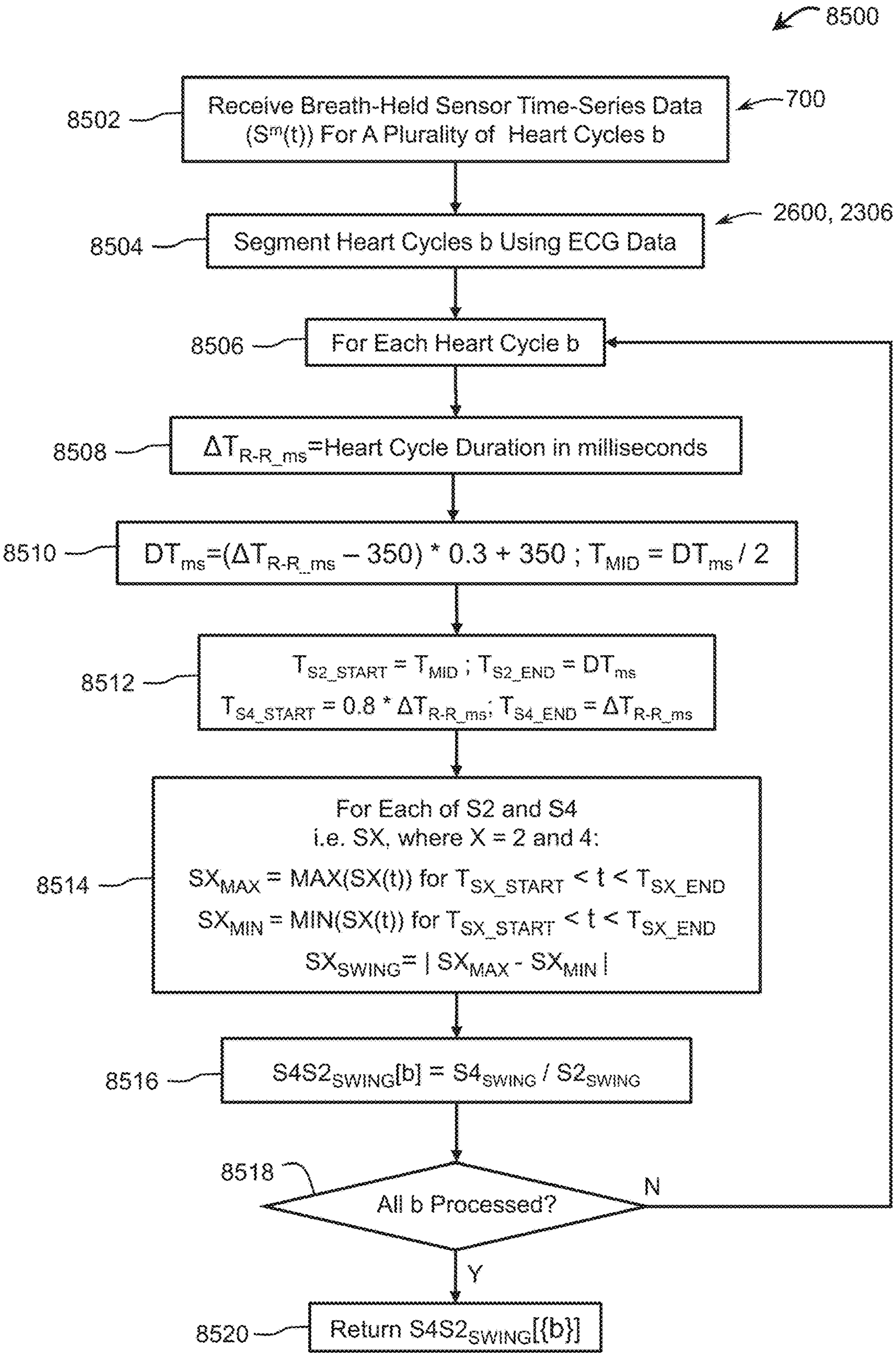
FIG. 85 illustrates a flow chart of a process for determining an array of values of the S4S2$_{SWING}$ metric used in the processes illustrated in FIGS. 84 and 87, the latter of which provides for detecting the presences of a fourth heart sound (S4) in an auscultatory sound signal.
Figure 86A:
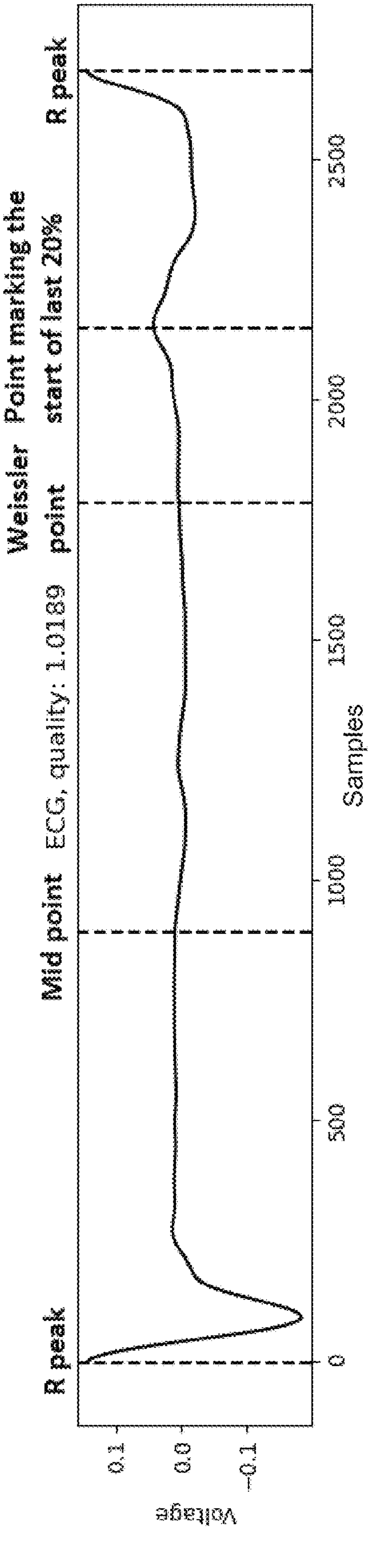
FIG. 86*a* illustrates an ECG signal associated with a single heart cycle.
Figure 86B:
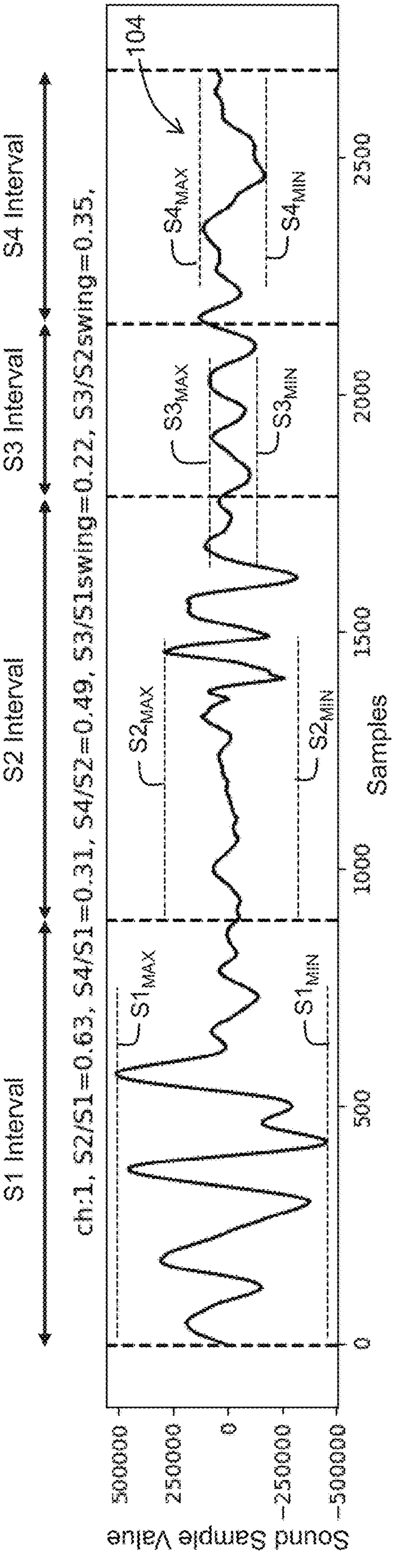
FIG. 86*b* illustrates band-pass-filtered auscultatory sound signal for purposes of illustrating the process illustrated in FIG. 85 for determining an array of values of the S4S2$_{SWING}$ metric.
Figure 87:
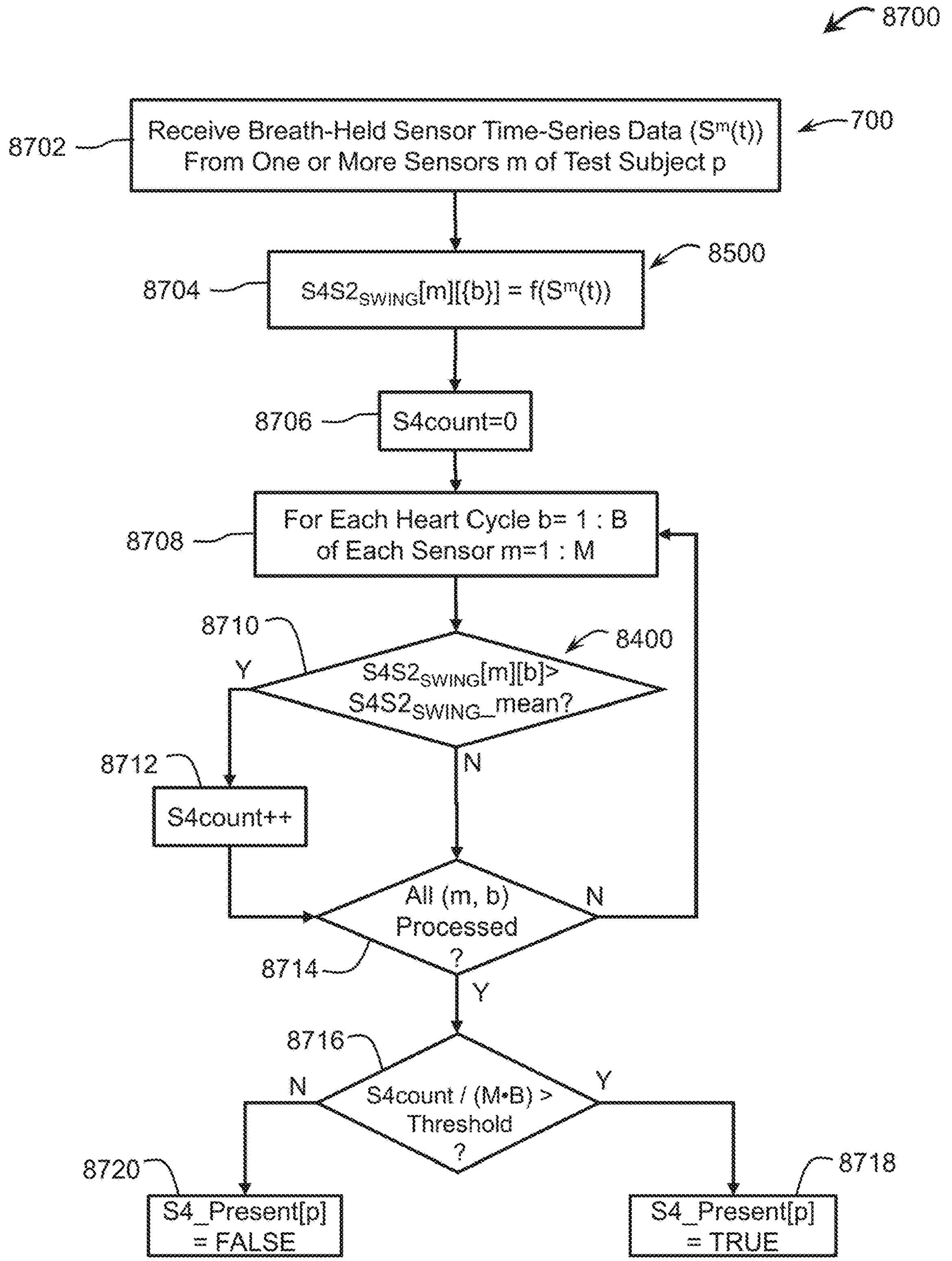
FIG. 87 illustrates a flow chart of a process for detecting the presence of a fourth heart sound (S4) in an auscultatory sound signal.

Referring to FIGS. 84-87, an S4 detection process 8700 illustrated in FIG. 87 provides for detecting whether or not a particular test-subject 22, *p* exhibits an S4 sound 104, based upon a value of $S4S2_{SWING}$—determined by an associated $S4S2_{SWING}$ determination process 8500 illustrated in FIG. 85 in respect of associated time intervals with a heart cycle 82, *b* illustrated in FIGS. 86*a* and 86*b*—in comparison with a mean value $S4S2_{SWING}$_mean of $S4S2_{SWING}$ across all heart cycles 82, *b* measured by all auscultatory sound sensors 12 *m* from all test-subjects 22, *p* as determined by the $S4S2_{SWING}$_mean determination process 8400 illustrated in FIG. 84, which utilizes the $S4S2_{SWING}$ determination process 8500 to determine the underlying values of $S4S2_{SWING}$ for each heart cycle 82, *b* measured by each auscultatory sound sensor 12, m for each test-subject 22, *p*.

More particularly, referring to FIG. 84, the $S4S2_{SWING}$_mean determination process 8400 commences with step (8402) for each of a plurality of test-subjects 22, *p* of a training set of test-subjects 22, $\{p\}_{TRAINING}$, the latter of which includes a first subset of test-subjects 22, p known a priori to exhibit the S4 sound 104, and includes a second subset of test-subjects 22, p known a priori to not exhibit an S4 sound 104. Then, in step (8404), breath-held sampled auscultatory sound data S'''[ ] containing a plurality of heart cycles 82, *b* for the selected test-subject 22, *p* is received from one or more auscultatory sound sensors 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ (counted by index m), and in step (8406), the associated values of $S4S2_{SWING}$ [p][m][{b}] are determined by the associated $S4S2_{SWING}$ determination process 8500 for each of the heart cycles 82, *b*, wherein braces "{ }" are used herein to indicate a plurality of values of an associated 1-dimensional vector. Then, from step (8408), the process of steps (8402) through (8408) is repeated form each of test-subjects 22, *p* and associated auscultatory sound sensors 12 *m*, after which, in step (8410), the mean value $S4S2_{SWING}$_mean of $S4S2_{SWING}$ of all heart cycles 82, *b* from all auscultatory sound sensors 12 *m* for all test-subjects 22, *p* is calculated.

Referring to FIG. 85, the $S4S2_{SWING}$ determination process 8500 commences in step (8502) with receipt of the breath-held sampled auscultatory sound data S'''[ ] for a particular auscultatory sound sensor 12, m of a particular test-subject 22, *p* that is passed on from either step (8404), or below-described step (8702). Then, in step (8504), the breath-held sampled auscultatory sound data S'''[ ] is segmented into separate heart cycles 82, *b* using the above-described heart-cycle segmentation and heart-phase identification process 2300 illustrated in FIG. 23 et seq, for example responsive to locations of the R-peaks 80' of the associated electrographic data 74 of the associated electrographic signal 37, wherein a particular heart cycle 82, *b* is assumed to start at one R-peak 80' and end at the next R-peak 80'. Then, beginning with step (8506), for each heart cycle 82, *b*, with the heart cycle 82, *b* starting at time 0, the heart cycle duration $\Delta T_{R\text{-}R\_ms}$ in milliseconds is given in step (8508) as the relative time of the next R-peak 80'. Then, in step (8510), the Weissler point $DT_{ms}$ is then calculated from equation (14) hereinabove, and an associated midpoint $T_{MID}$ is given as the midpoint in time between the start of the heart cycle 82, *b* and the Weissler point $DT_{ms}$, i.e. $T_{MID}=DT_{ms}/2$. Then, in step (8512), the start and end of each of the S2 and S4 intervals are defined for purposes of determining associated swing values as follows:

$$T_{S2\_START}=T_{MID};\quad T_{S2\_END}=DT_{ms};\quad T_{S4\_START}=0.8^*\Delta T_{R\text{-}R\_ms};\text{ and }T_{S4\_END}=\Delta T_{R\text{-}R\_ms}.$$

The rationale for these locations is that R-peak 80' provides the best estimate of the S4 end point and avoids leakage of the S1 sound into the S4 sound. The start of the S4 sound is synchronized with the P-wave of the ECG signal, which is not always apparent, so that the beginning of the last 20% of the heart cycle 82, *b* is used instead. The use of $T_{MID}$ and $DT_{ms}$ for the bounds of the S2 interval is sufficient to provide for determining the associated minimum and maximum values that occur therebetween. Following the definition of the S2 and S4 intervals in step (8512), in step (8514), maximum and minimum values of each of S2 and S4 are determined within their respective intervals, and the associated swing values $S2_{SWING}$ and $S4_{SWING}$ are respectively given by the absolute values of the corresponding differences between the corresponding associated maximum and minimum values within the corresponding associated intervals, respectively. Then, in step (8516), the corresponding associated ratio of swing values, i.e. $S4S2_{SWING}$ [b] for the particular heart cycle 82, *b* is determined from the ratio of $S4_{SWING}$ over $S2_{SWING}$, and saved as an element of the array $S4S2_{SWING}$ [b]. Then, from step (8518), the process of steps (8506) through (8518) is repeated for each heart cycle 82, *b*, followed by a return in step (8520) of the $S4S2_{SWING}$[{b}] array.

Referring to FIG. 87, the S4 detection process 8700 commences in step (8702) with receipt of breath-held sampled auscultatory sound data S'''[ ] containing a plurality of heart cycles 82, *b* from one or more auscultatory sound sensors m, 12, $\mathbf{12}^{1'}$, $\mathbf{12}^{2'}$, $\mathbf{12}^{3'}$, $\mathbf{12}^{1''}$, $\mathbf{12}^{2''}$, $\mathbf{12}^{3''}$ for a test-subject 22, *p* to be evaluated, after which, in step (8704), values of a corresponding associated $S4S2_{SWING}$ [m][{b}] array are determined for each of the auscultatory sound sensors 12 *m* in accordance with the $S4S2_{SWING}$ determination process 8500, supra. Then, in step (8706), and associated counter S4count is initialized to zero, after which, beginning with step (8708), for each heart cycle 82, *b* of each auscultatory sound sensor 12, *m*, from step (8710), if the corresponding value of $S4S2_{SWING}$ [m][b] is greater than the mean value $S4S2_{SWING}$_mean of $S4S2_{SWING}$ of all heart cycles 82, *b* from all auscultatory sound sensors 12 *m* for all test-subjects 22, *p* determined from step (8410), then, in step (8712), the counter S4count is incremented. Then, or otherwise from step (8710), in step (8714), the process of steps (8708) through (8714) is repeated for each heart cycle 82, *b* and auscultatory sound sensors 12, *m*, after which, in step (8716), if counter S4count as a fraction of the total number of combinations of heart cycles 82, *b* and auscultatory sound sensors 12, m is greater than a threshold, then, in step (8718), the flag S4_Present[p] is set to TRUE for the test-subject 22, *p* so as to indicate the presence of an S4 sound, otherwise, in step (8720), the flag S4_Present[p] is set to FALSE for the test-subject 22, *p* so as to indicate the lack of an S4 sound.

Figure 88:
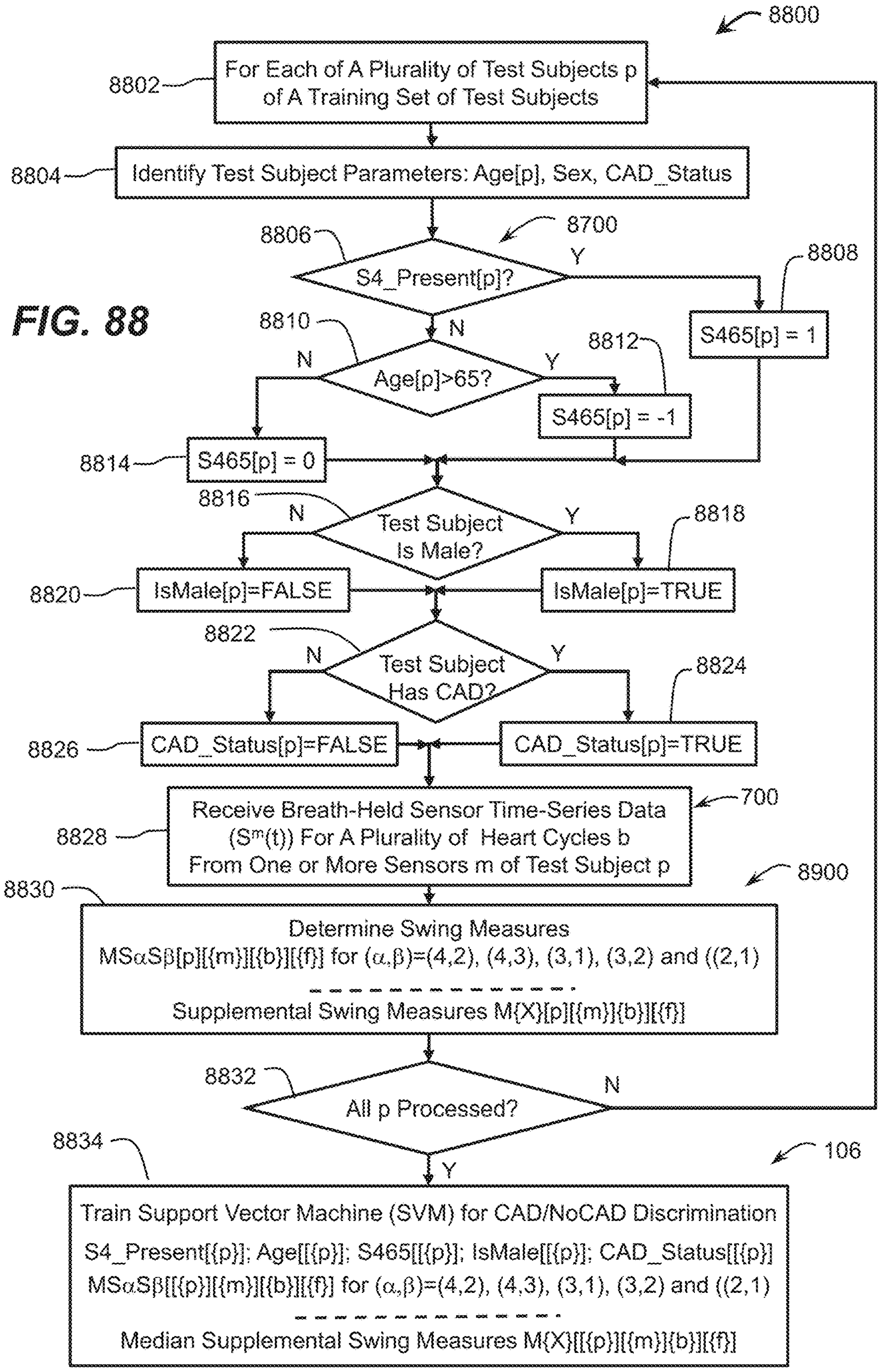
FIG. 88 illustrates a flow chart of a process for training a Support Vector Machine (SVM) to detect coronary artery disease (CAD) responsive to swing measure data associated with a test-subject.
Figure 89:
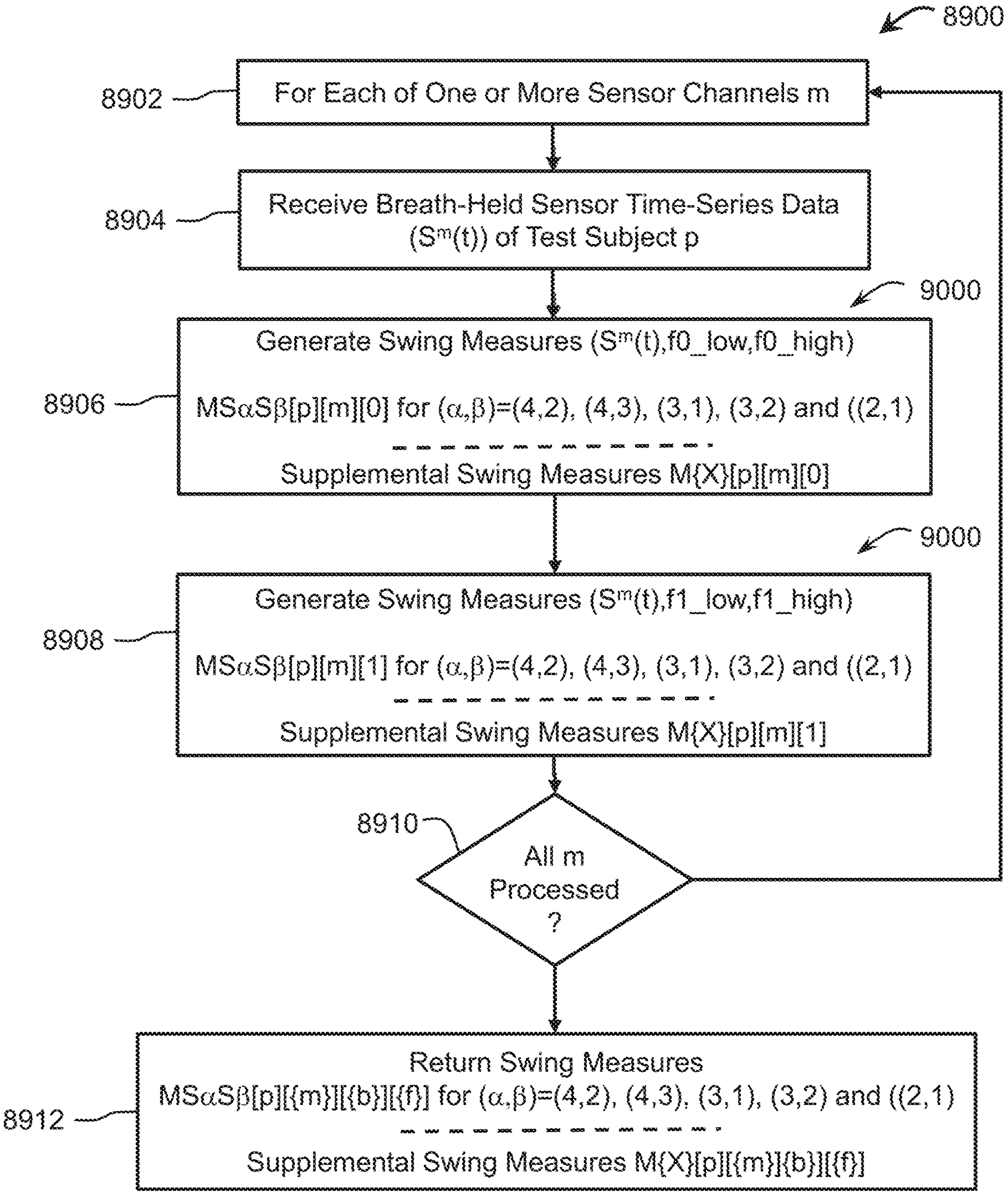
FIG. 89 illustrates a flow chart of a process for determining a plurality of swing measures for a plurality of frequency bands from auscultatory sound signals from one or more auscultatory sound sensors operatively associated with a given test-subject, called from the processes illustrated in FIGS. 88 and 93.
Figure 90:
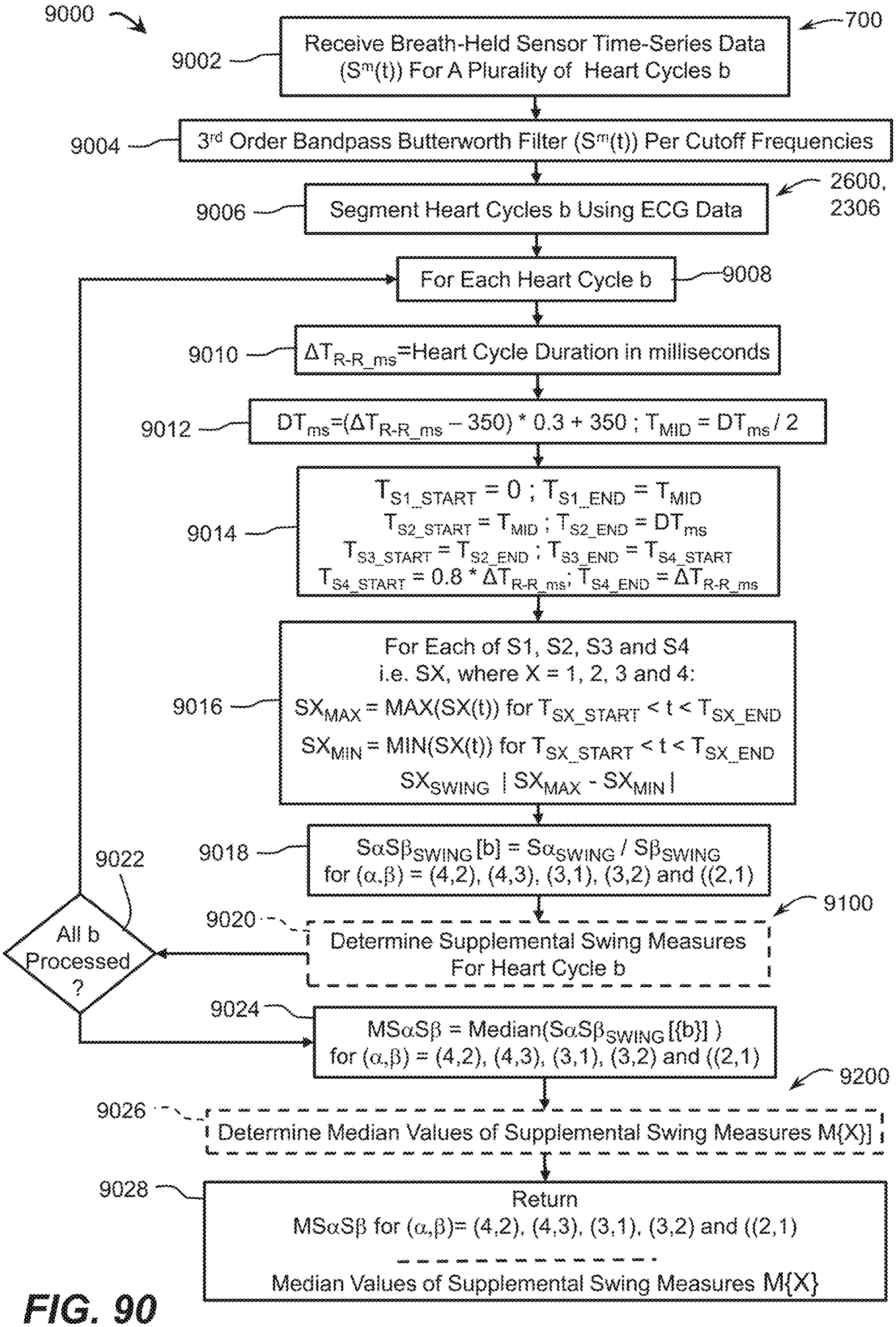
FIG. 90 illustrates a flow chart of a process for determining a plurality of swing measures from auscultatory sound signals from an auscultatory sound sensors operatively associated with a given test-subject, called from the process illustrated in FIG. 89.
Figure 93:
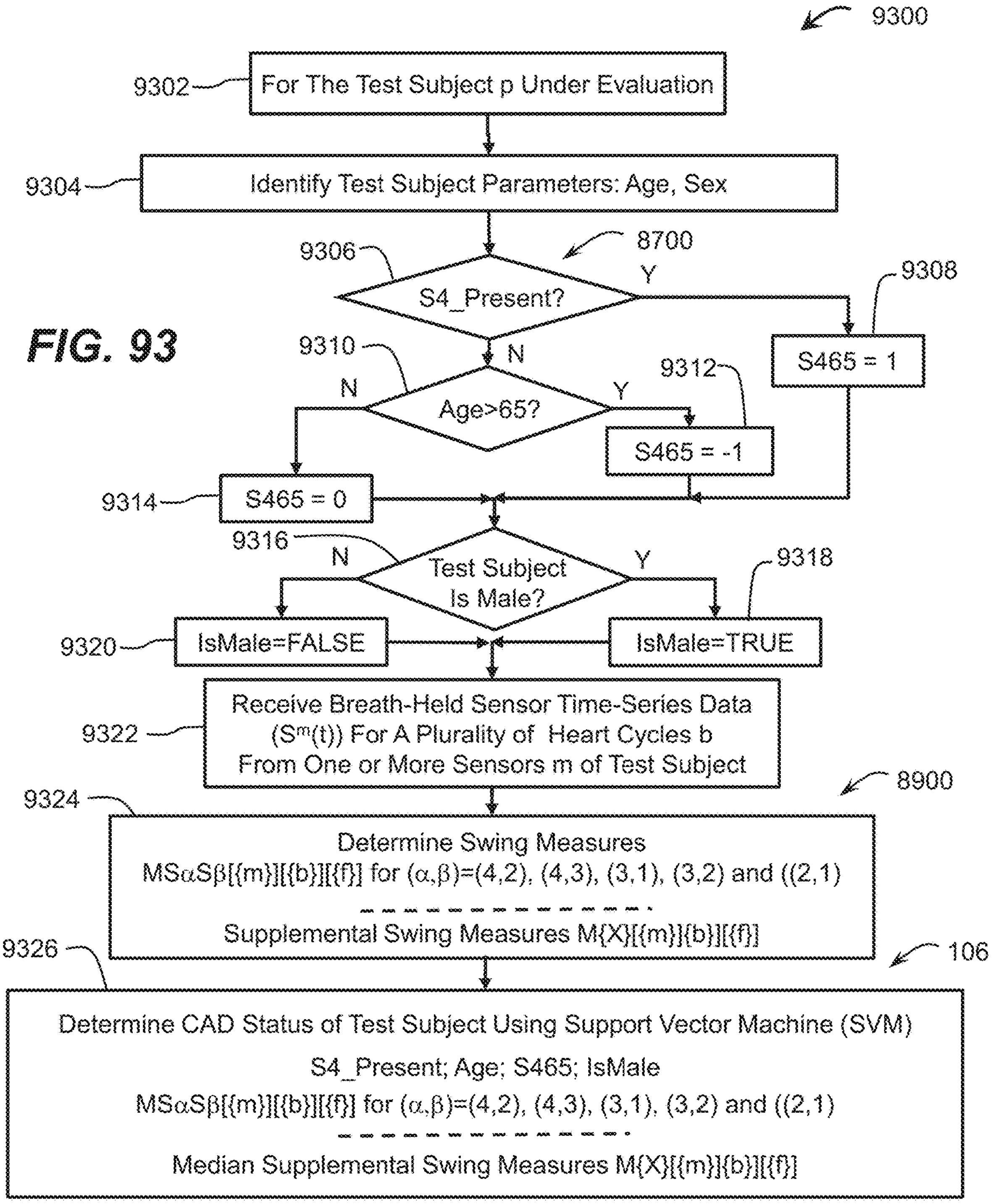
FIG. 93 illustrates flow chart of a process for detecting whether or not an auscultatory sound signal of a test-subject is associated with a condition of coronary artery disease, using the Support Vector Machine (SVM) that is trained by the process illustrated in FIG. 88, and that is responsive to swing-measure data determined from an auscultatory sound signal of the test-subject.

Referring to FIGS. 88-93, a first aspect of a CAD detection process 9300 illustrated in FIG. 93 provides for determining whether or not a particular test-subject 22, *p* is likely to exhibit coronary artery disease (CAD) responsive to parameters of a test-subject 22, *p* and responsive to swing measures determined from associated breath-held sampled auscultatory sound data S‴[ ] from one or more auscultatory sound sensors 12, 12$^{1'}$, 12$^{2'}$, 12$^{3'}$, 12$^{1''}$, 12$^{2''}$, 12$^{3''}$, responsive to a Support Vector Machine (SVM) 106 that is trained by an associated SVM training process 8800 illustrated in FIG. 88, in accordance with a supervised machine-learning process, wherein both the SVM training process 8800 and the CAD detection process 9300 utilize an executive swing-measure determination process 8900 illustrated in FIG. 89, to determine swing measures associated with a plurality of frequency ranges f, and the swing measures associated with a particular frequency range f are determined with a kernel swing-measure determination process 9000, infra, illustrated in FIG. 90 that provides for optionally utilizing one or more supplemental swing measures {X], for example, in accordance with FIGS. 91 and 92.

More particularly, referring to FIG. 88, the SVM training process 8800 commences with step (8802) for each of a plurality of test-subjects 22, *p* of a training set of test-subjects 22, $\{p\}_{TRAINING}$, the latter of which includes a first subset of test-subjects 22, *p* known a priori to exhibit coronary artery disease (CAD), and includes a second subset of test-subjects 22, *p* known a priori to not exhibit coronary artery disease (CAD). Then, in step (8804) various disease-relevant parameters of the test-subject 22, *p* are identified, including, inter alia, age (which is stored in an array Age [p]), sex (male or female) and their CAD status, i.e. known to exhibit coronary artery disease (CAD) or not. Then, from step (8806), if the test-subject 22, *p* exhibits an S4 sound 104 responsive to the S4 detection process 8700, then, in step (8808), an S465 parameter is set to a value of 1 for that test-subject 22, *p* to indicate the present of an S4 sound 104. Otherwise from step (8806), if, from step (8810), the age of the test-subject 22, *p* is greater than 65, then, in step (8812), the S465 parameter is set to a value of −1 for that test-subject 22, *p* to indicate that there is no S4 sound 104, and there also may be no coronary artery disease (CAD). Otherwise, from step (8810), in step (8814), the S465 parameter is set to a value of 0 for that test-subject 22, p to indicate that there is no S4 sound 104. Then, from steps (8808), (8812), or (8814), if, in step (8816), the test-subject 22, *p* is male, then, in step (8818), an IsMale parameter is set to TRUE for that test-subject 22, *p*, otherwise, in step (8820), the IsMale parameter is set to FALSE. Then, from step (8822), if the test-subject 22, *p* is known a priori to exhibit coronary artery disease (CAD), then, in step (8824), a CAD_Status parameter is set to TRUE for that test-subject 22, *p*, otherwise, in step (8826), the CAD_Status parameter is set to FALSE. Then, in step (8828), breath-held sampled auscultatory sound data S‴[ ] containing a plurality of heart cycles 82, b for the selected test-subject 22, *p* is received from one or more auscultatory sound sensors 12, 12$^{1'}$, 12$^{2'}$, 12$^{3'}$, 12$^{1''}$, 12$^{2''}$, 12$^{3''}$ (counted by index m), and in step (8830), a plurality of swing measures are determined therefrom by the below-described executive swing-measure determination process 8900, after which, from step (8832), the process of steps (8802) through (8832) is repeated for the next test-subject 22, *p*. Following step (8832), after all test-subjects 22, *p* of the training set have been processed, then, in step (8834), the associated Support Vector Machine (SVM) 106 is trained in accordance with a supervised machine learning process to distinguish between conditions with and without coronary artery disease (CAD) using inputs of S4_Present, Age, S465, IsMale, CAD_Status, swing measures, and possibly one or more supplemental swing measures, for each of the heart cycles 82, *b*, each of the frequency ranges f, each of the auscultatory sound sensors 12 *m*, and each of the test-subjects 22, *p*, In one set of embodiments, about 70% of the test-subjects 22, *p* are randomly picked for use in training the Support Vector Machine (SVM) 106, with the remainder used to test the Support Vector Machine (SVM) 106. Alternatively, others type of supervised machine learning systems could be used instead of, or in combination with, a Support Vector Machine (SVM) 106, including, but not limited to, LR (Logistic Regression) or RF (Random Forest).

Referring to FIG. 89, the above-referenced executive swing-measure determination process 8900 commences in step (8902), for each of the associated auscultatory sound sensors 12 *m*, with, in step (8904), receipt of the associated breath-held sampled auscultatory sound data S‴[ ] for the associated test-subject 22, *p*. Then, in step (8906), the swing measures are determined by the kernel swing-measure determination process 9000, infra, for a first range of frequencies, for example for an infrasound range of frequencies, for example, between f0_low=1 Hz and f0_high=20 Hz. Then, in step (8908), the swing measures are determined by the kernel swing-measure determination process 9000, infra, for a second range of frequencies, for example for an audible range of frequencies, for example, between a lower frequency bound f0_low of 20 to 25 Hz, and an upper frequency bound f1_high of 30 to 40 Hz. Then, from step (8910), the process of steps (8902) through (8910) is repeated until all of the auscultatory sound sensors 12 *m* have been processed for a given test-subject 22, *p*, after which, in step (8912), the resulting array(s) of swing measures are returned to the point of invocation.

Referring to FIG. 90, the kernel swing-measure determination process 9000 commences in step (9002) with receipt of the associated breath-held sampled auscultatory sound data S‴[ ] for a particular frequency range f, from a particular auscultatory sound sensor 12, *m*, for the associated test-subject 22, *p*. Then, in step (9004), the breath-held sampled auscultatory sound data S‴[ ] is bandpass filtered using a third order Butterworth filter with associated cutoff frequencies in accordance with the indicated frequency range f. The resulting filtered breath-held sampled auscultatory sound data S‴[ ] is then segmented in step (9006) into separate heart cycles 82, *b* using the above-described heart-cycle segmentation and heart-phase identification process 2300 illustrated in FIG. 23 et seq, for example, responsive to locations of the R-peaks 80' of the associated electrographic data 74 of the associated electrographic signal 37, wherein a particular heart cycle 82, *b* is assumed to start at one R-peak 80' and end at the next R-peak 80'. Beginning with step (9008), for each heart cycle 82, *b*, with the heart cycle 82, *b* starting at time 0, the heart cycle duration $\Delta T_{R\text{-}R\_ms}$ in milliseconds is given in step (9010) as the relative time of the next R-peak 80'. Then, in step (9012), the Weissler point $DT_{ms}$ is then calculated from equation (14) hereinabove, and an associated midpoint $T_{MID}$ is given as the midpoint in time between the start of the heart cycle 82, *b* and the Weissler point $DT_{ms}$, i.e. $T_{MID}=DT_{ms}/2$. Then, in step (9014), the start and end of each of the S1, S2, S3 and S4 intervals are defined for purposes of determining associated swing values as follows:

$T_{S1\_START}=0$; $T_{S1\_END}=T_{S2\_START}=T_{MID}$; $T_{S2\_END}=T_{S3\_START}=DT_{ms}$; $T_{S3\_END}=T_{S4\_START}=0.8*\Delta T_{R\text{-}R\_ms}$; and $T_{S4\_END}=\Delta T_{R\text{-}R\_ms}$.

Then, in step (9016), the associated swing values for each of $S1_{SWING}$, $S2_{SWING}$, $S3_{SWING}$, $S4_{SWING}$, i.e. $SX_{SWING}$ for X=1, 2, 3 and 4 respectively, are given by the absolute value of difference between the maximum and minimum values within the associate time intervals. Then, in step (9018), the following swing ratios are calculated and saved for the associated heart cycle 82, *b*: $S4_{SWING}/S2_{SWING}$, $S4_{SWING}/S3_{SWING}$, $S3_{SWING}/S1_{SWING}$, $S3_{SWING}/S2_{SWING}$, and $S2_{SWING}/S1_{SWING}$, after which, in step (9020), one or more of the supplemental swing measures listed in FIG. 91 may also be calculated and saved in step (9100) for the associated heart cycle 82, b. Then, from step (9022), the process of steps (9008) through (9020) is repeated for each heart cycle 82, b. From step (9022), after processing all of the heart cycles 82, *b*, in step (9024), and optionally in step (9026), the median values of the swing ratios and supplemental swing measures, the latter per step (9200) of FIG. 92, respectively, are calculated, and in step (9028), these median values are return to the point of invocation.

Referring to FIG. 93, the CAD detection process 9300 commences in step (9302) for a given test-subject 22, *p* to be evaluated, with the identification, in step (9304), of various disease-relevant parameters of the test-subject 22, *p*, including, inter alia, the age and sex (male or female). Then, from step (9306), if the test-subject 22, *p* exhibits an S4 sound 104 responsive to the S4 detection process 8700, then, in step (9308), an S465 parameter is set to a value of 1 for that test-subject 22, *p* to indicate the present of an S4 sound 104. Otherwise from step (9306), if, from step (9310), the age of the test-subject 22, *p* is greater than 65, then, in step (9312), the S465 parameter is set to a value of −1 for that test-subject 22, *p* to indicate that there is no S4 sound 104, and there also may be no coronary artery disease (CAD). Otherwise, from step (9310), in step (9314), the S465 parameter is set to a value of 0 for that test-subject 22, *p* to indicate that there is no S4 sound 104. Then, from steps (9308), (9312), or (9314), if, in step (9316), the test-subject 22, *p* is male, then, in step (9318), an IsMale parameter is set to TRUE for that test-subject 22, *p*, otherwise, in step (9320), the IsMale parameter is set to FALSE. Then, in step (9322), breath-held sampled auscultatory sound data S‴[ ] containing a plurality of heart cycles 82, *b* for the test-subject 22, *p* is received for one or more auscultatory sound sensors 12 *m*, and in step (9324), the plurality of swing measures are determined therefrom by above-described executive swing-measure determination process 8900, after which, in step (9326), the associated Support Vector Machine (SVM) 106 is evaluated to determine whether or not the test-subject 22, *p* is likely to exhibit coronary artery disease (CAD) using inputs of S4_Present, Age, S465, IsMale, the swing measures, and possibly one or more of the supplemental swing measures, for each of the heart cycles 82, *b*, each of the frequency ranges f, each of the auscultatory sound sensors 12 *m*, of the associated test-subject 22, *p*.

Figure 94:
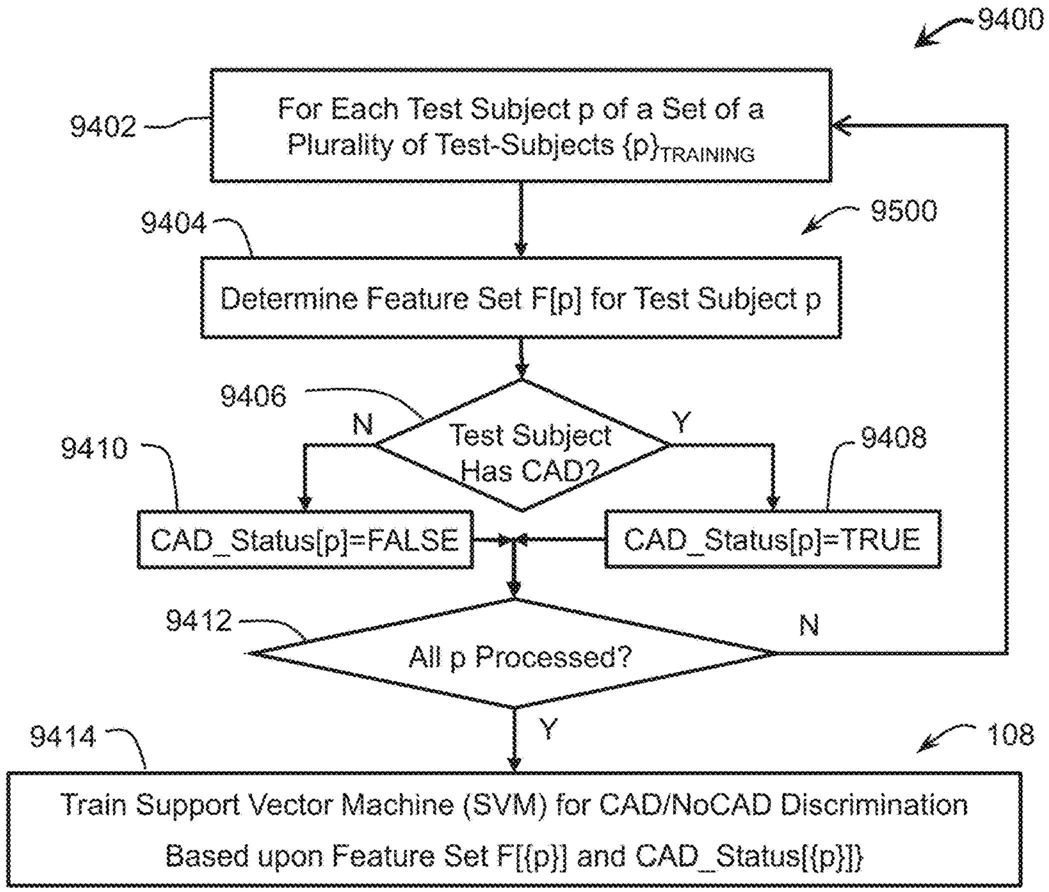
FIG. 94 illustrates a flowchart of a process for training a Support Vector Machine (SVM) to be used for detecting whether or not an auscultatory sound signal of a test-subject is associated with a condition of coronary artery disease, based upon energy within a plurality of time and frequency intervals of the auscultatory sound signal.
Figure 96:
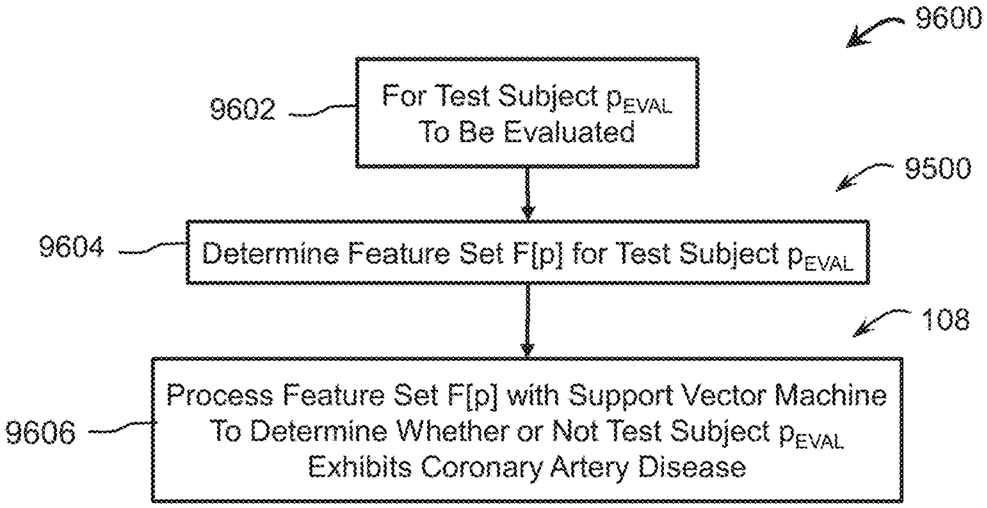
FIG. 96 illustrates a flow chart of a process for detecting whether or not an auscultatory sound signal of a test-subject is associated with a condition of coronary artery disease, based upon energy within a plurality of time and frequency intervals of the auscultatory sound signal, using the Support Vector Machine (SVM) that was trained in accordance with the associated training process illustrated in FIG. 94.
Figure 95:
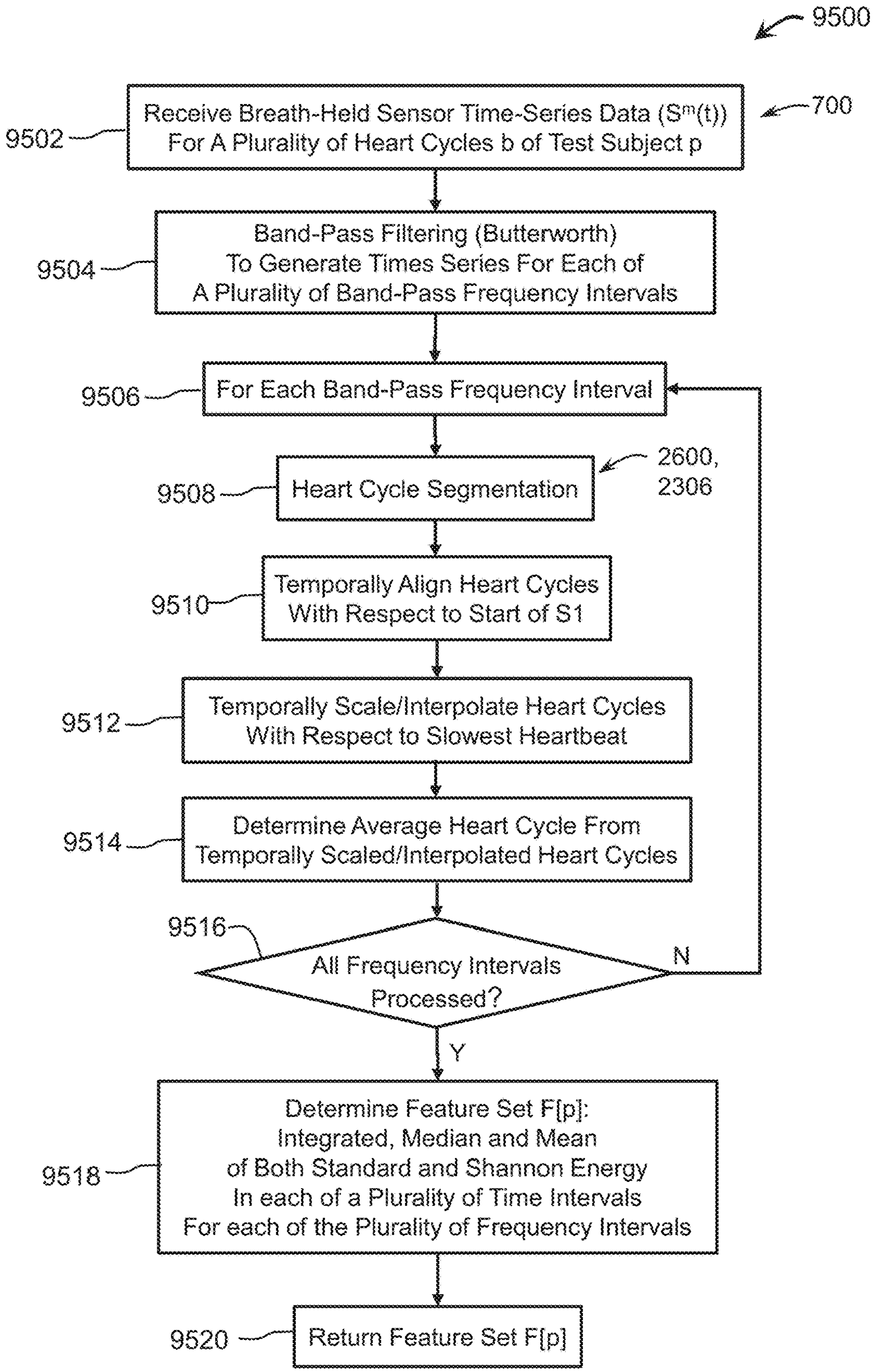
FIG. 95 illustrates a CAD-detection feature determination process that provides for determining a feature set for use by the Support Vector Machine (SVM) associated with the processes of each of FIGS. 94 and 96, responsive to an auscultatory sound signal of an associated test-subject.

Referring to FIGS. 94-96, in accordance with a second aspect, a CAD detection process 9600 utilizes a Support Vector Machine (SVM) 108 responsive to a set of features F[p] that are determined—for a particular test subject 22, $p_{EVAL}$ to be evaluated—by an associated CAD-detection feature-determination process 9500, the latter of which is also used by an associated CAD-detection training process

9400 to compile a set of features F[p] associated with a training set of test subjects 22, $\{p\}_{TRAINING}$—for whom a coronary-artery-disease status is also known—to train the Support Vector Machine (SVM) 108.

More particularly, referring to FIG. 94, the CAD-detection training process 9400 commences with step (9402), for each of a plurality of test subjects 22, *p*, with the determination from step (9404), by the CAD-detection feature-determination process 9500, of a set of features F[p] to be used, along with associated coronary artery disease (CAD) status, to train the associated Support Vector Machine (SVM) 108.

Referring to FIG. 95, in step (9502) of the CAD-detection feature-determination process 9500, breath-held sampled auscultatory sound data S‴[ ] containing a plurality of heart cycles 82, *b* for the test-subject 22, *p* is received, and, in step (9504), filtered using a bandpass Butterworth filter for each of the following five frequency intervals: 1) 1 Hz to 10 Hz; 2) 11 Hz to 30 Hz; 3) 3-31 Hz to 80 HZ; 4) 81 Hz to 120 Hz; and 5) 121 Hz to 1 KHz. Then, in step (9506), for each frequency interval, the resulting filtered breath-held sampled auscultatory sound data S‴[ ] is, in step (9508), segmented into separate heart cycles 82, *b* using the above-described heart-cycle segmentation and heart-phase identification process 2300 illustrated in FIG. 23 et seq, for example, responsive to locations of the R-peaks 80' of the associated electrographic data 74 of the associated electrographic signal 37, and in step (9510), the separate heart cycles 82, b are temporally aligned with respect to the start of S1, and, in step (9512), temporally scaled similar to steps (3724) and (3728) of the above-described auscultatory sound signal preprocessing and screening process 3700, but with application to the entire heart cycles 82, *b*, and not just to the diastolic portion thereof. Then, in step (9514), data from the separate heart cycles 82, *b* is averaged to form a single, waveform of average filtered breath-held sampled auscultatory sound data S‴[ ] for a single heart cycle 82, *b* for the associated frequency interval. Then, from step (9516), the process of steps (9506) through (9516) is repeated for each frequency interval. From step (9516), after the average filtered breath-held sampled auscultatory sound data S‴[ ] has been generated for each of the frequency intervals, then, in step (9518), the integral, median and mean of both the standard energy waveform and the Shannon energy waveform are calculated for each of the frequency intervals and within each of the seven time intervals identified hereinabove in and in conjunction with FIG. 77,—i.e. the S1 interval, the systolic interval, the S2 interval, the pre-S3 interval, the S3 interval, the diastasis interval, and the S4 interval,—so as to generate the associated set of features F[p] that are used as inputs to the Support Vector Machine (SVM) 108, wherein with the standard energy is defined by:

$$E_i = \frac{1}{N_W}\sum_{k=0}^{N_W-1}|x(k+i)|^2 \tag{38}$$

and the Shannon energy is defined by:

$$E_i = \frac{1}{N_W}\sum_{k=0}^{N_W-1}(x(k+i))^2\ln\left((x(k+i))^2\right) \tag{39}$$

for example, using a window length $N_W$ of 400 samples, (i.e. 10 milliseconds), after which, in step (9520), the resulting set of features F[p] are returned to the point of invocation.

Returning to FIG. 94, following the determination from step (9404) of the set of features F[p] for the selected test subject 22, *p* to be used to train the Support Vector Machine (SVM) 108, from step (9406), if the test subject 22, *p* is known a priori to exhibit coronary artery disease (CAD), then the value of an associated binary CAD_Status [p] flag is set to TRUE in step (9408). Otherwise, from step (9406), if the test subject 22, *p* is known a priori to not exhibit coronary artery disease (CAD), then the value of the associated binary CAD_Status [p] flag is set to FALSE in step (9410). Then, from either of steps (9410) or (9408), in step (9412), if all of the test subjects 22, *p* have not been processed, then steps (9402) through (9412) of the CAD-detection training process 9400 are repeated for the next test subject 22, *p*. From step (9412), after the sets of features FP[p} and associated CAD_Status [p] are determined for each of the test subjects 22, *p*, then, in step (9414), the Support Vector Machine (SVM) 108 is trained responsive thereto to detect coronary artery disease (CAD).

Referring to FIG. 95, following the training of the Support Vector Machine (SVM) 108 by the CAD-detection training process 9400, the Support Vector Machine (SVM) 108 may then be used to determine whether or not an arbitrary test subject 22, $p_{EVAL}$ exhibits coronary artery disease (CAD). More particularly, the CAD detection process 9600 commences in step (9602) with the input of heart data associated with the test subject 22, $p_{EVAL}$ to be evaluated. Then, in step (9604), the set of features FP[$p_{EVAL}$] is determined by the CAD-detection feature-determination process 9500, supra, for the test subject 22, $p_{EVAL}$ to be evaluated, after which, in step (9606), the Support Vector Machine (SVM) 108—as trained by the CAD-detection training process 9400—is then used to determine whether or not the test subject 22, $p_{EVAL}$ to be evaluated exhibits coronary artery disease (CAD).

While specific embodiments have been described in detail in the foregoing detailed description and illustrated in the accompanying drawings, those with ordinary skill in the art will appreciate that various modifications and alternatives to those details could be developed in light of the overall teachings of the disclosure. It should be understood, that any reference herein to the term "or" is intended to mean an "inclusive or" or what is also known as a "logical OR", wherein when used as a logic statement, the expression "A or B" is true if either A or B is true, or if both A and B are true, and when used as a list of elements, the expression "A, B or C" is intended to include all combinations of the elements recited in the expression, for example, any of the elements selected from the group consisting of A, B, C, (A, B), (A, C), (B, C), and (A, B, C); and so on if additional elements are listed. Furthermore, it should also be understood that the indefinite articles "a" or "an", and the corresponding associated definite articles "the" or "said", are each intended to mean one or more unless otherwise stated, implied, or physically impossible. Yet further, it should be understood that the expressions "at least one of A and B, etc.", "at least one of A or B, etc.", "selected from A and B, etc." and "selected from A or B, etc." are each intended to mean either any recited element individually or any combination of two or more elements, for example, any of the elements from the group consisting of "A", "B", and "A AND B together", etc. Yet further, it should be understood that the expressions "one of A and B, etc." and "one of A or B, etc." are each intended to mean any of the recited elements individually alone, for example, either A alone or B alone, etc., but not A AND B together. Furthermore, it should also be understood that unless indicated otherwise or unless physically impossible, that the above-described embodiments and aspects can be used in combination with one another and are not mutually exclusive. Accordingly, the particular arrangements disclosed are meant to be illustrative only and not limiting as to the scope of the invention, which is to be given the full breadth of the appended claim, and any and all equivalents thereof.

What is claimed is:

1. A computer-implemented method of detecting a cardiac condition from an auscultatory sound signal, comprising:

a. receiving an electrographic signal from an electrocardiogram (ECG) sensor;

b. receiving at least one auscultatory sound signal responsive to a corresponding at least one auscultatory sound sensor operatively associated with a test-subject;

c. generating a feature set of data responsive to said at least one auscultatory sound signal, wherein said feature set of data provides for input to a support vector machine (SVM) that is pretrained to detect the cardiac condition, wherein the operation of generating said feature set of data comprises:

i. for each frequency interval of a plurality of frequency intervals:

a) bandpass filtering said at least one auscultatory sound signal so as to generate a corresponding time series of bandpass-filtered data;

b) segmenting said corresponding time series of bandpass-filtered data responsive to said electrographic signal so as to associate a plurality of heart-cycle time series with said corresponding time series of bandpass-filtered data, wherein each heart-cycle time series of said plurality of heart-cycle time series spans a single corresponding heart cycle;

c) identifying a start of an S1 heart sound in each of said plurality of heart-cycle time series;

d) temporally aligning each of said plurality of heart-cycle time series with respect to said start of said S1 heart sound therein;

e) identifying a longest said heart-cycle time series of said plurality of heart-cycle time series corresponding to a slowest heart cycle of a plurality of heart cycles that correspond to said plurality of heart-cycle time series;

f) for each relatively-shorter said heart-cycle time series of said plurality of heart-cycle time series that is shorter in duration than said longest said heart-cycle time series, temporally scaling and temporally interpolating said each relatively-shorter said heart-cycle time series so as to generate a corresponding temporally-scaled heart-cycle time series that is temporally synchronized with, and of the same length, as said longest said heart-cycle time series;

g) determining an average heart-cycle time series for said frequency interval, wherein each sample of said average heart-cycle time series is responsive to an average of corresponding samples of a) each said heart-cycle time series of said plurality of heart-cycle time series having said same length as said longest said heart-cycle time series and b) each said corresponding temporally-scaled heart-cycle time series associated with remaining said heart-cycle time series of said plurality of heart-cycle time series;

h) determining at least one energy time series selected from the group of energy time series consisting of a standard-energy time series determined from said average heart-cycle time series, and a Shannon-energy time series determined from said average heart-cycle time series, wherein each sample of said standard-energy time series is responsive to a sum squares of values of samples of said average heart-cycle time series for a subset of samples of said average heart-cycle time series within an associated time interval within said average heart-cycle time series, and each sample of said Shannon-energy time series is responsive to a sum of products for a subset of said samples of said average heart-cycle time series within an associated time interval within said average heart-cycle time series;

i) locating at least one first time interval within said average heart-cycle time series, wherein a temporal duration of each first time interval of said at least one first time interval is shorter than a temporal duration of said average heart-cycle time series, and each said first time interval is selected from the group of first time intervals consisting of an S1-heart-sound time interval, a systolic time interval, an S2-heart-sound time interval, a pre-S3-heart-sound time interval, an S3-heart-sound time interval, a diastasis time interval, and an S4-heart-sound time interval; and j) determining a plurality of features of said feature set of data, wherein each feature of said plurality of features is selected from the group of energy measures consisting of a plurality of integrals of said standard-energy time series over a corresponding plurality of second time intervals, a plurality of mean values of said standard-energy time series over said corresponding plurality of second time intervals, a plurality of median values of said standard-energy time series over said corresponding plurality of second time intervals, a plurality of integrals of said Shannon-energy time series over said corresponding plurality of second time intervals, a plurality of mean values of said Shannon-energy time series over said corresponding plurality of second time intervals, and a plurality of median values of said Shannon-energy time series over said corresponding plurality of second time intervals, wherein each second time interval of said corresponding plurality of second time intervals is selected from the group of second time intervals consisting of the entirety of said at least one energy time series and said at least one first time interval; and d. using said support vector machine (SVM) to generate an estimate of whether or not said test-subject exhibits said cardiac condition responsive to said feature set of data.

2. A computer-implemented method of detecting a cardiac condition from an auscultatory sound signal as recited in claim 1, wherein at least one said frequency interval of said plurality of frequency intervals is selected from the group of frequency intervals consisting of within the range of 1 Hz to 10 Hz, within the range of 11 Hz to 30 Hz, within the range of starting at between 3 Hz and 31 Hz and ending at 80 Hz, within the range of 81 Hz to 120 Hz, and within the range of $12^1$ Hz to 1,000 Hz.

3. A computer-implemented method of detecting a cardiac condition from an auscultatory sound signal as recited in claim 1, wherein a start of each said time window is aligned with a corresponding sample of said at least one energy time series.

4. A computer-implemented method of detecting a cardiac condition from an auscultatory sound signal as recited in claim 1, wherein a start of said S1-heart-sound time interval is coincident with the beginning of said average heart-cycle time series, and an end of said S1-heart-sound time interval is responsive to a root of a quadratic equation model of an S1-heart-sound region of said average heart-cycle time series.

5. A computer-implemented method of detecting a cardiac condition from an auscultatory sound signal as recited in claim 4, wherein said end of said S1-heart-sound time interval is responsive to a second root of said quadratic equation model of said S1-heart-sound region of said average heart-cycle time series.

6. A computer-implemented method of detecting a cardiac condition from an auscultatory sound signal as recited in claim 1, wherein a start of said S2-heart-sound time interval is responsive to a first root of a quadratic equation model of an S2-heart-sound region of said average heart-cycle time series, and an end of said S2-heart-sound time interval is responsive to a second root of said quadratic equation model of said S2-heart-sound region of said average heart-cycle time series.

7. A computer-implemented method of detecting a cardiac condition from an auscultatory sound signal as recited in claim 1, wherein a start of said systolic time interval is coincident with the beginning of said average heart-cycle time series, and an end of said systolic time interval is coincident with the beginning of diastole in said average heart-cycle time series.

8. A computer-implemented method of detecting a cardiac condition from an auscultatory sound signal as recited in claim 7, wherein said beginning of said diastole in said average heart-cycle time series is responsive to a second root of a quadratic equation model of an S2-heart-sound region of said average heart-cycle time series.

9. A computer-implemented method of detecting a cardiac condition from an auscultatory sound signal as recited in claim 1, wherein a start of said S4-heart-sound time interval is assumed to occur at a point in time relative to the beginning of said average heart-cycle time series that is 80 percent of the duration of said average heart-cycle time series and an end of said S4-heart-sound time interval is coincident with the end of said average heart-cycle time series.

10. A computer-implemented method of detecting a cardiac condition from an auscultatory sound signal as recited in claim 1, wherein a start of said diastasis time interval is assumed to occur at a temporal offset relative to the beginning of said average heart-cycle time series, wherein said temporal offset is given in milliseconds by 350 plus 0.3 times the quantity (TRR-350), wherein said TRR is the duration of said average heart-cycle time series in milliseconds, and an end of said diastasis time interval is assumed to be coincident with a start of said S4-heart-sound time interval.

11. A computer-implemented method of detecting a cardiac condition from an auscultatory sound signal as recited in claim 10, wherein said start of said S4-heart-sound time interval is assumed to occur at a point in time relative to the beginning of said average heart-cycle time series that is 80 percent of the duration of said average heart-cycle time series.

12. A computer-implemented method of detecting a cardiac condition from an auscultatory sound signal as recited in claim 1, wherein a start of said S3-heart-sound time interval is assumed to occur at a first temporal offset prior to a start of said diastasis time interval, and an end of said S3-heart-sound time interval is assumed to occur at a second temporal offset after said start of said diastasis time interval, wherein said start of said diastasis time interval is assumed to occur at a third temporal offset relative to the beginning of said average heart-cycle time series, wherein said third temporal offset is given in milliseconds by 350 plus 0.3 times the quantity (TRR-350), wherein said TRR is the duration of said average heart-cycle time series in milliseconds.

13. A computer-implemented method of detecting a cardiac condition from an auscultatory sound signal as recited in claim 12, wherein said first temporal offset is within the range of 60 to 100 milliseconds, and said second temporal offset is within the range of 0 to 60 milliseconds.

14. A computer-implemented method of detecting a cardiac condition from an auscultatory sound signal as recited in claim 1, wherein a start of said pre-S3-heart-sound time interval is coincident with the beginning of diastole in said average heart-cycle time series, and an end of said pre-S3-heart-sound time interval is coincident with a start of said S3-heart-sound time interval.

15. A computer-implemented method of detecting a cardiac condition from an auscultatory sound signal as recited in claim 14, wherein said beginning of said diastole in said average heart-cycle time series is responsive to a second root of a quadratic equation model of an S2-heart-sound region of said average heart-cycle time series.

16. A computer-implemented method of detecting a cardiac condition from an auscultatory sound signal as recited in claim 14, wherein said start of said S3-heart-sound time interval is assumed to occur at a first temporal offset prior to a start of said diastasis time interval, said start of said diastasis time interval is assumed to occur at a second temporal offset relative to the beginning of said average heart-cycle time series, said second temporal offset is given in milliseconds by 350 plus 0.3 times the quantity (TRR-350), and said TRR is the duration of said average heart-cycle time series in milliseconds.

17. A computer-implemented metho of detecting a cardiac condition from an auscultatory sound signal as recited in claim 16, wherein said first temporal offset is within the range of 60 to 100 milliseconds.

18. A computer-implemented method of detecting a cardiac condition from an auscultatory sound signal as recited in claim 1, wherein each product of said sum of products of said Shannon-energy time series comprises a square of a value of a sample of said subset of samples of said average heart-cycle time series multiplied by a logarithm of said square of said value.

19. A computer-implemented method of detecting a cardiac condition from an auscultatory sound signal as recited in claim 1, further comprising:

a. repeating steps a-c of claim 1 for each training-test-subject of a plurality of training-test-subjects so as to generate a composite feature set of data, wherein said composite feature set of data comprises a composite of said feature set of data from said each training-test-subject of said plurality of training-test-subjects, a first non-null subset of said plurality of training-test-subjects is known a priori to exhibit said cardiac condition, and a remaining subset of said plurality of training-test-subjects is known a priori to not exhibit said cardiac condition;

b. for each said each training-test-subject of said plurality of training-test-subjects, including in said composite feature set of data an indication of whether or not said each training-test-subject exhibits said cardiac condition; and c. training said support vector machine (SVM) with said composite feature set of data from said plurality of training-test-subjects so as to provide for estimating therewith whether or not a test-subject exhibits said cardiac condition responsive to a corresponding feature set of data associated with said test-subject for the same features as had been incorporated for each said each training-test-subject in said composite feature set of data.

20. A computer-implemented method of detecting a cardiac condition from an auscultatory sound signal as recited in claim 19, wherein the features incorporated in said feature set of data used in step d of claim 1 are the same features used in step c of claim 19 to train said support vector machine (SVM).

21. A computer-implemented method of assessing the quality of an auscultatory sound signal for use in detecting a cardiac condition, comprising:

a. receiving an electrographic signal from an electrocardiogram (ECG) sensor;

b. receiving at least one auscultatory sound signal responsive to a corresponding at least one auscultatory sound sensor operatively associated with a test-subject;

c. segmenting said at least one auscultatory sound signal responsive to said electrographic signal so as to associate a plurality of heart-cycle time series with said at least one auscultatory sound signal, wherein each heart-cycle time series of said plurality of heart-cycle time series spans a single corresponding heart-cycle;

d. temporally aligning each of said plurality of heart-cycle time series with respect to a start of said single corresponding heart-cycle thereof;

e. identifying a longest said heart-cycle time series of said plurality of heart-cycle time series corresponding to a slowest heart-cycle of a plurality of heart-cycles that correspond to said plurality of heart-cycle time series;

f. for each relatively-shorter said heart-cycle time series of said plurality of heart-cycle time series that is shorter in duration than said longest said heart-cycle time series, forming a corresponding zero-padded heart-cycle time series from said each relatively-shorter said heart-cycle time series by also padding said each relatively-shorter said heart-cycle time series with a sufficient number of zero-valued samples at the end of said each relatively-shorter said heart-cycle time series so that a length of said corresponding zero-padded heart-cycle time series is the same as a length of said longest said heart-cycle time series;

g. determining a composite heart-cycle time series, wherein each sample of said composite heart-cycle time series is responsive to a composite of corresponding samples of a) each heart-cycle time series of said plurality of heart-cycle time series having the same said length as said longest said heart-cycle time series and b) each said corresponding zero-padded heart-cycle time series associated with remaining heart-cycle time series of said plurality of heart-cycle time series; and h. assessing a quality of said at least one auscultatory sound signal responsive to said composite heart-cycle time series, wherein the operation of assessing said quality of said at least one auscultatory sound signal is responsive to a value of at least one scaler selected from the group of scalers consisting of a difference-vector magnitude and an angular deviation, wherein said difference-vector magnitude is responsive to a vector distance between a first vector responsive to said composite heart-cycle time series and a second vector responsive to one of said plurality of heart-cycle time series, wherein said second vector is responsive to a time series selected from the group of time series consisting of one of said longest said heart-cycle time series and one of said corresponding zero-padded heart-cycle time series, and said angular deviation is responsive to a vector angle between said first and second vectors.

22. A computer-implemented method of assessing the quality of an auscultatory sound signal for use in detecting a cardiac condition as recited in claim 21, wherein said composite heart-cycle time series comprises a median heart-cycle time series, and each sample of said median heart-cycle time series is responsive to a median of values of corresponding samples of a) each said heart-cycle time series of said plurality of heart-cycle time series having the same said length as said longest said heart-cycle time series and b) each said corresponding zero-padded heart-cycle time series associated with said remaining heart-cycle time series of said plurality of heart-cycle time series.

23. A computer-implemented method of assessing the quality of an auscultatory sound signal for use in detecting a cardiac condition as recited in claim 21, wherein a cosine of said vector angle is responsive to a dot product of said first and second vectors divided by a product of magnitudes of said first and second vectors.

24. A computer-implemented method of assessing the quality of an auscultatory sound signal for use in detecting a cardiac condition as recited in claim 21, further comprising for each said heart-cycle time series of said plurality of heart-cycle time series, causing a corresponding heart-cycle corresponding to said each said heart-cycle time series to be ignored in subsequent calculations if a corresponding said difference-vector magnitude is in excess of a corresponding difference-vector-magnitude threshold.

25. A computer-implemented method of assessing the quality of an auscultatory sound signal for use in detecting a cardiac condition as recited in claim 21, further comprising for each said heart-cycle time series of said plurality of heart-cycle time series, causing a corresponding heart-cycle corresponding to said each said heart-cycle time series to be ignored in subsequent calculations if a corresponding said angular deviation is in excess of a corresponding angular-deviation threshold.

26. A computer-implemented method of assessing the quality of an auscultatory sound signal for use in detecting a cardiac condition as recited in claim 21, further comprising assessing said quality of said at least one auscultatory sound signal responsive to a heart-cycle-duration deviation of at least one said heart-cycle time series of said plurality of heart-cycle time series.

27. A computer-implemented method of assessing the quality of an auscultatory sound signal for use in detecting a cardiac condition as recited in claim 26, wherein said heart-cycle-duration deviation is responsive to a temporal deviation selected from the group of temporal deviations consisting of a first temporal deviation relative to said longest said heart-cycle time series, a second temporal deviation relative to a length of any of said plurality of heart-cycle time series, a third temporal deviation relative to a mean length of said plurality of heart-cycle time series, and a fourth temporal deviation relative to a composite length of said plurality of heart-cycle time series.

28. A computer-implemented method of assessing the quality of an auscultatory sound signal for use in detecting a cardiac condition as recited in claim 26, further comprising for each said heart-cycle time series of said plurality of heart-cycle time series, causing a corresponding heart-cycle corresponding to said at least one said heart-cycle time series to be ignored in subsequent calculations if a corresponding said heart-cycle-duration deviation is in excess of a corresponding heart-cycle-duration-deviation threshold.

* * * * *